US008465918B2

(12) United States Patent
Croce

(10) Patent No.: US 8,465,918 B2
(45) Date of Patent: Jun. 18, 2013

(54) ULTRACONSERVED REGIONS ENCODING NCRNAS

(75) Inventor: Carlo M. Croce, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 298 days.

(21) Appl. No.: 12/672,014

(22) PCT Filed: Aug. 4, 2008

(86) PCT No.: PCT/US2008/072081
§ 371 (c)(1),
(2), (4) Date: Feb. 22, 2010

(87) PCT Pub. No.: WO2009/020905
PCT Pub. Date: Feb. 12, 2009

(65) Prior Publication Data
US 2010/0184842 A1   Jul. 22, 2010

Related U.S. Application Data

(60) Provisional application No. 60/963,329, filed on Aug. 3, 2007.

(51) Int. Cl.
*C12Q 1/68*   (2006.01)

(52) U.S. Cl.
USPC ........................................................ 435/6.1

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |

(Continued)

FOREIGN PATENT DOCUMENTS

| | | |
|---|---|---|
| CA | 2587189 | 12/2006 |
| FR | 2877350 | 5/2006 |

(Continued)

OTHER PUBLICATIONS

Richler et al (Psychiatric Genetics, Feb. 2006, 16:19-23).*
Bejerano et al (Science, 2004, 304:1321-1325).*
Supplementary Table 1 from Bejerano et al (Science, 2004, 304:1321-1325).*
European Communication Pursuant to Article 94(3) EPC, Application No. 07810382.7, dated Dec. 8, 2010.
PCT International Preliminary Report on Patentability, PCT/US2009/065072 filed Nov. 19, 2009, dated Jun. 3, 2011.
European Communication Pursuant to Article 94(3) EPC, Application No. 08768266.2, dated Apr. 18, 2011.
European Search Report, Application No. 11151771-0, dated Feb. 8, 2011.
European Communication Pursuant to Article 94(3) EPC, Application No. 08767439.9, dated Mar. 15, 2011.
PCT International Preliminary Report on Patentability, PCT/US2010/025173 filed Feb. 24, 2010, dated Sep. 9, 2011.

(Continued)

*Primary Examiner* — Laura B Goddard
(74) *Attorney, Agent, or Firm* — MacMillan, Sobanski & Todd, LLC

(57) ABSTRACT

Described herein are methods for differentiate human cancers comprising using one or more transcribed ultraconserved regions (T-UCR) expression profiles where the association between the genomic location of UCRs and the analyzed cancer-related genomic elements is highly statistically significant and comparable to that reported for miRNAs.

3 Claims, 70 Drawing Sheets
(10 of 70 Drawing Sheet(s) Filed in Color)

U.S. PATENT DOCUMENTS

| Publication No. | Date | Inventor |
|---|---|---|
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 0076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005/020795 | 3/2005 |
| WO | 2005060661 | 7/2005 |
| WO | 2005/078139 | 8/2005 |
| WO | 2005/080601 | 9/2005 |
| WO | 2005111211 A2 | 11/2005 |
| WO | 2005/118806 | 12/2005 |
| WO | 2006/105486 | 10/2006 |
| WO | 2006/108718 | 10/2006 |
| WO | 2006108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007/033023 | 3/2007 |
| WO | 2007/044413 | 4/2007 |
| WO | 2007/081680 | 7/2007 |
| WO | 2007/081720 | 7/2007 |

| | | |
|---|---|---|
| WO | 2007/081740 | 7/2007 |
| WO | 2007/084486 | 7/2007 |
| WO | 2007/109236 | 9/2007 |
| WO | 2007112097 | 10/2007 |
| WO | 2007/127190 | 11/2007 |
| WO | 2008/008430 | 1/2008 |
| WO | 2008/036776 | 3/2008 |
| WO | 2008/054828 | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/18303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

European Search Report, Application No. 11151772-8, dated Feb. 8, 2011.
Chinese Office Action, Application No. 200680039776.8 dated Jun. 30, 2011.
Australian Office Action, Application No. 2006291165 dated Aug. 23, 2011.
PCT International Preliminary Report on Patentability, PCT/US2009/038214 filed Mar. 25, 2009, dated Jun. 16, 2011.
European Search Report, Application No. 08713330.2, dated Jul. 22, 2011.
Chinese Office Action, Application No. 200780005821.2 dated Jan. 26, 2011.
European Communication Pursuant to Article 94(3) EPC, Application No. 07867402.5, dated Jan. 5, 2011.
Chinese Office Action, Application No. 200680036598.3 dated Feb. 24, 2011.
Canadian Office Action, Application No. 2,621,441, dated Feb. 1, 2011.
European Search Report, Application No. 11151769-4, dated Feb. 8, 2011.
European Seach Report, Application No. 11151749.6, dated Feb. 8, 2011.
European Seach Report, Application No. 09714868.8 dated Aug. 1, 2011.
European Search Reoprt, Application No. 08841700.1, dated Jan. 4, 2011.
Canadian Office Action, Application No. 2,617,581, dated Feb. 1, 2011.
European Search Report, Application No. 09713926.5 dated Jul. 21, 2011.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Feng, G. et al., "Elevated Serum-Circulating RNA in Patients with Conventional Renal Cell Cancer," Anticancer Research, 2008, pp. 321-326, vol. 28.
Ford, L.P., "A MicroRNA Expression Signature of Human Solid Tumors Defines Cancer Gene Targets," Leukemia Research, 2006, pp. 511-513, vol. 30.
He, L. et al., "A MicroRNA Polycistron as a Potential Human Oncogene," Nature, Jun. 2005, pp. 828-833, vol. 435.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Landgraf, P. et al., "A Mammalian MicroRNA Expression Atlas Based on Small RNA Library Sequencing," Cell, Jun. 2007, pp. 1401-1414, vol. 129.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217.
Meng, F. et al., "MicroRNA-21 Regulates Expression of the PTEN Tumor Suppressor Gene in Human Hepatocellular Cancer," Gastroenterology, 2007, pp. 647-658, vol. 133.
Nam, E.J. et al., "MicroRNA Expression Profiles in Serous Ovarian Carcinoma," Clinical Cancer Research, 2008, pp. 2690-2695, vol. 14, No. 9.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tili, E. et al., "Expression and Function of Micro RNAs in Immune Cells During Normal or Disease State," International Journal of Medicine Sciences, 2008, pp. 73-79, vol. 5, No. 2.
Uil, T.G. et al., "Generation of an Adenoviral Vector Containing an Addition of a Heterologous Ligand to the Serotpe 3 Feber Knob," Cancer Gene Therapy, Feb. 2003, pp. 121-124, vol. 10, No. 2.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

Bartel, D. P., "MicroRNAs: Target Recognition and Regulatory Functions," Cell, Jan. 2009, pp. 215-233, vol. 136.

Bednarek, A. K. et al., "WWOX, the FRA16D Gene, Behaves as a Suppressor of Tumor Growth," Cancer Research, Nov. 2001, pp. 8068-8073, vol. 61.

Bejenaro, etal., "Ultraconserved Elements in the Human Genome," Electronic Suppl. Data, Science, 2004.

Bejerano, G. et al., "Ultraconserved Elements in the Human Genome," Science, May 2004, pp. 1321-1325, vol. 304.

Bell, D. A., "Origins and Molecular Pathology of Ovarian Cancer," Modern Pathology, 2005, pp. S19-S32, vol. 18.

Bichi, R. et al., "Human Chronic Lymphocytic Leukemia Modeled in Mouse by Targeted TCL1 Expression," PNAS, May 2002, pp. 6955-6960, vol. 99, No. 10.

Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.

Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.

Budhu, A. et al., "Identification of Metastasis-Related MicroRNAs in Hepatocellular Carcinoma," Hepatology, Mar. 2008, pp. 897-907, vol. 47, No. 3.

Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.

Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.

Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.

Calin, G. A. et al., "MicroRNA Signatures in Human Cancers," Nature Reviews Cancer, Nov. 2006, pp. 857-866, vol. 6.

Calin, G. A. et al., "MiR-15a and MiR-16-1 Cluster Functions in Human Leukemia," PNAS, Apr. 2008, pp. 5166-5171, vol. 105, No. 13.

Calin, G. A. et al., "Ultraconserved Regions Encoding ncRNAs are Altered in Human Leukemias and Carcinomas," Cancer Cell, Sep. 2007, pp. 215-229, vol. 12.

Chan, J. A. et al., "MicroRNA-21 is an Antiapoptotic Factor in Human Glioblastoma Cells," Cancer Research, Jul. 2005, pp. 6029-6033, vol. 65, No. 14.

Chang, N.-S. et al., "Molecular Mechanisms Underlying WOX1 Activation During Apoptotic and Stress Responses," Biochemical Pharmacology, 2003, pp. 1347-1354, vol. 66.

Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology, 2005, pp. 155-165, vol. 17.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Dalmay, T. et al., "MicroRNAs and the Hallmarks of Cancer," Oncogene, 2006, pp. 6170-6175, vol. 25.

Davies, F. E. et al., "Insights into the Multistep Transformation of MGUS to Myeloma Using Microarray Expression Analysis," Blood, Dec. 2003, pp. 4504-4511, vol. 102, No. 13.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

European Patent Application, EP 1795203 A2, Croce et al., Application No. 06010581.4, filed Feb. 7, 1997, published Jun. 13, 2007.

European Search Report, Application No. 06800599.0 dated Oct. 19, 2009.

European Search Report, Application No. 06814375.9 dated Oct. 8, 2009.

European Search Report, Application No. 06825457.2 dated Sep. 16, 2009.

European Search Report, Application No. 07716208.9 dated Nov. 10, 2009.

European Search Report, Application No. 07717734.3 dated Nov. 9, 2009.

European Search Report, Application No. 07717903.4 dated Oct. 23, 2009.

European Search Report, Application No. 07753450.1 dated Jan. 12, 2009.

European Search Report, Application No. 07810382.7 dated Sep. 14, 2009.

European Search Report, Application No. 07867402.5 dated Mar. 16, 2010.

European Search Report, Application No. 07872618.9 dated Jul. 5, 2010.

European Search Report, Application No. 08767439.6 dated May 12, 2010.

European Search Report, Application No. 08768266.2 dated Jul. 1, 2010.

European Search Report, Application No. 08796821.0 dated Aug. 4, 2010.

European Search Report, Application No. 08841700.1 dated Jun. 2, 2010.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," The Cancer Journal, Jan./Feb. 2008, pp. 1-6, vol. 14, No. 1.

Fabbri, M. et al., "WWOX Gene Restoration Prevents Lung Cancer Growth In Vitro and In Vivo," PNAS, Oct. 2005, pp. 15611-15616, vol. 102, No. 43.

Fong, Y. et al., "Muir-Torre-Like Syndrome in FHIT-Deficient Mice," PNAS, Apr. 2000, pp. 4742-4747, vol. 97, No. 9.

Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Fingerprints During Human Megakaryocytopoiesis," PNAS, Mar. 2006, pp. 5078-5083, vol. 103, No. 13.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.

Griffiths-Jones, S. et al., "miRBase: MicroRNA Sequences, Targets and Gene Nomenclature," Nucleic Acids Research, 2006, pp. D140-D144, vol. 34.

Guimaraes-Sternberg, C. et al., "MicroRNA Modulation of Megakaryoblast Fate Involves Cholinergic Signaling," Leukemia Research, 2006, pp. 583-595, vol. 30.

Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.

Havelange, V. et al., "MicroRNAs: New Players in Acute Myeloid Leukemia," British Journal of Cancer, 2009, pp. 743-748, vol. 101.

Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.

Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.
Lu, J. et al., "MicroRNA Expression Profiles Classify Human Cancers," Nature, Jun. 2005, pp. 834-838, vol. 435.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
McManus, M. T., "MicroRNAs and Cancer," Seminars in Cancer Biology, 2003, pp. 253-258, vol. 13.
Megraw, M. et al., "miRGen: A Database for the Study of Animal MicroRNA Genomic Organization and Function," Nucleic Acids Research, 2007, pp. D149-D155, vol. 35.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.

PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.

Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tang, X. et al., "A Simple Array Platform for MicroRNA Analysis and Its Application in Mouse Tissues," RNA, Aug. 2007, pp. 1-20, vol. 13.
Thomson, J. M. et al., "A Custom Microarray Platform for Analysis of MicroRNA Gene Expression," Nature Methods, Oct. 2004, pp. 1-7, vol. 1, No. 1.
Thorgeirsson, S. S. et al., "Functional Genomics of Hepatocellular Carcinoma," Hepatology, Feb. 2006, pp. S145-S150, vol. 43, No. 2, Suppl. 1.
Tockman, M. S. et al., "Considerations in Bringing a Cancer Biomarker to Clinical Application," Cancer Research, May 1992, pp. 2711s-2718s, vol. 52.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Valeri, N. et al., "Epigenetics, miRNAs, and Human Cancer: A New Chapter in Human Gene Regulation," Mamm Genome, Aug. 2009, pp. 573-580, vol. 20.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. pp. ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

Ambros, V. et al., "A Uniform System for MicroRNA Annotation," RNA, 2003, pp. 277-279, vol. 9.

Baira, E. et al., "Ultraconserved Elements: Genomics, Function and Disease," RNA Biology, Jul. 2008, pp. 132-134, vol. 5, No. 3.

Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.

Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.

Boland, C.R. et al., "Lynch Syndrome: Form, Function, Proteins, and Basketball," Gastroenterology, Aug. 2005, pp. 751-755, vol. 129, No. 2.

Caldas, C. et al., "Sizing Up miRNAs as Cancer Genes," Nature Medicine, Jul. 2005, pp. 712-714, vol. 11, No. 7.

Canadian Intellectual Property Office, Requisition by the Examiner, Application No. 2,635,616, Dated Feb. 21, 2011.

Chinese Office Action, Application No. 200780040146.7 dated May 25, 2011.

Cui, S. et al., "MicroRNAs that Underlie Ovarian Cancer Development and Response to Chemotherapy," 98th AACR Annual Meeting, Apr. 14-18, 2007, Los Angeles, CA.

Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.

EP Search Report, Application No. 08782609.5 dated Oct. 28, 2010.

Esquela-Kerscher, A. et al., "Oncomirs—MicroRNAs with a Role in Cancer," Nature Reviews:Cancer, Apr. 2006, pp. 259-269, vol. 6.

European Search Report, Application No. 08798444.9-2402, PCT/US2008/073964, dated Dec. 16, 2010.

European Search Report, Application No. 08799295.4-2402, PCT/US2008/075565, dated Nov. 9, 2010.

European Supplementary Search Report, Application No. 09715064.3 dated May 24, 2011.

Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.

Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.

Garzon, R. et al., "MicroRNA Expression and Function in Cancer," TRENDS in Molecular Medicine, Oct. 2006, pp. 580-587, vol. 12, No. 12.

Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.

Griffths-Jones, S. et al., "miRBase: Tools for MicroRNA Genomics," Nucleic Acids Research, 2008, pp. D154-D157, vol. 36.

Griffths-Jones, S., "The MicroRNA Registry," Nucleic Acids Research, 2004, pp. D109-D111, vol. 32.

He, X. et al., "MicroRNA and Esophageal Carcinoma," Journal of Nanjing Medical University, 2007, pp. 201-206, vol. 21, No. 4.

Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.

Kozomara, A. et al., "miRBase: Integrating MicroRNA Annotation and Deep-Sequencing Data," Nucleic Acids Research, 2011, pp. D152-D157, vol. 39.

Lagos-Quintana, M. et al., "Identification of Tissue-Specific MicroRNAs from Mouse" Current Biology, Apr. 2002, pp. 735-739, vol. 12.

Lanza, G. et al., "mRNA/microRNA Gene Expression Profile in Microsatellite Unstable Colorectal Cancer," Molecular Cancer, 2007, pp. 1-11, vol. 6, No. 54.

Li, S.-C. et al., "Bioinformatic Discovery of MicroRNA Precursors from Human ESTs and Introns," BMC Genomics, 2006, vol. 7.

Lujambio, A. et al., "A MicroRNA DNA Methylation Signature for Human Cancer Metastasis," PNAS, Sep. 2008, pp. 13556-13561, vol. 105, No. 36.

Medina, P.P. et al., "OncomiR Addiction in an In Vivo Model of MicroRNA-21-Induced Pre-B-Cell Lymphoma," Nature Letters, Sep. 2010, pp. 86-91, vol. 467.

Medina, P.P., "OncomiR Addicton in an in vivo Model of MicroRNA-21-Induced Pre-B-Cell Lymphoma," Supplementary Information, Sep. 2010, p. 1-22.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nicoloso, M.S. et al., "MicroRNAs—The Micro Steering Wheel of Tumour Metastases," Nature Reviews: Cancer, Apr. 2009, pp. 293-302, vol. 9.
Nurden, A.T., "Qualitative Disorders of Platelets and Megakaryocytes," Journal of Thrombosis and Haemostasis, 2005, vol. 3, pp. 1773-1782.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Saini, H.K. et al., "Annotation of Mammalian Primary MicroRNAs," BMC Genomics, 2008, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Slack, F.J., "Big Roles for Small RNAs," Nature, Feb. 2010, p. 616, vol. 463.
State Intellectual Property Office of the People's Republic of China, Notification of the First Office Action, Application No. 200780005791.5, dated Mar. 24, 2011.
Suarez-Saiz, F.J. et al., "MicroRNA Expression Profiling in Acute Myelogenous Leukemia," Canada Blood, Nov. 2004, Abstract #1131, p. 320A.
Taccioli, C. et al., "Ucbase & miRfunc: A Database of Ultraconserved Sequences and MicroRNA Function," Nucleic Acids Research, 2009, pp. D41-D48, vol. 37.
Valeri, N. et al., "Modulation of Mismatch Repair and Genomic Stability by miR-155," PNAS, Apr. 2010, pp. 6982-6987, vol. 107, No. 15.
Wijermans, P.W., "Low Dose Azanucleosidesfor High Risk (s) MDS and AML," Haematologica Reports,Nov. 2006, pp. 74-76. vol. 2, Issue, 15.
Australian Office Action, Application No. 2007205163 dated Nov. 15, 2012.
Chinese Office Action, Application No. 200880116343.7 dated Oct. 22, 2012.
Chinese Office Action, Application No. 200980111708.1 dated Aug. 27, 2012.
Chinese Office Action, Application No. 200880103023.8 dated Oct. 9, 2012.
Chinese Office Action, Application No. 200980112966.1 dated Sep. 20, 2012.
Chinese Office Action, Application No. 200880022612.3 dated Oct. 29, 2012.
EP Examination Report, Application No. 09715064.3 dated Nov. 5, 2012.
EP Search Report, Application No. 12154350.8 dated Sep. 27, 2012.
EP Search Report, Application No. 12165748.0 dated Aug. 23, 2012.
EP Search Report, Application No. 12154326.8 dated Sep. 6, 2012.
EP Search Report, Application No. 12165636.7 dated Sep. 25, 2012.
Ep Search Report, Application No. 12154327.6 dated Sep. 19, 2012.
EP Search Report, Application No. 12154347.4 dated Sep. 27, 2012.
EP Search Report, Application No. 12154354.0 dated Oct. 12, 2012.
EP Search Report, Application No. 12154337.5 dated Oct. 9, 2012.
EP Search Report, Application No. 12154339.1 dated Oct. 9, 2012.
EP Search Report, Application No. 12154322.7 dated Aug. 29, 2012.
EP Search Report, Application No. 12154329.2 dated Sep. 19, 2012.
EP Search Report, Application No. 12154344.1 dated Sep. 19, 2012.
EP Search Report, Application No. 12154334.2 dated Sep. 21, 2012.
EP Search Report, Application No. 12154345.8 dated Sep. 19, 2012.
EP Search Report, Application No. 12154352.4 dated Oct. 12, 2012.
EP Search Report, Application No. 12154346.6 dated Oct. 23, 2012.
EP Search Report, Application No. 12154349.0 dated Sep. 27, 2012.
EP Search Report, Application No. 12165638.3 dated Sep. 28, 2012.
EP Search Report, Application No. 12154341.7 dated Oct. 25, 2012.
EP Search Report, Application No. 12154351.6 dated Oct. 15, 2012.
EP Search Report, Application No. 12154353.2 dated Oct. 15, 2012.
EP Search Report, Application No. 12154332.6 dated Sep. 21, 2012.
Japanese Office Action, Application No. 2008-525107 dated Oct. 19, 2012.
PCT International Preliminary Report on Patentability, PCT/US2011/034451 filed Apr. 29, 2011, dated Nov. 15, 2012.
Ahmad, A. et al., "Distant Metastases of Nasopharyngeal Carcinoma: A Study of 256 Male Patients," Journal of Surgical Oncology, 1986, pp. 194-197, vol. 33.
Alberts, B. et al., Molecular Biology of the Cell, 3rd Edition, 1994, p. 465.
EP Search Report, Application No. 12154348.2 dated Oct. 9, 2012.
Eychene, A. et al., "A New MAFia in Cancer," Nature Reviews Cancer, Sep. 2008, pp. 683-693, vol. 8.
Greenbaum, D. et al., "Comparing Protein Abundance and mRNA Expression Levels on a Genomic Scale," Genome Biology, 2003, pp. 117.1-117.8, vol. 4, Issue 9.
Grier, D.G. et al., "The Pathophysiology of HIX Genes and Their Role in Cancer," Journal of Pathology, 2005, pp. 154-171, vol. 205.
He, H. et al., "The Role of MicroRNA Genes in Papillary Thyroid Carcinoma," PNAS, Dec. 2005, pp. 19075-19080, vol. 102, No. 52.
Hudlebusch, H. et al., "Expression of HOXA Genes in Patients with Multiple Myeloma," Leukemia & Lymphoma, Jun. 2004, pp. 1215-1217, vol. 45, No. 6.
Mascellani, N. et al., "Using miRNA Expression Data for the Study of Human Cancer," Minerva Biotec, 2008, pp. 23-30, vol. 20.
Pouponnot, C. et al., "Cell Context Reveals A Dual Role for Maf in Oncogenesis," Oncogene, 2006, pp. 1299-1310, vol. 25.
Sonoki, T. et al., "Insertion of MicroRNA-125b-1, A Human Homologue of lin-4, into a Rearranged Immunoglobulin Heavy Chain Gene Locus in a Patient with Precursor B-Cell Acute Lymphoblastic Leukemia," Leukemia, 2005, pp. 1-2, vol. 19.
Wu, D. et al., "Micro-RNA: A New Kind of Gene Regulators," Agricultural Sciences in China, Jan. 2006, pp. 77-80, vol. 5, No. 1.

* cited by examiner

```
5'- ACTTCCCCCT:TCTATTA:TACCATTAGCAACG    uc.346A
(bp.158)
      3' -GGGGATAG:TGCTATACGTAATT       miR-155

5'- TCAATGCACTATTGC:AAGACCATTATTGCAT    uc.160 (bp.184)
      3' -GGGGATAG:TCCTATACGTAATT       miR-155

5'- CCGCCATCTACCTGC:CTACTTAGCCCAAGGG    uc.160 (bp.136)
      3'- GACAAGGACGACTTGACTCGGT        miR-24

5'- CTAATGAGACTGAGTTTACA::GTGCCATAGA    uc.348 (bp.170)
      3'- TTGTGACTAAAGTTACCACGAT        miR-29b

5'- TGGAGATAC:AACAAGA:TAACATTAATGAGT    uc.348 (bp.111)
      3' -GGGGATAG:TGCTATACGTAATT       miR-155
```

Figure 3A

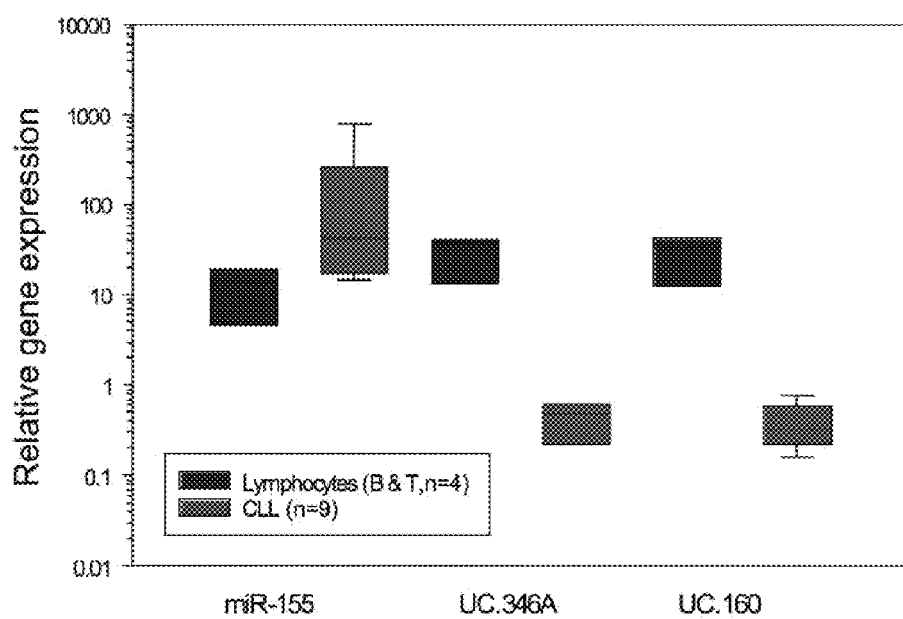

Figure 3B

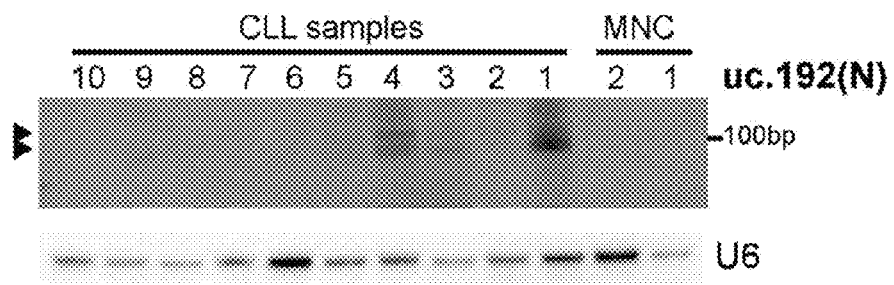
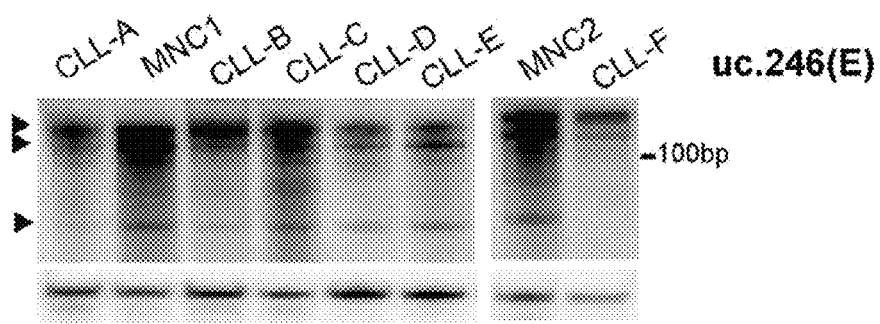
Figure 5

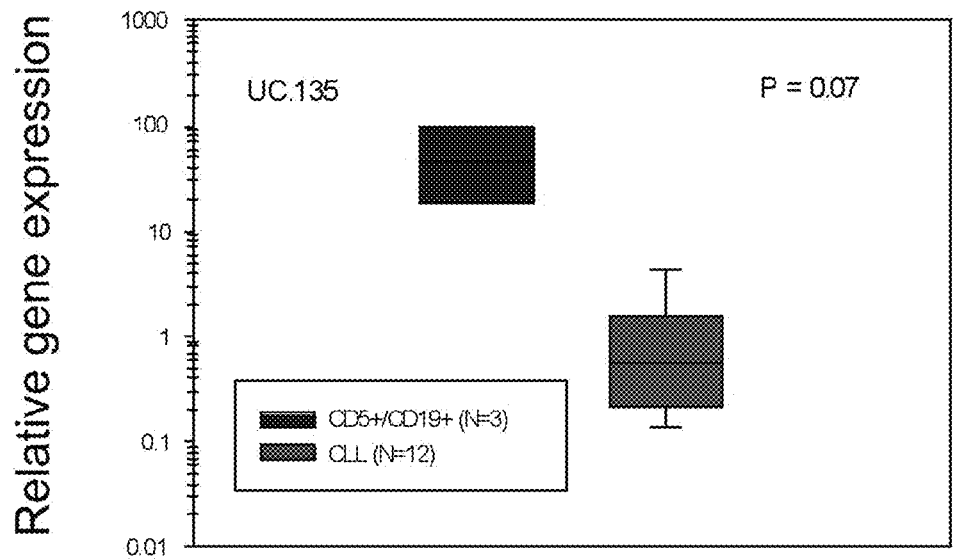
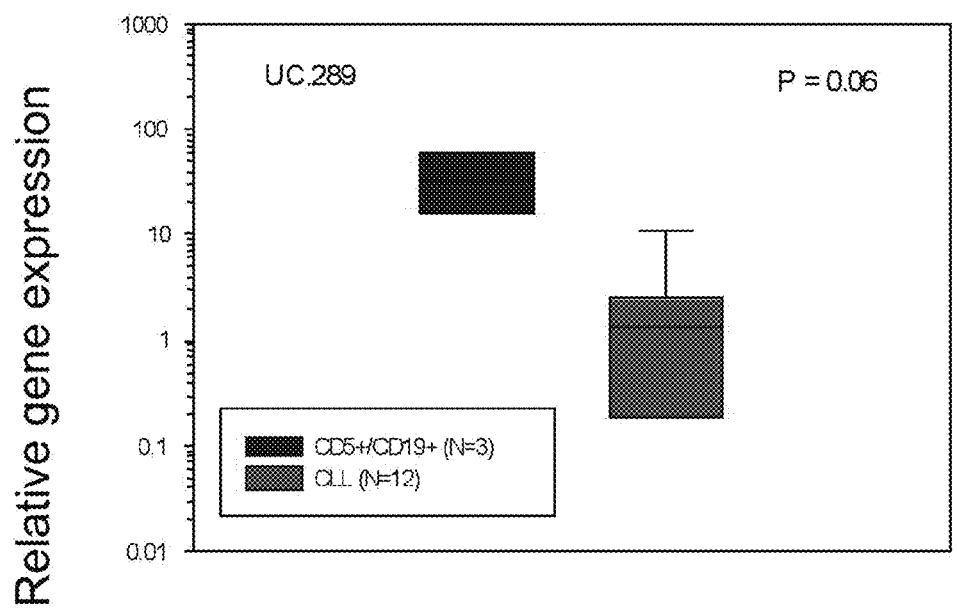
Figure 6

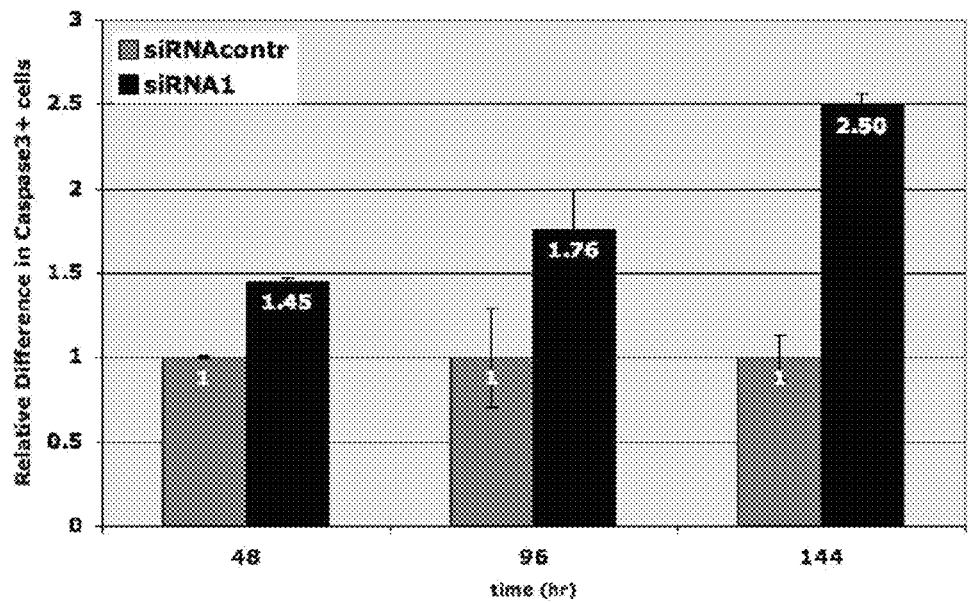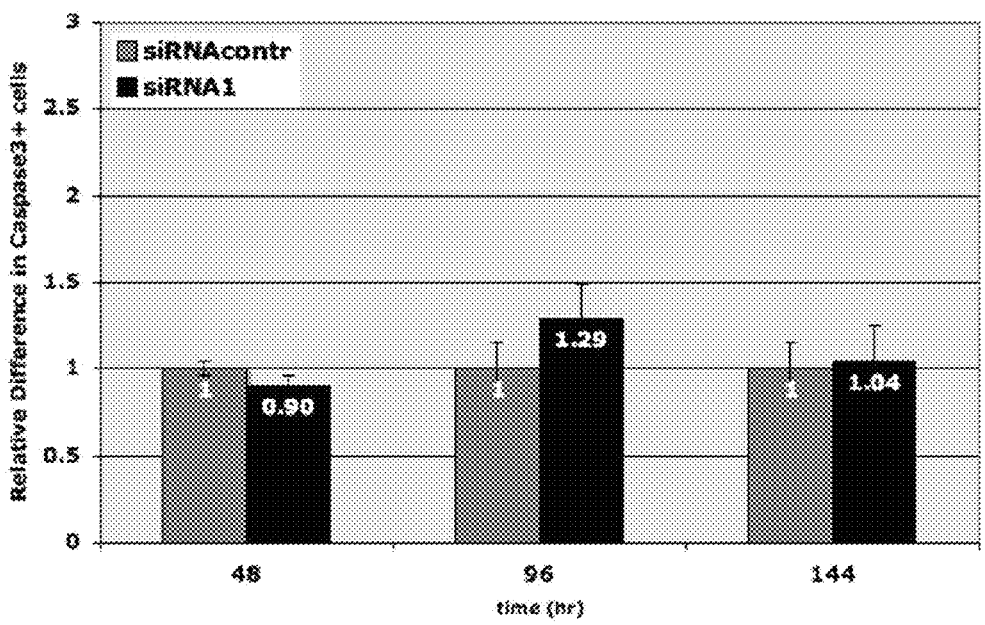
Figure 11

Table 1. Most significant differentially expressed UCRs in leukemias and carcinomas*.

| UCR name | Probe (T-UCR) | Type and location | Significance | Upstream, host and downstream genes | CAGR location and host gene cancer connection |
|---|---|---|---|---|---|
| uc.29 | uc.29+A | Non-exonic | high CRC vs norm | LMO4, N AF118089 | |
| uc.73 | uc.73+A | Possibly Exonic | low CLL vs CD5 high CRC vs norm | AK126774, BC017741 ZFHX1B | |
| uc.111 | uc.111+ | Possibly Exonic | high CRC vs norm | AK128398, N AB051544 | yes |
| uc.112 | uc.112+ | Non-exonic | high CRC vs norm | TBC1D5, N SATB1 | |
| uc.134 | uc.134+A | Possibly Exonic | high CRC vs norm | AF257098, MGC12197, MLF1 | |
| uc.135 | uc.135+ | Exonic | low CLL vs CD5 | GOLPH4, EVI1 ARPM1 | yes in antisense with EVI-1 oncogene overexpressed by t(3;21)(q26;q22) |
| uc.206 | uc.206+ | Non-exonic | high CRC vs norm | SP8, N SP4 | |
| uc.230 | uc.230+ | Possibly Exonic | high CRC vs norm | AK096400, N IFEC | |
| uc.233 | uc.233+ | Exonic | low CLL vs CD5 | C7orf21, CENTG3 ASB10 | in sense with CENTG3 |
| uc.291 | uc.291+ | Possibly Exonic | low CLL vs CD5 | AK024492, C10orf11 KCNMA1 | |

Figure 12

| | | | | |
|---|---|---|---|---|
| uc.292 | uc.292+ | Exonic | high CRC vs norm. | AF338191, MLR2, C10orf12 | in sense with MLR2 |
| uc.339 | uc.339+ | Possibly Exonic | high CRC vs norm. | ATP5G2, N KIAA1536 | yes |
| uc.341 | uc.341+ | Exonic | high CRC vs norm. | HOXC11, HOXC10 HOXC9 | yes in sense with HOXC10 |
| uc.388 | uc.388+ | Non-exonic | high CRC vs norm. | BX641000, TCF12 FLJ14957 | |
| uc.399 | uc.399+A | Non-exonic | high CRC vs norm. | CYLD, N SALL1 | |
| uc.420 | uc.420+A | Exonic | high CRC vs norm. | POLG2, DDX5 LOC90799 | in sense with DDX5, downregulated in colon |

*Note. Only UCRs at P<0.0001 were selected. For full list of UCRs, see Supplementary Table 3. CAGR – cancer associated genomic regions as reported by (Calin et al, 2004b). iN – intronic location Name of the genes as at www.ncbi.nlm.nih.gov/.

Figure 12 continued

Table 2. Mixed effect Poisson regression results of association of UCRs with regions of interest *.

| Region of interest | Ultraconserved regions | | | microRNAs | | | Zinc finger proteins | | |
|---|---|---|---|---|---|---|---|---|---|
| | IRR | 95% CI IRR | p | IRR | 95% CI IRR | p | IRR | 95% CI IRR | p |
| Fragile sites vs. non-fragile sites | 2.98 | 1.69, 5.07 | <0.001 | 9.12 | 6.22, 13.38 | <0.001 | 1.36 | 0.76, 2.44 | 0.29 |
| HPV16 insertion vs. all other | 5.07 | 3.37, 7.64 | <0.001 | 3.22 | 1.55, 6.68 | 0.002 | 0.50 | 0.07, 3.60 | 0.49 |
| Homeobox genes vs. all other | 2.39 | 1.69, 3.39 | <0.001 | 2.95 | 1.63, 5.34 | <0.001 | 0.16 | 0.02, 1.14 | 0.07 |
| HOX Cluster vs. all other | 7.09 | 3.61, 13.93 | <0.001 | 15.77 | 7.39, 33.62 | <0.001 | —† | — | — |
| Amplified regions vs. Non-amplified | 3.05 | 1.99, 4.67 | <0.001 | 3.97 | 2.31, 6.83 | <0.001 | 0.39 | 0.12, 1.23 | 0.11 |
| LOH vs. Other | 2.02 | 1.62, 2.53 | <0.001 | 4.08 | 2.99, 5.56 | <0.001 | 0.54 | 0.14, 2.10 | 0.37 |

* The comparison with a "positive" and a "negative" control class of genes each, microRNAs and Zinc Finger Proteins respectively, is presented. IRR = Incident Rate Ratio.
† Too few events; likelihood-based models are numerically unstable.

Figure 13

Table 3. T-UCRs whose expression inversely correlates with complementary miRNA differentially expressed in CLL patients*.

| T-UCR name | Type and location | T-UCR expression in ZAP-70 pos vs. neg | Complementary miRNAs | MiRNA expression in ZAP-70 pos vs. neg | Upstream, host, downstream genes |
|---|---|---|---|---|---|
| uc.269A | Non-exonic, chr 9 | downregulated | No complementary sites | | AK123000, KIAA1608, LHX2 |
| uc.160 | Non-exonic, chr 5 | downregulated | miR-155, miR-146a, miR-34 and miR-223 | upregulated | AK128395, N AP3B1 |
| uc.215 | Non-exonic, chr 7 | upregulated | No complementary sites | downregulated | INHBA, GLI3 C7orf25 |
| uc.346A | Possibly exonic, chr 12 | downregulated | miR-155 | upregulated | RPC2, N RFX4 |
| uc.348 | Non-exonic, chr 13 | upregulated | miR-29b, miR-29a, miR-29c, and miR-155, miR-24 | downregulated upregulated | KLHL1, DACH FLJ22624 gene desert |

*Among the UCRs differentially expressed between the 70-kD zeta-associated protein (ZAP-70) positive and negative CLLs we selected only the UCRs identified by three different algorithms -GeneSpring ANOVA, PAM (Prediction Analysis for Microarrays) and SAM (Significance Analysis of Microarrays)- and that had a complementary site for microRNAs differentially expressed among the same groups of CLLs.

Figure 14

Calin GA et al

Supplementary Table 1. List of T-UCRs expressed over the background in 19 human normal tissues (3 tissues are in two copies from different individuals). The filter was calculated using the average of blank spots + 2 standard deviations. Expression values were normalized by Lowess and on-chip median centered.

| Sample | Number of tissues in which the UCR pass the filter | B-cell 01 | B-cell 02 | Bladder | Brain | Breast | Esophagus A | Heart | Kidney | Liver | Lung | MNC 01 |
|---|---|---|---|---|---|---|---|---|---|---|---|---|
| uc.188+A | 19 | 3.299 | 2.322 | 1.020 | 1.111 | 0.945 | 1.322 | 0.981 | 0.942 | 1.041 | 1.294 | 1.402 |
| uc.177+A | 19 | 5.091 | 4.313 | 1.480 | 2.045 | 2.251 | 1.556 | 1.691 | 2.002 | 2.132 | 2.414 | 1.790 |
| uc.245+A | 19 | 1.719 | 1.643 | 1.006 | 1.058 | 1.140 | 1.141 | 1.379 | 0.944 | 1.008 | 1.080 | 0.996 |
| uc.426+ | 19 | 2.020 | 1.706 | 1.060 | 1.031 | 1.231 | 1.196 | 1.067 | 0.968 | 1.241 | 1.286 | 1.248 |
| uc.335+A | 19 | 2.179 | 1.898 | 1.740 | 1.156 | 1.116 | 1.568 | 1.097 | 1.289 | 1.053 | 1.637 | 1.241 |
| uc.97+A | 19 | 1.333 | 1.539 | 1.154 | 1.166 | 1.073 | 1.273 | 1.522 | 1.154 | 1.099 | 1.326 | 1.010 |
| uc.234+A | 19 | 1.709 | 1.248 | 0.945 | 1.041 | 1.038 | 1.043 | 0.953 | 0.907 | 0.985 | 1.039 | 1.152 |
| uc.422+ | 19 | 1.541 | 1.322 | 1.146 | 1.179 | 1.066 | 1.264 | 0.998 | 1.084 | 1.264 | 1.248 | 1.222 |
| uc.317+ | 19 | 0.903 | 0.969 | 1.193 | 1.319 | 1.222 | 1.177 | 1.086 | 1.001 | 1.025 | 1.292 | 1.255 |
| uc.206+ | 19 | 1.699 | 1.300 | 0.936 | 1.037 | 0.961 | 0.988 | 0.914 | 0.926 | 1.045 | 1.009 | 1.023 |
| uc.411+A | 19 | 3.420 | 1.843 | 1.010 | 1.098 | 1.011 | 1.051 | 0.995 | 0.944 | 1.079 | 1.080 | 1.135 |
| uc.400+A | 19 | 2.745 | 2.683 | 1.415 | 1.751 | 1.212 | 1.821 | 1.376 | 1.519 | 1.206 | 2.365 | 1.585 |
| uc.192+ | 19 | 0.967 | 0.925 | 1.178 | 1.106 | 1.228 | 1.252 | 1.021 | 0.964 | 0.994 | 1.202 | 1.038 |
| uc.343+A | 19 | 1.043 | 1.048 | 0.962 | 0.934 | 0.987 | 1.028 | 1.061 | 1.004 | 0.993 | 1.039 | 1.069 |
| uc.196+A | 19 | 2.448 | 1.227 | 0.953 | 1.024 | 0.961 | 0.950 | 0.938 | 0.906 | 0.927 | 0.999 | 1.236 |
| uc.346+A | 19 | 4.279 | 4.936 | 4.121 | 3.290 | 3.567 | 2.873 | 2.635 | 1.976 | 3.259 | 4.939 | 3.384 |
| uc.427+ | 19 | 3.093 | 3.142 | 2.218 | 2.363 | 1.878 | 1.879 | 2.129 | 2.315 | 2.871 | 2.662 | 2.370 |
| uc.50+A | 19 | 1.297 | 1.516 | 1.118 | 1.066 | 1.124 | 1.131 | 0.985 | 1.111 | 1.018 | 1.304 | 1.372 |
| uc.73+ | 19 | 0.893 | 0.914 | 1.245 | 1.086 | 1.335 | 0.997 | 1.162 | 1.004 | 1.027 | 1.114 | 1.124 |
| uc.321+A | 19 | 1.697 | 0.984 | 1.161 | 1.006 | 1.063 | 0.996 | 1.036 | 0.960 | 0.973 | 0.971 | 0.932 |
| uc.138+ | 19 | 0.927 | 0.909 | 1.001 | 1.026 | 1.020 | 0.978 | 1.688 | 1.434 | 1.745 | 1.278 | 1.182 |
| uc.310+ | 19 | 1.930 | 1.089 | 1.462 | 1.152 | 1.378 | 1.112 | 1.128 | 1.112 | 1.184 | 1.188 | 1.216 |
| uc.133+A | 19 | 2.558 | 2.571 | 1.074 | 1.258 | 1.130 | 1.202 | 1.445 | 1.249 | 1.521 | 1.352 | 1.273 |
| uc.456+ | 19 | 3.653 | 1.644 | 1.437 | 1.705 | 1.891 | 1.311 | 1.326 | 1.806 | 2.074 | 1.488 | 2.444 |
| uc.338+A | 19 | 2.960 | 2.304 | 0.982 | 1.459 | 1.068 | 1.346 | 0.974 | 1.059 | 0.972 | 1.533 | 1.487 |
| uc.128+ | 19 | 1.450 | 1.043 | 1.065 | 1.033 | 1.106 | 1.098 | 1.093 | 0.978 | 1.079 | 1.222 | 1.086 |
| uc.345+ | 19 | 1.207 | 0.981 | 1.035 | 1.025 | 1.073 | 1.013 | 0.982 | 0.936 | 0.967 | 1.036 | 1.126 |
| uc.248+A | 19 | 1.763 | 1.635 | 1.318 | 1.291 | 1.550 | 1.140 | 1.054 | 1.803 | 1.469 | 1.512 | 1.547 |
| uc.347+ | 19 | 0.898 | 0.917 | 1.089 | 0.954 | 1.086 | 1.122 | 1.024 | 0.958 | 1.007 | 1.059 | 0.993 |
| uc.346+ | 19 | 24.635 | 33.548 | 11.343 | 12.676 | 21.023 | 24.865 | 13.634 | 6.536 | 15.675 | 35.262 | 15.595 |
| uc.204+ | 19 | 1.825 | 2.176 | 2.903 | 1.616 | 2.385 | 2.462 | 2.284 | 1.888 | 1.612 | 2.510 | 2.145 |
| uc.391+A | 19 | 2.105 | 1.979 | 1.106 | 1.227 | 1.161 | 1.337 | 1.015 | 0.959 | 1.307 | 1.308 | 1.329 |
| uc.457+ | 19 | 2.156 | 1.853 | 1.413 | 1.706 | 1.438 | 1.422 | 1.765 | 1.857 | 2.215 | 2.149 | 1.824 |
| uc.316+A | 19 | 1.455 | 1.539 | 1.497 | 1.859 | 1.435 | 1.869 | 1.330 | 1.651 | 1.308 | 1.732 | 1.416 |
| uc.470+A | 19 | 6.553 | 5.553 | 6.978 | 11.972 | 8.041 | 7.532 | 8.759 | 3.437 | 5.064 | 15.702 | 5.131 |
| uc.417+A | 19 | 0.937 | 0.939 | 1.050 | 0.992 | 0.967 | 0.965 | 0.968 | 0.957 | 0.965 | 0.920 | 0.924 |
| uc.420+ | 19 | 6.291 | 5.773 | 2.604 | 3.135 | 3.480 | 3.992 | 2.900 | 2.713 | 3.062 | 7.049 | 4.790 |
| uc.327+A | 19 | 2.291 | 3.278 | 3.256 | 2.719 | 3.406 | 3.451 | 3.332 | 1.900 | 3.060 | 5.580 | 3.194 |
| uc.349+ | 19 | 1.771 | 2.209 | 1.802 | 1.457 | 1.494 | 1.527 | 1.328 | 1.440 | 1.426 | 3.688 | 1.784 |
| uc.223+A | 19 | 1.782 | 1.729 | 1.219 | 1.314 | 1.071 | 1.284 | 1.048 | 1.365 | 1.099 | 1.143 | 1.199 |
| uc.348+ | 19 | 1.134 | 1.337 | 1.641 | 1.675 | 2.082 | 2.004 | 1.623 | 1.267 | 1.902 | 1.859 | 1.259 |
| uc.16+ | 19 | 2.455 | 1.366 | 1.400 | 1.386 | 1.276 | 1.402 | 1.314 | 1.126 | 1.364 | 1.520 | 1.465 |
| uc.46+ | 19 | 1.245 | 1.134 | 0.951 | 1.031 | 0.976 | 0.973 | 0.949 | 0.978 | 0.929 | 1.005 | 0.996 |
| uc.275+ | 19 | 2.832 | 1.291 | 1.021 | 1.080 | 1.161 | 1.078 | 1.079 | 0.835 | 1.219 | 1.113 | 1.808 |
| uc.362+A | 19 | 3.420 | 2.761 | 1.723 | 2.045 | 2.044 | 2.062 | 2.658 | 1.846 | 3.457 | 3.562 | 2.318 |
| uc.131+ | 19 | 1.059 | 1.111 | 1.178 | 1.033 | 1.097 | 1.088 | 1.139 | 0.994 | 0.942 | 1.207 | 1.175 |
| uc.309+A | 19 | 2.576 | 2.460 | 3.077 | 3.334 | 4.134 | 2.815 | 3.026 | 1.906 | 2.487 | 3.122 | 3.066 |
| uc.383+ | 19 | 3.465 | 4.800 | 2.459 | 2.819 | 2.494 | 3.776 | 2.535 | 2.736 | 3.364 | 7.434 | 3.252 |
| uc.358+A | 19 | 1.462 | 1.454 | 1.513 | 2.183 | 2.364 | 2.182 | 1.337 | 1.204 | 1.478 | 1.950 | 2.825 |
| uc.167+ | 19 | 11.447 | 13.139 | 24.697 | 16.005 | 30.161 | 52.179 | 11.496 | 6.796 | 13.735 | 71.374 | 18.829 |
| uc.283+A | 19 | 24.122 | 23.244 | 12.128 | 15.535 | 17.655 | 21.088 | 12.781 | 5.894 | 8.923 | 46.720 | 14.112 |
| uc.21+A | 19 | 1.292 | 1.303 | 0.986 | 1.053 | 0.964 | 1.148 | 0.958 | 1.058 | 1.115 | 1.121 | 1.157 |
| uc.133+ | 19 | 1.629 | 1.545 | 0.961 | 1.051 | 1.026 | 1.049 | 0.941 | 0.901 | 0.993 | 1.083 | 0.997 |
| uc.48+ | 19 | 1.968 | 1.881 | 1.467 | 2.045 | 2.675 | 1.677 | 1.522 | 1.190 | 1.466 | 1.596 | 2.076 |
| uc.190+A | 19 | 3.073 | 3.861 | 1.745 | 2.444 | 1.974 | 2.161 | 2.471 | 2.442 | 3.109 | 3.237 | 3.196 |
| uc.134+ | 19 | 2.967 | 2.350 | 2.071 | 2.014 | 1.713 | 1.842 | 1.504 | 1.426 | 1.755 | 2.412 | 2.048 |
| uc.47+ | 19 | 2.281 | 2.351 | 1.744 | 1.964 | 1.552 | 1.585 | 1.911 | 1.639 | 2.187 | 2.147 | 1.735 |
| uc.10+A | 19 | 1.887 | 1.921 | 1.156 | 1.998 | 1.114 | 1.601 | 1.218 | 1.616 | 1.652 | 1.586 | 1.450 |
| uc.477+A | 19 | 9.461 | 8.824 | 2.869 | 4.881 | 3.248 | 3.748 | 4.869 | 3.374 | 6.340 | 6.680 | 5.091 |
| uc.278+ | 19 | 5.920 | 5.384 | 2.968 | 3.294 | 2.751 | 7.359 | 2.634 | 2.270 | 3.033 | 10.904 | 5.726 |
| uc.359+ | 19 | 2.495 | 2.491 | 1.137 | 1.531 | 1.057 | 1.214 | 1.294 | 1.513 | 1.660 | 1.597 | 1.281 |
| uc.118+A | 19 | 1.065 | 1.066 | 1.011 | 1.165 | 1.072 | 1.466 | 1.192 | 1.115 | 1.199 | 1.177 | 1.192 |
| uc.196+ | 19 | 1.050 | 1.084 | 1.074 | 1.068 | 1.277 | 1.031 | 1.265 | 1.392 | 1.239 | 1.203 | 1.140 |

Figure 15

| Sample | Number of tissues in which the UCR pass the filter | B-cell 01 | B-cell 02 | Bladder | Brain | Breast | Esophagus A | Heart | Kidney | Liver | Lung | MNC 01 |
|---|---|---|---|---|---|---|---|---|---|---|---|---|
| uc.75+ | 19 | 1.378 | 1.691 | 0.977 | 1.177 | 1.082 | 1.064 | 0.945 | 0.979 | 1.177 | 1.025 | 0.979 |
| uc.297+A | 19 | 1.315 | 1.272 | 1.007 | 0.988 | 1.001 | 1.002 | 1.115 | 0.961 | 0.940 | 1.018 | 1.015 |
| uc.161+ | 19 | 1.379 | 1.223 | 1.034 | 1.252 | 1.475 | 1.149 | 1.205 | 1.016 | 1.312 | 1.557 | 1.291 |
| uc.195+ | 19 | 1.256 | 1.199 | 1.235 | 1.531 | 1.443 | 1.021 | 1.975 | 1.399 | 2.458 | 1.644 | 1.225 |
| uc.275+A | 19 | 1.167 | 1.137 | 1.141 | 1.127 | 1.152 | 1.056 | 1.333 | 1.429 | 1.555 | 1.302 | 1.098 |
| uc.469+A | 19 | 1.394 | 1.535 | 1.294 | 1.757 | 1.790 | 1.256 | 2.256 | 1.833 | 2.939 | 2.334 | 1.683 |
| uc.160+ | 19 | 0.921 | 0.812 | 2.878 | 2.724 | 4.630 | 2.594 | 2.820 | 0.973 | 1.123 | 4.875 | 5.155 |
| uc.354+A | 19 | 2.216 | 1.932 | 1.907 | 1.829 | 1.872 | 1.920 | 2.031 | 1.746 | 3.044 | 2.528 | 1.902 |
| uc.43+ | 19 | 2.729 | 2.529 | 1.957 | 2.177 | 1.525 | 2.257 | 2.009 | 1.996 | 2.224 | 2.573 | 1.998 |
| uc.78+ | 19 | 2.967 | 3.917 | 1.678 | 1.567 | 1.961 | 2.435 | 1.688 | 1.695 | 2.423 | 3.432 | 2.083 |
| uc.182+A | 19 | 1.670 | 1.498 | 1.157 | 1.082 | 1.144 | 1.129 | 0.987 | 1.035 | 1.043 | 1.216 | 1.084 |
| uc.373+A | 19 | 1.081 | 1.176 | 0.979 | 0.954 | 0.922 | 1.056 | 0.996 | 0.974 | 0.934 | 0.996 | 0.977 |
| uc.44+ | 19 | 0.992 | 0.954 | 2.195 | 1.698 | 2.266 | 1.352 | 1.648 | 1.051 | 1.032 | 1.084 | 1.047 |
| uc.77+ | 19 | 5.741 | 7.487 | 2.978 | 4.447 | 3.316 | 5.482 | 2.823 | 3.354 | 4.181 | 7.342 | 3.715 |
| uc.13+A | 19 | 1.237 | 1.141 | 0.995 | 0.993 | 0.963 | 0.966 | 1.056 | 0.969 | 1.004 | 1.101 | 0.998 |
| uc.472+A | 19 | 2.846 | 1.710 | 1.117 | 1.161 | 1.017 | 0.954 | 0.931 | 0.919 | 0.984 | 1.278 | 1.210 |
| uc.382+ | 19 | 1.655 | 2.144 | 1.162 | 1.366 | 1.321 | 1.569 | 1.197 | 1.105 | 1.532 | 1.845 | 1.435 |
| uc.162+ | 19 | 1.427 | 1.026 | 0.947 | 0.986 | 0.957 | 0.939 | 1.013 | 1.027 | 0.990 | 1.079 | 1.047 |
| uc.117+A | 19 | 3.317 | 2.859 | 3.748 | 2.641 | 3.811 | 4.049 | 3.042 | 1.763 | 2.523 | 5.085 | 3.694 |
| uc.186+ | 19 | 1.311 | 1.137 | 0.932 | 1.121 | 0.926 | 0.955 | 0.927 | 1.123 | 0.994 | 1.029 | 1.097 |
| uc.46+A | 19 | 5.796 | 4.735 | 3.401 | 4.793 | 3.453 | 4.505 | 3.510 | 2.686 | 4.799 | 8.173 | 4.530 |
| uc.151+ | 19 | 2.230 | 1.345 | 1.060 | 0.989 | 1.076 | 1.046 | 1.023 | 0.965 | 1.075 | 1.386 | 1.301 |
| uc.295+ | 19 | 1.132 | 1.037 | 0.965 | 0.966 | 0.947 | 0.991 | 0.935 | 0.935 | 0.990 | 0.943 | 1.074 |
| uc.106+A | 19 | 1.608 | 1.432 | 1.205 | 1.294 | 1.646 | 1.008 | 1.457 | 1.382 | 1.801 | 1.677 | 1.644 |
| uc.63+ | 19 | 6.406 | 5.658 | 1.362 | 1.575 | 1.401 | 1.536 | 1.405 | 1.192 | 2.004 | 1.544 | 1.729 |
| uc.389+A | 19 | 0.994 | 0.915 | 1.089 | 0.976 | 0.997 | 1.004 | 1.015 | 0.938 | 0.969 | 1.015 | 1.047 |
| uc.285+A | 19 | 2.101 | 1.439 | 1.172 | 1.284 | 1.066 | 1.083 | 1.157 | 1.097 | 1.033 | 1.097 | 1.355 |
| uc.185+ | 19 | 1.319 | 1.257 | 1.226 | 1.145 | 0.960 | 1.264 | 1.079 | 1.210 | 1.113 | 1.143 | 1.174 |
| uc.181+A | 19 | 2.596 | 2.714 | 2.265 | 1.418 | 1.509 | 1.501 | 1.535 | 1.500 | 1.624 | 2.113 | 1.766 |
| uc.267+A | 19 | 1.294 | 1.215 | 0.908 | 1.136 | 0.939 | 1.017 | 0.960 | 1.057 | 0.961 | 0.928 | 0.977 |
| uc.443+A | 19 | 1.295 | 1.355 | 0.965 | 1.113 | 1.016 | 1.150 | 0.993 | 1.131 | 1.088 | 1.369 | 1.119 |
| uc.371+ | 19 | 1.397 | 1.594 | 1.581 | 1.217 | 1.339 | 1.334 | 1.239 | 1.035 | 1.057 | 1.376 | 1.458 |
| uc.153+ | 19 | 3.933 | 2.398 | 1.116 | 1.465 | 1.414 | 1.898 | 1.164 | 1.162 | 1.568 | 1.674 | 2.817 |
| uc.170+A | 19 | 2.296 | 1.539 | 0.918 | 1.010 | 0.902 | 1.196 | 0.944 | 1.022 | 1.137 | 1.133 | 1.202 |
| uc.128+A | 19 | 7.916 | 10.716 | 2.611 | 3.473 | 2.814 | 3.505 | 1.942 | 1.842 | 3.592 | 4.833 | 4.116 |
| uc.468+A | 19 | 3.115 | 1.443 | 1.010 | 1.207 | 1.007 | 1.033 | 0.975 | 0.944 | 1.082 | 1.224 | 1.517 |
| uc.189+ | 19 | 2.409 | 2.395 | 3.340 | 3.323 | 3.290 | 2.953 | 2.768 | 1.722 | 2.841 | 5.286 | 3.384 |
| uc.188+ | 19 | 1.381 | 1.369 | 1.157 | 1.138 | 1.011 | 1.011 | 1.156 | 1.142 | 1.491 | 1.460 | 1.277 |
| uc.95+ | 19 | 7.874 | 8.014 | 2.567 | 3.761 | 2.059 | 4.848 | 2.264 | 2.390 | 3.429 | 4.134 | 3.960 |
| uc.309+ | 19 | 2.063 | 1.161 | 1.166 | 1.136 | 1.118 | 1.068 | 1.114 | 0.935 | 1.096 | 1.085 | 1.337 |
| uc.277+A | 19 | 1.156 | 1.047 | 0.974 | 1.001 | 1.030 | 1.056 | 0.965 | 1.054 | 0.981 | 0.992 | 1.018 |
| uc.96+ | 19 | 1.309 | 1.450 | 1.276 | 1.755 | 1.558 | 1.458 | 1.656 | 1.575 | 2.293 | 1.755 | 1.581 |
| uc.241+A | 19 | 1.137 | 1.122 | 1.514 | 1.149 | 1.267 | 1.159 | 1.119 | 1.199 | 1.408 | 1.111 | 1.199 |
| uc.256+A | 19 | 5.431 | 8.578 | 2.521 | 2.901 | 1.884 | 3.411 | 2.081 | 2.821 | 2.192 | 3.495 | 2.858 |
| uc.334+A | 19 | 1.289 | 1.224 | 1.044 | 1.052 | 1.027 | 0.978 | 0.984 | 1.133 | 1.142 | 1.315 | 1.107 |
| uc.92+ | 19 | 1.455 | 1.309 | 1.016 | 1.079 | 1.013 | 1.139 | 1.017 | 0.961 | 0.973 | 1.057 | 1.155 |
| uc.268+A | 19 | 1.312 | 1.313 | 1.036 | 1.243 | 1.027 | 1.017 | 1.255 | 1.316 | 1.266 | 1.151 | 1.058 |
| uc.151+A | 19 | 1.467 | 1.487 | 1.130 | 1.550 | 1.363 | 1.105 | 1.396 | 1.190 | 1.807 | 1.354 | 1.503 |
| uc.183+ | 19 | 1.955 | 1.655 | 1.373 | 1.261 | 1.183 | 1.696 | 1.321 | 1.044 | 1.134 | 1.526 | 1.257 |
| uc.378+A | 19 | 5.865 | 5.882 | 3.190 | 6.598 | 4.521 | 8.591 | 5.668 | 5.232 | 9.471 | 13.484 | 6.133 |
| uc.291+ | 19 | 1.178 | 1.304 | 0.995 | 1.030 | 0.989 | 1.071 | 0.937 | 0.981 | 1.036 | 1.025 | 1.014 |
| uc.31+ | 19 | 1.487 | 2.185 | 1.559 | 1.331 | 1.852 | 1.823 | 1.460 | 1.613 | 1.641 | 1.391 | 1.631 |
| uc.263+A | 19 | 1.920 | 1.824 | 2.093 | 2.592 | 2.345 | 1.339 | 2.569 | 2.373 | 4.174 | 3.280 | 2.369 |
| uc.299+A | 19 | 5.935 | 7.807 | 3.976 | 5.207 | 5.001 | 5.415 | 3.687 | 3.588 | 5.083 | 13.250 | 5.531 |
| uc.181+ | 19 | 1.035 | 1.664 | 1.044 | 1.025 | 1.091 | 0.974 | 1.090 | 1.063 | 1.215 | 0.984 | 1.059 |
| uc.345+A | 19 | 1.645 | 1.121 | 1.248 | 1.016 | 1.121 | 1.208 | 1.318 | 1.193 | 1.412 | 1.258 | 1.114 |
| uc.331+A | 19 | 3.955 | 2.266 | 2.691 | 1.875 | 1.990 | 1.747 | 1.934 | 1.528 | 2.012 | 2.456 | 2.027 |
| uc.252+A | 19 | 1.138 | 1.189 | 1.393 | 1.077 | 1.067 | 1.105 | 1.137 | 1.104 | 1.163 | 1.178 | 1.168 |
| uc.182+ | 19 | 4.215 | 1.794 | 1.282 | 1.194 | 1.465 | 1.428 | 1.299 | 1.186 | 1.229 | 1.604 | 1.931 |
| uc.378+ | 19 | 2.975 | 1.965 | 1.701 | 2.523 | 1.722 | 1.972 | 1.466 | 1.429 | 1.903 | 2.224 | 2.457 |
| uc.462+A | 19 | 8.768 | 6.357 | 4.006 | 7.407 | 4.339 | 6.553 | 6.064 | 4.677 | 7.351 | 10.334 | 6.303 |
| uc.233+ | 19 | 0.942 | 1.007 | 1.186 | 1.774 | 1.266 | 1.047 | 2.299 | 2.076 | 1.185 | 1.197 | 1.023 |
| uc.150+A | 19 | 1.224 | 1.487 | 1.199 | 1.188 | 1.219 | 1.067 | 1.210 | 1.218 | 1.334 | 1.573 | 1.301 |
| uc.234+ | 19 | 2.728 | 2.617 | 1.574 | 2.068 | 1.551 | 1.826 | 2.712 | 2.365 | 3.415 | 2.467 | 2.304 |
| uc.215+A | 19 | 1.105 | 1.037 | 0.993 | 1.085 | 0.977 | 1.046 | 1.168 | 1.025 | 1.482 | 1.046 | 1.010 |
| uc.258+ | 19 | 3.141 | 3.086 | 1.440 | 2.378 | 1.238 | 1.744 | 1.888 | 1.742 | 2.323 | 1.789 | 1.752 |
| uc.20+A | 19 | 2.854 | 1.304 | 0.957 | 1.085 | 1.093 | 1.151 | 1.058 | 1.025 | 1.032 | 1.102 | 1.074 |
| uc.342+ | 19 | 1.264 | 1.234 | 1.058 | 1.252 | 1.296 | 1.308 | 1.376 | 1.299 | 1.463 | 1.349 | 1.256 |
| uc.450+ | 19 | 1.360 | 1.339 | 1.095 | 1.686 | 1.196 | 1.097 | 1.203 | 1.273 | 1.611 | 1.452 | 1.197 |
| uc.453+ | 19 | 2.184 | 1.387 | 1.633 | 1.359 | 1.526 | 1.971 | 1.226 | 1.027 | 1.204 | 1.292 | 1.359 |
| uc.237+A | 19 | 1.423 | 1.451 | 0.940 | 1.003 | 0.963 | 0.964 | 1.004 | 1.090 | 1.026 | 0.995 | 0.946 |

Figure 15 Continued

| Sample | Number of tissues in which the UCR pass the filter | B-cell 01 | B-cell 02 | Bladder | Brain | Breast | Esophagus A | Heart | Kidney | Liver | Lung | MNC 01 |
|---|---|---|---|---|---|---|---|---|---|---|---|---|
| uc.452+ | 19 | 1.438 | 1.394 | 1.019 | 1.160 | 1.013 | 1.260 | 1.021 | 1.265 | 1.071 | 1.118 | 1.018 |
| uc.41+ | 19 | 1.227 | 1.339 | 1.150 | 1.267 | 1.161 | 1.248 | 1.171 | 1.312 | 1.368 | 1.195 | 1.164 |
| uc.200+ | 19 | 6.017 | 4.815 | 2.040 | 3.308 | 2.252 | 3.152 | 2.342 | 2.922 | 2.729 | 2.817 | 2.877 |
| uc.305+A | 19 | 2.510 | 2.410 | 1.531 | 2.232 | 1.327 | 1.725 | 1.385 | 1.689 | 1.694 | 1.720 | 1.774 |
| uc.343+ | 19 | 1.165 | 1.159 | 0.966 | 0.967 | 0.989 | 1.063 | 0.994 | 1.014 | 1.012 | 1.028 | 1.046 |
| uc.383+A | 19 | 1.418 | 1.141 | 0.954 | 0.992 | 0.926 | 0.977 | 1.060 | 0.953 | 1.000 | 0.974 | 1.083 |
| uc.122+A | 19 | 1.623 | 1.273 | 0.968 | 0.987 | 0.962 | 1.113 | 1.032 | 1.136 | 0.996 | 1.083 | 1.101 |
| uc.473+A | 19 | 6.485 | 4.115 | 4.231 | 5.594 | 5.543 | 4.103 | 7.036 | 3.836 | 10.952 | 16.614 | 4.492 |
| uc.229+A | 19 | 1.724 | 1.767 | 1.821 | 2.065 | 1.859 | 1.544 | 2.207 | 1.883 | 2.623 | 1.865 | 2.040 |
| uc.372+ | 19 | 2.034 | 1.909 | 1.090 | 1.370 | 1.170 | 1.364 | 1.129 | 1.290 | 1.296 | 1.277 | 1.336 |
| uc.465+A | 19 | 9.943 | 14.994 | 5.270 | 7.080 | 5.869 | 7.987 | 5.044 | 4.957 | 7.991 | 11.358 | 8.276 |
| uc.292+A | 19 | 9.618 | 17.358 | 7.878 | 9.769 | 13.558 | 16.494 | 8.609 | 5.974 | 15.622 | 57.165 | 8.412 |
| uc.478+A | 19 | 3.785 | 3.532 | 1.954 | 2.908 | 1.647 | 2.681 | 1.604 | 1.801 | 1.795 | 3.137 | 2.632 |
| uc.299+ | 19 | 3.573 | 2.948 | 2.824 | 3.696 | 3.583 | 2.543 | 2.038 | 1.731 | 2.663 | 3.681 | 3.972 |
| uc.192+A | 19 | 1.340 | 1.531 | 1.482 | 1.107 | 1.011 | 1.261 | 1.239 | 1.196 | 1.035 | 1.268 | 1.077 |
| uc.33+ | 19 | 2.159 | 1.957 | 1.813 | 2.172 | 1.934 | 1.795 | 2.205 | 2.600 | 2.825 | 2.009 | 2.433 |
| uc.54+ | 19 | 1.529 | 1.159 | 0.983 | 1.016 | 0.981 | 0.961 | 0.968 | 1.018 | 1.155 | 1.025 | 1.458 |
| uc.34+A | 19 | 1.662 | 1.752 | 1.272 | 1.193 | 1.473 | 1.249 | 1.533 | 1.617 | 2.117 | 1.682 | 1.535 |
| uc.158+ | 19 | 2.932 | 1.211 | 1.167 | 1.181 | 1.139 | 1.151 | 1.029 | 0.995 | 1.222 | 1.327 | 1.261 |
| uc.440+A | 19 | 1.242 | 1.237 | 0.971 | 1.066 | 1.050 | 1.008 | 1.066 | 1.039 | 1.176 | 1.089 | 1.207 |
| uc.57+ | 19 | 1.312 | 1.259 | 1.075 | 1.173 | 1.041 | 1.095 | 1.758 | 1.152 | 1.026 | 1.088 | 1.127 |
| uc.42+A | 19 | 1.427 | 1.724 | 1.054 | 1.114 | 0.976 | 1.092 | 0.984 | 1.162 | 1.053 | 1.316 | 1.096 |
| uc.340+ | 19 | 2.921 | 2.797 | 1.683 | 2.141 | 1.913 | 2.363 | 1.684 | 1.723 | 2.103 | 2.360 | 1.977 |
| uc.319+A | 19 | 0.951 | 0.941 | 1.147 | 1.137 | 1.045 | 1.155 | 1.080 | 1.263 | 1.051 | 1.099 | 1.002 |
| uc.483+ | 19 | 1.697 | 1.369 | 1.511 | 1.444 | 1.614 | 1.501 | 1.489 | 1.545 | 1.938 | 2.779 | 1.623 |
| uc.263+ | 19 | 2.926 | 1.592 | 1.054 | 1.261 | 1.267 | 1.297 | 0.909 | 1.016 | 1.387 | 1.419 | 1.643 |
| uc.204+A | 19 | 3.523 | 2.777 | 2.162 | 1.698 | 1.987 | 2.552 | 1.964 | 1.456 | 1.747 | 1.702 | 2.066 |
| uc.230+ | 19 | 1.291 | 1.655 | 3.488 | 11.308 | 5.278 | 4.831 | 5.044 | 3.187 | 5.279 | 5.932 | 1.999 |
| uc.292+A | 19 | 1.543 | 1.604 | 1.101 | 1.111 | 0.997 | 1.125 | 0.939 | 1.415 | 0.975 | 1.300 | 1.053 |
| uc.220+ | 19 | 0.959 | 1.604 | 0.956 | 1.071 | 1.094 | 0.906 | 1.011 | 1.192 | 1.351 | 1.032 | 1.083 |
| uc.473+ | 19 | 5.476 | 5.222 | 1.170 | 2.177 | 1.293 | 2.111 | 1.128 | 1.713 | 2.043 | 1.739 | 1.903 |
| uc.329+A | 19 | 2.042 | 1.657 | 1.390 | 1.392 | 1.281 | 1.514 | 1.256 | 1.512 | 1.280 | 1.461 | 1.329 |
| uc.203+A | 19 | 1.077 | 0.973 | 0.934 | 0.935 | 0.930 | 0.947 | 1.154 | 0.929 | 0.946 | 0.985 | 0.925 |
| uc.472+ | 19 | 1.438 | 1.273 | 1.119 | 1.308 | 1.193 | 1.439 | 1.150 | 1.089 | 1.247 | 1.522 | 1.281 |
| uc.475+A | 19 | 3.519 | 2.136 | 2.063 | 2.354 | 2.175 | 1.660 | 1.765 | 1.179 | 1.860 | 2.431 | 2.447 |
| uc.146+ | 19 | 1.627 | 1.186 | 1.059 | 1.150 | 1.072 | 1.104 | 1.302 | 1.222 | 1.264 | 1.226 | 1.203 |
| uc.27+ | 19 | 0.879 | 0.929 | 1.031 | 1.024 | 1.011 | 1.055 | 0.994 | 1.080 | 1.044 | 1.054 | 0.967 |
| uc.111+ | 19 | 1.389 | 1.263 | 1.216 | 1.138 | 1.176 | 1.231 | 1.152 | 1.086 | 1.049 | 1.327 | 1.186 |
| uc.362+A | 19 | 2.287 | 1.652 | 1.422 | 1.267 | 1.221 | 1.248 | 1.154 | 1.694 | 1.505 | 1.230 | 1.625 |
| uc.331+ | 19 | 2.161 | 2.163 | 1.597 | 2.434 | 1.446 | 1.906 | 1.779 | 1.689 | 1.865 | 1.670 | 1.554 |
| uc.455+A | 19 | 1.930 | 1.160 | 1.202 | 1.073 | 0.986 | 0.991 | 1.001 | 0.988 | 1.049 | 1.105 | 1.151 |
| uc.476+ | 19 | 1.599 | 1.216 | 1.365 | 1.138 | 1.247 | 1.189 | 1.134 | 0.992 | 1.147 | 1.403 | 1.225 |
| uc.19+ | 19 | 0.993 | 1.042 | 1.003 | 0.989 | 0.987 | 1.030 | 0.962 | 1.120 | 1.008 | 1.054 | 0.955 |
| uc.48+ | 19 | 1.167 | 1.399 | 1.259 | 1.480 | 1.309 | 1.239 | 1.342 | 1.305 | 1.617 | 1.569 | 1.421 |
| uc.330+ | 19 | 1.410 | 1.365 | 1.234 | 1.510 | 1.020 | 1.509 | 1.178 | 1.245 | 1.439 | 1.166 | 1.195 |
| uc.281+A | 19 | 4.319 | 5.865 | 2.535 | 3.939 | 2.456 | 5.342 | 2.566 | 4.029 | 3.090 | 6.196 | 4.496 |
| uc.77+A | 19 | 2.153 | 1.241 | 1.162 | 0.995 | 1.086 | 1.061 | 1.128 | 1.116 | 1.041 | 1.164 | 1.233 |
| uc.475+ | 19 | 8.863 | 11.423 | 4.463 | 6.384 | 5.046 | 8.229 | 5.408 | 4.406 | 6.394 | 12.610 | 8.528 |
| uc.396+ | 19 | 0.939 | 0.963 | 1.160 | 1.220 | 1.071 | 1.152 | 1.135 | 1.176 | 1.054 | 1.091 | 1.074 |
| uc.374+A | 19 | 1.073 | 0.985 | 0.954 | 0.903 | 1.019 | 0.956 | 1.133 | 1.057 | 1.280 | 1.007 | 1.020 |
| uc.206+A | 19 | 2.480 | 1.295 | 1.314 | 1.252 | 1.160 | 1.162 | 1.350 | 1.117 | 1.878 | 1.367 | 1.456 |
| uc.22+A | 19 | 2.349 | 2.260 | 1.053 | 1.141 | 1.036 | 1.536 | 1.018 | 1.141 | 1.047 | 1.437 | 1.364 |
| uc.180+A | 19 | 1.074 | 1.065 | 1.007 | 0.986 | 0.959 | 0.964 | 0.986 | 0.929 | 1.677 | 1.159 | 1.024 |
| uc.250+ | 19 | 1.264 | 1.343 | 0.973 | 1.090 | 0.966 | 0.978 | 1.044 | 1.124 | 1.078 | 1.089 | 0.973 |
| uc.363+A | 19 | 3.628 | 2.940 | 1.311 | 1.233 | 1.215 | 1.266 | 1.568 | 1.619 | 1.693 | 1.513 | 1.536 |
| uc.20+ | 19 | 3.417 | 2.994 | 2.046 | 2.978 | 2.322 | 1.905 | 2.758 | 2.118 | 3.727 | 2.718 | 2.848 |
| uc.138+A | 19 | 1.198 | 1.045 | 0.906 | 0.933 | 0.920 | 0.958 | 0.909 | 0.972 | 0.997 | 0.933 | 1.086 |
| uc.142+ | 19 | 1.642 | 1.464 | 1.091 | 1.045 | 1.055 | 1.058 | 1.092 | 0.962 | 0.938 | 1.018 | 1.324 |
| uc.228+A | 19 | 1.124 | 0.961 | 1.024 | 1.017 | 1.007 | 1.049 | 1.029 | 0.973 | 0.946 | 1.020 | 0.947 |
| uc.398+ | 19 | 23.405 | 27.414 | 19.585 | 19.964 | 21.304 | 48.460 | 19.979 | 8.140 | 11.515 | 56.962 | 39.263 |
| uc.464+A | 19 | 2.621 | 2.235 | 1.336 | 1.483 | 1.193 | 1.635 | 1.147 | 1.189 | 1.546 | 1.605 | 1.855 |
| uc.149+ | 19 | 1.062 | 1.145 | 1.023 | 1.021 | 1.037 | 1.047 | 1.054 | 1.065 | 1.129 | 1.055 | 0.987 |
| uc.44+A | 19 | 4.251 | 4.877 | 2.815 | 3.948 | 2.602 | 4.374 | 2.776 | 2.393 | 3.207 | 7.170 | 4.756 |
| uc.217+A | 19 | 3.240 | 2.267 | 2.147 | 2.432 | 2.237 | 2.234 | 2.712 | 1.836 | 4.090 | 3.238 | 2.588 |
| uc.453+A | 19 | 8.414 | 9.429 | 2.130 | 5.289 | 2.032 | 5.673 | 2.265 | 2.655 | 5.004 | 5.203 | 5.100 |
| uc.295+A | 19 | 1.264 | 1.091 | 1.012 | 1.047 | 1.067 | 1.054 | 1.038 | 1.091 | 1.020 | 1.103 | 1.084 |
| uc.145+ | 19 | 1.168 | 0.978 | 1.087 | 1.063 | 1.103 | 1.035 | 1.107 | 0.966 | 0.960 | 1.062 | 1.091 |
| uc.33+A | 19 | 2.557 | 1.579 | 1.438 | 1.108 | 1.436 | 1.279 | 1.329 | 0.993 | 1.166 | 1.580 | 2.116 |
| uc.144+ | 19 | 1.318 | 1.133 | 1.110 | 1.026 | 1.054 | 0.995 | 1.097 | 1.029 | 0.966 | 1.057 | 1.106 |
| uc.447+ | 19 | 1.665 | 1.549 | 1.036 | 1.087 | 0.995 | 1.069 | 1.006 | 1.083 | 1.112 | 1.304 | 1.093 |
| uc.338+ | 19 | 4.418 | 4.023 | 3.565 | 3.277 | 3.598 | 3.286 | 2.372 | 2.101 | 5.761 | 5.742 | 3.615 |

Figure 15 Continued

| Sample | Number of tissues in which the UCR pass the filter | B-cell 01 | B-cell 02 | Bladder | Brain | Breast | Esophagus A | Heart | Kidney | Liver | Lung | MNC 01 |
|---|---|---|---|---|---|---|---|---|---|---|---|---|
| uc.269+A | 19 | 1.743 | 2.019 | 5.273 | 3.715 | 4.911 | 5.814 | 4.741 | 2.206 | 3.115 | 10.031 | 7.565 |
| uc.301+A | 19 | 0.967 | 0.983 | 0.967 | 1.007 | 1.043 | 1.056 | 1.142 | 1.014 | 0.952 | 1.033 | 0.993 |
| uc.339+ | 19 | 15.197 | 22.611 | 7.585 | 40.922 | 8.522 | 23.904 | 8.153 | 6.947 | 15.017 | 75.435 | 9.369 |
| uc.5+ | 19 | 2.001 | 1.055 | 1.222 | 0.989 | 1.189 | 1.126 | 1.115 | 1.240 | 1.052 | 0.926 | 1.087 |
| uc.445+ | 19 | 1.979 | 1.701 | 1.774 | 1.193 | 1.345 | 1.694 | 1.025 | 1.139 | 1.425 | 1.438 | 1.449 |
| uc.132+A | 19 | 0.915 | 0.931 | 1.053 | 1.044 | 1.067 | 0.993 | 1.134 | 1.060 | 1.063 | 1.067 | 1.026 |
| uc.411+ | 19 | 2.155 | 1.971 | 1.417 | 1.320 | 1.347 | 1.324 | 1.221 | 1.509 | 1.197 | 1.284 | 1.423 |
| uc.446+ | 19 | 1.477 | 1.502 | 1.115 | 1.168 | 1.179 | 1.212 | 1.161 | 1.262 | 1.307 | 1.259 | 1.303 |
| uc.312+A | 19 | 1.115 | 1.129 | 0.994 | 0.963 | 0.949 | 1.205 | 0.939 | 1.116 | 1.098 | 1.063 | 1.097 |
| uc.413+ | 19 | 1.081 | 0.972 | 1.066 | 0.984 | 0.985 | 1.018 | 1.205 | 0.923 | 0.914 | 0.943 | 0.987 |
| uc.359+A | 19 | 0.967 | 1.515 | 1.002 | 1.206 | 1.544 | 0.945 | 1.012 | 0.901 | 0.945 | 1.019 | 0.895 |
| uc.402+A | 19 | 2.434 | 1.431 | 0.960 | 0.922 | 0.956 | 1.029 | 0.925 | 0.920 | 1.044 | 0.986 | 1.059 |
| uc.91+ | 19 | 1.768 | 1.551 | 0.979 | 1.089 | 0.961 | 1.037 | 1.015 | 0.945 | 0.987 | 1.060 | 1.143 |
| uc.412+ | 19 | 3.427 | 2.069 | 1.860 | 1.592 | 2.229 | 2.197 | 1.515 | 1.336 | 1.517 | 2.458 | 2.215 |
| uc.448+ | 19 | 2.450 | 1.229 | 1.266 | 1.370 | 1.344 | 1.212 | 1.119 | 1.013 | 1.152 | 1.523 | 1.921 |
| uc.9+A | 19 | 1.801 | 0.969 | 1.041 | 1.010 | 1.069 | 1.050 | 0.992 | 1.169 | 1.060 | 1.145 | 1.093 |
| uc.505+ | 19 | 2.359 | 1.354 | 1.189 | 1.256 | 1.455 | 1.581 | 1.175 | 1.060 | 1.233 | 1.268 | 1.523 |
| uc.233+A | 19 | 2.795 | 3.089 | 1.124 | 1.855 | 1.495 | 1.488 | 0.977 | 1.112 | 1.536 | 1.955 | 1.787 |
| uc.304+A | 19 | 1.512 | 1.671 | 1.022 | 1.013 | 1.030 | 1.056 | 0.961 | 1.063 | 0.950 | 1.042 | 1.081 |
| uc.369+ | 19 | 3.938 | 4.798 | 4.691 | 2.681 | 4.221 | 4.141 | 3.301 | 2.075 | 2.274 | 4.028 | 4.047 |
| uc.88+A | 19 | 11.292 | 12.414 | 1.698 | 4.652 | 1.925 | 6.634 | 2.506 | 2.516 | 3.390 | 4.627 | 4.434 |
| uc.2+ | 19 | 0.936 | 0.955 | 1.020 | 0.974 | 1.013 | 0.955 | 1.025 | 1.270 | 0.922 | 0.935 | 0.985 |
| uc.110+A | 19 | 3.631 | 5.255 | 4.457 | 4.067 | 4.018 | 5.847 | 3.794 | 1.774 | 2.708 | 4.292 | 4.268 |
| uc.461+A | 19 | 1.004 | 1.076 | 1.261 | 1.266 | 1.190 | 1.139 | 1.174 | 1.355 | 1.062 | 1.127 | 1.223 |
| uc.419+A | 19 | 1.896 | 1.947 | 2.182 | 1.676 | 1.836 | 1.674 | 1.644 | 1.815 | 1.383 | 2.195 | 1.643 |
| uc.449+ | 19 | 1.149 | 1.026 | 1.018 | 1.013 | 0.951 | 0.926 | 0.931 | 0.942 | 0.933 | 0.953 | 1.021 |
| uc.478+ | 19 | 1.518 | 1.296 | 1.844 | 1.709 | 1.717 | 1.824 | 1.268 | 1.651 | 1.202 | 1.850 | 1.429 |
| uc.1+ | 19 | 3.470 | 3.635 | 3.574 | 2.570 | 3.012 | 2.862 | 3.719 | 2.840 | 2.311 | 2.445 | 2.353 |
| uc.4+ | 19 | 1.839 | 1.290 | 1.166 | 1.246 | 1.280 | 1.086 | 1.471 | 1.462 | 1.619 | 1.217 | 1.276 |
| uc.335+ | 19 | 1.362 | 1.459 | 1.135 | 1.465 | 1.103 | 1.373 | 1.045 | 1.074 | 1.031 | 1.260 | 1.250 |
| uc.483+A | 19 | 1.594 | 1.840 | 2.676 | 3.699 | 2.774 | 3.535 | 2.635 | 2.009 | 2.875 | 5.520 | 2.646 |
| uc.6+ | 19 | 2.169 | 3.013 | 9.916 | 16.582 | 5.625 | 12.980 | 8.160 | 2.464 | 9.704 | 2.855 | 5.435 |
| uc.63+A | 19 | 2.937 | 3.482 | 1.057 | 1.316 | 1.198 | 1.606 | 0.976 | 1.223 | 1.086 | 1.437 | 1.535 |
| uc.443+ | 19 | 1.252 | 1.142 | 1.021 | 0.967 | 0.992 | 1.008 | 1.086 | 0.931 | 0.936 | 0.990 | 0.983 |
| uc.117+ | 19 | 5.433 | 6.885 | 5.491 | 5.302 | 6.179 | 6.823 | 5.232 | 4.995 | 4.695 | 8.902 | 5.933 |
| uc.477+ | 19 | 2.604 | 1.353 | 0.998 | 1.737 | 0.995 | 1.045 | 0.933 | 0.955 | 1.092 | 1.144 | 1.421 |
| uc.205+A | 19 | 2.895 | 1.682 | 1.413 | 1.309 | 1.292 | 1.710 | 1.524 | 1.016 | 1.242 | 1.899 | 1.596 |
| uc.3+ | 19 | 1.053 | 0.965 | 1.243 | 1.257 | 1.248 | 1.175 | 1.797 | 1.554 | 1.713 | 1.202 | 1.211 |
| uc.322+ | 19 | 1.224 | 1.259 | 0.935 | 1.090 | 1.034 | 0.959 | 0.978 | 0.907 | 0.992 | 1.032 | 1.220 |
| uc.213+ | 19 | 10.045 | 15.102 | 6.177 | 5.492 | 7.526 | 6.915 | 5.834 | 3.246 | 6.766 | 9.875 | 5.788 |
| uc.249+ | 19 | 1.994 | 1.967 | 2.087 | 2.545 | 2.133 | 1.931 | 2.288 | 1.666 | 2.047 | 2.013 | 1.355 |
| uc.503+A | 19 | 1.139 | 1.195 | 1.168 | 1.276 | 1.291 | 1.256 | 1.202 | 1.267 | 1.533 | 1.353 | 1.163 |
| uc.323+ | 19 | 1.320 | 1.365 | 1.016 | 1.173 | 1.056 | 1.056 | 1.161 | 1.697 | 1.305 | 1.220 | 1.158 |
| uc.248+ | 19 | 2.110 | 1.283 | 0.937 | 0.962 | 0.978 | 0.984 | 0.960 | 1.001 | 1.044 | 1.046 | 1.238 |
| uc.465+ | 19 | 1.459 | 1.069 | 1.077 | 1.026 | 1.185 | 0.955 | 1.616 | 0.903 | 1.016 | 1.019 | 0.982 |
| uc.134+ | 19 | 2.470 | 2.089 | 2.654 | 3.207 | 2.084 | 4.696 | 2.562 | 2.987 | 1.607 | 4.478 | 4.298 |
| uc.214+ | 19 | 1.189 | 1.286 | 1.111 | 1.146 | 1.169 | 1.366 | 1.201 | 1.153 | 1.548 | 1.435 | 1.236 |
| uc.145+A | 19 | 2.657 | 3.014 | 11.933 | 10.163 | 15.697 | 15.905 | 10.732 | 3.298 | 7.588 | 22.091 | 17.102 |
| uc.329+A | 19 | 1.156 | 0.966 | 1.162 | 1.044 | 1.161 | 1.014 | 1.525 | 1.175 | 1.927 | 1.242 | 1.106 |
| uc.217+ | 19 | 5.617 | 4.299 | 1.550 | 2.139 | 1.630 | 2.735 | 1.311 | 1.303 | 2.558 | 2.893 | 2.793 |
| uc.325+ | 19 | 13.837 | 20.922 | 16.216 | 9.218 | 10.185 | 16.609 | 8.718 | 5.053 | 9.349 | 13.644 | 9.529 |
| uc.435+ | 19 | 1.552 | 1.801 | 1.335 | 1.473 | 1.342 | 1.235 | 1.576 | 1.377 | 1.894 | 1.458 | 1.380 |
| uc.326+ | 19 | 2.817 | 3.238 | 1.754 | 1.741 | 1.641 | 3.019 | 1.303 | 1.912 | 1.562 | 2.767 | 2.590 |
| uc.106+ | 19 | 4.035 | 1.443 | 0.985 | 1.045 | 1.072 | 1.177 | 0.924 | 0.955 | 1.029 | 1.420 | 2.445 |
| uc.468+ | 19 | 1.408 | 1.171 | 1.385 | 1.846 | 1.528 | 1.616 | 1.904 | 1.560 | 2.165 | 1.494 | 1.933 |
| uc.213+A | 19 | 1.490 | 1.604 | 2.324 | 2.477 | 2.591 | 1.935 | 2.617 | 2.046 | 3.249 | 3.618 | 2.286 |
| uc.95+A | 19 | 1.178 | 1.076 | 0.979 | 0.988 | 1.014 | 1.042 | 0.909 | 0.934 | 0.933 | 1.011 | 1.027 |
| uc.246+A | 19 | 1.922 | 1.374 | 1.361 | 1.236 | 1.335 | 1.459 | 1.148 | 1.132 | 1.030 | 1.348 | 1.434 |
| uc.43+A | 19 | 1.655 | 1.165 | 0.950 | 1.066 | 1.033 | 1.034 | 0.983 | 0.950 | 1.002 | 1.005 | 1.369 |
| uc.389+ | 19 | 1.332 | 1.299 | 1.228 | 1.293 | 1.237 | 1.419 | 1.600 | 1.166 | 1.419 | 1.634 | 1.215 |
| uc.159+A | 19 | 3.485 | 3.462 | 3.925 | 4.120 | 3.696 | 3.593 | 1.586 | 2.256 | 3.162 | 4.458 | 4.754 |
| uc.100+ | 19 | 1.575 | 1.769 | 1.354 | 1.278 | 1.838 | 1.784 | 1.206 | 1.168 | 1.792 | 1.626 | 1.410 |
| uc.462+ | 19 | 2.441 | 1.892 | 2.094 | 1.775 | 1.869 | 1.531 | 1.455 | 1.312 | 1.402 | 1.830 | 1.953 |
| uc.352+ | 19 | 5.661 | 5.806 | 2.825 | 2.453 | 3.361 | 3.656 | 2.754 | 1.741 | 2.804 | 5.951 | 3.903 |
| uc.386+ | 19 | 4.497 | 1.918 | 1.191 | 1.492 | 1.407 | 1.636 | 1.114 | 1.568 | 1.993 | 1.653 | 2.461 |
| uc.125+A | 19 | 1.088 | 0.984 | 0.994 | 1.051 | 1.042 | 0.992 | 0.986 | 0.993 | 1.519 | 1.084 | 1.035 |
| uc.136+ | 19 | 1.688 | 2.509 | 1.535 | 1.245 | 1.232 | 1.602 | 1.219 | 1.321 | 1.039 | 1.534 | 1.645 |
| uc.344+ | 19 | 1.179 | 1.296 | 0.969 | 1.036 | 1.036 | 0.972 | 0.956 | 0.983 | 1.093 | 1.023 | 1.023 |
| uc.138+ | 19 | 1.451 | 1.352 | 0.992 | 1.092 | 0.987 | 1.180 | 1.015 | 1.300 | 1.047 | 1.147 | 1.312 |
| uc.291+A | 19 | 1.219 | 1.031 | 1.531 | 1.257 | 2.102 | 1.128 | 1.686 | 1.051 | 1.275 | 2.536 | 1.076 |
| uc.249+A | 19 | 2.356 | 1.484 | 1.122 | 1.151 | 1.154 | 1.137 | 1.038 | 0.982 | 1.161 | 1.233 | 1.322 |

Figure 15 Continued

| Calin GA et al | | | | | | 5 | | | | | |
|---|---|---|---|---|---|---|---|---|---|---|---|
| Sample | Number of tissues in which the UCR pass the filter | B-cell 01 | B-cell 02 | Bladder | Brain | Breast | Esophagus A | Heart | Kidney | Liver | Lung | MNC 01 |
| uc.469+ | 19 | 1.160 | 0.994 | 0.968 | 0.983 | 0.961 | 0.975 | 0.930 | 0.961 | 0.933 | 0.981 | 1.051 |
| uc.18+ | 19 | 5.139 | 6.741 | 2.912 | 4.286 | 4.056 | 5.620 | 3.577 | 2.919 | 6.117 | 5.931 | 3.189 |
| uc.245+ | 19 | 1.153 | 1.162 | 0.955 | 1.449 | 1.090 | 1.190 | 1.333 | 1.177 | 1.026 | 1.084 | 1.074 |
| uc.280+A | 19 | 1.450 | 1.415 | 1.078 | 1.118 | 0.962 | 1.173 | 0.993 | 1.065 | 1.049 | 1.079 | 1.193 |
| uc.14+ | 19 | 0.969 | 1.180 | 1.059 | 1.164 | 1.011 | 1.117 | 1.003 | 1.111 | 1.062 | 1.136 | 1.023 |
| uc.134+A | 19 | 4.401 | 5.256 | 2.803 | 2.033 | 2.004 | 2.437 | 1.875 | 1.472 | 1.698 | 1.962 | 2.025 |
| uc.386+ | 19 | 5.160 | 5.479 | 3.346 | 6.561 | 3.695 | 5.679 | 3.786 | 4.593 | 5.518 | 4.774 | 3.610 |
| uc.15+ | 19 | 2.675 | 2.369 | 1.438 | 1.914 | 1.316 | 1.698 | 1.490 | 1.739 | 1.717 | 1.894 | 1.658 |
| uc.391+ | 19 | 1.060 | 1.191 | 1.207 | 1.238 | 1.242 | 1.306 | 1.136 | 1.131 | 1.119 | 1.296 | 1.207 |
| uc.262+A | 19 | 3.912 | 3.639 | 3.198 | 3.937 | 2.964 | 4.984 | 2.868 | 5.025 | 2.621 | 5.453 | 5.133 |
| uc.458+A | 19 | 4.226 | 5.363 | 3.251 | 3.260 | 2.906 | 2.899 | 3.647 | 2.856 | 3.611 | 6.068 | 3.096 |
| uc.53+ | 19 | 0.863 | 1.046 | 1.031 | 1.317 | 1.031 | 1.018 | 1.615 | 1.208 | 1.184 | 0.942 | 1.119 |
| uc.89+ | 19 | 1.175 | 0.983 | 1.014 | 1.050 | 1.036 | 1.003 | 1.270 | 1.171 | 1.667 | 1.353 | 1.196 |
| uc.390+ | 19 | 2.266 | 2.168 | 1.194 | 1.342 | 1.089 | 1.506 | 1.071 | 1.092 | 1.208 | 1.729 | 1.454 |
| uc.183+A | 19 | 4.222 | 3.333 | 1.423 | 1.597 | 1.242 | 1.738 | 1.367 | 1.769 | 1.529 | 1.814 | 1.581 |
| uc.377+A | 19 | 1.638 | 1.230 | 1.117 | 1.192 | 1.160 | 1.157 | 1.337 | 1.011 | 1.054 | 1.245 | 1.095 |
| uc.368+A | 19 | 1.868 | 1.660 | 1.734 | 2.172 | 1.700 | 1.393 | 1.827 | 1.356 | 2.525 | 2.175 | 1.984 |
| uc.173+ | 19 | 1.914 | 1.388 | 1.062 | 1.040 | 1.007 | 1.090 | 0.961 | 0.925 | 0.972 | 1.093 | 1.168 |
| uc.478+A | 19 | 4.673 | 4.251 | 3.632 | 6.523 | 4.011 | 5.537 | 3.849 | 4.033 | 5.148 | 10.162 | 5.340 |
| uc.47+A | 19 | 2.567 | 1.934 | 1.102 | 1.212 | 1.191 | 1.357 | 1.197 | 1.134 | 1.346 | 1.400 | 1.416 |
| uc.393+ | 19 | 1.023 | 1.309 | 1.220 | 1.179 | 1.434 | 1.126 | 1.266 | 1.123 | 1.245 | 1.106 | 1.103 |
| uc.315+A | 19 | 1.382 | 1.390 | 1.052 | 1.037 | 1.168 | 1.037 | 1.017 | 1.132 | 1.023 | 1.032 | 1.104 |
| uc.177+ | 19 | 3.037 | 2.810 | 2.021 | 2.033 | 2.137 | 1.981 | 1.656 | 1.539 | 2.052 | 2.264 | 2.313 |
| uc.392+ | 19 | 1.447 | 1.187 | 0.944 | 0.969 | 1.005 | 1.045 | 0.921 | 0.969 | 0.946 | 1.075 | 1.024 |
| uc.341+A | 19 | 1.158 | 1.095 | 1.036 | 1.007 | 1.011 | 0.958 | 0.995 | 0.996 | 0.942 | 0.944 | 0.981 |
| uc.88+ | 19 | 3.506 | 1.594 | 2.521 | 2.275 | 2.326 | 1.955 | 2.133 | 1.489 | 2.138 | 3.369 | 2.367 |
| uc.285+ | 19 | 2.164 | 2.424 | 2.603 | 2.393 | 2.312 | 3.085 | 2.128 | 1.801 | 3.209 | 5.867 | 2.786 |
| uc.420+A | 19 | 2.046 | 1.671 | 1.183 | 1.317 | 1.079 | 1.219 | 0.980 | 0.945 | 1.054 | 1.340 | 1.315 |
| uc.164+A | 19 | 1.253 | 1.360 | 1.027 | 1.036 | 0.948 | 1.038 | 1.061 | 1.107 | 1.041 | 1.260 | 1.144 |
| uc.300+A | 19 | 19.467 | 25.679 | 6.912 | 9.169 | 6.818 | 16.260 | 6.685 | 5.466 | 6.485 | 17.350 | 11.134 |
| uc.153+A | 19 | 1.854 | 1.736 | 1.855 | 2.320 | 2.180 | 1.439 | 2.633 | 1.961 | 4.238 | 2.789 | 2.369 |
| uc.448+A | 19 | 8.965 | 10.577 | 3.801 | 4.849 | 2.938 | 3.573 | 4.106 | 3.254 | 5.187 | 7.430 | 3.942 |
| uc.17+A | 19 | 1.028 | 1.161 | 1.047 | 1.304 | 1.056 | 1.061 | 1.034 | 1.083 | 1.218 | 2.016 | 1.166 |
| uc.436+ | 19 | 1.262 | 1.544 | 1.099 | 1.175 | 1.089 | 1.191 | 1.080 | 1.064 | 1.096 | 1.207 | 1.087 |
| uc.142+A | 19 | 4.770 | 7.363 | 2.914 | 4.927 | 2.807 | 3.560 | 3.168 | 3.271 | 5.981 | 4.971 | 4.119 |
| uc.73+A | 19 | 3.522 | 5.222 | 2.880 | 3.811 | 2.964 | 3.665 | 2.947 | 3.081 | 4.295 | 5.430 | 3.600 |
| uc.404+ | 19 | 1.039 | 1.865 | 0.975 | 1.140 | 1.032 | 0.963 | 1.327 | 1.187 | 1.368 | 1.228 | 1.103 |
| uc.54+A | 19 | 2.818 | 2.794 | 6.772 | 5.866 | 6.605 | 9.429 | 4.983 | 2.851 | 6.425 | 17.692 | 4.198 |
| uc.280+ | 19 | 1.773 | 1.353 | 1.041 | 1.038 | 1.054 | 1.108 | 1.043 | 1.033 | 1.119 | 1.068 | 1.177 |
| uc.172+A | 19 | 10.788 | 16.805 | 4.384 | 6.111 | 4.931 | 11.485 | 5.924 | 6.007 | 15.330 | 26.972 | 5.607 |
| uc.287+A | 19 | 3.860 | 3.866 | 2.522 | 3.700 | 2.857 | 3.232 | 4.413 | 3.350 | 6.478 | 5.313 | 3.575 |
| uc.54+ | 19 | 0.905 | 0.915 | 1.029 | 0.985 | 0.969 | 0.959 | 0.983 | 1.004 | 0.945 | 1.000 | 0.993 |
| uc.445+A | 19 | 1.989 | 1.499 | 1.387 | 1.601 | 1.661 | 1.268 | 2.499 | 1.678 | 2.961 | 1.698 | 1.771 |
| uc.407+ | 19 | 1.525 | 1.422 | 1.192 | 1.336 | 1.141 | 1.174 | 1.202 | 1.253 | 1.418 | 1.788 | 1.428 |
| uc.412+A | 19 | 3.861 | 4.442 | 2.870 | 2.995 | 2.430 | 2.991 | 3.362 | 2.850 | 3.831 | 3.906 | 3.033 |
| uc.387+A | 19 | 1.167 | 1.440 | 1.316 | 1.095 | 1.396 | 1.336 | 1.305 | 1.559 | 1.516 | 1.416 | 1.353 |
| uc.87+ | 19 | 1.148 | 1.325 | 1.011 | 1.211 | 0.982 | 1.136 | 1.157 | 1.114 | 1.139 | 1.078 | 1.144 |
| uc.176+ | 19 | 4.728 | 2.962 | 2.106 | 2.846 | 2.456 | 2.423 | 1.874 | 1.746 | 2.687 | 2.483 | 2.613 |
| uc.181+A | 19 | 3.885 | 4.183 | 2.241 | 3.023 | 1.908 | 2.308 | 1.780 | 1.905 | 1.841 | 2.602 | 2.565 |

Figure 15 Continued

| Sample | Number of tissues in which the UCR pass the filter | MNC 02 | Ovary | Pancreatic | Placenta | Prostate | Skeletal muscle | Spleen | T-cell 01 | T-cell 02 | Testicule | Thymus |
|---|---|---|---|---|---|---|---|---|---|---|---|---|
| uc.188+A | 19 | 1.523 | 1.056 | 1.059 | 1.215 | 1.195 | 1.109 | 1.071 | 1.961 | 3.386 | 1.116 | 1.150 |
| uc.177+A | 19 | 1.959 | 1.658 | 2.833 | 2.269 | 1.924 | 2.574 | 1.852 | 1.970 | 2.344 | 2.119 | 2.187 |
| uc.345+A | 19 | 1.107 | 0.971 | 1.128 | 1.049 | 1.062 | 1.054 | 1.053 | 2.095 | 4.229 | 1.060 | 1.054 |
| uc.426+ | 19 | 1.509 | 1.043 | 0.956 | 1.095 | 1.179 | 0.973 | 1.564 | 1.872 | 4.504 | 1.176 | 1.124 |
| uc.335+A | 19 | 1.516 | 1.050 | 0.965 | 1.443 | 1.441 | 1.432 | 1.115 | 1.079 | 1.379 | 1.171 | 1.072 |
| uc.97+A | 19 | 1.206 | 1.132 | 1.322 | 1.272 | 1.397 | 1.329 | 1.095 | 1.019 | 0.962 | 1.254 | 1.152 |
| uc.234+A | 19 | 1.358 | 0.915 | 0.980 | 1.028 | 0.975 | 0.933 | 0.962 | 1.585 | 1.752 | 0.962 | 0.941 |
| uc.422+ | 19 | 1.277 | 1.044 | 0.998 | 1.256 | 1.246 | 1.136 | 1.329 | 1.219 | 1.372 | 1.223 | 1.138 |
| uc.317+ | 19 | 1.104 | 1.137 | 0.969 | 1.003 | 1.042 | 1.084 | 0.961 | 1.056 | 0.998 | 0.971 | 1.002 |
| uc.206+ | 19 | 0.995 | 0.990 | 0.917 | 0.994 | 0.963 | 0.998 | 0.905 | 1.236 | 1.445 | 1.095 | 1.012 |
| uc.411+A | 19 | 1.098 | 1.047 | 1.051 | 0.978 | 1.022 | 1.055 | 1.015 | 2.136 | 3.236 | 1.017 | 1.053 |
| uc.400+A | 19 | 2.185 | 1.196 | 1.275 | 1.658 | 1.711 | 2.121 | 1.453 | 1.586 | 1.511 | 1.284 | 1.121 |
| uc.193+ | 19 | 0.989 | 1.093 | 1.300 | 2.037 | 1.554 | 1.080 | 1.637 | 3.054 | 1.183 | 1.279 | 1.537 |
| uc.343+A | 19 | 1.016 | 0.917 | 0.972 | 0.957 | 0.950 | 1.025 | 0.931 | 0.926 | 0.980 | 0.954 | 0.971 |
| uc.196+A | 19 | 1.193 | 0.914 | 0.973 | 1.052 | 1.021 | 0.976 | 1.056 | 1.879 | 2.715 | 1.116 | 0.952 |
| uc.346+A | 19 | 3.839 | 3.284 | 9.153 | 3.219 | 2.985 | 3.118 | 4.932 | 9.129 | 6.721 | 4.381 | 4.538 |
| uc.427+ | 19 | 2.355 | 1.715 | 1.571 | 1.736 | 2.196 | 2.566 | 1.639 | 1.612 | 1.717 | 2.050 | 2.073 |
| uc.50+A | 19 | 1.203 | 1.019 | 0.930 | 1.177 | 1.244 | 1.233 | 1.155 | 0.933 | 0.903 | 1.086 | 1.144 |
| uc.73+ | 19 | 1.315 | 1.211 | 1.311 | 1.645 | 1.222 | 1.129 | 1.351 | 1.277 | 1.095 | 1.235 | 1.379 |
| uc.321+A | 19 | 0.931 | 0.964 | 1.022 | 0.967 | 0.955 | 1.027 | 1.018 | 0.997 | 1.055 | 0.968 | 0.969 |
| uc.238+ | 19 | 1.203 | 1.156 | 1.161 | 1.073 | 1.140 | 1.213 | 0.967 | 0.936 | 0.945 | 1.026 | 1.129 |
| uc.310+ | 19 | 1.174 | 1.094 | 1.114 | 0.942 | 0.981 | 1.233 | 1.105 | 1.624 | 1.804 | 1.155 | 1.098 |
| uc.133+A | 19 | 1.337 | 1.248 | 1.082 | 1.058 | 1.229 | 1.466 | 1.127 | 1.170 | 1.246 | 1.130 | 1.067 |
| uc.456+ | 19 | 2.252 | 1.501 | 2.051 | 1.765 | 1.675 | 1.450 | 1.841 | 2.841 | 3.798 | 1.465 | 2.004 |
| uc.336+A | 19 | 1.790 | 0.953 | 1.033 | 1.213 | 1.226 | 1.691 | 1.624 | 1.547 | 1.592 | 1.093 | 1.135 |
| uc.128+ | 19 | 0.948 | 0.931 | 1.091 | 1.042 | 0.927 | 1.011 | 0.953 | 1.299 | 1.779 | 0.997 | 1.099 |
| uc.345+ | 19 | 1.027 | 1.068 | 0.982 | 0.966 | 0.948 | 0.933 | 0.949 | 1.364 | 1.449 | 0.961 | 1.124 |
| uc.248+A | 19 | 1.584 | 1.363 | 1.632 | 1.230 | 1.619 | 1.677 | 1.633 | 1.224 | 1.096 | 1.642 | 1.646 |
| uc.347+ | 19 | 1.030 | 0.983 | 1.015 | 1.035 | 0.979 | 0.973 | 0.952 | 1.056 | 0.988 | 0.983 | 0.999 |
| uc.346+ | 19 | 14.364 | 8.615 | 17.557 | 9.276 | 8.670 | 9.897 | 8.334 | 12.290 | 14.745 | 11.466 | 14.697 |
| uc.204+ | 19 | 2.516 | 2.101 | 2.231 | 4.205 | 2.075 | 2.326 | 1.941 | 3.723 | 2.478 | 2.266 | 2.894 |
| uc.391+A | 19 | 1.557 | 1.059 | 1.107 | 1.155 | 1.134 | 1.058 | 1.103 | 1.762 | 2.149 | 1.026 | 1.147 |
| uc.457+ | 19 | 1.828 | 1.514 | 1.387 | 1.509 | 1.809 | 2.146 | 1.817 | 1.614 | 1.462 | 1.792 | 1.453 |
| uc.310+A | 19 | 1.538 | 1.743 | 1.365 | 1.456 | 1.572 | 1.707 | 1.415 | 1.511 | 1.434 | 1.317 | 1.769 |
| uc.470+A | 19 | 3.994 | 12.430 | 5.221 | 5.656 | 8.459 | 5.114 | 5.014 | 4.462 | 3.776 | 9.171 | 6.962 |
| uc.417+A | 19 | 0.957 | 0.944 | 1.005 | 1.024 | 0.985 | 1.034 | 1.304 | 1.024 | 1.008 | 1.148 | 1.035 |
| uc.420+ | 19 | 2.071 | 2.130 | 2.760 | 3.404 | 3.448 | 3.500 | 2.183 | 2.516 | 2.319 | 2.730 | 2.514 |
| uc.327+A | 19 | 3.260 | 2.835 | 5.073 | 4.119 | 3.604 | 3.341 | 3.093 | 3.728 | 3.064 | 4.084 | 4.606 |
| uc.349+ | 19 | 1.423 | 1.415 | 1.183 | 1.477 | 1.543 | 1.820 | 1.533 | 1.132 | 1.142 | 1.236 | 1.845 |
| uc.223+A | 19 | 1.184 | 1.152 | 1.189 | 1.018 | 1.119 | 1.209 | 1.194 | 1.290 | 1.256 | 1.139 | 1.035 |
| uc.348+ | 19 | 1.268 | 1.508 | 1.697 | 1.549 | 1.581 | 1.457 | 1.537 | 1.363 | 1.147 | 1.793 | 2.074 |
| uc.10+ | 19 | 1.728 | 1.100 | 1.213 | 1.613 | 1.798 | 1.268 | 1.467 | 2.209 | 2.307 | 1.546 | 1.372 |
| uc.46+ | 19 | 1.021 | 0.991 | 0.965 | 1.300 | 0.986 | 0.909 | 0.956 | 1.632 | 1.017 | 0.935 | 0.935 |
| uc.275+ | 19 | 2.528 | 1.164 | 1.218 | 0.963 | 1.088 | 1.114 | 1.134 | 2.609 | 3.100 | 1.048 | 1.031 |
| uc.362+A | 19 | 2.457 | 1.667 | 2.263 | 1.705 | 2.203 | 2.720 | 1.361 | 2.326 | 3.273 | 2.664 | 2.277 |
| uc.131+ | 19 | 0.980 | 0.929 | 1.359 | 1.056 | 0.971 | 1.025 | 1.013 | 1.010 | 0.961 | 1.179 | 1.068 |
| uc.309+A | 19 | 3.136 | 2.360 | 2.831 | 3.819 | 2.886 | 1.682 | 1.664 | 1.630 | 1.526 | 2.194 | 3.169 |
| uc.383+ | 19 | 3.150 | 3.775 | 3.916 | 3.266 | 2.910 | 3.993 | 2.962 | 3.493 | 2.326 | 3.368 | 3.568 |
| uc.398+A | 19 | 2.063 | 1.486 | 1.297 | 1.934 | 2.156 | 1.244 | 2.326 | 1.884 | 1.458 | 2.022 | 1.880 |
| uc.167+ | 19 | 14.211 | 12.406 | 15.961 | 20.443 | 13.270 | 8.197 | 6.118 | 8.518 | 5.869 | 11.896 | 12.398 |
| uc.283+A | 19 | 12.275 | 7.926 | 21.491 | 9.641 | 13.435 | 14.193 | 7.481 | 20.563 | 13.651 | 13.268 | 14.464 |
| uc.21+A | 19 | 0.996 | 0.934 | 0.970 | 1.027 | 1.129 | 1.095 | 0.994 | 0.931 | 0.943 | 0.930 | 1.010 |
| uc.133+ | 19 | 1.000 | 0.946 | 1.039 | 0.914 | 0.903 | 0.983 | 0.912 | 1.580 | 2.325 | 0.978 | 0.983 |
| uc.49+ | 19 | 2.323 | 1.253 | 1.663 | 1.783 | 1.526 | 1.497 | 1.654 | 3.224 | 2.809 | 2.097 | 1.562 |
| uc.190+A | 19 | 2.974 | 1.989 | 2.338 | 1.767 | 2.324 | 3.929 | 1.961 | 1.502 | 1.754 | 2.192 | 2.055 |
| uc.154+ | 19 | 2.062 | 1.209 | 1.544 | 2.188 | 1.976 | 1.726 | 1.398 | 2.056 | 2.399 | 2.961 | 1.989 |
| uc.47+ | 19 | 1.770 | 1.239 | 1.516 | 1.522 | 1.741 | 1.727 | 1.407 | 1.546 | 1.736 | 1.720 | 1.608 |
| uc.10+A | 19 | 1.354 | 0.985 | 1.313 | 1.120 | 1.154 | 1.345 | 1.365 | 1.193 | 1.269 | 1.048 | 1.266 |
| uc.477+A | 19 | 4.958 | 3.046 | 4.192 | 3.073 | 3.390 | 5.724 | 2.936 | 3.595 | 4.156 | 3.450 | 3.446 |
| uc.278+ | 19 | 8.195 | 2.624 | 2.278 | 4.226 | 3.745 | 2.859 | 5.817 | 2.933 | 2.039 | 2.626 | 2.691 |
| uc.350+ | 19 | 1.429 | 1.231 | 1.335 | 1.132 | 1.397 | 1.995 | 1.385 | 1.188 | 1.154 | 1.341 | 1.195 |
| uc.118+A | 19 | 1.375 | 1.149 | 1.215 | 1.426 | 1.165 | 1.155 | 1.183 | 1.116 | 0.968 | 1.061 | 1.028 |
| uc.196+ | 19 | 1.125 | 1.293 | 1.191 | 1.391 | 1.081 | 1.373 | 1.143 | 1.037 | 0.942 | 1.113 | 1.115 |

| Sample | Number of tissues in which the UCR pass the filter | MNC 02 | Ovary | Pancreatic | Placenta | Prostate | Skeletal muscle | Spleen | T-cell 01 | T-cell 02 | Testicule | Thymus |
|---|---|---|---|---|---|---|---|---|---|---|---|---|
| uc.452+ | 19 | 1.205 | 1.171 | 0.996 | 1.117 | 1.624 | 1.463 | 1.155 | 1.176 | 1.325 | 0.998 | 1.142 |
| uc.41+ | 19 | 1.269 | 1.278 | 1.133 | 1.142 | 1.110 | 1.227 | 1.143 | 1.262 | 0.916 | 1.144 | 1.131 |
| uc.200+ | 19 | 3.237 | 2.051 | 2.652 | 2.664 | 2.513 | 3.066 | 2.578 | 2.629 | 3.037 | 2.439 | 2.267 |
| uc.305+A | 19 | 1.776 | 1.513 | 1.263 | 1.611 | 1.562 | 1.820 | 1.344 | 1.280 | 1.442 | 1.090 | 1.167 |
| uc.343+ | 19 | 1.006 | 0.977 | 0.939 | 1.191 | 1.013 | 1.016 | 0.938 | 1.010 | 0.902 | 0.968 | 0.960 |
| uc.363+ | 19 | 1.190 | 1.027 | 1.025 | 1.031 | 1.118 | 1.098 | 1.010 | 0.974 | 1.254 | 1.053 | 1.000 |
| uc.122+A | 19 | 1.073 | 1.037 | 1.038 | 1.119 | 1.054 | 1.150 | 0.957 | 1.155 | 1.096 | 0.955 | 0.857 |
| uc.473+A | 19 | 4.289 | 3.154 | 4.522 | 3.629 | 4.163 | 5.880 | 2.963 | 4.842 | 6.286 | 4.375 | 3.911 |
| uc.209+A | 19 | 1.733 | 1.367 | 2.003 | 1.309 | 1.559 | 1.936 | 1.444 | 1.294 | 1.293 | 1.822 | 1.667 |
| uc.372+ | 19 | 1.293 | 1.046 | 1.070 | 1.225 | 1.220 | 1.414 | 1.153 | 1.143 | 1.337 | 1.097 | 1.011 |
| uc.465+A | 19 | 5.119 | 5.262 | 5.826 | 5.094 | 5.482 | 8.347 | 4.420 | 5.633 | 5.290 | 5.650 | 5.375 |
| uc.282+A | 19 | 10.295 | 9.817 | 27.695 | 9.776 | 9.015 | 11.141 | 9.206 | 18.238 | 12.357 | 13.227 | 14.094 |
| uc.476+A | 19 | 2.673 | 1.803 | 1.653 | 1.715 | 1.966 | 2.481 | 1.690 | 2.319 | 2.136 | 1.764 | 1.133 |
| uc.299+ | 19 | 3.453 | 2.601 | 3.325 | 2.724 | 2.860 | 2.347 | 2.904 | 3.309 | 3.461 | 3.295 | 3.264 |
| uc.192+A | 19 | 1.562 | 1.095 | 1.128 | 1.342 | 1.402 | 1.828 | 1.086 | 1.086 | 0.988 | 1.050 | 1.214 |
| uc.33+ | 19 | 1.920 | 1.677 | 2.069 | 1.712 | 1.925 | 2.290 | 1.691 | 1.517 | 1.652 | 1.829 | 1.789 |
| uc.34+ | 19 | 1.236 | 0.919 | 1.050 | 0.998 | 0.964 | 0.957 | 1.066 | 1.340 | 1.707 | 1.020 | 0.950 |
| uc.34+A | 19 | 1.396 | 1.371 | 1.403 | 1.142 | 1.323 | 1.565 | 1.378 | 1.387 | 0.955 | 1.274 | 1.380 |
| uc.158+ | 19 | 1.041 | 0.982 | 1.211 | 1.242 | 1.263 | 1.087 | 1.505 | 1.226 | 1.594 | 1.142 | 1.275 |
| uc.440+A | 19 | 0.979 | 1.072 | 1.019 | 0.953 | 0.970 | 0.972 | 0.940 | 0.995 | 1.508 | 1.033 | 1.037 |
| uc.37+ | 19 | 1.124 | 0.998 | 1.153 | 1.045 | 1.596 | 1.176 | 1.418 | 1.114 | 1.040 | 1.129 | 1.064 |
| uc.42+A | 19 | 1.175 | 1.138 | 0.957 | 0.997 | 0.967 | 1.312 | 1.058 | 0.941 | 0.950 | 1.007 | 1.015 |
| uc.340+ | 19 | 2.155 | 1.573 | 1.832 | 1.584 | 1.351 | 1.886 | 1.631 | 1.904 | 1.545 | 1.372 | 1.319 |
| uc.319+A | 19 | 1.030 | 1.065 | 1.663 | 1.607 | 1.036 | 1.087 | 1.956 | 1.088 | 1.062 | 1.061 | 1.068 |
| uc.483+ | 19 | 1.117 | 1.659 | 1.819 | 1.183 | 1.116 | 1.334 | 1.192 | 1.043 | 1.197 | 1.258 | 1.204 |
| uc.263+ | 19 | 2.064 | 1.143 | 0.998 | 1.277 | 1.047 | 1.041 | 1.024 | 2.311 | 3.298 | 1.340 | 1.099 |
| uc.204+A | 19 | 2.285 | 1.738 | 2.294 | 1.950 | 2.118 | 2.572 | 2.071 | 3.113 | 2.006 | 2.024 | 1.938 |
| uc.230+ | 19 | 2.597 | 5.186 | 3.153 | 3.353 | 6.241 | 2.259 | 5.755 | 2.392 | 1.506 | 4.436 | 4.043 |
| uc.292+A | 19 | 1.053 | 1.053 | 1.371 | 1.041 | 1.061 | 1.451 | 1.096 | 1.070 | 0.956 | 1.069 | 1.027 |
| uc.220+ | 19 | 1.193 | 1.171 | 1.121 | 0.925 | 1.041 | 1.234 | 1.058 | 0.953 | 0.898 | 1.127 | 1.125 |
| uc.473+ | 19 | 2.203 | 1.555 | 1.492 | 1.419 | 1.600 | 2.132 | 1.953 | 2.605 | 3.274 | 1.514 | 1.224 |
| uc.329+A | 19 | 1.618 | 1.286 | 1.510 | 1.582 | 1.354 | 1.671 | 1.238 | 1.178 | 1.490 | 1.162 | 1.157 |
| uc.203+A | 19 | 1.015 | 0.929 | 0.997 | 1.091 | 0.995 | 1.034 | 0.987 | 1.015 | 1.029 | 0.950 | 1.016 |
| uc.472+ | 19 | 1.156 | 1.416 | 1.290 | 1.171 | 1.118 | 1.055 | 1.146 | 1.246 | 1.252 | 1.048 | 1.302 |
| uc.475+A | 19 | 2.841 | 1.689 | 1.374 | 1.610 | 2.241 | 1.820 | 2.191 | 3.056 | 3.024 | 1.856 | 1.967 |
| uc.146+ | 19 | 0.969 | 1.038 | 1.212 | 1.169 | 1.231 | 1.596 | 1.091 | 0.962 | 0.967 | 1.221 | 1.161 |
| uc.27+ | 19 | 0.986 | 1.031 | 1.116 | 1.059 | 1.046 | 1.060 | 1.079 | 0.966 | 0.890 | 0.941 | 0.974 |
| uc.111+ | 19 | 1.149 | 1.198 | 0.972 | 1.538 | 1.327 | 1.218 | 1.194 | 1.026 | 1.108 | 1.081 | 0.996 |
| uc.382+A | 19 | 1.477 | 1.048 | 1.689 | 1.290 | 1.471 | 1.583 | 1.044 | 1.802 | 2.802 | 1.711 | 1.256 |
| uc.331+ | 19 | 1.687 | 1.785 | 1.833 | 3.173 | 1.799 | 2.205 | 2.049 | 1.590 | 1.550 | 1.686 | 1.701 |
| uc.450+A | 19 | 1.132 | 1.072 | 0.959 | 0.926 | 1.064 | 1.136 | 1.048 | 1.222 | 1.658 | 1.031 | 0.989 |
| uc.476+ | 19 | 1.245 | 1.017 | 1.051 | 1.591 | 1.366 | 1.055 | 1.146 | 1.199 | 1.305 | 1.081 | 1.110 |
| uc.29+ | 19 | 0.946 | 0.915 | 0.973 | 0.962 | 1.298 | 0.965 | 1.028 | 0.947 | 0.927 | 1.097 | 0.960 |
| uc.26+ | 19 | 1.526 | 1.134 | 1.415 | 1.284 | 1.652 | 1.620 | 1.272 | 1.075 | 1.019 | 1.284 | 1.291 |
| uc.330+ | 19 | 1.467 | 1.335 | 1.273 | 2.086 | 1.424 | 1.382 | 1.174 | 1.022 | 1.640 | 1.219 | 1.274 |
| uc.281+A | 19 | 4.443 | 2.837 | 2.459 | 4.318 | 3.177 | 4.804 | 3.467 | 2.556 | 1.917 | 2.146 | 2.555 |
| uc.77+A | 19 | 1.505 | 0.999 | 1.573 | 0.989 | 1.031 | 1.106 | 0.992 | 1.819 | 1.703 | 1.117 | 1.091 |
| uc.475+ | 19 | 6.941 | 4.399 | 5.240 | 4.769 | 4.529 | 5.520 | 4.472 | 4.177 | 3.240 | 4.767 | 4.995 |
| uc.396+ | 19 | 1.044 | 1.096 | 1.089 | 1.902 | 1.556 | 1.136 | 2.054 | 1.065 | 0.939 | 1.313 | 1.136 |
| uc.374+A | 19 | 0.914 | 0.962 | 1.024 | 1.339 | 0.981 | 1.178 | 0.956 | 0.962 | 0.945 | 1.035 | 1.525 |
| uc.206+A | 19 | 1.270 | 1.027 | 1.254 | 1.280 | 1.316 | 1.429 | 1.291 | 1.767 | 2.710 | 1.344 | 1.478 |
| uc.22+A | 19 | 1.363 | 1.223 | 1.130 | 1.294 | 1.267 | 1.261 | 1.521 | 1.489 | 1.343 | 1.177 | 1.330 |
| uc.160+A | 19 | 1.058 | 0.952 | 1.039 | 0.979 | 1.103 | 1.046 | 1.021 | 1.028 | 1.204 | 1.086 | 1.030 |
| uc.250+ | 19 | 1.093 | 1.024 | 1.061 | 1.089 | 0.945 | 1.206 | 0.961 | 1.052 | 1.036 | 0.997 | 1.058 |
| uc.363+A | 19 | 1.216 | 1.120 | 1.243 | 0.964 | 0.949 | 1.181 | 1.086 | 1.164 | 1.459 | 1.089 | 1.114 |
| uc.20+ | 19 | 2.099 | 1.922 | 1.997 | 1.480 | 1.866 | 2.212 | 1.841 | 1.552 | 1.872 | 1.825 | 2.113 |
| uc.138+A | 19 | 1.342 | 1.238 | 0.945 | 0.952 | 0.960 | 0.933 | 0.923 | 1.350 | 1.245 | 0.957 | 1.002 |
| uc.142+ | 19 | 1.384 | 0.900 | 1.079 | 1.096 | 0.990 | 0.963 | 1.063 | 1.991 | 1.599 | 1.079 | 1.143 |
| uc.228+A | 19 | 1.016 | 0.979 | 1.200 | 0.965 | 0.967 | 0.991 | 1.094 | 1.225 | 1.052 | 0.998 | 1.026 |
| uc.398+ | 19 | 10.839 | 10.397 | 23.531 | 12.466 | 12.512 | 9.475 | 10.736 | 17.514 | 9.802 | 12.372 | 14.021 |
| uc.464+A | 19 | 1.547 | 1.406 | 1.476 | 1.795 | 1.483 | 1.485 | 1.578 | 1.284 | 1.721 | 1.421 | 1.378 |
| uc.149+ | 19 | 1.021 | 1.049 | 1.073 | 0.964 | 0.941 | 0.972 | 0.951 | 0.964 | 0.975 | 0.970 | 0.964 |
| uc.44+A | 19 | 4.564 | 2.233 | 2.843 | 3.383 | 3.869 | 2.917 | 2.832 | 2.732 | 2.679 | 2.841 | 2.430 |
| uc.217+A | 19 | 2.783 | 1.954 | 1.913 | 1.919 | 2.596 | 2.111 | 2.083 | 2.061 | 1.903 | 2.271 | 2.531 |
| uc.453+A | 19 | 4.134 | 3.752 | 3.131 | 4.288 | 2.832 | 4.706 | 2.407 | 3.423 | 3.235 | 2.486 | 2.352 |
| uc.295+A | 19 | 1.071 | 0.963 | 1.105 | 0.985 | 1.004 | 1.068 | 1.029 | 0.961 | 1.071 | 1.068 | 0.950 |
| uc.145+ | 19 | 1.361 | 1.031 | 0.988 | 0.998 | 1.321 | 0.944 | 1.051 | 1.235 | 1.275 | 1.069 | 0.996 |
| uc.33+A | 19 | 2.344 | 1.132 | 1.226 | 1.048 | 1.366 | 1.025 | 1.201 | 2.062 | 3.061 | 1.185 | 1.223 |
| uc.144+ | 19 | 0.955 | 0.981 | 0.927 | 1.338 | 1.197 | 1.055 | 0.968 | 0.944 | 0.801 | 1.027 | 1.106 |
| uc.447+ | 19 | 1.247 | 0.974 | 1.031 | 1.529 | 1.301 | 1.273 | 1.195 | 1.588 | 1.983 | 1.435 | 1.102 |
| uc.338+ | 19 | 4.241 | 3.146 | 3.195 | 4.692 | 3.857 | 3.410 | 2.586 | 2.726 | 2.793 | 4.111 | 3.565 |

Figure 15 Continued

Cain GA et al

| Sample | Number of tissues in which the UCR pass the filter | MNC 02 | Ovary | Pancreatic | Placenta | Prostate | Skeletal muscle | Spleen | T-cell 01 | T-cell 02 | Testicule | Thymus |
|---|---|---|---|---|---|---|---|---|---|---|---|---|
| uc.269+A | 19 | 6.573 | 2.898 | 3.533 | 2.003 | 3.120 | 2.569 | 6.861 | 2.945 | 1.834 | 2.903 | 3.063 |
| uc.301+A | 19 | 1.029 | 0.956 | 1.072 | 0.919 | 0.968 | 1.028 | 1.004 | 0.964 | 1.036 | 0.941 | 0.933 |
| uc.339+ | 19 | 12.865 | 7.763 | 11.640 | 13.797 | 17.123 | 11.131 | 15.608 | 16.259 | 11.467 | 12.505 | 10.631 |
| uc.5+ | 19 | 1.169 | 1.079 | 1.147 | 1.118 | 1.046 | 1.067 | 1.273 | 2.066 | 1.996 | 1.252 | 1.246 |
| uc.445+ | 19 | 1.647 | 1.286 | 1.244 | 1.118 | 1.470 | 1.153 | 1.592 | 1.910 | 2.764 | 1.466 | 1.397 |
| uc.132+A | 19 | 1.145 | 1.003 | 0.978 | 0.974 | 1.077 | 1.196 | 1.015 | 1.025 | 0.907 | 1.033 | 1.081 |
| uc.411+ | 19 | 1.381 | 1.375 | 1.715 | 1.584 | 1.698 | 2.604 | 1.798 | 1.356 | 1.251 | 1.823 | 1.303 |
| uc.446+ | 19 | 1.306 | 1.150 | 1.079 | 1.126 | 1.177 | 1.240 | 1.295 | 1.136 | 1.025 | 1.356 | 1.137 |
| uc.312+A | 19 | 0.890 | 1.151 | 0.992 | 0.985 | 1.062 | 1.142 | 1.047 | 0.980 | 0.946 | 0.957 | 1.051 |
| uc.413+ | 19 | 1.073 | 0.904 | 1.040 | 0.954 | 0.971 | 1.023 | 1.003 | 1.000 | 0.987 | 0.937 | 0.949 |
| uc.359+A | 19 | 1.006 | 0.959 | 1.557 | 1.617 | 1.440 | 1.057 | 1.054 | 0.961 | 1.139 | 1.048 | 1.043 |
| uc.402+A | 19 | 1.017 | 0.971 | 0.849 | 0.957 | 0.966 | 0.964 | 0.971 | 1.802 | 2.720 | 1.019 | 0.995 |
| uc.91+ | 19 | 1.169 | 0.971 | 0.951 | 1.145 | 1.006 | 1.054 | 1.126 | 1.416 | 1.303 | 1.055 | |
| uc.412+ | 19 | 2.068 | 1.494 | 1.581 | 1.653 | 1.457 | 1.459 | 1.781 | 2.691 | 3.006 | 1.651 | 1.934 |
| uc.448+ | 19 | 2.279 | 1.275 | 1.233 | 1.301 | 1.387 | 1.280 | 1.222 | 2.586 | 2.391 | 1.221 | 1.281 |
| uc.9+A | 19 | 1.059 | 1.025 | 1.086 | 1.081 | 1.253 | 1.011 | 0.905 | 0.951 | 0.936 | 1.049 | |
| uc.305+ | 19 | 1.951 | 1.062 | 1.038 | 1.270 | 1.317 | 1.153 | 1.203 | 1.939 | 3.336 | 1.123 | 1.246 |
| uc.233+A | 19 | 2.397 | 1.283 | 1.253 | 1.125 | 1.321 | 1.297 | 1.283 | 1.866 | 2.504 | 1.272 | 1.252 |
| uc.304+A | 19 | 0.965 | 0.944 | 0.951 | 1.029 | 1.056 | 1.207 | 1.007 | 0.935 | 0.963 | 0.963 | 1.007 |
| uc.369+ | 19 | 3.072 | 2.308 | 3.652 | 2.792 | 2.864 | 2.664 | 2.784 | 3.419 | 2.495 | 2.211 | 2.496 |
| uc.88+A | 19 | 4.283 | 2.710 | 2.677 | 3.448 | 3.575 | 3.959 | 2.770 | 3.599 | 4.043 | 2.716 | 2.154 |
| uc.2+ | 19 | 0.976 | 0.993 | 1.006 | 1.103 | 1.048 | 1.071 | 1.031 | 0.997 | 0.920 | 0.952 | 0.939 |
| uc.110+A | 19 | 4.142 | 2.701 | 3.240 | 3.795 | 2.845 | 2.222 | 2.861 | 2.311 | 1.831 | 3.107 | 3.625 |
| uc.461+A | 19 | 1.153 | 1.132 | 1.009 | 1.041 | 1.039 | 1.337 | 1.136 | 1.212 | 1.744 | 1.052 | 1.256 |
| uc.419+A | 19 | 1.809 | 1.175 | 1.092 | 1.929 | 1.914 | 1.113 | 1.081 | 1.016 | 0.943 | 1.354 | 1.366 |
| uc.440+ | 19 | 1.015 | 0.925 | 0.940 | 0.979 | 0.957 | 0.995 | 1.012 | 1.018 | 0.978 | 0.913 | 1.030 |
| uc.478+ | 19 | 2.399 | 1.508 | 1.665 | 2.880 | 1.931 | 1.062 | 1.346 | 4.275 | 1.996 | 1.614 | 1.926 |
| uc.1+ | 19 | 1.868 | 2.443 | 3.644 | 3.343 | 3.860 | 3.191 | 3.457 | 3.139 | 2.046 | 4.055 | 3.857 |
| uc.4+ | 19 | 1.161 | 1.090 | 1.161 | 1.061 | 1.144 | 1.596 | 1.217 | 1.427 | 1.336 | 1.350 | |
| uc.335+ | 19 | 1.517 | 1.519 | 1.014 | 1.637 | 1.117 | 1.427 | 1.237 | 1.031 | 0.966 | 1.102 | 1.106 |
| uc.483+A | 19 | 2.476 | 2.419 | 3.509 | 1.857 | 2.114 | 2.707 | 2.662 | 1.871 | 1.904 | 2.341 | 2.587 |
| uc.8+ | 19 | 5.871 | 3.216 | 6.693 | 17.981 | 8.321 | 7.728 | 10.597 | 4.058 | 2.772 | 12.067 | 10.934 |
| uc.63+A | 19 | 1.444 | 1.193 | 1.153 | 1.509 | 1.309 | 1.535 | 1.445 | 1.573 | 1.914 | 1.054 | 1.050 |
| uc.443+ | 19 | 1.024 | 0.918 | 1.057 | 0.954 | 1.036 | 1.078 | 1.031 | 1.191 | 1.272 | 1.004 | 0.986 |
| uc.117+ | 19 | 6.267 | 3.642 | 4.697 | 4.206 | 4.847 | 6.134 | 3.149 | 4.091 | 3.576 | 3.145 | 3.286 |
| uc.477+ | 19 | 1.959 | 1.134 | 1.032 | 1.118 | 1.050 | 1.073 | 1.162 | 2.319 | 2.875 | 1.274 | 1.649 |
| uc.200+A | 19 | 1.847 | 1.225 | 1.191 | 1.580 | 1.648 | 1.142 | 1.477 | 2.421 | 2.636 | 1.454 | 1.441 |
| uc.3+ | 19 | 1.155 | 1.396 | 1.150 | 1.145 | 1.185 | 1.312 | 1.106 | 1.062 | 1.106 | 1.274 | 1.239 |
| uc.322+ | 19 | 0.939 | 0.976 | 0.990 | 0.944 | 0.928 | 0.949 | 0.943 | 0.955 | 1.088 | 0.999 | 0.989 |
| uc.213+ | 19 | 5.487 | 4.939 | 5.060 | 7.083 | 3.264 | 3.856 | 5.529 | 5.875 | 5.520 | 6.395 | 7.742 |
| uc.349+ | 19 | 1.478 | 1.919 | 1.666 | 1.701 | 2.103 | 1.535 | 1.996 | 2.016 | 1.562 | 2.004 | 2.139 |
| uc.303+A | 19 | 1.432 | 1.245 | 1.347 | 1.144 | 1.147 | 1.120 | 1.129 | 0.996 | 1.038 | 1.102 | 1.049 |
| uc.323+ | 19 | 0.986 | 1.150 | 1.108 | 0.994 | 0.999 | 1.041 | 0.958 | 1.009 | 0.968 | 0.939 | 1.023 |
| uc.248+ | 19 | 1.509 | 1.053 | 1.007 | 0.924 | 0.939 | 0.964 | 0.987 | 1.700 | 1.953 | 0.945 | 0.954 |
| uc.465+ | 19 | 1.182 | 0.955 | 0.982 | 1.047 | 1.045 | 1.006 | 1.096 | 1.307 | 1.492 | 1.125 | 1.049 |
| uc.139+ | 19 | 5.475 | 1.949 | 1.576 | 2.984 | 2.659 | 2.715 | 2.813 | 1.848 | 1.336 | 1.628 | 2.006 |
| uc.214+ | 19 | 1.394 | 1.509 | 1.623 | 1.472 | 1.279 | 1.345 | 1.229 | 1.164 | 1.974 | 1.214 | 1.447 |
| uc.145+A | 19 | 7.250 | 5.579 | 5.641 | 15.593 | 4.461 | 4.560 | 7.546 | 3.766 | 2.756 | 10.465 | 9.467 |
| uc.325+A | 19 | 1.002 | 0.967 | 1.291 | 0.926 | 1.004 | 1.193 | 1.012 | 0.964 | 1.148 | 1.152 | 1.040 |
| uc.217+ | 19 | 2.930 | 1.575 | 1.524 | 2.214 | 1.190 | 1.626 | 2.009 | 4.305 | 4.295 | 2.191 | 1.919 |
| uc.525+ | 19 | 7.184 | 9.000 | 12.195 | 7.353 | 7.299 | 5.588 | 5.881 | 7.133 | 8.944 | 7.447 | 10.892 |
| uc.435+ | 19 | 1.298 | 1.129 | 1.820 | 1.112 | 1.290 | 1.554 | 1.301 | 1.323 | 1.662 | 1.281 | 1.280 |
| uc.526+ | 19 | 2.679 | 1.758 | 1.413 | 1.755 | 1.831 | 2.695 | 2.346 | 1.719 | 1.309 | 1.621 | 1.462 |
| uc.106+ | 19 | 3.375 | 1.913 | 1.341 | 0.987 | 1.025 | 1.177 | 0.998 | 4.189 | 5.963 | 1.298 | 1.157 |
| uc.468+ | 19 | 1.599 | 1.565 | 1.409 | 1.097 | 1.283 | 1.325 | 1.292 | 1.448 | 1.253 | 1.553 | 1.361 |
| uc.213+A | 19 | 2.222 | 1.634 | 2.054 | 1.982 | 1.928 | 2.327 | 1.911 | 1.618 | 1.613 | 2.136 | 2.295 |
| uc.62+A | 19 | 0.982 | 0.922 | 1.051 | 1.005 | 0.995 | 1.143 | 1.014 | 1.017 | 1.007 | 1.012 | 0.937 |
| uc.246+A | 19 | 1.481 | 1.115 | 1.391 | 1.220 | 1.205 | 1.095 | 1.287 | 2.474 | 2.031 | 1.346 | 1.366 |
| uc.43+A | 19 | 1.499 | 1.045 | 1.081 | 1.025 | 1.053 | 1.048 | 1.043 | 1.973 | 1.790 | 1.039 | 0.931 |
| uc.389+ | 19 | 1.447 | 1.567 | 1.795 | 1.210 | 1.153 | 1.419 | 1.185 | 2.047 | 1.824 | 1.206 | 1.256 |
| uc.159+A | 19 | 3.358 | 2.353 | 2.208 | 3.616 | 2.644 | 2.957 | 2.511 | 2.209 | 2.211 | 2.632 | 2.538 |
| uc.100+ | 19 | 1.191 | 1.373 | 1.823 | 1.276 | 1.259 | 1.312 | 1.584 | 1.488 | 1.069 | 1.434 | 1.795 |
| uc.462+ | 19 | 2.063 | 1.395 | 1.507 | 1.613 | 1.745 | 1.397 | 1.521 | 2.569 | 2.365 | 1.648 | 1.788 |
| uc.352+ | 19 | 4.335 | 2.225 | 3.942 | 2.334 | 2.486 | 3.094 | 1.866 | 5.051 | 3.683 | 2.394 | 3.026 |
| uc.388+ | 19 | 2.326 | 1.321 | 1.296 | 1.204 | 1.405 | 1.256 | 1.459 | 3.842 | 5.143 | 1.554 | 1.373 |
| uc.125+A | 19 | 1.484 | 1.068 | 1.101 | 1.030 | 1.045 | 1.018 | 0.990 | 0.983 | 1.279 | 1.050 | 1.122 |
| uc.136+ | 19 | 2.327 | 1.037 | 1.573 | 1.609 | 1.550 | 2.018 | 1.905 | 2.904 | 2.828 | 1.675 | 1.799 |
| uc.244+ | 19 | 1.177 | 1.059 | 0.988 | 0.925 | 1.074 | 1.137 | 1.256 | 1.029 | 0.929 | 0.932 | 1.033 |
| uc.138+ | 19 | 0.925 | 1.013 | 0.874 | 0.982 | 1.046 | 1.137 | 0.968 | 0.959 | 1.136 | 0.959 | 1.126 |
| uc.291+A | 19 | 0.908 | 1.176 | 1.377 | 1.263 | 2.262 | 1.140 | 1.597 | 1.055 | 1.103 | 2.199 | 1.743 |
| uc.249+A | 19 | 1.447 | 1.142 | 1.286 | 1.083 | 1.172 | 1.050 | 1.152 | 2.314 | 2.122 | 1.132 | 1.186 |

Figure 15 Continued

Calin GA et al                                                  10

| Sample | Number of tissues in which the UCR pass the filter | MNC 02 | Ovary | Pancreatic | Placenta | Prostate | Skeletal muscle | Spleen | T-cell 01 | T-cell 02 | Testicule | Thymus |
|---|---|---|---|---|---|---|---|---|---|---|---|---|
| uc.469+ | 19 | 1.166 | 0.907 | 0.989 | 0.936 | 0.926 | 0.935 | 0.963 | 1.244 | 1.458 | 0.988 | 0.929 |
| uc.19+ | 19 | 3.390 | 3.614 | 4.712 | 2.379 | 2.944 | 3.843 | 3.323 | 3.911 | 3.271 | 5.127 | 5.072 |
| uc.245+ | 19 | 0.966 | 1.132 | 1.114 | 0.986 | 1.374 | 1.111 | 1.053 | 1.059 | 1.091 | 0.980 | 0.957 |
| uc.280+A | 19 | 1.126 | 1.096 | 0.997 | 1.120 | 1.121 | 1.154 | 1.140 | 1.288 | 1.469 | 1.130 | 0.991 |
| uc.14+ | 19 | 1.102 | 1.133 | 1.102 | 1.325 | 1.162 | 1.283 | 1.221 | 1.032 | 0.942 | 1.147 | 1.027 |
| uc.134+A | 19 | 2.530 | 1.679 | 1.470 | 2.176 | 2.492 | 1.965 | 3.879 | 2.293 | 2.548 | 2.426 | 2.572 |
| uc.246+ | 19 | 3.279 | 3.477 | 3.665 | 4.015 | 2.975 | 5.144 | 2.441 | 3.318 | 2.669 | 2.711 | 2.959 |
| uc.16+ | 19 | 1.697 | 1.430 | 1.296 | 1.133 | 1.270 | 1.425 | 1.439 | 1.347 | 1.633 | 1.274 | 1.203 |
| uc.391+ | 19 | 1.156 | 1.032 | 1.323 | 1.377 | 1.216 | 1.183 | 1.174 | 1.077 | 0.938 | 1.142 | 1.141 |
| uc.262+A | 19 | 5.156 | 3.671 | 2.332 | 2.333 | 2.827 | 3.992 | 3.690 | 2.254 | 1.668 | 2.634 | 2.310 |
| uc.456+A | 19 | 3.191 | 2.290 | 2.816 | 2.374 | 2.219 | 4.331 | 2.106 | 2.124 | 2.338 | 2.345 | 2.119 |
| uc.53+ | 19 | 1.129 | 1.363 | 1.178 | 1.131 | 1.139 | 1.077 | 1.125 | 1.106 | 0.971 | 1.171 | 1.151 |
| uc.89+ | 19 | 1.172 | 1.057 | 1.062 | 1.116 | 1.137 | 1.194 | 1.077 | 1.177 | 1.579 | 1.115 | 1.127 |
| uc.390+ | 19 | 1.556 | 1.155 | 1.252 | 1.265 | 1.204 | 1.496 | 1.504 | 1.347 | 1.137 | 1.262 | 1.235 |
| uc.103+A | 19 | 1.078 | 1.509 | 1.189 | 1.762 | 1.117 | 2.269 | 1.367 | 2.675 | 2.909 | 1.212 | 1.253 |
| uc.377+A | 19 | 1.337 | 1.144 | 1.059 | 1.383 | 1.414 | 1.169 | 1.143 | 1.240 | 1.463 | 1.134 | 1.099 |
| uc.306+A | 19 | 1.853 | 1.181 | 1.582 | 1.202 | 1.469 | 1.452 | 1.197 | 1.590 | 1.781 | 1.473 | 1.391 |
| uc.173+ | 19 | 1.171 | 0.943 | 1.036 | 0.919 | 0.909 | 0.971 | 0.959 | 1.794 | 2.257 | 0.985 | 0.993 |
| uc.478+A | 19 | 5.702 | 5.841 | 7.227 | 3.697 | 4.289 | 6.193 | 4.162 | 5.264 | 3.696 | 4.023 | 3.658 |
| uc.47+A | 19 | 1.787 | 1.355 | 1.147 | 1.338 | 1.295 | 1.149 | 1.109 | 1.944 | 2.304 | 0.982 | 1.100 |
| uc.393+ | 19 | 1.159 | 1.002 | 1.233 | 1.141 | 1.041 | 1.079 | 1.158 | 0.955 | 0.928 | 1.138 | 1.128 |
| uc.315+A | 19 | 1.168 | 0.962 | 0.982 | 1.194 | 1.039 | 1.141 | 1.018 | 0.996 | 1.027 | 1.048 | 1.077 |
| uc.177+ | 19 | 2.075 | 1.574 | 2.310 | 1.484 | 1.459 | 1.453 | 1.822 | 2.510 | 2.125 | 1.988 | 1.927 |
| uc.392+ | 19 | 1.048 | 0.978 | 0.922 | 0.951 | 0.955 | 0.938 | 1.020 | 1.435 | 3.546 | 1.037 | 0.969 |
| uc.341+A | 19 | 0.965 | 0.956 | 1.139 | 0.996 | 0.960 | 1.065 | 0.978 | 1.502 | 1.152 | 1.041 | 0.983 |
| uc.98+ | 19 | 2.495 | 1.782 | 1.825 | 1.803 | 2.100 | 2.176 | 1.817 | 3.178 | 4.193 | 2.068 | 2.042 |
| uc.205+ | 19 | 3.559 | 1.753 | 2.019 | 2.296 | 2.232 | 2.191 | 1.954 | 2.129 | 2.927 | 2.162 | 2.171 |
| uc.420+A | 19 | 1.610 | 1.144 | 1.103 | 0.970 | 1.042 | 1.023 | 1.140 | 1.999 | 2.100 | 1.250 | 1.025 |
| uc.164+A | 19 | 1.248 | 1.111 | 0.979 | 1.344 | 1.127 | 1.252 | 1.039 | 0.998 | 0.984 | 1.005 | 1.112 |
| uc.300+A | 19 | 11.305 | 6.271 | 10.132 | 8.366 | 5.453 | 7.133 | 6.574 | 10.990 | 7.640 | 4.684 | 5.212 |
| uc.153+A | 19 | 2.353 | 1.594 | 2.235 | 1.284 | 1.811 | 2.085 | 1.585 | 1.552 | 1.985 | 1.960 | 1.651 |
| uc.446+A | 19 | 3.772 | 2.983 | 4.117 | 2.371 | 3.175 | 4.683 | 2.819 | 4.244 | 4.399 | 3.509 | 2.721 |
| uc.17+A | 19 | 1.243 | 1.118 | 1.237 | 1.154 | 1.637 | 1.139 | 0.997 | 0.923 | 0.887 | 1.025 | 1.491 |
| uc.436+ | 19 | 1.117 | 1.114 | 1.188 | 1.159 | 1.008 | 1.045 | 1.217 | 1.102 | 0.984 | 1.110 | 1.103 |
| uc.142+A | 19 | 4.748 | 2.818 | 4.135 | 2.708 | 2.427 | 3.569 | 2.338 | 4.838 | 3.344 | 2.433 | 2.828 |
| uc.73+A | 19 | 4.743 | 2.904 | 4.313 | 3.258 | 3.532 | 3.693 | 3.955 | 2.572 | 2.781 | 3.182 | 2.997 |
| uc.404+ | 19 | 1.022 | 1.012 | 0.992 | 0.989 | 1.024 | 1.096 | 0.951 | 0.963 | 1.014 | 0.998 | 0.997 |
| uc.84+A | 19 | 3.780 | 4.511 | 6.438 | 5.964 | 4.908 | 3.053 | 4.186 | 5.387 | 2.647 | 4.585 | 4.175 |
| uc.280+ | 19 | 1.355 | 1.067 | 1.678 | 1.874 | 1.293 | 1.204 | 1.049 | 1.135 | 1.463 | 1.146 | 1.211 |
| uc.172+A | 19 | 6.390 | 7.669 | 18.509 | 8.125 | 6.448 | 9.018 | 7.936 | 6.680 | 4.294 | 8.306 | 7.605 |
| uc.267+A | 19 | 3.526 | 2.591 | 2.773 | 2.302 | 2.976 | 4.556 | 2.617 | 2.152 | 2.331 | 2.832 | 3.052 |
| uc.54+ | 19 | 0.966 | 0.952 | 1.040 | 1.006 | 1.028 | 1.069 | 1.083 | 1.271 | 0.980 | 0.996 | 0.995 |
| uc.445+A | 19 | 1.844 | 1.264 | 1.607 | 1.490 | 1.567 | 2.044 | 1.196 | 1.317 | 2.809 | 1.283 | 1.487 |
| uc.407+ | 19 | 1.749 | 1.246 | 1.195 | 1.303 | 1.406 | 1.441 | 1.200 | 1.129 | 1.119 | 1.121 | 1.124 |
| uc.412+A | 19 | 2.549 | 1.942 | 1.868 | 2.179 | 2.402 | 3.570 | 2.145 | 1.987 | 1.911 | 2.426 | 2.074 |
| uc.347+A | 19 | 1.326 | 1.317 | 1.559 | 1.057 | 1.081 | 1.524 | 1.248 | 1.422 | 1.183 | 1.167 | 1.166 |
| uc.87+ | 19 | 1.119 | 1.070 | 1.116 | 1.426 | 1.164 | 1.250 | 1.182 | 1.046 | 0.940 | 1.264 | 1.089 |
| uc.170+ | 19 | 2.879 | 1.322 | 2.229 | 2.103 | 2.783 | 2.699 | 1.959 | 4.648 | 5.083 | 2.809 | 3.014 |
| uc.161+A | 19 | 3.148 | 1.741 | 1.161 | 2.979 | 2.830 | 4.067 | 1.895 | 1.787 | 1.988 | 2.126 | 2.196 |

Figure 15 Continued

Calin GA et al

Supplementary table 2. T-UCRs differentially expressed (ANOVA at p<0.005) among each cancer type with the corresponding normal tissues.

| Comparison | Probe | P-value | Expression Tumor/Normal | Significance | UCR name | UCR type |
|---|---|---|---|---|---|---|
| CLL vs CD5+ | uc.289+ | 0.00097 | 0.22 | down in tumors | uc.289 | N |
| CLL vs CD5+ | uc.285+ | 0.00021 | 0.39 | down in tumors | uc.285 | E |
| CLL vs CD5+ | uc.73+A | 1.36E-07 | 0.58 | down in tumors | uc.73 | P |
| CLL vs CD5+ | uc.291+ | 1.12E-06 | 0.58 | down in tumors | uc.291 | P |
| CLL vs CD5+ | uc.231+ | 0.000106 | 0.58 | down in tumors | uc.231 | N |
| CLL vs CD5+ | uc.233+ | 4.42E-05 | 0.68 | down in tumors | uc.233 | E |
| CLL vs CD5+ | uc.435+ | 0.00426 | 0.69 | down in tumors | uc.435 | N |
| CLL vs CD5+ | uc.183+ | 0.00481 | 0.81 | down in tumors | uc.183 | E |
| CLL vs CD5+ | uc.135+ | 8.91E-06 | 0.85 | down in tumors | uc.135 | E |
| CLL vs CD5+ | uc.349+A | 0.000699 | 0.88 | down in tumors | uc.349 | P |
| CLL vs CD5+ | uc.316+ | 0.00166 | 0.92 | down in tumors | uc.316 | N |
| CLL vs CD5+ | uc.122+ | 0.000553 | 1.15 | up in tumors | uc.122 | N |
| CLL vs CD5+ | uc.422+A | 8.46E-05 | 1.20 | up in tumors | uc.422 | P |
| CLL vs CD5+ | uc.144+ | 0.000352 | 1.21 | up in tumors | uc.144 | E |
| CLL vs CD5+ | uc.377+A | 0.000352 | 1.21 | up in tumors | uc.377 | E |
| CLL vs CD5+ | uc.262+ | 0.000847 | 1.48 | up in tumors | uc.262 | N |
| CLL vs CD5+ | uc.352+ | 0.000537 | 1.61 | up in tumors | uc.352 | N |
| CLL vs CD5+ | uc.192+ | 0.000106 | 2.34 | up in tumors | uc.192 | N |
| CLL vs CD5+ | uc.160+ | 0.000115 | 2.48 | up in tumors | uc.160 | N |
| Comparison | Probe | P-value | Tumor/Normal | Tumor/Normal | UCR name | UCR type |
| CRC vs colon mucosa | uc.43+ | 0.00342 | 0.84 | down in tumors | uc.43 | N |
| CRC vs colon mucosa | uc.3+ | 0.00429 | 0.94 | down in tumors | uc.3 | P |
| CRC vs colon mucosa | uc.204+A | 0.00353 | 1.07 | up in tumors | uc.204 | N |
| CRC vs colon mucosa | uc.305+A | 0.00341 | 1.08 | up in tumors | uc.305 | P |
| CRC vs colon mucosa | uc.9+ | 0.0044 | 1.08 | up in tumors | uc.9 | N |
| CRC vs colon mucosa | uc.340+A | 0.00121 | 1.09 | up in tumors | uc.340 | N |
| CRC vs colon mucosa | uc.198+A | 0.000842 | 1.09 | up in tumors | uc.198 | N |
| CRC vs colon mucosa | uc.330+ | 0.000934 | 1.09 | up in tumors | uc.330 | E |
| CRC vs colon mucosa | uc.249+A | 0.000253 | 1.09 | up in tumors | uc.249 | N |
| CRC vs colon mucosa | uc.221+A | 0.00191 | 1.10 | up in tumors | uc.221 | P |
| CRC vs colon mucosa | uc.422+A | 0.00497 | 1.10 | up in tumors | uc.422 | P |
| CRC vs colon mucosa | uc.427+A | 0.000973 | 1.10 | up in tumors | uc.427 | P |
| CRC vs colon mucosa | uc.413+A | 0.00176 | 1.11 | up in tumors | uc.413 | E |
| CRC vs colon mucosa | uc.29+A | 3.26E-05 | 1.11 | up in tumors | uc.29 | N |
| CRC vs colon mucosa | uc.292+ | 0.000013 | 1.11 | up in tumors | uc.292 | E |
| CRC vs colon mucosa | uc.92+ | 0.0039 | 1.12 | up in tumors | uc.92 | N |
| CRC vs colon mucosa | uc.144+ | 0.000223 | 1.12 | up in tumors | uc.144 | E |
| CRC vs colon mucosa | uc.206+ | 2.16E-05 | 1.14 | up in tumors | uc.206 | N |
| CRC vs colon mucosa | uc.202+A | 0.00441 | 1.14 | up in tumors | uc.202 | N |
| CRC vs colon mucosa | uc.310+ | 0.0049 | 1.14 | up in tumors | uc.310 | N |
| CRC vs colon mucosa | uc.296+A | 7.37E-05 | 1.14 | up in tumors | uc.298 | N |
| CRC vs colon mucosa | uc.249+ | 0.000208 | 1.15 | up in tumors | uc.249 | N |
| CRC vs colon mucosa | uc.234+A | 0.00139 | 1.16 | up in tumors | uc.234 | P |
| CRC vs colon mucosa | uc.91+ | 0.00424 | 1.16 | up in tumors | uc.91 | N |
| CRC vs colon mucosa | uc.435+A | 0.00201 | 1.17 | up in tumors | uc.435 | N |
| CRC vs colon mucosa | uc.338+A | 0.000673 | 1.17 | up in tumors | uc.338 | E |
| CRC vs colon mucosa | uc.10+ | 0.00322 | 1.18 | up in tumors | uc.10 | N |
| CRC vs colon mucosa | uc.457+A | 0.00281 | 1.19 | up in tumors | uc.457 | E |
| CRC vs colon mucosa | uc.426+ | 0.00497 | 1.19 | up in tumors | uc.426 | P |
| CRC vs colon mucosa | uc.281+ | 0.00237 | 1.19 | up in tumors | uc.281 | P |
| CRC vs colon mucosa | uc.399+A | 9.97E-06 | 1.20 | up in tumors | uc.399 | N |
| CRC vs colon mucosa | uc.445+ | 0.00322 | 1.20 | up in tumors | uc.445 | N |
| CRC vs colon mucosa | uc.1+ | 0.00429 | 1.20 | up in tumors | uc.1 | P |

Figure 16

Calin GA et al  2

| Comparison | Probe | P-value | Expression Tumor/Normal | Significance | UCR name | UCR type |
|---|---|---|---|---|---|---|
| CRC vs colon mucosa | uc.158+ | 0.00156 | 1.20 | up in tumors | uc.158 | N |
| CRC vs colon mucosa | uc.326+ | 0.000355 | 1.21 | up in tumors | uc.326 | P |
| CRC vs colon mucosa | uc.111+ | 4.04E-05 | 1.21 | up in tumors | uc.111 | P |
| CRC vs colon mucosa | uc.182+ | 0.000355 | 1.22 | up in tumors | uc.182 | P |
| CRC vs colon mucosa | uc.63+ | 0.000511 | 1.22 | up in tumors | uc.63 | E |
| CRC vs colon mucosa | uc.468+A | 0.000198 | 1.23 | up in tumors | uc.468 | P |
| CRC vs colon mucosa | uc.475+ | 0.00455 | 1.24 | up in tumors | uc.475 | E |
| CRC vs colon mucosa | uc.200+ | 0.000763 | 1.24 | up in tumors | uc.200 | N |
| CRC vs colon mucosa | uc.341+ | 0.000045 | 1.24 | up in tumors | uc.341 | E |
| CRC vs colon mucosa | uc.420+A | 0.000013 | 1.27 | up in tumors | uc.420 | E |
| CRC vs colon mucosa | uc.106+ | 0.00137 | 1.28 | up in tumors | uc.106 | P |
| CRC vs colon mucosa | uc.246+ | 0.000511 | 1.28 | up in tumors | uc.246 | E |
| CRC vs colon mucosa | uc.470+A | 0.000253 | 1.29 | up in tumors | uc.470 | N |
| CRC vs colon mucosa | uc.362+ | 0.000603 | 1.29 | up in tumors | uc.362 | P |
| CRC vs colon mucosa | uc.383+ | 0.000308 | 1.31 | up in tumors | uc.383 | N |
| CRC vs colon mucosa | uc.73+A | 0.000972 | 1.31 | up in tumors | uc.73 | P |
| CRC vs colon mucosa | uc.412+ | 0.000105 | 1.31 | up in tumors | uc.412 | N |
| CRC vs colon mucosa | uc.266+A | 0.00081 | 1.36 | up in tumors | uc.266 | P |
| CRC vs colon mucosa | uc.63+A | 0.00305 | 1.36 | up in tumors | uc.63 | E |
| CRC vs colon mucosa | uc.308+ | 3.05E-06 | 1.37 | up in tumors | uc.308 | N |
| CRC vs colon mucosa | uc.300+A | 0.000208 | 1.37 | up in tumors | uc.300 | N |
| CRC vs colon mucosa | uc.230+ | 3.16E-06 | 1.40 | up in tumors | uc.230 | P |
| CRC vs colon mucosa | uc.18+ | 0.000536 | 1.50 | up in tumors | uc.18 | N |
| CRC vs colon mucosa | uc.134+A | 2.92E-08 | 1.53 | up in tumors | uc.134 | P |
| CRC vs colon mucosa | uc.398+ | 0.000777 | 1.54 | up in tumors | uc.398 | P |
| CRC vs colon mucosa | uc.112+ | 1.88E-14 | 1.71 | up in tumors | uc.112 | N |
| CRC vs colon mucosa | uc.145+A | 0.000253 | 1.79 | up in tumors | uc.145 | N |
| CRC vs colon mucosa | uc.339+ | 2.33E-09 | 2.17 | up in tumors | uc.339 | P |

| Comparison | Probe | P-value* | Tumor/Normal | Tumor/Normal | UCR name | UCR type |
|---|---|---|---|---|---|---|
| HCC vs Normal liver | uc.198+ | 0.000477 | 0.89 | down in tumors | uc.198 | N |
| HCC vs Normal liver | uc.23+ | 0.00221 | 0.90 | down in tumors | uc.23 | N |
| HCC vs Normal liver | uc.27+ | 0.00175 | 0.93 | down in tumors | uc.27 | N |
| HCC vs Normal liver | uc.274+ | 0.00367 | 0.93 | down in tumors | uc.274 | P |
| HCC vs Normal liver | uc.396+ | 0.00105 | 0.95 | down in tumors | uc.396 | N |
| HCC vs Normal liver | uc.252+A | 0.00152 | 1.17 | up in tumors | uc.252 | N |
| HCC vs Normal liver | uc.20+A | 0.00373 | 1.38 | up in tumors | uc.20 | P |
| HCC vs Normal liver | uc.402+A | 0.00141 | 1.38 | up in tumors | uc.402 | P |

*Statistical comparison was performed without Benjamini and Hochberg correction.

Figure 16 Continued

Calin GA et al

Supplemental Table 3. Genomic location of UCRs is correlated with CAGR (Cancer Associated Genomic Regions) (databases as in Bejerano G et al, Science 2004; Calin GA et al, PNAS 2004)

| ultra conserved element name | type | Build 34 coords | LOH exact | FRA <2Mb | AMPLIF exact | HPV 16 <2.5Mb | HOX clusters | HOX genes |
|---|---|---|---|---|---|---|---|---|
| uc.1 | p | chr1:10307243-10307449 | ■ | | ▨ | | ▨ | |
| uc.2 | n | chr1:10442089-10442295 | ■ | | | | | |
| uc.3 | p | chr1:10460711-10460935 | ■ | | | | | |
| uc.4 | n | chr1:10467795-10468153 | ■ | | | | | |
| uc.5 | n | chr1:10490897-10491110 | ■ | | | | | |
| uc.6 | p | chr1:10504667-10504967 | ■ | | | | | |
| uc.7 | p | chr1:10545679-10545934 | ■ | | | | | |
| uc.8 | n | chr1:10561364-10561579 | ■ | | | | | |
| uc.9 | n | chr1:10634956-10635157 | ■ | | | | | |
| uc.10 | n | chr1:10675120-10675394 | ■ | | | | | |
| uc.12 | p | chr1:35077889-35078089 | | | | | | |
| uc.13 | e | chr1:35786852-35787086 | | | | | | |
| uc.14 | p | chr1:37908296-37908510 | | | | | | |
| uc.15 | n | chr1:37974370-37974602 | | | | | | |
| uc.16 | p | chr1:38041493-38041703 | | | | | | |
| uc.17 | n | chr1:38215445-38215681 | | | | | | |
| uc.18 | n | chr1:44128955-44129192 | | | | | | |
| uc.19 | n | chr1:44403606-44403861 | | | | | | |
| uc.20 | p | chr1:44415666-44415934 | | | | | | |
| uc.21 | n | chr1:48482903-48483137 | ■ | | | | | |
| uc.22 | n | chr1:50376149-50376456 | ■ | | | | | |
| uc.23 | n | chr1:50405695-50405923 | ■ | | | | | |
| uc.24 | n | chr1:50469063-50469398 | ■ | | | | | |
| uc.25 | n | chr1:50535952-50536186 | ■ | | | | | |
| uc.26 | n | chr1:62739563-62739774 | ■ | | | | | |
| uc.27 | n | chr1:62739797-62740086 | ■ | | | | | |
| uc.28 | e | chr1:70066629-70066983 | ▨ | ■ | | | | |
| uc.29 | n | chr1:87244976-87245194 | | | | | | |
| uc.30 | n | chr1:87451593-87451835 | | | | | | |
| uc.31 | n | chr1:88395168-88395420 | | | | | | |
| uc.33 | e | chr1:96743538-96743849 | | | | | | |
| uc.34 | e | chr1:96751973-96752180 | | | | | | |
| uc.35 | p | chr1:97465205-97465409 | ▨ | | | | | |
| uc.36 | p | chr1:108587040-108587303 | | | | | | |
| uc.37 | e | chr1:114578780-114578981 | | | | | | |
| uc.38 | n | chr1:161127332-161127555 | | ■ | | | | |
| uc.39 | n | chr1:161210912-161211267 | | ■ | | | | |
| uc.40 | p | chr1:161825339-161825585 | | | | | | |
| uc.41 | n | chr1:210655265-210655480 | | | | | | |
| uc.42 | n | chr1:213945530-213945795 | | | | | | |
| uc.43 | n | chr1:240842759-240843015 | | | | | | |
| uc.44 | e | chr1:241164431-241164660 | | | | | | |
| uc.45 | e | chr1:241963410-241963612 | | | | | | |
| uc.46 | e | chr1:241964327-241964543 | | | | | | |
| uc.47 | n | chr2:7796390-7796616 | | | | | | |
| uc.48 | e | chr2:20463845-20463142 | | | | | | |
| uc.49 | e | chr2:33787944-33788150 | | | | | | |
| uc.50 | e | chr2:38950836-38951057 | | | | | | |

Figure 17

Calin GA et al 2

| ultra conserved element name | type | Build 34 coords | LOH exact | FRA <2Mb | AMPLIF exact | HPV 10 <2.5Mb | HOX clusters | HOX genes |
|---|---|---|---|---|---|---|---|---|
| uc.51 | n | chr2:57947093-57947299 | | | | | | |
| uc.52 | n | chr2:59062720-59062893 | | | | | | |
| uc.53 | n | chr2:59107845-59108076 | | | | | | |
| uc.54 | n | chr2:59173937-59174145 | | | | | | |
| uc.55 | n | chr2:59721112-59721351 | | | | | | |
| uc.56 | n | chr2:59922365-59922566 | | | | | | |
| uc.57 | n | chr2:60113774-60114019 | | | | | | |
| uc.58 | n | chr2:60272497-60272699 | | | | | | |
| uc.59 | n | chr2:60272917-60273136 | | | | | | |
| uc.60 | n | chr2:60416094-60416310 | | | | | | |
| uc.61 | e | chr2:60662107-60662432 | | | | | | |
| uc.62 | e | chr2:60755216-60755449 | | ■ | | | | |
| uc.63 | e | chr2:61727035-61727312 | | ■ | | | | |
| uc.64 | p | chr2:63168525-63168869 | | | | | | |
| uc.65 | n | chr2:66273125-66273336 | | | | | | ■ |
| uc.66 | n | chr2:73149541-73149787 | | | | | | ■ |
| uc.67 | n | chr2:104358126-104358342 | | | | | | |
| uc.68 | n | chr2:144125491-144125745 | | | | | | |
| uc.69 | n | chr2:144322879-144323179 | | | | | | |
| uc.70 | p | chr2:144648108-144648344 | | | | | | |
| uc.71 | n | chr2:144923625-144923872 | | | | | | |
| uc.72 | n | chr2:144925741-144926147 | | | | | | |
| uc.73 | p | chr2:144973082-144973282 | | | | | | |
| uc.74 | p | chr2:145036732-145037269 | | | | | | |
| uc.75 | e | chr2:145356619-145356854 | | | | | | |
| uc.76 | n | chr2:145371902-145372236 | | | | | | |
| uc.77 | e | chr2:145396534-145396829 | | | | | | |
| uc.78 | n | chr2:145399123-145399370 | | | | | | |
| uc.79 | p | chr2:145407946-145408240 | | | | | | |
| uc.80 | n | chr2:145411621-145411914 | | | | | | |
| uc.81 | n | chr2:147344834-147345044 | | | | | | |
| uc.82 | n | chr2:156929644-156929853 | | | | | | |
| uc.83 | n | chr2:157194172-157194467 | | | | | | |
| uc.84 | p | chr2:157397251-157397459 | | | | | | |
| uc.85 | n | chr2:157753959-157764206 | | | | | | |
| uc.86 | n | chr2:157862655-157862994 | | | | | | |
| uc.87 | n | chr2:158102814-158103103 | | | | | | |
| uc.88 | n | chr2:162297586-162297897 | | | | | | |
| uc.89 | p | chr2:162441217-162441523 | | | | | | |
| uc.90 | e | chr2:162475571-162475776 | | | | | | |
| uc.91 | n | chr2:163247566-163247772 | | | | | | |
| uc.92 | n | chr2:164653223-164653531 | | | | | | |
| uc.93 | n | chr2:164864451-164864713 | | | | | | |
| uc.94 | n | chr2:165046714-165046913 | | | | | | |
| uc.95 | p | chr2:171774074-171774324 | | | ■ | | | |
| uc.96 | p | chr2:173023218-173023478 | | | | | | ■ |
| uc.97 | e | chr2:173025175-173025616 | | | | | | ■ |
| uc.98 | n | chr2:173159062-173159299 | | | | | | |
| uc.99 | n | chr2:173160925-173161322 | | | | | | |
| uc.100 | n | chr2:174317324-174317530 | | | | | | |
| uc.101 | e | chr2:174977025-174977278 | | | | | | |
| uc.102 | e | chr2:175148953-175149290 | | | | | | |
| uc.103 | p | chr2:175172216-175172448 | | | | | | |
| uc.104 | n | chr2:175183478-175189693 | | | | | | |
| uc.105 | n | chr2:175192331-175192553 | | | | | | |
| uc.106 | p | chr2:175227967-175228172 | | | | | | |
| uc.107 | n | chr2:175410152-175410388 | | | | | | |
| uc.108 | n | chr2:177142901-177143274 | | | | | ■ | |
| uc.109 | n | chr2:177705882-177706105 | | | | | | |
| uc.110 | n | chr2:237358132-237358374 | | | | | | ■ |
| uc.111 | p | chr3:9446461-9446756 | ■ | | | | | |
| uc.483 | p | chr3:17567733-17568134 | | | | | | |

Figure 17 Continued

Calin GA et al  3

| ultra conserved element name | type | Build 34 coords | LOH exact | FRA <2Mb | AMPLIF exact | HPV 16 <2.5Mb | HOX clusters | HOX genes |
|---|---|---|---|---|---|---|---|---|
| uc.112 | n | chr3:18144568-18144913 | ■ | | ▨ | | ■ | ▨ |
| uc.113 | p | chr3:18651408-18651654 | | | | | | |
| uc.114 | n | chr3:18819454-18819747 | | | | | | |
| uc.115 | n | chr3:19009162-19009380 | | | | | | |
| uc.116 | n | chr3:70499494-70499699 | ■ | | | | | |
| uc.117 | n | chr3:70793683-70793933 | ■ | | | | | |
| uc.118 | n | chr3:70792935-70793153 | | | | | | |
| uc.119 | n | chr3:115754368-115754668 | | | | | | |
| uc.120 | p | chr3:115755940-115756209 | | | | | | |
| uc.121 | n | chr3:115896375-115896667 | | | | | | |
| uc.122 | n | chr3:115932792-115933006 | | | | | | |
| uc.123 | n | chr3:138304453-138304944 | | | | | | |
| uc.124 | n | chr3:138369353-138369639 | | | | | | |
| uc.125 | n | chr3:138389226-138389490 | | | | | | |
| uc.126 | n | chr3:138446557-138446827 | | | | | | |
| uc.127 | n | chr3:148351617-148351888 | | | | | | |
| uc.128 | p | chr3:148370547-148370845 | | | | | | |
| uc.129 | e | chr3:153485296-153485507 | | | | | | |
| uc.130 | p | chr3:159097487-159097710 | | | | | | |
| uc.131 | n | chr3:159310953-159311159 | | | | | | |
| uc.132 | n | chr3:159347072-159347279 | | | | | | |
| uc.133 | n | chr3:159347391-159347667 | | | | | | |
| uc.134 | n | chr3:159566817-159567027 | | | | | | |
| uc.135 | e | chr3:170155196-170155396 | ■ | | | | | |
| uc.136 | p | chr3:170514865-170515211 | | | | | | |
| uc.137 | n | chr3:181757778-181758154 | | | | ▨ | | |
| uc.138 | e | chr3:186970209-186970627 | | | | | | |
| uc.139 | p | chr4:4587982-4588319 | | | | | | ▨ |
| uc.140 | n | chr4:12760753-12760975 | | | | | | |
| uc.141 | e | chr4:24280045-24280339 | ■ | | | | | |
| uc.142 | p | chr4:41665611-41665869 | | | | | | |
| uc.143 | e | chr4:77037519-77037736 | | | | | | |
| uc.144 | e | chr4:83805060-83805264 | | | | | | |
| uc.145 | n | chr4:105805133-105805380 | ■ | | | | | |
| uc.146 | n | chr4:112375296-112375569 | | | | | | ▨ |
| uc.147 | p | chr4:151814010-151814317 | | | | | | |
| uc.148 | p | chr4:152071579-152071818 | | | | | | |
| uc.149 | p | chr4:152071820-152072023 | | | | | | |
| uc.150 | n | chr5:3565359-3565620 | | | | ▨ | | |
| uc.151 | e | chr5:32425638-32425851 | | | ▨ | | | ▨ |
| uc.152 | n | chr5:50351523-50351723 | | ■ | | | | |
| uc.153 | e | chr5:72379759-72379998 | | | | | | |
| uc.154 | p | chr5:72294086-72294290 | | | | | | |
| uc.155 | p | chr5:77018437-77018643 | | | | | | |
| uc.156 | p | chr5:77019492-77019704 | | | | | | |
| uc.157 | n | chr5:77025234-77025440 | | | | | | |
| uc.158 | n | chr5:77234326-77234549 | | | | | | |
| uc.159 | n | chr5:77232005-77232476 | | | | | | |
| uc.160 | n | chr5:77352917-77353238 | | | | | | |
| uc.161 | p | chr5:77442602-77442879 | | | | | | |
| uc.162 | p | chr5:81331434-81331651 | | | | | | |
| uc.163 | n | chr5:87252696-87253071 | | | | | | |
| uc.164 | n | chr5:87324478-87324680 | | | | | | |
| uc.165 | n | chr5:87777006-87777229 | | | | | | |
| uc.166 | p | chr5:88045878-88046187 | | | | | | |
| uc.167 | n | chr5:88263697-88263897 | | | | | | |
| uc.168 | n | chr5:91012866-91013085 | | | | | | |
| uc.169 | e | chr5:92895090-92895293 | | | | | | |
| uc.170 | n | chr5:93301743-93302052 | | | | | | |
| uc.171 | n | chr5:93649920-93650127 | | | | | | |
| uc.172 | n | chr5:93724792-93725009 | | | | | | |
| uc.173 | e | chr5:133802376-133802651 | | | ■ | ■ | | |

Figure 17 Continued

Calin GA et al

| ultra conserved element name | type | Build 34 coords | LOH exact | FRA <2Mb | AMPLIF exact | HPV 16 <2.5Mb | HOX clusters | HOX genes |
|---|---|---|---|---|---|---|---|---|
| uc.174 | e | chr5:138719870-138720129 | | | | | | |
| uc.175 | n | chr5:158322733-158322982 | | | | | | |
| uc.176 | n | chr5:167313590-167313835 | | | | | | |
| uc.177 | n | chr5:170398551-170398807 | | | | ■ | | |
| uc.178 | n | chr5:170398920-170399168 | | | | ■ | | |
| uc.179 | n | chr5:170609134-170609352 | | | | ■ | | |
| uc.180 | n | chr5:170609411-170609635 | | | | ■ | | |
| uc.181 | n | chr5:170610401-170610678 | | | | ■ | | |
| uc.182 | p | chr5:170684001-170684239 | | | | ■ | | |
| uc.183 | e | chr5:171365442-171365677 | | | | | | ▨ |
| uc.184 | e | chr5:173366215-173366444 | | | | | | |
| uc.185 | e | chr5:178157908-178158318 | | | | | | |
| uc.186 | e | chr5:179155889-179156193 | | | | | | |
| uc.187 | n | chr6:10502663-10502874 | | | | | | |
| uc.188 | e | chr6:16407363-16407577 | | | | | | |
| uc.189 | e | chr6:36614372-36614944 | | | | | | |
| uc.190 | n | chr6:41570295-41570494 | | | | | | |
| uc.191 | n | chr6:51123630-51123837 | | | | | | |
| uc.192 | n | chr6:51195833-51196076 | | | | | | |
| uc.193 | e | chr6:86317282-86317600 | ■ | | | | | |
| uc.194 | e | chr6:93964662-93964862 | | | | | | |
| uc.195 | p | chr6:97708954-97709226 | | | | | | |
| uc.196 | n | chr6:98162138-98162358 | | | | | | |
| uc.197 | n | chr6:98408397-98408620 | | | | | | |
| uc.198 | n | chr6:98765487-98765793 | | | | | | |
| uc.199 | n | chr6:98859453-98859708 | | | | | | |
| uc.200 | n | chr6:99041131-99041384 | | | | | | |
| uc.201 | n | chr6:100097582-100097821 | | | | | | |
| uc.202 | n | chr6:101019581-101019810 | | | | | | |
| uc.203 | e | chr6:163990992-163901194 | ■ | | | | | |
| uc.204 | n | chr7:1010242-1010443 | | | | | | |
| uc.205 | n | chr7:20574185-20574356 | | | | | | |
| uc.206 | n | chr7:20748081-20748579 | | | | | | |
| uc.207 | n | chr7:21555889-21556038 | | | | | | |
| uc.208 | e | chr7:23303942-23304159 | | | | | | |
| uc.209 | e | chr7:23304166-23304409 | | | | | | |
| uc.210 | p | chr7:26439350-26439606 | | | | | ▨ | |
| uc.211 | n | chr7:26471744-26472034 | | | | | ▨ | |
| uc.212 | p | chr7:26884210-26884414 | | | | | ▨ | |
| uc.213 | e | chr7:26925484-26925604 | | | | | ▨ | |
| uc.214 | n | chr7:31144676-31144911 | | | | | | |
| uc.215 | n | chr7:41933365-41933626 | | | | | | |
| uc.216 | p | chr7:50102955-50103266 | | | | | | |
| uc.217 | p | chr7:54378405-54378625 | | | | | | |
| uc.218 | p | chr7:69215092-69215377 | | | | | | |
| uc.219 | p | chr7:69392897-69393106 | | | | | | |
| uc.220 | n | chr7:96245647-96245903 | | | | | | ▨ |
| uc.221 | p | chr7:96253032-96253380 | | | | | | |
| uc.222 | n | chr7:113611674-113611874 | | | | ■ | | |
| uc.223 | n | chr7:113612688-113612955 | | | | ■ | | |
| uc.224 | n | chr7:113617522-113617816 | | | | ■ | | |
| uc.225 | n | chr7:113627358-113627558 | | | | ■ | | |
| uc.226 | n | chr7:113763821-113764025 | | | | ■ | | |
| uc.227 | n | chr7:113849819-113850049 | | | | ■ | | |
| uc.228 | n | chr7:114671200-114671464 | ■ | | | | | |
| uc.229 | n | chr7:114689148-114689443 | | | | ■ | | |
| uc.230 | p | chr7:114873964-114874201 | | | | ■ | | |
| uc.231 | n | chr7:115136620-115136843 | | | | | | |
| uc.232 | p | chr7:121499109-121499355 | | | | | | |
| uc.233 | e | chr7:150220055-150220330 | | | | | | |
| uc.234 | p | chr7:156229240-156229511 | | | | | | |
| uc.235 | n | chr8:25797831-25798057 | ■ | | | | | |

Figure 17 Continued

Calin GA et al

| ultra conserved element name | type | Build 34 coords | LOH exact | FRA <2Mb | AMPLIF exact | HPV 16 <2.5Mb | HOX clusters | HOX genes |
|---|---|---|---|---|---|---|---|---|
| uc.236 | n | chr8:37307753-37308015 | | | | | | |
| uc.237 | p | chr8:53187862-53188329 | | | | | | |
| uc.238 | p | chr8:53217077-53217434 | | | | | | |
| uc.239 | p | chr8:59992334-59992633 | | | | | | |
| uc.240 | p | chr8:65542580-65542785 | | | | | | |
| uc.241 | n | chr8:65547091-65547292 | | | | | | |
| uc.242 | n | chr8:66199258-66199532 | | | | | | |
| uc.243 | p | chr8:77740924-77741139 | | | | ▓ | | |
| uc.244 | n | chr8:105918932-105919252 | | | | | | |
| uc.245 | n | chr8:106290415-106290753 | | | | | | |
| uc.246 | e | chr8:119079806-119080089 | ■ | ▓ | | | | |
| uc.247 | p | chr9:959154-959514 | | | | | | |
| uc.248 | n | chr9:964189-964410 | | | | | | |
| uc.249 | n | chr9:8085728-8085967 | | | | | | |
| uc.250 | n | chr9:13929910-13930118 | | | | | | |
| uc.251 | n | chr9:15864309-15864521 | | | | | | |
| uc.252 | n | chr9:16700753-16700983 | | | | | | |
| uc.253 | n | chr9:17322212-17322433 | | | | | | |
| uc.254 | n | chr9:23456725-23457003 | | | | | | |
| uc.255 | e | chr9:23681768-23681999 | | | | | | |
| uc.256 | e | chr9:23682234-23682439 | | | | | | |
| uc.257 | n | chr9:37305204-37305467 | | | | | | |
| uc.258 | p | chr9:37314424-37314624 | | | | | | |
| uc.259 | p | chr9:75084998-75085305 | | | | | | |
| uc.260 | n | chr9:76929543-76929773 | | | | | | |
| uc.261 | n | chr9:77328693-77329093 | | | | | | |
| uc.262 | n | chr9:79184841-79185095 | | | | | | |
| uc.263 | e | chr9:82047403-82047609 | | | | | | |
| uc.264 | e | chr9:82047611-82047877 | | | | | | |
| uc.265 | e | chr9:103498309-103498525 | ■ | | | | | |
| uc.266 | p | chr9:104758130-104758372 | | | | | | |
| uc.267 | e | chr9:120429935-120430137 | ■ | | | | | |
| uc.268 | p | chr9:120982873-120983123 | ■ | | | | | |
| uc.269 | n | chr9:121913982-121914198 | ■ | | | | | |
| uc.270 | p | chr9:123680114-123680391 | ■ | | | | | |
| uc.271 | p | chr9:123680397-123680607 | ■ | | | | | |
| uc.272 | n | chr9:123808633-123808845 | ■ | | | | | |
| uc.273 | p | chr9:123893643-123893963 | ■ | | | | | |
| uc.274 | p | chr9:123897916-123898242 | ■ | | | | | |
| uc.275 | n | chr9:123960161-123960415 | ■ | | | | | |
| uc.276 | p | chr9:123981857-123982288 | ■ | | | | | |
| uc.277 | p | chr9:123983755-123984030 | ■ | | | | | |
| uc.278 | p | chr9:124022210-124022446 | ■ | | | | | |
| uc.279 | n | chr9:124048604-124048933 | ■ | | | | | |
| uc.280 | e | chr9:124054051-124054270 | ■ | | | | | |
| uc.281 | p | chr9:130771570-130771807 | | | | | | |
| uc.282 | e | chr9:135399783-135399989 | | | | ■ | | |
| uc.283 | n | chr10:49949360-49949636 | | | | | | |
| uc.284 | p | chr10:49951459-49951667 | | | | | | |
| uc.285 | e | chr10:69860594-69860825 | | | | | | |
| uc.286 | n | chr10:76483627-76483878 | | | | | | |
| uc.287 | p | chr10:76840546-76840802 | | | | | | |
| uc.288 | n | chr10:77071706-77072008 | | | | | | |
| uc.289 | n | chr10:77335142-77335395 | | | | | | |
| uc.290 | e | chr10:77386885-77387090 | | | | | | |
| uc.291 | p | chr10:77628227-77628457 | | | | | | |
| uc.292 | e | chr10:98380042-98380258 | | | | | | |
| uc.293 | n | chr10:102037356-102037498 | ■ | | | | | ▓ |
| uc.294 | n | chr10:102038204-102038647 | ■ | | | | | ▓ |
| uc.295 | n | chr10:102039687-102039895 | ■ | | | | | ▓ |
| uc.296 | n | chr10:102079693-102080153 | ■ | | | | | ▓ |
| uc.297 | n | chr10:102083857-102084178 | ■ | | | | | ▓ |

Figure 17 Continued

| ultra conserved element name | type | Build 34 coords | LOH exact | FRA <2Mb | AMPLIF exact | HPV 18 <2.5Mb | HOX clusters | HOX genes |
|---|---|---|---|---|---|---|---|---|
| uc.298 | n | chr10:102112245-102112503 | | | | | | ▨ |
| uc.299 | e | chr10:102174022-102174231 | | | | | | ▨ |
| uc.300 | n | chr10:102211705-102211912 | | | | | | ▨ |
| uc.301 | p | chr10:102232378-102232661 | | | | | | ▨ |
| uc.302 | n | chr10:102643767-102644107 | | | | | | ▨ |
| uc.303 | n | chr10:102717014-102717385 | | | | | | ▨ |
| uc.304 | p | chr10:102747091-102747362 | | | | | | ▨ |
| uc.305 | p | chr10:102876022-102876326 | | | | | | ▨ |
| uc.306 | p | chr10:102876626-102876849 | | | | | | ▨ |
| uc.307 | p | chr10:102908570-102908801 | | | | | | ▨ |
| uc.308 | p | chr10:102910399-102910675 | | | | | | ▨ |
| uc.309 | n | chr10:102931618-102931885 | | | | | | ▨ |
| uc.310 | n | chr10:114068810-114069038 | ■ | | | | | ▨ |
| uc.311 | p | chr10:119738989-119739207 | | | | | | ▨ |
| uc.312 | p | chr10:119741124-119741443 | | | | | | ▨ |
| uc.313 | e | chr10:121004761-121004991 | | | | | | |
| uc.314 | n | chr10:124392535-124392736 | | | | | | |
| uc.315 | n | chr10:124392947-124393181 | | | | | | |
| uc.316 | n | chr10:126479965-126480204 | | | | | | |
| uc.317 | n | chr10:130920738-130920955 | ■ | | | | | |
| uc.318 | p | chr10:131165986-131166306 | | | | | | |
| uc.319 | n | chr11:8269004-8269318 | | | | | | |
| uc.320 | n | chr11:8282143-8282477 | | | | | | |
| uc.321 | n | chr11:15588733-15588936 | | | | | | |
| uc.322 | n | chr11:16280660-16280982 | | | | | | |
| uc.323 | p | chr11:16439645-16439844 | | | | | | |
| uc.324 | e | chr11:30521830-30522054 | | | | | | |
| uc.325 | n | chr11:31649953-31650187 | | | | | | |
| uc.326 | p | chr11:31749989-31750303 | | | | | | |
| uc.327 | n | chr11:31750593-31750860 | | | | | | |
| uc.328 | p | chr11:31789972-31790202 | | | | | | |
| uc.329 | n | chr11:32162301-32162607 | | | | | | |
| uc.330 | e | chr11:66169256-66169462 | | ■ | | | | |
| uc.331 | e | chr11:82931467-82921684 | | | | | | |
| uc.332 | n | chr11:115770342-115770678 | | | | | | |
| uc.333 | e | chr11:124182298-124182568 | ▨ | | | | | |
| uc.334 | n | chr11:131405597-131405818 | | | | | | |
| uc.335 | n | chr12:16606601-16606894 | | | | | | |
| uc.336 | n | chr12:24183273-24183523 | | | | | | |
| uc.337 | n | chr12:40035446-40035663 | | | | | | |
| uc.338 | e | chr12:52144756-52144978 | | | ■ | | | |
| uc.339 | p | chr12:52357363-52357614 | | | ■ | | | |
| uc.340 | n | chr12:52377099-52377357 | | | | | | |
| uc.341 | e | chr12:52669185-52669498 | | | ■ | | | |
| uc.342 | e | chr12:52698761-52698987 | | | ■ | | | |
| uc.343 | e | chr12:52708708-52709095 | | | ■ | | | |
| uc.344 | e | chr12:52713153-52713406 | | | ■ | | | |
| uc.345 | e | chr12:52733867-52734167 | | | ■ | | | |
| uc.346 | p | chr13:105478977-105479178 | | | | | | |
| uc.347 | n | chr13:69591989-69592197 | | | | | | |
| uc.348 | n | chr13:69861358-69861597 | | | | | | |
| uc.349 | p | chr13:69919303-69919505 | | | | | | |
| uc.350 | n | chr13:70054101-70054340 | | | ■ | | ■ | |
| uc.351 | n | chr13:70466901-70467155 | | | | | ■ | |
| uc.352 | n | chr13:70493166-70493365 | | | | | ■ | |
| uc.353 | n | chr13:70569554-70569876 | | | | | | |
| uc.354 | p | chr13:76774830-76775064 | | | | | | |
| uc.355 | n | chr13:93316863-93317110 | ■ | | | ▨ | | |
| uc.356 | e | chr13:95706821-95707871 | | | | ▨ | | |
| uc.357 | p | chr13:110664338-110664579 | ■ | | | | | |
| uc.358 | n | chr14:24368163-24368387 | | | | | | |
| uc.359 | e | chr14:24905096-24905419 | | | | | | |

Figure 17 Continued

Calin GA et al  7

| ultra conserved element name | type | Build 34 coords | LOH exact | FRA <2Mb | AMPLIF exact | HPV 16 <2.5Mb | HOX cluster | HOX genes |
|---|---|---|---|---|---|---|---|---|
| uc.360 | e | chr14:24905510-24905796 | | | | | | |
| uc.361 | p | chr14:27233174-27233448 | ■ | | | | | |
| uc.362 | p | chr14:27338791-27339029 | ■ | | | | | |
| uc.363 | n | chr14:27851358-27851622 | ■ | | | | | |
| uc.364 | n | chr14:28703798-28703004 | ■ | | | | | |
| uc.365 | n | chr14:28732401-28732678 | ■ | | | | | |
| uc.366 | e | chr14:29372746-29372947 | ■ | | | | | |
| uc.367 | p | chr14:31834502-31834799 | ■ | | | | | |
| uc.368 | n | chr14:32050615-32058842 | | | | ▨ | | |
| uc.369 | n | chr14:32112656-32112968 | | | | | | |
| uc.370 | n | chr14:32192610-32193002 | | | | ▨ | | |
| uc.371 | n | chr14:34010228-34010523 | | | | | | |
| uc.372 | n | chr14:34033074-34033350 | | | | ▨ | | |
| uc.373 | n | chr14:34571846-34572239 | | | | | | |
| uc.374 | p | chr14:35705952-35706175 | | | | | | |
| uc.375 | e | chr14:35767259-35767558 | | | | ▨ | | |
| uc.376 | e | chr14:43555788-43556077 | | | | | | |
| uc.377 | e | chr14:43569061-43569277 | | | | | | |
| uc.378 | e | chr14:78317518-78317763 | | | | | | |
| uc.379 | n | chr14:95421409-95421660 | ■ | | | | | |
| uc.380 | n | chr14:95752635-95752866 | | | | | | |
| uc.381 | n | chr14:95869331-95869568 | ■ | | | | | |
| uc.382 | n | chr15:33634568-33635167 | ■ | | | | | |
| uc.383 | n | chr15:34535983-34536251 | ■ | | | | | |
| uc.384 | p | chr15:34681449-34681714 | ■ | | | | | |
| uc.385 | p | chr15:34901726-34901934 | ■ | | | | | |
| uc.386 | n | chr15:35238065-35238267 | | | | | | |
| uc.387 | e | chr15:39748110-39748347 | | | | | | |
| uc.388 | n | chr15:55141581-55141878 | | | | | | |
| uc.389 | n | chr15:65381203-65381473 | | | | | | |
| uc.390 | e | chr15:65593983-65594193 | | | | | | |
| uc.391 | e | chr15:65756132-65756432 | | | | | | |
| uc.392 | n | chr15:68107952-68108207 | | | | | | |
| uc.393 | e | chr15:72630059-72630333 | | | | | | |
| uc.394 | n | chr15:94965868-94966069 | | | | | | |
| uc.395 | e | chr16:24545554-24545802 | | | | | | |
| uc.396 | n | chr16:48872692-48872899 | | | | | | |
| uc.397 | p | chr16:49513876-49514186 | | | | | | |
| uc.398 | p | chr16:49668919-49685240 | | | | | | |
| uc.399 | n | chr16:50627024-50627237 | | | | | | |
| uc.400 | n | chr16:51450888-51450393 | | | | | | |
| uc.401 | p | chr16:52273380-52273549 | | | | | | |
| uc.402 | p | chr16:53433987-53433231 | | | | | | |
| uc.403 | p | chr16:54102457-54102662 | | | | | | |
| uc.404 | p | chr16:55001959-55002193 | | | | | | |
| uc.405 | n | chr16:59350792-59351001 | | | | | | |
| uc.406 | e | chr16:69456552-69456762 | | | | | | |
| uc.407 | e | chr16:69457343-69457669 | | | | | | |
| uc.408 | e | chr16:72597321-72597572 | | | | | | |
| uc.409 | e | chr16:72869147-72869390 | | | | | | |
| uc.410 | n | chr17:35207780-35207998 | | | | | | |
| uc.411 | n | chr17:35525169-35525397 | | | | | | |
| uc.412 | n | chr17:35532036-35532303 | | | | | | |
| uc.413 | e | chr17:37941482-37941753 | | | ▨ | | | |
| uc.414 | e | chr17:38624137-38634382 | | | | | | |
| uc.415 | n | chr17:47138544-47138750 | | | | | ▨ | ▨ |
| uc.416 | e | chr17:47145525-47145810 | | | | | ▨ | ▨ |
| uc.417 | e | chr17:47156950-47157171 | | | | | | |
| uc.418 | e | chr17:56556866-56557082 | | | ■ | ■ | | |
| uc.419 | e | chr17:56557353-56557641 | | | ■ | | | |
| uc.420 | e | chr17:63046872-63047104 | | | | | | |
| uc.421 | n | chr18:20945142-20945486 | | | | | | |

Figure 17 Continued

| ultra conserved element name | type | Build 34 coords | LOH exact | FRA <2Mb | AMPLIF exact | HPV 16 <3.5Mb | HOX clusters | HOX genes |
|---|---|---|---|---|---|---|---|---|
| uc.422 | p | chr18:21000175-21000400 | | | | | | |
| uc.423 | n | chr18:21008342-21008564 | | | | | | |
| uc.424 | p | chr18:21019766-21019980 | | | | | | |
| uc.425 | n | chr18:21117194-21117518 | | | | | | |
| uc.426 | p | chr18:22167579-22167840 | | | | | | |
| uc.427 | p | chr18:22489166-22489400 | | | | | | |
| uc.428 | p | chr18:28605196-28605434 | | | | | | |
| uc.429 | n | chr18:32732528-32732765 | | | | | | |
| uc.430 | n | chr18:33315637-33315845 | | | | | | |
| uc.431 | n | chr18:33430587-33430816 | | | | | | |
| uc.432 | n | chr18:33816919-33817129 | | | | | | |
| uc.433 | n | chr18:34315619-34315824 | | | | | | |
| uc.434 | n | chr18:43022775-43023023 | | | | | | |
| uc.435 | n | chr18:51238918-51239144 | | | | | | |
| uc.436 | e | chr18:51403228-51403437 | | | | | | |
| uc.437 | n | chr18:70484635-70484849 | | | | | | |
| uc.438 | n | chr18:70484951-70485091 | | | | | | |
| uc.439 | n | chr18:70490008-70490270 | | | | | | |
| uc.440 | n | chr18:70490342-70490670 | | | | | | |
| uc.441 | p | chr18:70695569-70695816 | | | | | | |
| uc.442 | n | chr18:70719689-70719937 | | | | | | |
| uc.443 | e | chr19:8433269-8433507 | | | | | | |
| uc.444 | n | chr19:35186619-35187006 | | | | ▨ | | |
| uc.445 | n | chr19:35258275-35258584 | | | | | | |
| uc.446 | p | chr19:35439694-35439965 | | | | ▨ | | |
| uc.447 | n | chr19:35459621-35459893 | | | | ▨ | | |
| uc.448 | n | chr19:35533376-35533601 | | | | | | |
| uc.449 | n | chr19:35695381-35695670 | | | | | | |
| uc.450 | n | chr19:36279466-36279676 | | | | | | |
| uc.451 | n | chr19:36498460-36498684 | | | | | | |
| uc.452 | e | chr19:36519787-36519990 | | | | | | |
| uc.453 | n | chr19:47129157-47129481 | | | | | | |
| uc.454 | e | chr20:4861440-4861647 | | | | | | |
| uc.455 | e | chr20:35043808-35044053 | | | | | | |
| uc.456 | e | chr20:42773185-42773504 | | | | | | |
| uc.457 | e | chr22:17770463-17770673 | | | | | | |
| uc.458 | e | chr22:34420305-34420508 | ■ | | | | | |
| uc.459 | e | chrX:20895986-20896240 | | | | | | |
| uc.460 | p | chrX:24184937-24185211 | | | | | | |
| uc.461 | n | chrX:24226223-24226619 | | | | | | |
| uc.462 | p | chrX:24256252-24257030 | | | | | | |
| uc.463 | n | chrX:24277308-24277582 | | | | | | |
| uc.464 | n | chrX:24277584-24278353 | | | | | | |
| uc.465 | n | chrX:24278907-24279216 | | | | | | |
| uc.466 | n | chrX:24307884-24308232 | | | | | | |
| uc.467 | n | chrX:24369780-24370510 | | | | | | |
| uc.468 | p | chrX:24378989-24379477 | | | | | | |
| uc.469 | p | chrX:24379479-24379700 | | | | | | |
| uc.470 | n | chrX:24762642-24762962 | | | | | | |
| uc.471 | e | chrX:40239309-40239547 | | | | | | |
| uc.472 | e | chrX:40410244-40410445 | | | | | | |
| uc.473 | e | chrX:69240015-69240236 | | | | | | |
| uc.474 | e | chrX:69335634-69335843 | | | | | | |
| uc.475 | e | chrX:69632845-69633342 | | | | | | |
| uc.476 | n | chrX:80545473-80545710 | | | | | | |
| uc.477 | e | chrX:101813348-101813556 | | | | | | |
| uc.478 | e | chrX:121297212-121297463 | | | | | | |
| uc.479 | e | chrX:121311506-121311807 | | | | | | |
| uc.480 | e | chrX:121933027-121933228 | | | | | | |
| uc.481 | e | chrX:121933230-121933433 | | | | | | |
| uc.482 | n | chrX:137876095-137876389 | | | | | | |

Figure 17 Continued

Calin GA

Supplementary Table 4. Negative correlations between the expression of miRNAs and T-UCRs in CLL patients. All validated negative correlations by FDR method at 0.01 treshold, or 1% false positive results, and with an R correlation lower as -0.040 were considered.

The probe complementary to the genomic orientation is named "+", while the probe to the complementary sequence is named "A+".

| miRNA probe on array | UCR probe on array | Correlations (Spearman Method) | miRNA |
|---|---|---|---|
| hsa-let-7a-1-prec | uc.420+ | -0.7315 | hsa-let-7a |
| hsa-let-7a-2-precNo2 | uc.73+A | -0.7284 | hsa-let-7a |
| hsa-let-7a-1-prec | uc.189+ | -0.6855 | hsa-let-7a |
| hsa-let-7a-1-prec | uc.285+ | -0.6832 | hsa-let-7a |
| hsa-let-7a-1-prec | uc.299+A | -0.6717 | hsa-let-7a |
| hsa-let-7a-2-precNo2 | uc.462+A | -0.6683 | hsa-let-7a |
| hsa-let-7a-1-prec | uc.73+A | -0.6596 | hsa-let-7a |
| hsa-let-7a-2-precNo2 | uc.477+A | -0.6569 | hsa-let-7a |
| hsa-let-7a-2-precNo2 | uc.456+A | -0.6518 | hsa-let-7a |
| hsa-let-7a-2-precNo2 | uc.200+ | -0.6496 | hsa-let-7a |
| hsa-let-7a-2-precNo2 | uc.449+A | -0.6475 | hsa-let-7a |
| hsa-let-7a-2-precNo2 | uc.287+A | -0.6465 | hsa-let-7a |
| hsa-let-7a-2-precNo2 | uc.190+A | -0.6443 | hsa-let-7a |
| hsa-let-7a-1-prec | uc.388+A | -0.6234 | hsa-let-7a |
| hsa-let-7a-1-prec | uc.462+A | -0.6077 | hsa-let-7a |
| hsa-let-7a-1-prec | uc.153+A | -0.6059 | hsa-let-7a |
| hsa-let-7a-2-precNo2 | uc.217+ | -0.6049 | hsa-let-7a |
| hsa-let-7a-3-prec | uc.420+ | -0.603 | hsa-let-7a |
| hsa-let-7a-1-prec | uc.33+ | -0.598 | hsa-let-7a |
| hsa-let-7a-2-precNo2 | uc.378+A | -0.594 | hsa-let-7a |
| hsa-let-7a-1-prec | uc.412+A | -0.5928 | hsa-let-7a |
| hsa-let-7a-2-precNo2 | uc.151+A | -0.5936 | hsa-let-7a |
| hsa-let-7a-3-prec | uc.262+A | -0.5889 | hsa-let-7a |
| hsa-let-7a-1-prec | uc.354+A | -0.5867 | hsa-let-7a |
| hsa-let-7a-1-prec | uc.8+ | -0.5855 | hsa-let-7a |
| hsa-let-7a-2-precNo2 | uc.88+A | -0.593 | hsa-let-7a |
| hsa-let-7a-2-precNo2 | uc.412+ | -0.5829 | hsa-let-7a |
| hsa-let-7a-1-prec | uc.234+ | -0.5827 | hsa-let-7a |
| hsa-let-7a-2-precNo2 | uc.378+ | -0.5826 | hsa-let-7a |
| hsa-let-7a-2-precNo2 | uc.338+ | -0.5807 | hsa-let-7a |
| hsa-let-7a-3-prec | uc.8+ | -0.5782 | hsa-let-7a |
| hsa-let-7a-3-prec | uc.161+A | -0.577 | hsa-let-7a |
| hsa-let-7a-2-precNo2 | uc.145+A | -0.5761 | hsa-let-7a |
| hsa-let-7a-1-prec | uc.151+A | -0.5756 | hsa-let-7a |
| hsa-let-7a-3-prec | uc.145+A | -0.5745 | hsa-let-7a |
| hsa-let-7a-1-prec | uc.456+A | -0.5716 | hsa-let-7a |
| hsa-let-7a-1-prec | uc.33+A | -0.5702 | hsa-let-7a |
| hsa-let-7a-2-precNo2 | uc.427+ | -0.5685 | hsa-let-7a |
| hsa-let-7a-1-prec | uc.468+ | -0.5659 | hsa-let-7a |
| hsa-let-7a-3-prec | uc.160+ | -0.5658 | hsa-let-7a |
| hsa-let-7a-2-precNo2 | uc.412+A | -0.5634 | hsa-let-7a |
| hsa-let-7a-3-prec | uc.134+ | -0.5563 | hsa-let-7a |
| hsa-let-7a-1-prec | uc.134+ | -0.554 | hsa-let-7a |
| hsa-let-7a-1-prec | uc.338+ | -0.5524 | hsa-let-7a |
| hsa-let-7a-2-precNo2 | uc.420+ | -0.5507 | hsa-let-7a |
| hsa-let-7a-2-precNo2 | uc.189+ | -0.5502 | hsa-let-7a |
| hsa-let-7a-2-precNo2 | uc.95+ | -0.5486 | hsa-let-7a |
| hsa-let-7a-3-prec | uc.117+ | -0.5479 | hsa-let-7a |
| hsa-let-7a-1-prec | uc.44+A | -0.5461 | hsa-let-7a |
| hsa-let-7a-2-precNo2 | uc.281+A | -0.5384 | hsa-let-7a |
| hsa-let-7a-1-prec | uc.190+A | -0.5302 | hsa-let-7a |
| hsa-let-7a-3-prec | uc.478+A | -0.5285 | hsa-let-7a |
| hsa-let-7a-3-prec | uc.183+ | -0.5275 | hsa-let-7a |
| hsa-let-7a-3-prec | uc.299+A | -0.5255 | hsa-let-7a |
| hsa-let-7a-1-prec | uc.445+A | -0.5253 | hsa-let-7a |
| hsa-let-7a-2-precNo2 | uc.234+ | -0.5203 | hsa-let-7a |
| hsa-let-7a-1-prec | uc.420+A | -0.5185 | hsa-let-7a |
| hsa-let-7a-1-prec | uc.183+ | -0.5149 | hsa-let-7a |
| hsa-let-7a-1-prec | uc.378+A | -0.5138 | hsa-let-7a |
| hsa-let-7a-3-prec | uc.353+ | -0.5131 | hsa-let-7a |
| hsa-let-7a-1-prec | uc.252+A | -0.5101 | hsa-let-7a |
| hsa-let-7a-1-prec | uc.43+ | -0.5074 | hsa-let-7a |
| hsa-let-7a-1-prec | uc.217+A | -0.5033 | hsa-let-7a |
| hsa-let-7a-2-precNo2 | uc.44+A | -0.5027 | hsa-let-7a |
| hsa-let-7a-2-precNo2 | uc.354+A | -0.5016 | hsa-let-7a |
| hsa-let-7a-1-prec | uc.275+ | -0.4998 | hsa-let-7a |
| hsa-let-7a-2-precNo2 | uc.159+A | -0.4975 | hsa-let-7a |
| hsa-let-7a-3-prec | uc.338+ | -0.4951 | hsa-let-7a |
| hsa-let-7a-1-prec | uc.388+ | -0.495 | hsa-let-7a |
| hsa-let-7a-2-precNo2 | uc.456+ | -0.4948 | hsa-let-7a |
| hsa-let-7a-3-prec | uc.189+ | -0.4939 | hsa-let-7a |
| hsa-let-7a-2-precNo2 | uc.285+ | -0.4917 | hsa-let-7a |
| hsa-let-7a-2-precNo2 | uc.275+ | -0.4882 | hsa-let-7a |
| hsa-let-7a-3-prec | uc.462+A | -0.4878 | hsa-let-7a |
| hsa-let-7a-3-prec | uc.285+ | -0.4856 | hsa-let-7a |
| hsa-let-7a-2-precNo2 | uc.299+A | -0.4848 | hsa-let-7a |
| hsa-let-7a-2-precNo2 | uc.153+A | -0.494 | hsa-let-7a |
| hsa-let-7a-3-prec | uc.234+ | -0.4836 | hsa-let-7a |

Figure 18

Calin GA

| miRNA probe on array | UCR probe on array | Correlations (Spearman Method) | miRNA |
|---|---|---|---|
| hsa-let-7a-2-precNo2 | uc.190+ | -0.4768 | hsa-let-7a |
| hsa-let-7a-2-precNo2 | uc.78+ | -0.4758 | hsa-let-7a |
| hsa-let-7a-3-prec | uc.73+A | -0.4754 | hsa-let-7a |
| hsa-let-7a-1-prec | uc.173+ | -0.4738 | hsa-let-7a |
| hsa-let-7a-1-prec | uc.117+ | -0.4697 | hsa-let-7a |
| hsa-let-7a-1-prec | uc.477+A | -0.466 | hsa-let-7a |
| hsa-let-7a-3-prec | uc.78+ | -0.4656 | hsa-let-7a |
| hsa-let-7a-2-precNo2 | uc.473+A | -0.4646 | hsa-let-7a |
| hsa-let-7a-1-prec | uc.331+A | -0.4591 | hsa-let-7a |
| hsa-let-7a-1-prec | uc.190+ | -0.4586 | hsa-let-7a |
| hsa-let-7a-1-prec | uc.233+A | -0.4572 | hsa-let-7a |
| hsa-let-7a-1-prec | uc.106+ | -0.4547 | hsa-let-7a |
| hsa-let-7a-3-prec | uc.368+ | -0.4545 | hsa-let-7a |
| hsa-let-7a-1-prec | uc.287+A | -0.4538 | hsa-let-7a |
| hsa-let-7a-2-precNo2 | uc.170+ | -0.4518 | hsa-let-7a |
| hsa-let-7a-1-prec | uc.427+ | -0.4493 | hsa-let-7a |
| hsa-let-7a-2-precNo2 | uc.368+ | -0.4484 | hsa-let-7a |
| hsa-let-7c-prec | uc.145+A | -0.5297 | hsa-let-7c |
| hsa-let-7c-prec | uc.352+ | -0.5169 | hsa-let-7c |
| hsa-let-7c-prec | uc.281+A | -0.4844 | hsa-let-7c |
| hsa-let-7c-prec | uc.262+A | -0.4484 | hsa-let-7c |
| hsa-let-7d-prec | uc.352+ | -0.6191 | hsa-let-7d |
| hsa-let-7d-prec | uc.145+A | -0.5737 | hsa-let-7d |
| hsa-let-7d-prec | uc.269+A | -0.5569 | hsa-let-7d |
| hsa-let-7d-prec | uc.262+A | -0.5485 | hsa-let-7d |
| hsa-let-7d-prec | uc.479+A | -0.5376 | hsa-let-7d |
| hsa-let-7d-prec | uc.362+ | -0.5259 | hsa-let-7d |
| hsa-let-7d-prec | uc.160+ | -0.4846 | hsa-let-7d |
| hsa-let-7d-prec | uc.78+ | -0.484 | hsa-let-7d |
| hsa-let-7d-prec | uc.283+A | -0.4636 | hsa-let-7d |
| hsa-let-7d-prec | uc.161+A | -0.458 | hsa-let-7d |
| hsa-let-7d-prec | uc.398+ | -0.4513 | hsa-let-7d |
| hsa-let-7d-prec | uc.339+ | -0.4495 | hsa-let-7d |
| hsa-let-7e-prec | uc.473+ | -0.6242 | hsa-let-7e |
| hsa-let-7e-prec | uc.95+ | -0.5034 | hsa-let-7e |
| hsa-let-7e-prec | uc.453+A | -0.4873 | hsa-let-7e |
| hsa-let-7e-prec | uc.88+A | -0.4812 | hsa-let-7e |
| hsa-let-7f-2-prec3 | uc.420+ | -0.7661 | hsa-let-7f |
| hsa-let-7f-2-prec2 | uc.299+A | -0.7152 | hsa-let-7f |
| hsa-let-7f-1-precNo2 | uc.352+ | -0.6966 | hsa-let-7f |
| hsa-let-7f-2-prec3 | uc.189+ | -0.6916 | hsa-let-7f |
| hsa-let-7f-2-prec2 | uc.285+ | -0.6809 | hsa-let-7f |
| hsa-let-7f-2-prec3 | uc.78+ | -0.6496 | hsa-let-7f |
| hsa-let-7f-2-prec2 | uc.8+ | -0.6458 | hsa-let-7f |
| hsa-let-7f-2-prec3 | uc.462+A | -0.6427 | hsa-let-7f |
| hsa-let-7f-2-prec2 | uc.151+ | -0.631 | hsa-let-7f |
| hsa-let-7f-2-prec2 | uc.33+A | -0.6246 | hsa-let-7f |
| hsa-let-7f-2-prec2 | uc.33+ | -0.581 | hsa-let-7f |
| hsa-let-7f-2-prec2 | uc.44+A | -0.5784 | hsa-let-7f |
| hsa-let-7f-2-prec3 | uc.73+A | -0.5747 | hsa-let-7f |
| hsa-let-7f-1-precNo2 | uc.283+A | -0.5705 | hsa-let-7f |
| hsa-let-7f-2-prec2 | uc.327+A | -0.5608 | hsa-let-7f |
| hsa-let-7f-1-precNo2 | uc.282+ | -0.5535 | hsa-let-7f |
| hsa-let-7f-2-prec2 | uc.177+ | -0.5533 | hsa-let-7f |
| hsa-let-7f-2-prec2 | uc.153+ | -0.5486 | hsa-let-7f |
| hsa-let-7f-2-prec2 | uc.412+ | -0.5483 | hsa-let-7f |
| hsa-let-7f-2-prec3 | uc.234+ | -0.5431 | hsa-let-7f |
| hsa-let-7f-2-prec2 | uc.134+ | -0.5385 | hsa-let-7f |
| hsa-let-7f-2-prec2 | uc.412+A | -0.5381 | hsa-let-7f |
| hsa-let-7f-2-prec2 | uc.338+ | -0.5376 | hsa-let-7f |
| hsa-let-7f-2-prec2 | uc.153+A | -0.5346 | hsa-let-7f |
| hsa-let-7f-2-prec3 | uc.183+ | -0.532 | hsa-let-7f |
| hsa-let-7f-2-prec2 | uc.88+ | -0.5177 | hsa-let-7f |
| hsa-let-7f-2-prec3 | uc.106+ | -0.5168 | hsa-let-7f |
| hsa-let-7f-2-prec2 | uc.378+ | -0.5126 | hsa-let-7f |
| hsa-let-7f-2-prec2 | uc.151+A | -0.4967 | hsa-let-7f |
| hsa-let-7f-2-prec3 | uc.368+A | -0.4963 | hsa-let-7f |
| hsa-let-7f-2-prec2 | uc.173+ | -0.4842 | hsa-let-7f |
| hsa-let-7f-2-prec3 | uc.477+A | -0.4775 | hsa-let-7f |
| hsa-let-7f-2-prec2 | uc.331+A | -0.4771 | hsa-let-7f |
| hsa-let-7f-2-prec2 | uc.167+ | -0.4762 | hsa-let-7f |
| hsa-let-7f-2-prec2 | uc.190+A | -0.4672 | hsa-let-7f |
| hsa-let-7f-2-prec2 | uc.420+A | -0.465 | hsa-let-7f |
| hsa-let-7f-1-precNo2 | uc.269+A | -0.4637 | hsa-let-7f |
| hsa-let-7f-2-prec2 | uc.354+A | -0.4595 | hsa-let-7f |
| hsa-let-7f-2-prec2 | uc.378+A | -0.4592 | hsa-let-7f |
| hsa-let-7f-2-prec2 | uc.10+ | -0.4591 | hsa-let-7f |
| hsa-let-7f-2-prec3 | uc.456+A | -0.4518 | hsa-let-7f |
| hsa-let-7f-2-prec2 | uc.43+ | -0.4493 | hsa-let-7f |
| hsa-let-7g-precNo1 | uc.420+ | -0.7906 | hsa-let-7g |
| hsa-let-7g-precNo1 | uc.234+ | -0.7436 | hsa-let-7g |
| hsa-let-7g-precNo1 | uc.412+A | -0.7325 | hsa-let-7g |
| hsa-let-7g-precNo1 | uc.73+A | -0.7293 | hsa-let-7g |
| hsa-let-7g-precNo1 | uc.354+A | -0.7201 | hsa-let-7g |

Figure 18 Continued

Calin GA

| mRNA probe on array | UCR probe on array | Correlations (Spearman Method) | miRNA |
|---|---|---|---|
| hsa-let-7g-precNo1 | uc.198+A | -0.7168 | hsa-let-7g |
| hsa-let-7g-precNo1 | uc.153+A | -0.7122 | hsa-let-7g |
| hsa-let-7g-precNo1 | uc.189+ | -0.7059 | hsa-let-7g |
| hsa-let-7g-precNo1 | uc.285+ | -0.6953 | hsa-let-7g |
| hsa-let-7g-precNo1 | uc.456+A | -0.6835 | hsa-let-7g |
| hsa-let-7g-precNo1 | uc.33+A | -0.6647 | hsa-let-7g |
| hsa-let-7g-precNo1 | uc.427+ | -0.6627 | hsa-let-7g |
| hsa-let-7g-precNo1 | uc.105+ | -0.6607 | hsa-let-7g |
| hsa-let-7g-precNo1 | uc.43+ | -0.6584 | hsa-let-7g |
| hsa-let-7g-precNo1 | uc.462+A | -0.6574 | hsa-let-7g |
| hsa-let-7g-precNo1 | uc.299+A | -0.6537 | hsa-let-7g |
| hsa-let-7g-precNo1 | uc.33+ | -0.6498 | hsa-let-7g |
| hsa-let-7g-precNo1 | uc.8+ | -0.6443 | hsa-let-7g |
| hsa-let-7g-precNo1 | uc.378+A | -0.6308 | hsa-let-7g |
| hsa-let-7g-precNo1 | uc.388+A | -0.6239 | hsa-let-7g |
| hsa-let-7g-precNo1 | uc.477+A | -0.6184 | hsa-let-7g |
| hsa-let-7g-precNo1 | uc.468+ | -0.6132 | hsa-let-7g |
| hsa-let-7g-precNo1 | uc.287+A | -0.6008 | hsa-let-7g |
| hsa-let-7g-precNo1 | uc.153+ | -0.5961 | hsa-let-7g |
| hsa-let-7g-precNo1 | uc.445+A | -0.5906 | hsa-let-7g |
| hsa-let-7g-precNo1 | uc.217+A | -0.5796 | hsa-let-7g |
| hsa-let-7g-precNo1 | uc.378+ | -0.5785 | hsa-let-7g |
| hsa-let-7g-precNo1 | uc.44+A | -0.572 | hsa-let-7g |
| hsa-let-7g-precNo1 | uc.200+ | -0.5646 | hsa-let-7g |
| hsa-let-7g-precNo1 | uc.233+A | -0.5626 | hsa-let-7g |
| hsa-let-7g-precNo1 | uc.473+A | -0.5579 | hsa-let-7g |
| hsa-let-7g-precNo1 | uc.327+A | -0.5546 | hsa-let-7g |
| hsa-let-7g-precNo1 | uc.18+ | -0.5523 | hsa-let-7g |
| hsa-let-7g-precNo1 | uc.190+ | -0.546 | hsa-let-7g |
| hsa-let-7g-precNo1 | uc.388+ | -0.5406 | hsa-let-7g |
| hsa-let-7g-precNo1 | uc.420+A | -0.5365 | hsa-let-7g |
| hsa-let-7g-precNo1 | uc.20+ | -0.5357 | hsa-let-7g |
| hsa-let-7g-precNo1 | uc.448+A | -0.5327 | hsa-let-7g |
| hsa-let-7g-precNo1 | uc.78+ | -0.5237 | hsa-let-7g |
| hsa-let-7g-precNo1 | uc.275+ | -0.5215 | hsa-let-7g |
| hsa-let-7g-precNo1 | uc.468+A | -0.5211 | hsa-let-7g |
| hsa-let-7g-precNo1 | uc.213+ | -0.5193 | hsa-let-7g |
| hsa-let-7g-precNo1 | uc.161+A | -0.5192 | hsa-let-7g |
| hsa-let-7g-precNo1 | uc.363+ | -0.5128 | hsa-let-7g |
| hsa-let-7g-precNo1 | uc.412+ | -0.5076 | hsa-let-7g |
| hsa-let-7g-precNo1 | uc.10+ | -0.5064 | hsa-let-7g |
| hsa-let-7g-precNo1 | uc.263+ | -0.5059 | hsa-let-7g |
| hsa-let-7g-precNo1 | uc.151+A | -0.5047 | hsa-let-7g |
| hsa-let-7g-precNo1 | uc.88+ | -0.5042 | hsa-let-7g |
| hsa-let-7g-precNo1 | uc.456+ | -0.5034 | hsa-let-7g |
| hsa-let-7g-precNo1 | uc.263+A | -0.5023 | hsa-let-7g |
| hsa-let-7g-precNo1 | uc.217+ | -0.5018 | hsa-let-7g |
| hsa-let-7g-precNo1 | uc.134+ | -0.499 | hsa-let-7g |
| hsa-let-7g-precNo1 | uc.338+ | -0.4948 | hsa-let-7g |
| hsa-let-7g-precNo1 | uc.173+ | -0.4869 | hsa-let-7g |
| hsa-let-7g-precNo1 | uc.177+ | -0.4836 | hsa-let-7g |
| hsa-let-7g-precNo1 | uc.172+A | -0.4752 | hsa-let-7g |
| hsa-let-7g-precNo1 | uc.20+A | -0.4696 | hsa-let-7g |
| hsa-let-7g-precNo1 | uc.466+A | -0.4696 | hsa-let-7g |
| hsa-let-7g-precNo1 | uc.362+A | -0.4632 | hsa-let-7g |
| hsa-let-7g-precNo1 | uc.151+ | -0.4573 | hsa-let-7g |
| hsa-let-7g-precNo1 | uc.262+A | -0.4494 | hsa-let-7g |
| hsa-let-7iNo1 | uc.325+ | -0.5234 | hsa-let-7i |
| hsa-let-7iNo1 | uc.262+A | -0.5231 | hsa-let-7i |
| hsa-let-7iNo1 | uc.135+A | -0.4855 | hsa-let-7i |
| hsa-let-7iNo1 | uc.136+ | -0.4768 | hsa-let-7i |
| hsa-let-7iNo1 | uc.345+A | -0.4675 | hsa-let-7i |
| hsa-let-7iNo1 | uc.278+ | -0.4673 | hsa-let-7i |
| hsa-mir-103-prec-5=103-1 | uc.346+A | -0.6765 | hsa-miR-103 |
| hsa-mir-103-prec-5=103-1 | uc.282+A | -0.6633 | hsa-miR-103 |
| hsa-mir-103-prec-5=103-1 | uc.325+ | -0.6073 | hsa-miR-103 |
| hsa-mir-103-prec-5=103-1 | uc.34+A | -0.5571 | hsa-miR-103 |
| hsa-mir-103-prec-5=103-1 | uc.283+A | -0.5373 | hsa-miR-103 |
| hsa-mir-103-prec-5=103-1 | uc.339+ | -0.5287 | hsa-miR-103 |
| hsa-mir-103-prec-5=103-1 | uc.393+ | -0.5028 | hsa-miR-103 |
| hsa-mir-103-prec-5=103-1 | uc.465+A | -0.5 | hsa-miR-103 |
| hsa-mir-103-prec-5=103-1 | uc.269+A | -0.482 | hsa-miR-103 |
| hsa-mir-103-prec-5=103-1 | uc.478+A | -0.4723 | hsa-miR-103 |
| hsa-mir-106-prec-X | uc.167+ | -0.6399 | hsa-miR-106a |
| hsa-mir-106aNo1 | uc.48+A | -0.6329 | hsa-miR-106a |
| hsa-mir-106aNo1 | uc.283+A | -0.6323 | hsa-miR-106a |
| hsa-mir-106-prec-X | uc.478+A | -0.6299 | hsa-miR-106a |
| hsa-mir-106aNo1 | uc.382+A | -0.6256 | hsa-miR-106a |
| hsa-mir-106aNo1 | uc.478+A | -0.6253 | hsa-miR-106a |
| hsa-mir-106-prec-X | uc.48+A | -0.6244 | hsa-miR-106a |
| hsa-mir-106aNo1 | uc.160+ | -0.6177 | hsa-miR-106a |
| hsa-mir-106aNo1 | uc.327+A | -0.6067 | hsa-miR-106a |
| hsa-mir-106aNo1 | uc.465+A | -0.6057 | hsa-miR-106a |
| hsa-mir-106aNo1 | uc.167+ | -0.6024 | hsa-miR-106a |

Figure 18 Continued

Calin GA

| miRNA probe on array | UCR probe on array | Correlations (Spearman Method) | miRNA |
|---|---|---|---|
| hsa-mir-106-prec-X | uc.160+ | -0.59 | hsa-miR-106a |
| hsa-mir-106-prec-X | uc.283+A | -0.58 | hsa-miR-106a |
| hsa-mir-106-prec-X | uc.283+A | -0.5735 | hsa-miR-106a |
| hsa-mir-106aNo1 | uc.339+ | -0.5724 | hsa-miR-106a |
| hsa-mir-106-prec-X | uc.465+A | -0.5685 | hsa-miR-106a |
| hsa-mir-106aNo1 | uc.325+ | -0.565 | hsa-miR-106a |
| hsa-mir-106aNo1 | uc.117+ | -0.5566 | hsa-miR-106a |
| hsa-mir-106-prec-X | uc.339+ | -0.5533 | hsa-miR-106a |
| hsa-mir-106-prec-X | uc.327+A | -0.5461 | hsa-miR-106a |
| hsa-mir-106-prec-X | uc.325+ | -0.5384 | hsa-miR-106a |
| hsa-mir-106aNo1 | uc.213+ | -0.5257 | hsa-miR-106a |
| hsa-mir-106aNo1 | uc.84+A | -0.5242 | hsa-miR-106a |
| hsa-mir-106-prec-X | uc.117+ | -0.5217 | hsa-miR-106a |
| hsa-mir-106-prec-X | uc.84+A | -0.5149 | hsa-miR-106a |
| hsa-mir-106-prec-X | uc.170+ | -0.5004 | hsa-miR-106a |
| hsa-mir-106-prec-X | uc.213+ | -0.4948 | hsa-miR-106a |
| hsa-mir-106aNo1 | uc.170+ | -0.4931 | hsa-miR-106a |
| hsa-mir-106aNo1 | uc.300+A | -0.485 | hsa-miR-106a |
| hsa-mir-106aNo1 | uc.263+ | -0.4845 | hsa-miR-106a |
| hsa-mir-106-prec-X | uc.299+ | -0.4857 | hsa-miR-106a |
| hsa-mir-106aNo1 | uc.269+A | -0.4782 | hsa-miR-106a |
| hsa-mir-106-prec-X | uc.300+ | -0.4742 | hsa-miR-106a |
| hsa-mir-106aNo1 | uc.153+A | -0.4735 | hsa-miR-106a |
| hsa-mir-106aNo1 | uc.153+ | -0.4728 | hsa-miR-106a |
| hsa-mir-106-prec-X | uc.88+A | -0.4711 | hsa-miR-106a |
| hsa-mir-106-prec-X | uc.427+ | -0.4703 | hsa-miR-106a |
| hsa-mir-106aNo1 | uc.427+ | -0.4654 | hsa-miR-106a |
| hsa-mir-106-prec-X | uc.448+A | -0.4608 | hsa-miR-106a |
| hsa-mir-106-prec-X | uc.263+ | -0.4606 | hsa-miR-106a |
| hsa-mir-106-prec-X | uc.300+A | -0.4559 | hsa-miR-106a |
| hsa-mir-106aNo1 | uc.285+ | -0.454 | hsa-miR-106a |
| hsa-mir-106aNo1 | uc.346+A | -0.4533 | hsa-miR-106a |
| hsa-mir-106-prec-X | uc.346+A | -0.452 | hsa-miR-106a |
| hsa-mir-106bNo1 | uc.478+A | -0.6573 | hsa-miR-106b |
| hsa-mir-106bNo1 | uc.48+A | -0.6432 | hsa-miR-106b |
| hsa-mir-106bNo1 | uc.465+A | -0.6366 | hsa-miR-106b |
| hsa-mir-106bNo1 | uc.327+A | -0.613 | hsa-miR-106b |
| hsa-mir-106bNo1 | uc.167+ | -0.6037 | hsa-miR-106b |
| hsa-mir-106bNo1 | uc.117+ | -0.5939 | hsa-miR-106b |
| hsa-mir-106bNo1 | uc.160+ | -0.5934 | hsa-miR-106b |
| hsa-mir-106bNo1 | uc.325+ | -0.5738 | hsa-miR-106b |
| hsa-mir-106bNo1 | uc.283+A | -0.569 | hsa-miR-106b |
| hsa-mir-106bNo1 | uc.346+ | -0.5522 | hsa-miR-106b |
| hsa-mir-106bNo1 | uc.282+A | -0.5496 | hsa-miR-106b |
| hsa-mir-106bNo1 | uc.84+A | -0.5416 | hsa-miR-106b |
| hsa-mir-106bNo1 | uc.339+ | -0.5323 | hsa-miR-106b |
| hsa-mir-106bNo1 | uc.110+A | -0.5313 | hsa-miR-106b |
| hsa-mir-106bNo1 | uc.153+ | -0.5296 | hsa-miR-106b |
| hsa-mir-106bNo1 | uc.285+ | -0.5289 | hsa-miR-106b |
| hsa-mir-106bNo1 | uc.151+A | -0.5224 | hsa-miR-106b |
| hsa-mir-106bNo1 | uc.213+ | -0.522 | hsa-miR-106b |
| hsa-mir-106bNo1 | uc.153+A | -0.5214 | hsa-miR-106b |
| hsa-mir-106bNo1 | uc.106+ | -0.5074 | hsa-miR-106b |
| hsa-mir-106bNo1 | uc.117+A | -0.4977 | hsa-miR-106b |
| hsa-mir-106bNo1 | uc.300+A | -0.4952 | hsa-miR-106b |
| hsa-mir-106bNo1 | uc.18+ | -0.4794 | hsa-miR-106b |
| hsa-mir-106bNo1 | uc.33+ | -0.4706 | hsa-miR-106b |
| hsa-mir-106bNo1 | uc.462+A | -0.4705 | hsa-miR-106b |
| hsa-mir-106bNo1 | uc.369+A | -0.4634 | hsa-miR-106b |
| hsa-mir-106bNo1 | uc.172+A | -0.4623 | hsa-miR-106b |
| hsa-mir-106bNo1 | uc.234+ | -0.4571 | hsa-miR-106b |
| hsa-mir-106bNo1 | uc.33+A | -0.4569 | hsa-miR-106b |
| hsa-mir-106bNo1 | uc.388+A | -0.4555 | hsa-miR-106b |
| hsa-mir-106bNo1 | uc.263+ | -0.4542 | hsa-miR-106b |
| hsa-mir-106bNo1 | uc.170+ | -0.4533 | hsa-miR-106b |
| hsa-mir-106bNo1 | uc.88+ | -0.4517 | hsa-miR-106b |
| hsa-mir-106bNo1 | uc.352+ | -0.4478 | hsa-miR-106b |
| hsa-mir-107No1 | uc.282+A | -0.665 | hsa-miR-107 |
| hsa-mir-107No1 | uc.346+A | -0.6312 | hsa-miR-107 |
| hsa-mir-107-prec-10 | uc.282+A | -0.6273 | hsa-miR-107 |
| hsa-mir-107No1 | uc.283+A | -0.616 | hsa-miR-107 |
| hsa-mir-107-prec-10 | uc.346+A | -0.6094 | hsa-miR-107 |
| hsa-mir-107-prec-10 | uc.283+A | -0.5694 | hsa-miR-107 |
| hsa-mir-107No1 | uc.325+ | -0.551 | hsa-miR-107 |
| hsa-mir-107-prec-10 | uc.325+ | -0.5381 | hsa-miR-107 |
| hsa-mir-107No1 | uc.339+ | -0.5338 | hsa-miR-107 |
| hsa-mir-107-prec-10 | uc.143+A | -0.5334 | hsa-miR-107 |
| hsa-mir-107No1 | uc.34+A | -0.5257 | hsa-miR-107 |
| hsa-mir-107-prec-10 | uc.339+ | -0.5191 | hsa-miR-107 |
| hsa-mir-107No1 | uc.478+A | -0.5133 | hsa-miR-107 |
| hsa-mir-107No1 | uc.84+A | -0.5122 | hsa-miR-107 |
| hsa-mir-107No1 | uc.398+ | -0.5097 | hsa-miR-107 |
| hsa-mir-107No1 | uc.465+A | -0.5005 | hsa-miR-107 |
| hsa-mir-107-prec-10 | uc.84+A | -0.4869 | hsa-miR-107 |

Figure 18 Continued

Calin G4

| miRNA probe on array | UCR probe on array | Correlations (Spearman Method) | miRNA |
|---|---|---|---|
| hsa-mir-107-prec-10 | uc.34+A | -0.4807 | hsa-miR-107 |
| hsa-mir-107No1 | uc.353+ | -0.479 | hsa-miR-107 |
| hsa-mir-107-prec-10 | uc.478+A | -0.4774 | hsa-miR-107 |
| hsa-mir-107-prec-10 | uc.204+A | -0.4658 | hsa-miR-107 |
| hsa-mir-107No1 | uc.142+A | -0.4655 | hsa-miR-107 |
| hsa-mir-107No1 | uc.269+A | -0.4565 | hsa-miR-107 |
| hsa-mir-107-prec-10 | uc.48+A | -0.4559 | hsa-miR-107 |
| hsa-mir-107No1 | uc.48+A | -0.4535 | hsa-miR-107 |
| hsa-mir-122a-prec | uc.230+ | -0.6636 | hsa-miR-122a |
| hsa-mir-122a-prec | uc.366+ | -0.6077 | hsa-miR-122a |
| hsa-mir-122a-prec | uc.192+ | -0.6018 | hsa-miR-122a |
| hsa-mir-122a-prec | uc.389+ | -0.5285 | hsa-miR-122a |
| hsa-mir-122a-prec | uc.345+A | -0.5157 | hsa-miR-122a |
| hsa-mir-122a-prec | uc.125+A | -0.4675 | hsa-miR-122a |
| hsa-mir-122a-prec | uc.73+ | -0.4493 | hsa-miR-122a |
| hsa-mir-122a-prec | uc.181+A | -0.448 | hsa-miR-122a |
| hsa-mir-122a-prec | uc.310+A | -0.448 | hsa-miR-122a |
| hsa-mir-128a-precNo1 | uc.420+ | -0.5341 | hsa-mir-128a |
| hsa-mir-128a-precNo1 | uc.299+A | -0.5232 | hsa-mir-128a |
| hsa-mir-128a-precNo1 | uc.134+ | -0.5068 | hsa-mir-128a |
| hsa-mir-128a-precNo1 | uc.33+A | -0.4685 | hsa-mir-128a |
| hsa-mir-129-precNo1 | uc.466+A | -0.479 | hsa-miR-129 |
| hsa-mir-130bNo2 | uc.6+ | -0.6653 | hsa-mir-130b |
| hsa-mir-130bNo2 | uc.420+ | -0.605 | hsa-mir-130b |
| hsa-mir-130bNo2 | uc.189+ | -0.5375 | hsa-mir-130b |
| hsa-mir-130bNo2 | uc.33+ | -0.5232 | hsa-mir-130b |
| hsa-mir-130bNo2 | uc.388+A | -0.5015 | hsa-mir-130b |
| hsa-mir-130bNo1 | uc.48+A | -0.4947 | hsa-miR-130b |
| hsa-mir-130bNo2 | uc.468+ | -0.4887 | hsa-mir-130b |
| hsa-mir-130bNo2 | uc.229+ | -0.4844 | hsa-mir-130b |
| hsa-mir-130bNo2 | uc.299+A | -0.4723 | hsa-mir-130b |
| hsa-mir-130bNo2 | uc.466+A | -0.4686 | hsa-mir-130b |
| hsa-mir-130bNo1 | uc.167+ | -0.4682 | hsa-miR-130b |
| hsa-mir-130bNo1 | uc.142+A | -0.4661 | hsa-mir-130b |
| hsa-mir-130bNo2 | uc.177+ | -0.4529 | hsa-mir-130b |
| hsa-mir-130bNo1 | uc.84+A | -0.4503 | hsa-mir-130b |
| hsa-mir-130bNo2 | uc.134+ | -0.4479 | hsa-mir-130b |
| hsa-mir-136-precNo2 | uc.379+ | -0.4528 | hsa-miR-136 |
| hsa-mir-138-2-prec | uc.20+ | -0.5607 | hsa-miR-138 |
| hsa-mir-138-2-prec | uc.477+ | -0.5512 | hsa-miR-138 |
| hsa-mir-138-2-prec | uc.20+A | -0.5388 | hsa-miR-138 |
| hsa-mir-138-2-prec | uc.362+ | -0.4761 | hsa-miR-138 |
| hsa-mir-138-2-prec | uc.263+ | -0.469 | hsa-miR-138 |
| hsa-mir-140No2 | uc.465+A | -0.575 | hsa-mir-140 |
| hsa-mir-140No2 | uc.299+A | -0.5569 | hsa-mir-140 |
| hsa-mir-140No2 | uc.388+A | -0.5525 | hsa-mir-140 |
| hsa-mir-140No2 | uc.151+A | -0.5378 | hsa-mir-140 |
| hsa-mir-140No2 | uc.18+ | -0.5346 | hsa-mir-140 |
| hsa-mir-140No2 | uc.420+ | -0.5319 | hsa-mir-140 |
| hsa-mir-140No2 | uc.213+ | -0.5249 | hsa-mir-140 |
| hsa-mir-140No2 | uc.153+A | -0.5216 | hsa-mir-140 |
| hsa-mir-140No2 | uc.33+A | -0.519 | hsa-mir-140 |
| hsa-mir-140No2 | uc.337+A | -0.5149 | hsa-mir-140 |
| hsa-mir-140No2 | uc.172+A | -0.5107 | hsa-mir-140 |
| hsa-mir-140No2 | uc.151+ | -0.5103 | hsa-mir-140 |
| hsa-mir-140No2 | uc.325+ | -0.5074 | hsa-mir-140 |
| hsa-mir-140No2 | uc.77+ | -0.499 | hsa-mir-140 |
| hsa-mir-140No2 | uc.173+ | -0.4987 | hsa-mir-140 |
| hsa-mir-140No2 | uc.285+ | -0.4973 | hsa-mir-140 |
| hsa-mir-140No2 | uc.117+ | -0.4921 | hsa-mir-140 |
| hsa-mir-140No2 | uc.128+A | -0.4741 | hsa-mir-140 |
| hsa-mir-140No2 | uc.468+ | -0.4735 | hsa-mir-140 |
| hsa-mir-140No2 | uc.234+ | -0.4726 | hsa-mir-140 |
| hsa-mir-140No2 | uc.462+A | -0.4707 | hsa-mir-140 |
| hsa-mir-140No2 | uc.478+A | -0.4692 | hsa-mir-140 |
| hsa-mir-140No2 | uc.106+ | -0.4635 | hsa-mir-140 |
| hsa-mir-140No2 | uc.354+A | -0.4628 | hsa-mir-140 |
| hsa-mir-140No2 | uc.346+ | -0.4618 | hsa-mir-140 |
| hsa-mir-140No2 | uc.339+ | -0.4597 | hsa-mir-140 |
| hsa-mir-140No2 | uc.427+ | -0.4596 | hsa-mir-140 |
| hsa-mir-140No2 | uc.44+A | -0.4561 | hsa-mir-140 |
| hsa-mir-140No2 | uc.8+ | -0.4517 | hsa-mir-140 |
| hsa-mir-140No2 | uc.177+ | -0.4477 | hsa-mir-140 |
| hsa-mir-142-prec | uc.420+ | -0.8325 | hsa-miR-142-5p |
| hsa-mir-142-prec | uc.33+A | -0.8101 | hsa-miR-142-5p |
| hsa-mir-142-prec | uc.462+A | -0.7796 | hsa-miR-142-5p |
| hsa-mir-142-prec | uc.189+ | -0.775 | hsa-miR-142-5p |
| hsa-mir-142-prec | uc.106+ | -0.7498 | hsa-miR-142-5p |
| hsa-mir-142-prec | uc.363+ | -0.7397 | hsa-miR-142-5p |
| hsa-mir-142-prec | uc.456+A | -0.7304 | hsa-miR-142-5p |
| hsa-mir-142-prec | uc.153+A | -0.7288 | hsa-miR-142-5p |
| hsa-mir-142-prec | uc.73+A | -0.7259 | hsa-miR-142-5p |
| hsa-mir-142-prec | uc.468+ | -0.7169 | hsa-miR-142-5p |
| hsa-mir-142-prec | uc.275+ | -0.7114 | hsa-miR-142-5p |

Figure 18 Continued

Calin GA

| miRNA probe on array | UCR probe on array | Correlations (Spearman Method) | miRNA |
|---|---|---|---|
| hsa-mir-142-prec | uc.354+A | -0.7079 | hsa-miR-142-5p |
| hsa-mir-142-prec | uc.378+A | -0.7073 | hsa-miR-142-5p |
| hsa-mir-142-prec | uc.190+A | -0.7067 | hsa-miR-142-5p |
| hsa-mir-142-prec | uc.33+ | -0.701 | hsa-miR-142-5p |
| hsa-mir-142-prec | uc.412+A | -0.6934 | hsa-miR-142-5p |
| hsa-mir-142-prec | uc.234+ | -0.688 | hsa-miR-142-5p |
| hsa-mir-142-prec | uc.299+A | -0.6812 | hsa-miR-142-5p |
| hsa-mir-142-prec | uc.88+ | -0.6807 | hsa-miR-142-5p |
| hsa-mir-142-prec | uc.473+A | -0.6767 | hsa-miR-142-5p |
| hsa-mir-142-prec | uc.153+ | -0.6735 | hsa-miR-142-5p |
| hsa-mir-142-prec | uc.6+ | -0.6726 | hsa-miR-142-5p |
| hsa-mir-142-prec | uc.317+A | -0.6688 | hsa-miR-142-5p |
| hsa-mir-142-prec | uc.477+A | -0.6672 | hsa-miR-142-5p |
| hsa-mir-142-prec | uc.18+ | -0.6586 | hsa-miR-142-5p |
| hsa-mir-142-prec | uc.388+ | -0.6484 | hsa-miR-142-5p |
| hsa-mir-142-prec | uc.44+A | -0.6436 | hsa-miR-142-5p |
| hsa-mir-142-prec | uc.287+A | -0.643 | hsa-miR-142-5p |
| hsa-mir-142-prec | uc.378+ | -0.6406 | hsa-miR-142-5p |
| hsa-mir-142-prec | uc.388+A | -0.6403 | hsa-miR-142-5p |
| hsa-mir-142-prec | uc.427+ | -0.6392 | hsa-miR-142-5p |
| hsa-mir-142-prec | uc.20+ | -0.6283 | hsa-miR-142-5p |
| hsa-mir-142-prec | uc.263+ | -0.6193 | hsa-miR-142-5p |
| hsa-mir-142-prec | uc.265+ | -0.614 | hsa-miR-142-5p |
| hsa-mir-142-prec | uc.213+ | -0.6089 | hsa-miR-142-5p |
| hsa-mir-142-prec | uc.217+ | -0.6062 | hsa-miR-142-5p |
| hsa-mir-142-prec | uc.43+ | -0.6049 | hsa-miR-142-5p |
| hsa-mir-142-prec | uc.445+A | -0.6041 | hsa-miR-142-5p |
| hsa-mir-142-prec | uc.468+A | -0.5924 | hsa-miR-142-5p |
| hsa-mir-142-prec | uc.20+A | -0.5842 | hsa-miR-142-5p |
| hsa-mir-142-prec | uc.327+A | -0.5712 | hsa-miR-142-5p |
| hsa-mir-142-prec | uc.456+ | -0.5614 | hsa-miR-142-5p |
| hsa-mir-142-prec | uc.151+A | -0.5488 | hsa-miR-142-5p |
| hsa-mir-142-prec | uc.170+ | -0.5193 | hsa-miR-142-5p |
| hsa-mir-142-prec | uc.448+A | -0.519 | hsa-miR-142-5p |
| hsa-mir-142-prec | uc.412+ | -0.5176 | hsa-miR-142-5p |
| hsa-mir-142-prec | uc.10+ | -0.5173 | hsa-miR-142-5p |
| hsa-mir-142-prec | uc.331+A | -0.5152 | hsa-miR-142-5p |
| hsa-mir-142-prec | uc.420+A | -0.5145 | hsa-miR-142-5p |
| hsa-mir-142-prec | uc.448+ | -0.5103 | hsa-miR-142-5p |
| hsa-mir-142-prec | uc.338+ | -0.5096 | hsa-miR-142-5p |
| hsa-mir-142-prec | uc.190+ | -0.5058 | hsa-miR-142-5p |
| hsa-mir-142-prec | uc.182+ | -0.5 | hsa-miR-142-5p |
| hsa-mir-142-prec | uc.362+A | -0.4983 | hsa-miR-142-5p |
| hsa-mir-142-prec | uc.363+A | -0.4789 | hsa-miR-142-5p |
| hsa-mir-142-prec | uc.260+ | -0.4748 | hsa-miR-142-5p |
| hsa-mir-142-prec | uc.177+ | -0.4718 | hsa-miR-142-5p |
| hsa-mir-142-prec | uc.173+ | -0.4716 | hsa-miR-142-5p |
| hsa-mir-142-prec | uc.183+ | -0.4633 | hsa-miR-142-5p |
| hsa-mir-142-prec | uc.134+ | -0.4615 | hsa-miR-142-5p |
| hsa-mir-142-prec | uc.128+A | -0.45 | hsa-miR-142-5p |
| hsa-mir-142-prec | uc.151+ | -0.4493 | hsa-miR-142-5p |
| hsa-mir-145-prec | uc.223+A | -0.5491 | hsa-miR-145 |
| hsa-mir-145-prec | uc.278+A | -0.5047 | hsa-miR-145 |
| hsa-mir-145-prec | uc.291+ | -0.4904 | hsa-miR-145 |
| hsa-mir-145-prec | uc.90+A | -0.4836 | hsa-miR-145 |
| hsa-mir-145-prec | uc.298+ | -0.4764 | hsa-miR-145 |
| hsa-mir-146-prec | uc.478+A | -0.4815 | hsa-miR-146a |
| hsa-mir-146-prec | uc.160+ | -0.4667 | hsa-miR-146a |
| hsa-mir-146-prec | uc.325+ | -0.4649 | hsa-miR-146a |
| hsa-mir-148-prec | uc.145+A | -0.5377 | hsa-miR-148a |
| hsa-mir-148-prec | uc.478+A | -0.4857 | hsa-miR-148a |
| hsa-mir-148-prec | uc.475+ | -0.4615 | hsa-miR-148a |
| hsa-mir-149-prec | uc.8+ | -0.5258 | hsa-miR-149 |
| hsa-mir-149-prec | uc.299+A | -0.466 | hsa-miR-149 |
| hsa-mir-149-prec | uc.420+ | -0.4481 | hsa-miR-149 |
| hsa-mir-150-prec | uc.8+ | -0.7279 | hsa-miR-150 |
| hsa-mir-150-prec | uc.466+A | -0.657 | hsa-miR-150 |
| hsa-mir-150-prec | uc.189+ | -0.6232 | hsa-miR-150 |
| hsa-mir-150-prec | uc.420+ | -0.577 | hsa-miR-150 |
| hsa-mir-150-prec | uc.299+A | -0.5766 | hsa-miR-150 |
| hsa-mir-150-prec | uc.468+ | -0.5347 | hsa-miR-150 |
| hsa-mir-150-prec | uc.134+A | -0.5124 | hsa-miR-150 |
| hsa-mir-150-prec | uc.195+A | -0.4915 | hsa-miR-150 |
| hsa-mir-150-prec | uc.73+A | -0.4885 | hsa-miR-150 |
| hsa-mir-150-prec | uc.412+A | -0.4814 | hsa-miR-150 |
| hsa-mir-150-prec | uc.43+ | -0.477 | hsa-miR-150 |
| hsa-mir-150-prec | uc.412+ | -0.4661 | hsa-miR-150 |
| hsa-mir-150-prec | uc.177+ | -0.4644 | hsa-miR-150 |
| hsa-mir-150-prec | uc.229+ | -0.4602 | hsa-miR-150 |
| hsa-mir-150-prec | uc.462+A | -0.4546 | hsa-miR-150 |
| hsa-mir-150-prec | uc.456+A | -0.4474 | hsa-miR-150 |
| hsa-mir-151-prec | uc.412+ | -0.5811 | hsa-miR-151 |
| hsa-mir-151-prec | uc.189+ | -0.5673 | hsa-miR-151 |
| hsa-mir-151-prec | uc.8+ | -0.5411 | hsa-miR-151 |

Figure 18 Continued

Calin GA

7

| miRNA probe on array | UCR probe on array | Correlations (Spearman Method) | miRNA |
|---|---|---|---|
| hsa-mir-151-prec | uc.299+A | -0.5331 | hsa-miR-151 |
| hsa-mir-151-prec | uc.338+ | -0.4979 | hsa-miR-151 |
| hsa-mir-151-prec | uc.73+A | -0.4795 | hsa-miR-151 |
| hsa-mir-151-prec | uc.477+A | -0.471 | hsa-miR-151 |
| hsa-mir-151-prec | uc.134+A | -0.467 | hsa-miR-151 |
| hsa-mir-151-prec | uc.420+ | -0.4534 | hsa-miR-151 |
| hsa-mir-152-precNo1 | uc.229+ | -0.7536 | hsa-miR-152 |
| hsa-mir-152-precNo1 | uc.466+A | -0.734 | hsa-miR-152 |
| hsa-mir-152-precNo1 | uc.349+ | -0.7155 | hsa-miR-152 |
| hsa-mir-152-precNo1 | uc.177+ | -0.7128 | hsa-miR-152 |
| hsa-mir-152-precNo1 | uc.262+A | -0.6541 | hsa-miR-152 |
| hsa-mir-152-precNo1 | uc.278+ | -0.6345 | hsa-miR-152 |
| hsa-mir-152-precNo1 | uc.8+ | -0.63 | hsa-miR-152 |
| hsa-mir-152-precNo1 | uc.134+A | -0.6118 | hsa-miR-152 |
| hsa-mir-152-precNo2 | uc.388+ | -0.5947 | hsa-mir-152 |
| hsa-mir-152-precNo1 | uc.346+ | -0.5874 | hsa-miR-152 |
| hsa-mir-152-precNo2 | uc.463+A | -0.5752 | hsa-mir-152 |
| hsa-mir-152-precNo1 | uc.128+A | -0.5626 | hsa-miR-152 |
| hsa-mir-152-precNo1 | uc.426+ | -0.5546 | hsa-miR-152 |
| hsa-mir-152-precNo1 | uc.462+ | -0.5515 | hsa-miR-152 |
| hsa-mir-152-precNo2 | uc.473+A | -0.5506 | hsa-mir-152 |
| hsa-mir-152-precNo1 | uc.183+ | -0.5492 | hsa-miR-152 |
| hsa-mir-152-precNo1 | uc.172+A | -0.5416 | hsa-miR-152 |
| hsa-mir-152-precNo1 | uc.151+ | -0.5342 | hsa-miR-152 |
| hsa-mir-152-precNo3 | uc.477+ | -0.5269 | hsa-mir-152 |
| hsa-mir-152-precNo2 | uc.310+ | -0.5167 | hsa-mir-152 |
| hsa-mir-152-precNo1 | uc.77+ | -0.5107 | hsa-miR-152 |
| hsa-mir-152-precNo1 | uc.204+ | -0.5101 | hsa-miR-152 |
| hsa-mir-152-precNo2 | uc.18+ | -0.5099 | hsa-mir-152 |
| hsa-mir-152-precNo2 | uc.20+A | -0.5056 | hsa-mir-152 |
| hsa-mir-152-precNo2 | uc.20+ | -0.5030 | hsa-mir-152 |
| hsa-mir-152-precNo2 | uc.363+ | -0.4976 | hsa-mir-152 |
| hsa-mir-152-precNo1 | uc.186+A | -0.4883 | hsa-miR-152 |
| hsa-mir-152-precNo2 | uc.153+ | -0.4859 | hsa-mir-152 |
| hsa-mir-152-precNo1 | uc.136+ | -0.485 | hsa-miR-152 |
| hsa-mir-152-precNo2 | uc.362+ | -0.4786 | hsa-mir-152 |
| hsa-mir-152-precNo1 | uc.165+ | -0.4775 | hsa-miR-152 |
| hsa-mir-152-precNo1 | uc.134+ | -0.4751 | hsa-miR-152 |
| hsa-mir-152-precNo2 | uc.445+A | -0.475 | hsa-mir-152 |
| hsa-mir-152-precNo1 | uc.73+ | -0.4741 | hsa-miR-152 |
| hsa-mir-152-precNo2 | uc.106+ | -0.4678 | hsa-mir-152 |
| hsa-mir-152-precNo1 | uc.420+A | -0.4643 | hsa-miR-152 |
| hsa-mir-152-precNo1 | uc.465+A | -0.4641 | hsa-miR-152 |
| hsa-mir-152-precNo2 | uc.88+ | -0.4619 | hsa-mir-152 |
| hsa-mir-152-precNo1 | uc.139+ | -0.4518 | hsa-miR-152 |
| hsa-mir-152-precNo2 | uc.63+ | -0.4495 | hsa-mir-152 |
| hsa-mir-153-1-prec1 | uc.465+A | -0.7389 | hsa-miR-153 |
| hsa-mir-153-1-prec1 | uc.229+ | -0.7232 | hsa-miR-153 |
| hsa-mir-153-1-prec1 | uc.349+ | -0.7215 | hsa-miR-153 |
| hsa-mir-153-1-prec1 | uc.177+ | -0.6679 | hsa-miR-153 |
| hsa-mir-153-1-prec1 | uc.262+A | -0.6193 | hsa-miR-153 |
| hsa-mir-153-1-prec1 | uc.426+ | -0.605 | hsa-miR-153 |
| hsa-mir-153-1-prec1 | uc.278+ | -0.5817 | hsa-miR-153 |
| hsa-mir-153-1-prec1 | uc.8+ | -0.5706 | hsa-miR-153 |
| hsa-mir-153-1-prec1 | uc.73+ | -0.5675 | hsa-miR-153 |
| hsa-mir-153-1-prec1 | uc.346+ | -0.5664 | hsa-miR-153 |
| hsa-mir-153-1-prec1 | uc.136+ | -0.5601 | hsa-miR-153 |
| hsa-mir-153-1-prec1 | uc.204+ | -0.5479 | hsa-miR-153 |
| hsa-mir-153-1-prec1 | uc.134+A | -0.5266 | hsa-miR-153 |
| hsa-mir-153-1-prec1 | uc.462+ | -0.5212 | hsa-miR-153 |
| hsa-mir-153-1-prec1 | uc.172+A | -0.5128 | hsa-miR-153 |
| hsa-mir-153-1-prec1 | uc.165+ | -0.5083 | hsa-miR-153 |
| hsa-mir-153-1-prec1 | uc.128+A | -0.4974 | hsa-miR-153 |
| hsa-mir-153-1-prec1 | uc.77+ | -0.4872 | hsa-miR-153 |
| hsa-mir-153-1-prec1 | uc.483+ | -0.4773 | hsa-miR-153 |
| hsa-mir-155-prec | uc.282+A | -0.6215 | hsa-miR-155 |
| hsa-mir-155-prec | uc.283+A | -0.6176 | hsa-miR-155 |
| hsa-mir-155-prec | uc.346+A | -0.528 | hsa-miR-155 |
| hsa-mir-155-prec | uc.465+A | -0.525 | hsa-miR-155 |
| hsa-mir-155-prec | uc.84+A | -0.4589 | hsa-miR-155 |
| hsa-mir-15aNo1 | uc.420+ | -0.7206 | hsa-miR-15a |
| hsa-mir-015a-2-precNo1 | uc.420+ | -0.7013 | hsa-miR-15a |
| hsa-mir-15aNo1 | uc.285+ | -0.6703 | hsa-miR-15a |
| hsa-mir-15aNo1 | uc.33+A | -0.6354 | hsa-miR-15a |
| hsa-mir-015a-2-precNo1 | uc.285+ | -0.6268 | hsa-miR-15a |
| hsa-mir-15aNo1 | uc.151+ | -0.6262 | hsa-miR-15a |
| hsa-mir-015a-2-precNo1 | uc.327+A | -0.612 | hsa-miR-15a |
| hsa-mir-15aNo1 | uc.8+ | -0.604 | hsa-miR-15a |
| hsa-mir-15aNo1 | uc.327+A | -0.6035 | hsa-miR-15a |
| hsa-mir-015a-2-precNo1 | uc.462+A | -0.601 | hsa-miR-15a |
| hsa-mir-15aNo1 | uc.262+A | -0.596 | hsa-miR-15a |
| hsa-mir-015a-2-precNo1 | uc.78+ | -0.5834 | hsa-miR-15a |
| hsa-mir-15aNo1 | uc.189+ | -0.582 | hsa-miR-15a |
| hsa-mir-15aNo1 | uc.177+ | -0.5817 | hsa-miR-15a |

Figure 18 Continued

Calin GA

| miRNA probe on array | UCR probe on array | Correlations (Spearman Method) | miRNA |
|---|---|---|---|
| hsa-mir-015a-2-precNo1 | uc.8+ | -0.58 | hsa-miR-15a |
| hsa-mir-015a-2-precNo1 | uc.427+ | -0.5784 | hsa-miR-15a |
| hsa-mir-015a-2-precNo1 | uc.73+A | -0.5784 | hsa-miR-15a |
| hsa-mir-015a-2-precNo1 | uc.44+A | -0.5756 | hsa-miR-15a |
| hsa-mir-015a-2-precNo1 | uc.33+A | -0.5754 | hsa-miR-15a |
| hsa-mir-15aNo1 | uc.465+A | -0.571 | hsa-miR-15a |
| hsa-mir-015a-2-precNo1 | uc.189+ | -0.5684 | hsa-miR-15a |
| hsa-mir-15aNo1 | uc.172+A | -0.5603 | hsa-miR-15a |
| hsa-mir-15aNo1 | uc.44+A | -0.5494 | hsa-miR-15a |
| hsa-mir-15aNo1 | uc.346+ | -0.5457 | hsa-miR-15a |
| hsa-mir-15aNo1 | uc.189+ | -0.5437 | hsa-miR-15a |
| hsa-mir-015a-2-precNo1 | uc.299+A | -0.5333 | hsa-miR-15a |
| hsa-mir-15aNo1 | uc.153+A | -0.5317 | hsa-miR-15a |
| hsa-mir-015a-2-precNo1 | uc.456+A | -0.529 | hsa-miR-15a |
| hsa-mir-15aNo1 | uc.462+A | -0.527 | hsa-miR-15a |
| hsa-mir-15aNo1 | uc.78+ | -0.5231 | hsa-miR-15a |
| hsa-mir-015a-2-precNo1 | uc.151+ | -0.5195 | hsa-miR-15a |
| hsa-mir-15aNo1 | uc.183+ | -0.5163 | hsa-miR-15a |
| hsa-mir-15aNo1 | uc.388+A | -0.5151 | hsa-miR-15a |
| hsa-mir-15aNo1 | uc.299+A | -0.5148 | hsa-miR-15a |
| hsa-mir-15aNo1 | uc.420+A | -0.5139 | hsa-miR-15a |
| hsa-mir-15aNo1 | uc.427+ | -0.5125 | hsa-miR-15a |
| hsa-mir-015a-2-precNo1 | uc.153+A | -0.5114 | hsa-miR-15a |
| hsa-mir-015a-2-precNo1 | uc.378+A | -0.5087 | hsa-miR-15a |
| hsa-mir-015a-2-precNo1 | uc.354+A | -0.5078 | hsa-miR-15a |
| hsa-mir-15aNo1 | uc.234+ | -0.5078 | hsa-miR-15a |
| hsa-mir-15aNo1 | uc.77+ | -0.5067 | hsa-miR-15a |
| hsa-mir-15aNo1 | uc.354+A | -0.5051 | hsa-miR-15a |
| hsa-mir-015a-2-precNo1 | uc.161+A | -0.5041 | hsa-miR-15a |
| hsa-mir-15aNo1 | uc.33+ | -0.5038 | hsa-miR-15a |
| hsa-mir-015a-2-precNo1 | uc.338+ | -0.5031 | hsa-miR-15a |
| hsa-mir-15aNo1 | uc.412+A | -0.5026 | hsa-miR-15a |
| hsa-mir-015a-2-precNo1 | uc.167+ | -0.5 | hsa-miR-15a |
| hsa-mir-015a-2-precNo1 | uc.412+A | -0.4977 | hsa-miR-15a |
| hsa-mir-015a-2-precNo1 | uc.234+ | -0.4949 | hsa-miR-15a |
| hsa-mir-15aNo1 | uc.456+A | -0.4865 | hsa-miR-15a |
| hsa-mir-15aNo1 | uc.173+ | -0.4856 | hsa-miR-15a |
| hsa-mir-15aNo1 | uc.128+A | -0.4826 | hsa-miR-15a |
| hsa-mir-15aNo1 | uc.456+ | -0.4819 | hsa-miR-15a |
| hsa-mir-015a-2-precNo1 | uc.477+A | -0.477 | hsa-miR-15a |
| hsa-mir-015a-2-precNo1 | uc.331+A | -0.4758 | hsa-miR-15a |
| hsa-mir-015a-2-precNo1 | uc.160+ | -0.4755 | hsa-miR-15a |
| hsa-mir-015a-2-precNo1 | uc.190+A | -0.475 | hsa-miR-15a |
| hsa-mir-015a-2-precNo1 | uc.217+A | -0.4722 | hsa-miR-15a |
| hsa-mir-15aNo1 | uc.73+A | -0.4695 | hsa-miR-15a |
| hsa-mir-015a-2-precNo1 | uc.213+ | -0.4641 | hsa-miR-15a |
| hsa-mir-15aNo1 | uc.331+A | -0.4633 | hsa-miR-15a |
| hsa-mir-015a-2-precNo1 | uc.478+A | -0.4612 | hsa-miR-15a |
| hsa-mir-15aNo1 | uc.106+ | -0.4601 | hsa-miR-15a |
| hsa-mir-015a-2-precNo1 | uc.263+A | -0.4597 | hsa-miR-15a |
| hsa-mir-015a-2-precNo1 | uc.465+A | -0.4593 | hsa-miR-15a |
| hsa-mir-15aNo1 | uc.134+ | -0.4567 | hsa-miR-15a |
| hsa-mir-15aNo1 | uc.213+ | -0.4553 | hsa-miR-15a |
| hsa-mir-015a-2-precNo1 | uc.378+ | -0.4546 | hsa-miR-15a |
| hsa-mir-15aNo1 | uc.151+A | -0.45 | hsa-miR-15a |
| hsa-mir-015a-2-precNo1 | uc.33+ | -0.4495 | hsa-miR-15a |
| hsa-mir-15aNo1 | uc.217+A | -0.4481 | hsa-miR-15a |
| hsa-mir-15aNo1 | uc.378+A | -0.4475 | hsa-miR-15a |
| hsa-mir-015b-precNo1 | uc.420+ | -0.7727 | hsa-miR-15b |
| hsa-mir-015b-precNo1 | uc.462+A | -0.7277 | hsa-miR-15b |
| hsa-mir-015b-precNo1 | uc.189+ | -0.7125 | hsa-miR-15b |
| hsa-mir-015b-precNo1 | uc.73+A | -0.6877 | hsa-miR-15b |
| hsa-mir-015b-precNo1 | uc.338+ | -0.6657 | hsa-miR-15b |
| hsa-mir-015b-precNo1 | uc.78+ | -0.6637 | hsa-miR-15b |
| hsa-mir-015b-precNo1 | uc.44+A | -0.6532 | hsa-miR-15b |
| hsa-mir-015b-precNo1 | uc.299+A | -0.646 | hsa-miR-15b |
| hsa-mir-015b-precNo1 | uc.263+ | -0.6458 | hsa-miR-15b |
| hsa-mir-015b-precNo1 | uc.412+ | -0.6146 | hsa-miR-15b |
| hsa-mir-015b-precNo1 | uc.8+ | -0.6097 | hsa-miR-15b |
| hsa-mir-015b-precNo1 | uc.331+A | -0.6019 | hsa-miR-15b |
| hsa-mir-015b-precNo1 | uc.456+ | -0.5974 | hsa-miR-15b |
| hsa-mir-015b-precNo1 | uc.477+A | -0.5942 | hsa-miR-15b |
| hsa-mir-015b-precNo1 | uc.379+ | -0.591 | hsa-miR-15b |
| hsa-mir-015b-precNo1 | uc.378+A | -0.5734 | hsa-miR-15b |
| hsa-mir-015b-precNo1 | uc.427+ | -0.5729 | hsa-miR-15b |
| hsa-mir-015b-precNo1 | uc.33+A | -0.5723 | hsa-miR-15b |
| hsa-mir-015b-precNo1 | uc.327+A | -0.5714 | hsa-miR-15b |
| hsa-mir-015b-precNo1 | uc.217+ | -0.5697 | hsa-miR-15b |
| hsa-mir-015b-precNo1 | uc.456+A | -0.5693 | hsa-miR-15b |
| hsa-mir-015b-precNo1 | uc.412+A | -0.5626 | hsa-miR-15b |
| hsa-mir-015b-precNo1 | uc.161+A | -0.5595 | hsa-miR-15b |
| hsa-mir-015b-precNo1 | uc.88+ | -0.5592 | hsa-miR-15b |
| hsa-mir-015b-precNo1 | uc.275+ | -0.5508 | hsa-miR-15b |
| hsa-mir-015b-precNo1 | uc.153+ | -0.5415 | hsa-miR-15b |

Figure 18 Continued

Calin GA

| miRNA probe on array | UCR probe on array | Correlations (Spearman Method) | miRNA |
|---|---|---|---|
| hsa-mir-015b-predNo1 | uc.190+A | -0.5337 | hsa-miR-15b |
| hsa-mir-015b-predNo1 | uc.234+ | -0.5316 | hsa-miR-15b |
| hsa-mir-015b-predNo1 | uc.151+ | -0.5265 | hsa-miR-15b |
| hsa-mir-015b-predNo1 | uc.167+ | -0.5187 | hsa-miR-15b |
| hsa-mir-015b-predNo1 | uc.363+ | -0.5174 | hsa-miR-15b |
| hsa-mir-015b-predNo1 | uc.473+A | -0.5071 | hsa-miR-15b |
| hsa-mir-015b-predNo1 | uc.354+A | -0.5015 | hsa-miR-15b |
| hsa-mir-015b-predNo1 | uc.145+A | -0.4998 | hsa-miR-15b |
| hsa-mir-015b-predNo1 | uc.153+A | -0.499 | hsa-miR-15b |
| hsa-mir-015b-predNo1 | uc.448+A | -0.4979 | hsa-miR-15b |
| hsa-mir-015b-predNo1 | uc.170+ | -0.497 | hsa-miR-15b |
| hsa-mir-015b-predNo1 | uc.287+A | -0.4894 | hsa-miR-15b |
| hsa-mir-015b-predNo1 | uc.448+ | -0.482 | hsa-miR-15b |
| hsa-mir-015b-predNo1 | uc.106+ | -0.4731 | hsa-miR-15b |
| hsa-mir-015b-predNo1 | uc.33+ | -0.4706 | hsa-miR-15b |
| hsa-mir-015b-predNo1 | uc.388+ | -0.4693 | hsa-miR-15b |
| hsa-mir-015b-predNo1 | uc.317+A | -0.4608 | hsa-miR-15b |
| hsa-mir-015b-predNo1 | uc.313+ | -0.4576 | hsa-miR-15b |
| hsa-mir-015b-predNo1 | uc.134+ | -0.4548 | hsa-miR-15b |
| hsa-mir-015b-predNo1 | uc.88+A | -0.4513 | hsa-miR-15b |
| hsa-mir-16-2No1 | uc.420+ | -0.7565 | hsa-miR-16 |
| hsa-mir-016b-chr3 | uc.420+ | -0.741 | hsa-miR-16 |
| hsa-mir-16-1No1 | uc.420+ | -0.7116 | hsa-miR-16 |
| hsa-mir-016a-chr13 | uc.420+ | -0.7036 | hsa-miR-16 |
| hsa-mir-16-2No1 | uc.8+ | -0.6632 | hsa-miR-16 |
| hsa-mir-016a-chr13 | uc.177+ | -0.668 | hsa-miR-16 |
| hsa-mir-016b-chr3 | uc.8+ | -0.6536 | hsa-miR-16 |
| hsa-mir-016b-chr3 | uc.151+ | -0.636 | hsa-miR-16 |
| hsa-mir-016a-chr13 | uc.8+ | -0.6347 | hsa-miR-16 |
| hsa-mir-16-1No1 | uc.8+ | -0.6272 | hsa-miR-16 |
| hsa-mir-016b-chr3 | uc.33+A | -0.6254 | hsa-miR-16 |
| hsa-mir-16-1No1 | uc.33+A | -0.6236 | hsa-miR-16 |
| hsa-mir-16-2No1 | uc.151+ | -0.6215 | hsa-miR-16 |
| hsa-mir-16-2No1 | uc.33+A | -0.6215 | hsa-miR-16 |
| hsa-mir-016a-chr13 | uc.466+A | -0.6213 | hsa-miR-16 |
| hsa-mir-016a-chr13 | uc.33+A | -0.613 | hsa-miR-16 |
| hsa-mir-16-2No1 | uc.189+ | -0.6116 | hsa-miR-16 |
| hsa-mir-016a-chr13 | uc.151+ | -0.6068 | hsa-miR-16 |
| hsa-mir-16-1No1 | uc.189+ | -0.6024 | hsa-miR-16 |
| hsa-mir-016b-chr3 | uc.189+ | -0.5978 | hsa-miR-16 |
| hsa-mir-16-1No1 | uc.151+ | -0.5912 | hsa-miR-16 |
| hsa-mir-16-1No1 | uc.436+ | -0.5902 | hsa-miR-16 |
| hsa-mir-16-1No1 | uc.437+ | -0.5896 | hsa-miR-16 |
| hsa-mir-16-1No1 | uc.462+A | -0.5804 | hsa-miR-16 |
| hsa-mir-016a-chr13 | uc.173+A | -0.5797 | hsa-miR-16 |
| hsa-mir-16-2No1 | uc.177+ | -0.5791 | hsa-miR-16 |
| hsa-mir-16-1No1 | uc.456+A | -0.5694 | hsa-miR-16 |
| hsa-mir-16-1No1 | uc.412+A | -0.5687 | hsa-miR-16 |
| hsa-mir-16-2No1 | uc.413+A | -0.5627 | hsa-miR-16 |
| hsa-mir-16-2No1 | uc.299+A | -0.5607 | hsa-miR-16 |
| hsa-mir-016a-chr13 | uc.346+ | -0.5605 | hsa-miR-16 |
| hsa-mir-16-2No1 | uc.456+A | -0.5557 | hsa-miR-16 |
| hsa-mir-016a-chr13 | uc.363+A | -0.555 | hsa-miR-16 |
| hsa-mir-16-2No1 | uc.462+A | -0.5523 | hsa-miR-16 |
| hsa-mir-16-1No1 | uc.299+A | -0.5521 | hsa-miR-16 |
| hsa-mir-016b-chr3 | uc.177+ | -0.551 | hsa-miR-16 |
| hsa-mir-016b-chr3 | uc.299+A | -0.5477 | hsa-miR-16 |
| hsa-mir-016b-chr3 | uc.412+A | -0.5468 | hsa-miR-16 |
| hsa-mir-16-1No1 | uc.327+A | -0.546 | hsa-miR-16 |
| hsa-mir-016a-chr13 | uc.285+ | -0.5458 | hsa-miR-16 |
| hsa-mir-016b-chr3 | uc.456+A | -0.5453 | hsa-miR-16 |
| hsa-mir-016b-chr3 | uc.285+ | -0.5431 | hsa-miR-16 |
| hsa-mir-16-2No1 | uc.466+A | -0.5399 | hsa-miR-16 |
| hsa-mir-016b-chr3 | uc.462+A | -0.5382 | hsa-miR-16 |
| hsa-mir-016a-chr13 | uc.128+A | -0.5375 | hsa-miR-16 |
| hsa-mir-016a-chr13 | uc.189+ | -0.5355 | hsa-miR-16 |
| hsa-mir-16-2No1 | uc.354+A | -0.5236 | hsa-miR-16 |
| hsa-mir-16-1No1 | uc.190+A | -0.523 | hsa-miR-16 |
| hsa-mir-16-1No1 | uc.383+ | -0.5206 | hsa-miR-16 |
| hsa-mir-16-2No1 | uc.305+ | -0.5192 | hsa-miR-16 |
| hsa-mir-016b-chr3 | uc.172+A | -0.5183 | hsa-miR-16 |
| hsa-mir-16-1No1 | uc.378+ | -0.5182 | hsa-miR-16 |
| hsa-mir-16-1No1 | uc.78+ | -0.5177 | hsa-miR-16 |
| hsa-mir-016a-chr13 | uc.77+ | -0.5143 | hsa-miR-16 |
| hsa-mir-16-2No1 | uc.420+A | -0.5135 | hsa-miR-16 |
| hsa-mir-16-1No1 | uc.234+ | -0.5117 | hsa-miR-16 |
| hsa-mir-16-2No1 | uc.106+ | -0.5098 | hsa-miR-16 |
| hsa-mir-16-1No1 | uc.378+A | -0.5074 | hsa-miR-16 |
| hsa-mir-16-2No1 | uc.173+ | -0.5068 | hsa-miR-16 |
| hsa-mir-016b-chr3 | uc.173+ | -0.5064 | hsa-miR-16 |
| hsa-mir-16-2No1 | uc.10+ | -0.5059 | hsa-miR-16 |
| hsa-mir-16-2No1 | uc.172+A | -0.5049 | hsa-miR-16 |
| hsa-mir-16-2No1 | uc.234+ | -0.5038 | hsa-miR-16 |
| hsa-mir-16-2No1 | uc.153+A | -0.5036 | hsa-miR-16 |

Figure 18 Continued

Calin GA

| miRNA probe on array | UCR probe on array | Correlations (Spearman Method) | miRNA |
|---|---|---|---|
| hsa-mir-16-2No1 | uc.190+A | -0.5022 | hsa-miR-16 |
| hsa-mir-16-1No1 | uc.44+A | -0.5005 | hsa-miR-16 |
| hsa-mir-016b-chr3 | uc.466+A | -0.4986 | hsa-miR-16 |
| hsa-mir-016b-chr3 | uc.78+ | -0.4982 | hsa-miR-16 |
| hsa-mir-16-1No1 | uc.73+A | -0.4975 | hsa-miR-16 |
| hsa-mir-16-1No1 | uc.20+ | -0.4966 | hsa-miR-16 |
| hsa-mir-16-1No1 | uc.477+A | -0.4958 | hsa-miR-16 |
| hsa-mir-16-1No1 | uc.106+ | -0.495 | hsa-miR-16 |
| hsa-mir-016b-chr3 | uc.354+A | -0.4944 | hsa-miR-16 |
| hsa-mir-016b-chr3 | uc.427+ | -0.494 | hsa-miR-16 |
| hsa-mir-016a-chr13 | uc.173+ | -0.4939 | hsa-miR-16 |
| hsa-mir-016b-chr3 | uc.234+ | -0.4927 | hsa-miR-16 |
| hsa-mir-016b-chr3 | uc.456+ | -0.4908 | hsa-miR-16 |
| hsa-mir-16-1No1 | uc.354+A | -0.4897 | hsa-miR-16 |
| hsa-mir-016a-chr13 | uc.229+ | -0.4894 | hsa-miR-16 |
| hsa-mir-016a-chr13 | uc.420+A | -0.4894 | hsa-miR-16 |
| hsa-mir-016b-chr3 | uc.420+A | -0.489 | hsa-miR-16 |
| hsa-mir-16-1No1 | uc.153+A | -0.4884 | hsa-miR-16 |
| hsa-mir-016b-chr3 | uc.190+A | -0.4881 | hsa-miR-16 |
| hsa-mir-16-1No1 | uc.285+ | -0.4871 | hsa-miR-16 |
| hsa-mir-016b-chr3 | uc.327+A | -0.4863 | hsa-miR-16 |
| hsa-mir-016b-chr3 | uc.10+ | -0.4856 | hsa-miR-16 |
| hsa-mir-016a-chr13 | uc.299+A | -0.484 | hsa-miR-16 |
| hsa-mir-16-1No1 | uc.412+ | -0.4833 | hsa-miR-16 |
| hsa-mir-16-1No1 | uc.153+ | -0.4824 | hsa-miR-16 |
| hsa-mir-16-2No1 | uc.33+ | -0.4824 | hsa-miR-16 |
| hsa-mir-16-1No1 | uc.173+ | -0.4805 | hsa-miR-16 |
| hsa-mir-16-1No1 | uc.263+ | -0.4786 | hsa-miR-16 |
| hsa-mir-16-1No1 | uc.213+ | -0.4774 | hsa-miR-16 |
| hsa-mir-016b-chr3 | uc.106+ | -0.4768 | hsa-miR-16 |
| hsa-mir-16-2No1 | uc.262+A | -0.4756 | hsa-miR-16 |
| hsa-mir-16-2No1 | uc.427+ | -0.4749 | hsa-miR-16 |
| hsa-mir-016b-chr3 | uc.153+A | -0.4736 | hsa-miR-16 |
| hsa-mir-16-2No1 | uc.78+ | -0.4717 | hsa-miR-16 |
| hsa-mir-16-1No1 | uc.88+ | -0.4711 | hsa-miR-16 |
| hsa-mir-16-1No1 | uc.473+A | -0.4701 | hsa-miR-16 |
| hsa-mir-16-1No1 | uc.18+ | -0.4699 | hsa-miR-16 |
| hsa-mir-16-2No1 | uc.128+A | -0.4694 | hsa-miR-16 |
| hsa-mir-16-2No1 | uc.177+ | -0.4686 | hsa-miR-16 |
| hsa-mir-16-2No1 | uc.134+ | -0.465 | hsa-miR-16 |
| hsa-mir-016b-chr3 | uc.128+A | -0.4648 | hsa-miR-16 |
| hsa-mir-016b-chr3 | uc.262+A | -0.4645 | hsa-miR-16 |
| hsa-mir-16-2No1 | uc.378+A | -0.4637 | hsa-miR-16 |
| hsa-mir-16-2No1 | uc.456+ | -0.4627 | hsa-miR-16 |
| hsa-mir-16-1No1 | uc.172+A | -0.4617 | hsa-miR-16 |
| hsa-mir-16-2No1 | uc.182+ | -0.4612 | hsa-miR-16 |
| hsa-mir-016b-chr3 | uc.378+A | -0.4608 | hsa-miR-16 |
| hsa-mir-16-1No1 | uc.275+ | -0.4596 | hsa-miR-16 |
| hsa-mir-16-2No1 | uc.327+A | -0.4587 | hsa-miR-16 |
| hsa-mir-16-2No1 | uc.388+A | -0.458 | hsa-miR-16 |
| hsa-mir-16-2No1 | uc.77+ | -0.4571 | hsa-miR-16 |
| hsa-mir-16-1No1 | uc.161+A | -0.4558 | hsa-miR-16 |
| hsa-mir-16-2No1 | uc.161+A | -0.4556 | hsa-miR-16 |
| hsa-mir-016b-chr3 | uc.44+A | -0.4512 | hsa-miR-16 |
| hsa-mir-016a-chr13 | uc.465+A | -0.4509 | hsa-miR-16 |
| hsa-mir-16-1No1 | uc.331+A | -0.4506 | hsa-miR-16 |
| hsa-mir-016a-chr13 | uc.134+A | -0.4495 | hsa-miR-16 |
| hsa-mir-016a-chr13 | uc.327+A | -0.4494 | hsa-miR-16 |
| hsa-mir-16-2No1 | uc.18+ | -0.4493 | hsa-miR-16 |
| hsa-mir-017-precNo1 | uc.420+ | -0.5894 | hsa-miR-17-3p |
| hsa-mir-017-precNo1 | uc.299+A | -0.5716 | hsa-miR-17-3p |
| hsa-mir-017-precNo1 | uc.462+A | -0.5506 | hsa-miR-17-3p |
| hsa-mir-017-precNo1 | uc.338+ | -0.5454 | hsa-miR-17-3p |
| hsa-mir-017-precNo1 | uc.8+ | -0.5347 | hsa-miR-17-3p |
| hsa-mir-017-precNo1 | uc.78+ | -0.5153 | hsa-miR-17-3p |
| hsa-mir-017-precNo1 | uc.145+A | -0.4627 | hsa-miR-17-3p |
| hsa-mir-017-precNo1 | uc.412+ | -0.4624 | hsa-miR-17-3p |
| hsa-mir-017-precNo1 | uc.73+A | -0.4577 | hsa-miR-17-3p |
| hsa-mir-017-precNo1 | uc.161+A | -0.451 | hsa-miR-17-3p |
| hsa-mir-017-precNo1 | uc.189+ | -0.4488 | hsa-miR-17-3p |
| hsa-mir-017-precNo2 | uc.160+ | -0.6241 | hsa-miR-17-5p |
| hsa-mir-017-precNo2 | uc.48+A | -0.6134 | hsa-miR-17-5p |
| hsa-mir-017-precNo2 | uc.478+A | -0.5866 | hsa-miR-17-5p |
| hsa-mir-017-precNo2 | uc.167+ | -0.5711 | hsa-miR-17-5p |
| hsa-mir-017-precNo2 | uc.170+ | -0.5611 | hsa-miR-17-5p |
| hsa-mir-017-precNo2 | uc.448+A | -0.529 | hsa-miR-17-5p |
| hsa-mir-017-precNo2 | uc.325+ | -0.5271 | hsa-miR-17-5p |
| hsa-mir-017-precNo2 | uc.427+ | -0.5219 | hsa-miR-17-5p |
| hsa-mir-017-precNo2 | uc.117+ | -0.5114 | hsa-miR-17-5p |
| hsa-mir-017-precNo2 | uc.153+A | -0.5091 | hsa-miR-17-5p |
| hsa-mir-017-precNo2 | uc.262+A | -0.506 | hsa-miR-17-5p |
| hsa-mir-017-precNo2 | uc.327+A | -0.501 | hsa-miR-17-5p |
| hsa-mir-017-precNo2 | uc.263+A | -0.499 | hsa-miR-17-5p |
| hsa-mir-017-precNo2 | uc.88+A | -0.4971 | hsa-miR-17-5p |

Figure 18 Continued

| miRNA probe on array | UCR probe on array | Correlations (Spearman Method) | miRNA |
|---|---|---|---|
| hsa-mir-017-precNo2 | uc.339+ | -0.4912 | hsa-miR-17-5p |
| hsa-mir-017-precNo2 | uc.263+ | -0.4901 | hsa-miR-17-5p |
| hsa-mir-017-precNo2 | uc.84+A | -0.4843 | hsa-miR-17-5p |
| hsa-mir-017-precNo2 | uc.473+A | -0.4792 | hsa-miR-17-5p |
| hsa-mir-017-precNo2 | uc.465+A | -0.4764 | hsa-miR-17-5p |
| hsa-mir-017-precNo2 | uc.217+A | -0.4747 | hsa-miR-17-5p |
| hsa-mir-017-precNo2 | uc.106+ | -0.4741 | hsa-miR-17-5p |
| hsa-mir-017-precNo2 | uc.200+ | -0.4718 | hsa-miR-17-5p |
| hsa-mir-017-precNo2 | uc.213+ | -0.464 | hsa-miR-17-5p |
| hsa-mir-017-precNo2 | uc.153+ | -0.4632 | hsa-miR-17-5p |
| hsa-mir-017-precNo2 | uc.448+ | -0.4586 | hsa-miR-17-5p |
| hsa-mir-017-precNo2 | uc.234+ | -0.4565 | hsa-miR-17-5p |
| hsa-mir-017-precNo2 | uc.86+ | -0.4548 | hsa-miR-17-5p |
| hsa-mir-017-precNo2 | uc.151+A | -0.4526 | hsa-miR-17-5p |
| hsa-mir-017-precNo2 | uc.269+A | -0.4498 | hsa-miR-17-5p |
| hsa-mir-181a-precNo1 | uc.95+ | -0.6264 | hsa-miR-181a |
| hsa-mir-181a-precNo1 | uc.281+A | -0.6145 | hsa-miR-181a |
| hsa-mir-181a-precNo1 | uc.475+ | -0.6131 | hsa-miR-181a |
| hsa-mir-181a-precNo1 | uc.142+A | -0.5892 | hsa-miR-181a |
| hsa-mir-181a-precNo1 | uc.88+A | -0.5668 | hsa-miR-181a |
| hsa-mir-181a-precNo1 | uc.159+A | -0.5604 | hsa-miR-181a |
| hsa-mir-181a-precNo1 | uc.299+ | -0.5529 | hsa-miR-181a |
| hsa-mir-181a-precNo1 | uc.117+ | -0.5251 | hsa-miR-181a |
| hsa-mir-181a-precNo1 | uc.200+ | -0.5183 | hsa-miR-181a |
| hsa-mir-181a-precNo1 | uc.64+A | -0.5006 | hsa-miR-181a |
| hsa-mir-181b-precNo1 | uc.338+ | -0.4732 | hsa-miR-181a |
| hsa-mir-181b-precNo1 | uc.427+ | -0.4671 | hsa-miR-181a |
| hsa-mir-181a-precNo1 | uc.167+ | -0.4658 | hsa-miR-181a |
| hsa-mir-181a-precNo1 | uc.473+ | -0.4656 | hsa-miR-181a |
| hsa-mir-181a-precNo1 | uc.73+A | -0.4654 | hsa-miR-181a |
| hsa-mir-181a-precNo1 | uc.291+ | -0.4629 | hsa-miR-181a |
| hsa-mir-181a-precNo1 | uc.448+A | -0.4598 | hsa-miR-181a |
| hsa-mir-181a-precNo1 | uc.448+ | -0.4555 | hsa-miR-181a |
| hsa-mir-181a-precNo1 | uc.145+A | -0.4513 | hsa-miR-181a |
| hsa-mir-181a-precNo1 | uc.78+ | -0.4495 | hsa-miR-181a |
| hsa-mir-213-precNo1 | uc.204+ | -0.7109 | hsa-miR-181b |
| hsa-mir-213-precNo1 | uc.73+ | -0.7034 | hsa-miR-181b |
| hsa-mir-213-precNo1 | uc.41+ | -0.6853 | hsa-miR-181b |
| hsa-mir-213-precNo1 | uc.165+ | -0.6522 | hsa-miR-181b |
| hsa-mir-213-precNo1 | uc.366+ | -0.6408 | hsa-miR-181b |
| hsa-mir-213-precNo1 | uc.349+ | -0.6308 | hsa-miR-181b |
| hsa-mir-213-precNo1 | uc.483+ | -0.6172 | hsa-miR-181b |
| hsa-mir-213-precNo1 | uc.278+ | -0.6149 | hsa-miR-181b |
| hsa-mir-213-precNo1 | uc.329+ | -0.6035 | hsa-miR-181b |
| hsa-mir-213-precNo1 | uc.426+ | -0.5906 | hsa-miR-181b |
| hsa-mir-213-precNo1 | uc.346+ | -0.5627 | hsa-miR-181b |
| hsa-mir-213-precNo1 | uc.345+ | -0.5573 | hsa-miR-181b |
| hsa-mir-213-precNo1 | uc.136+ | -0.5534 | hsa-miR-181b |
| hsa-mir-213-precNo1 | uc.345+A | -0.5449 | hsa-miR-181b |
| hsa-mir-181b-1No1 | uc.44+A | -0.5289 | hsa-miR-181b |
| hsa-mir-213-precNo1 | uc.77+ | -0.5244 | hsa-miR-181b |
| hsa-mir-213-precNo1 | uc.139+ | -0.5213 | hsa-miR-181b |
| hsa-mir-213-precNo1 | uc.465+A | -0.5145 | hsa-miR-181b |
| hsa-mir-181b-1No1 | uc.338+ | -0.5071 | hsa-miR-181b |
| hsa-mir-213-precNo1 | uc.192+ | -0.4984 | hsa-miR-181b |
| hsa-mir-213-precNo1 | uc.125+A | -0.4954 | hsa-miR-181b |
| hsa-mir-213-precNo1 | uc.262+A | -0.495 | hsa-miR-181b |
| hsa-mir-213-precNo1 | uc.172+A | -0.4932 | hsa-miR-181b |
| hsa-mir-181b-1No1 | uc.299+A | -0.4913 | hsa-miR-181b |
| hsa-mir-213-precNo1 | uc.177+ | -0.4886 | hsa-miR-181b |
| hsa-mir-181b-1No1 | uc.117+ | -0.4882 | hsa-miR-181b |
| hsa-mir-181b-2No1 | uc.165+ | -0.4896 | hsa-miR-181b |
| hsa-mir-181b-2No1 | uc.419+A | -0.4865 | hsa-miR-181b |
| hsa-mir-213-precNo1 | uc.466+A | -0.4847 | hsa-miR-181b |
| hsa-mir-181b-1No1 | uc.419+A | -0.4828 | hsa-miR-181b |
| hsa-mir-213-precNo1 | uc.346+A | -0.4822 | hsa-miR-181b |
| hsa-mir-213-precNo1 | uc.463+ | -0.4723 | hsa-miR-181b |
| hsa-mir-213-precNo1 | uc.34+A | -0.4583 | hsa-miR-181b |
| hsa-mir-181b-1No1 | uc.285+ | -0.4539 | hsa-miR-181b |
| hsa-mir-213-precNo1 | uc.339+ | -0.4538 | hsa-miR-181b |
| hsa-mir-213-precNo1 | uc.24+A | -0.4518 | hsa-miR-181b |
| hsa-mir-213-precNo1 | uc.128+A | -0.4508 | hsa-miR-181b |
| hsa-mir-213-precNo1 | uc.389+ | -0.4494 | hsa-miR-181b |
| hsa-mir-213-precNo1 | uc.31+ | -0.4489 | hsa-miR-181b |
| hsa-mir-184-precNo2 | uc.366+ | -0.6711 | hsa-mir-184 |
| hsa-mir-184-precNo2 | uc.389+ | -0.6576 | hsa-mir-184 |
| hsa-mir-184-precNo2 | uc.193+ | -0.6345 | hsa-mir-184 |
| hsa-mir-184-precNo2 | uc.478+ | -0.5881 | hsa-mir-184 |
| hsa-mir-184-precNo2 | uc.346+A | -0.5472 | hsa-mir-184 |
| hsa-mir-184-precNo2 | uc.24+A | -0.5016 | hsa-mir-184 |
| hsa-mir-184-precNo2 | uc.341+A | -0.479 | hsa-mir-184 |
| hsa-mir-184-precNo2 | uc.34+A | -0.4743 | hsa-mir-184 |
| hsa-mir-184-precNo2 | uc.73+ | -0.4685 | hsa-mir-184 |
| hsa-mir-184-precNo2 | uc.310+A | -0.4608 | hsa-mir-184 |

Figure 18 Continued

Calin 8A

| miRNA probe on array | UCR probe on array | Correlations (Spearman Method) | miRNA |
|---|---|---|---|
| hsa-mir-185-precNo2 | uc.462- | -0.553 | hsa-miR-185 |
| hsa-mir-185-precNo2 | uc.345+ | -0.5482 | hsa-miR-185 |
| hsa-mir-185-precNo2 | uc.204- | -0.5346 | hsa-miR-185 |
| hsa-mir-185-precNo2 | uc.229+ | -0.5101 | hsa-miR-185 |
| hsa-mir-185-precNo2 | uc.131- | -0.4978 | hsa-miR-185 |
| hsa-mir-185-precNo2 | uc.177+ | -0.4969 | hsa-miR-185 |
| hsa-mir-185-precNo2 | uc.346+ | -0.4961 | hsa-miR-185 |
| hsa-mir-185-precNo2 | uc.41+ | -0.4817 | hsa-miR-185 |
| hsa-mir-185-precNo2 | uc.349+ | -0.4518 | hsa-miR-185 |
| hsa-mir-191-prec | uc.41- | -0.5999 | hsa-miR-191 |
| hsa-mir-191-prec | uc.465+A | -0.5892 | hsa-miR-191 |
| hsa-mir-191-prec | uc.142- | -0.4801 | hsa-miR-191 |
| hsa-mir-191-prec | uc.73+ | -0.4703 | hsa-miR-191 |
| hsa-mir-191-prec | uc.282+A | -0.4678 | hsa-miR-191 |
| hsa-mir-191-prec | uc.241-A | -0.4531 | hsa-miR-191 |
| hsa-mir-193-precNo2 | uc.388+ | -0.7732 | hsa-miR-193a |
| hsa-mir-193-precNo2 | uc.477+A | -0.7699 | hsa-miR-193a |
| hsa-mir-193-precNo2 | uc.387+A | -0.7676 | hsa-miR-193a |
| hsa-mir-193-precNo2 | uc.190-A | -0.7657 | hsa-miR-193a |
| hsa-mir-193-precNo2 | uc.20+A | -0.7459 | hsa-miR-193a |
| hsa-mir-193-precNo2 | uc.477+ | -0.7449 | hsa-miR-193a |
| hsa-mir-193-precNo2 | uc.456+A | -0.7433 | hsa-miR-193a |
| hsa-mir-193-precNo2 | uc.20+ | -0.7382 | hsa-miR-193a |
| hsa-mir-193-precNo2 | uc.378- | -0.7376 | hsa-miR-193a |
| hsa-mir-193-precNo2 | uc.468+A | -0.729 | hsa-miR-193a |
| hsa-mir-193-precNo2 | uc.378-A | -0.7006 | hsa-miR-193a |
| hsa-mir-193-precNo2 | uc.217+ | -0.6952 | hsa-miR-193a |
| hsa-mir-193-precNo2 | uc.43+ | -0.6917 | hsa-miR-193a |
| hsa-mir-193-precNo2 | uc.473+A | -0.6852 | hsa-miR-193a |
| hsa-mir-193-precNo2 | uc.362+ | -0.6841 | hsa-miR-193a |
| hsa-mir-193-precNo2 | uc.354+A | -0.6795 | hsa-miR-193a |
| hsa-mir-193-precNo2 | uc.190+ | -0.6704 | hsa-miR-193a |
| hsa-mir-193-precNo2 | uc.263- | -0.6594 | hsa-miR-193a |
| hsa-mir-193-precNo2 | uc.106+ | -0.6571 | hsa-miR-193a |
| hsa-mir-193-precNo2 | uc.462+A | -0.6558 | hsa-miR-193a |
| hsa-mir-193-precNo2 | uc.448+A | -0.6482 | hsa-miR-193a |
| hsa-mir-193-precNo2 | uc.275+ | -0.6458 | hsa-miR-193a |
| hsa-mir-193-precNo2 | uc.153+ | -0.6408 | hsa-miR-193a |
| hsa-mir-193-precNo2 | uc.456+ | -0.6334 | hsa-miR-193a |
| hsa-mir-193-precNo2 | uc.73-A | -0.6307 | hsa-miR-193a |
| hsa-mir-193-precNo2 | uc.362+A | -0.6287 | hsa-miR-193a |
| hsa-mir-193-precNo2 | uc.63+ | -0.6291 | hsa-miR-193a |
| hsa-mir-193-precNo2 | uc.427+ | -0.6069 | hsa-miR-193a |
| hsa-mir-193-precNo2 | uc.338- | -0.5993 | hsa-miR-193a |
| hsa-mir-193-precNo2 | uc.412+A | -0.5972 | hsa-miR-193a |
| hsa-mir-193-precNo2 | uc.448+ | -0.5929 | hsa-miR-193a |
| hsa-mir-193-precNo2 | uc.153+A | -0.5863 | hsa-miR-193a |
| hsa-mir-193-precNo2 | uc.234+ | -0.5721 | hsa-miR-193a |
| hsa-mir-193-precNo2 | uc.95- | -0.5709 | hsa-miR-193a |
| hsa-mir-193-precNo2 | uc.170+ | -0.5703 | hsa-miR-193a |
| hsa-mir-193-precNo2 | uc.413+ | -0.5652 | hsa-miR-193a |
| hsa-mir-193-precNo2 | uc.182+ | -0.5558 | hsa-miR-193a |
| hsa-mir-193-precNo2 | uc.445+A | -0.5488 | hsa-miR-193a |
| hsa-mir-193-precNo2 | uc.280- | -0.5483 | hsa-miR-193a |
| hsa-mir-193-precNo2 | uc.468+ | -0.5482 | hsa-miR-193a |
| hsa-mir-193-precNo2 | uc.248+ | -0.545 | hsa-miR-193a |
| hsa-mir-193-precNo2 | uc.383+ | -0.5417 | hsa-miR-193a |
| hsa-mir-193-precNo2 | uc.88- | -0.5295 | hsa-miR-193a |
| hsa-mir-193-precNo2 | uc.88+A | -0.5215 | hsa-miR-193a |
| hsa-mir-193-precNo2 | uc.475+A | -0.5077 | hsa-miR-193a |
| hsa-mir-193-precNo2 | uc.44-A | -0.5047 | hsa-miR-193a |
| hsa-mir-193-precNo2 | uc.189+ | -0.5009 | hsa-miR-193a |
| hsa-mir-193-precNo2 | uc.48-A | -0.4902 | hsa-miR-193a |
| hsa-mir-193-precNo2 | uc.159+A | -0.4807 | hsa-miR-193a |
| hsa-mir-193-precNo2 | uc.217-A | -0.479 | hsa-miR-193a |
| hsa-mir-193-precNo2 | uc.177+A | -0.4761 | hsa-miR-193a |
| hsa-mir-193-precNo2 | uc.18- | -0.4545 | hsa-miR-193a |
| hsa-mir-193-precNo2 | uc.263+A | -0.454 | hsa-miR-193a |
| hsa-mir-194-precNo1 | uc.159+A | -0.6811 | hsa-miR-194 |
| hsa-mir-194-precNo1 | uc.95- | -0.6761 | hsa-miR-194 |
| hsa-mir-194-precNo1 | uc.287+A | -0.6403 | hsa-miR-194 |
| hsa-mir-194-precNo1 | uc.88-A | -0.6004 | hsa-miR-194 |
| hsa-mir-194-precNo1 | uc.200+ | -0.5876 | hsa-miR-194 |
| hsa-mir-194-precNo1 | uc.477-A | -0.5561 | hsa-miR-194 |
| hsa-mir-194-precNo1 | uc.217- | -0.5458 | hsa-miR-194 |
| hsa-mir-194-precNo1 | uc.73+A | -0.5439 | hsa-miR-194 |
| hsa-mir-194-precNo1 | uc.475+A | -0.5427 | hsa-miR-194 |
| hsa-mir-194-precNo1 | uc.448+ | -0.5099 | hsa-miR-194 |
| hsa-mir-194-precNo1 | uc.475- | -0.506 | hsa-miR-194 |
| hsa-mir-194-precNo1 | uc.448+A | -0.4951 | hsa-miR-194 |
| hsa-mir-194-precNo1 | uc.473+ | -0.4945 | hsa-miR-194 |
| hsa-mir-194-precNo1 | uc.362+A | -0.4914 | hsa-miR-194 |
| hsa-mir-194-precNo1 | uc.413+ | -0.4779 | hsa-miR-194 |
| hsa-mir-194-2Nc1 | uc.1+ | -0.4717 | hsa-miR-194 |

Figure 18 Continued

| miRNA probe on array | UCR probe on array | Correlations (Spearman Method) | miRNA |
|---|---|---|---|
| hsa-mir-194-2No1 | uc.453+A | -0.462 | hsa-miR-194 |
| hsa-mir-194-precNo1 | uc.388+ | -0.4574 | hsa-miR-194 |
| hsa-mir-194-precNo1 | uc.462+A | -0.4567 | hsa-miR-194 |
| hsa-mir-194-precNo1 | uc.281+A | -0.456 | hsa-miR-194 |
| hsa-mir-194-precNo1 | uc.63+ | -0.4508 | hsa-miR-194 |
| hsa-mir-195-prec | uc.420+ | -0.7876 | hsa-miR-195 |
| hsa-mir-195-prec | uc.189+ | -0.7078 | hsa-miR-195 |
| hsa-mir-195-prec | uc.299+A | -0.6535 | hsa-miR-195 |
| hsa-mir-195-prec | uc.44+A | -0.6169 | hsa-miR-195 |
| hsa-mir-195-prec | uc.78+ | -0.6154 | hsa-miR-195 |
| hsa-mir-195-prec | uc.412+A | -0.6149 | hsa-miR-195 |
| hsa-mir-195-prec | uc.462+A | -0.6119 | hsa-miR-195 |
| hsa-mir-195-prec | uc.33+A | -0.6097 | hsa-miR-195 |
| hsa-mir-195-prec | uc.412+ | -0.6071 | hsa-miR-195 |
| hsa-mir-195-prec | uc.8+ | -0.5817 | hsa-miR-195 |
| hsa-mir-195-prec | uc.338+ | -0.5741 | hsa-miR-195 |
| hsa-mir-195-prec | uc.456+A | -0.5716 | hsa-miR-195 |
| hsa-mir-195-prec | uc.285+ | -0.5596 | hsa-miR-195 |
| hsa-mir-195-prec | uc.151+ | -0.5445 | hsa-miR-195 |
| hsa-mir-195-prec | uc.161+A | -0.5436 | hsa-miR-195 |
| hsa-mir-195-prec | uc.190+A | -0.5413 | hsa-miR-195 |
| hsa-mir-195-prec | uc.354+A | -0.5353 | hsa-miR-195 |
| hsa-mir-195-prec | uc.73+A | -0.5318 | hsa-miR-195 |
| hsa-mir-195-prec | uc.331+A | -0.5276 | hsa-miR-195 |
| hsa-mir-195-prec | uc.427+ | -0.5234 | hsa-miR-195 |
| hsa-mir-195-prec | uc.456+ | -0.5217 | hsa-miR-195 |
| hsa-mir-195-prec | uc.477+A | -0.5094 | hsa-miR-195 |
| hsa-mir-195-prec | uc.378+A | -0.5092 | hsa-miR-195 |
| hsa-mir-195-prec | uc.10+ | -0.4824 | hsa-miR-195 |
| hsa-mir-195-prec | uc.134+ | -0.4814 | hsa-miR-195 |
| hsa-mir-195-prec | uc.88+ | -0.467 | hsa-miR-195 |
| hsa-mir-195-prec | uc.378+ | -0.4667 | hsa-miR-195 |
| hsa-mir-195-prec | uc.275+ | -0.4599 | hsa-miR-195 |
| hsa-mir-195-prec | uc.448+ | -0.4581 | hsa-miR-195 |
| hsa-mir-195-prec | uc.234+ | -0.4533 | hsa-miR-195 |
| hsa-mir-195-prec | uc.33+ | -0.4519 | hsa-miR-195 |
| hsa-mir-195-prec | uc.153+A | -0.4503 | hsa-miR-195 |
| hsa-mir-196-2-precNo2 | uc.366+ | -0.674 | hsa-miR-196a |
| hsa-mir-196-2-precNo2 | uc.192+ | -0.653 | hsa-miR-196a |
| hsa-mir-196-2-precNo2 | uc.230+ | -0.5495 | hsa-miR-196a |
| hsa-mir-196-2-precNo2 | uc.478+ | -0.5265 | hsa-miR-196a |
| hsa-mir-196-2-precNo2 | uc.181+A | -0.5243 | hsa-miR-196a |
| hsa-mir-196-2-precNo2 | uc.473+ | -0.4941 | hsa-miR-196a |
| hsa-mir-196-2-precNo2 | uc.125+A | -0.4886 | hsa-miR-196a |
| hsa-mir-196-2-precNo2 | uc.345+A | -0.4551 | hsa-miR-196a |
| hsa-mir-196-2-precNo2 | uc.131+ | -0.4493 | hsa-miR-196a |
| hsa-mir-196bNo2 | uc.192+ | -0.5465 | hsa-miR-196b |
| hsa-mir-196bNo2 | uc.341+A | -0.5396 | hsa-miR-196b |
| hsa-mir-196bNo2 | uc.204+ | -0.4733 | hsa-miR-196b |
| hsa-mir-196bNo2 | uc.41+ | -0.4731 | hsa-miR-196b |
| hsa-mir-196bNo2 | uc.366+ | -0.454 | hsa-miR-196b |
| hsa-mir-197-prec | uc.229+ | -0.745 | hsa-miR-197 |
| hsa-mir-197-prec | uc.466+A | -0.6606 | hsa-miR-197 |
| hsa-mir-197-prec | uc.73+ | -0.6459 | hsa-miR-197 |
| hsa-mir-197-prec | uc.345+ | -0.6329 | hsa-miR-197 |
| hsa-mir-197-prec | uc.349+ | -0.6289 | hsa-miR-197 |
| hsa-mir-197-prec | uc.426+ | -0.6162 | hsa-miR-197 |
| hsa-mir-197-prec | uc.483+ | -0.6125 | hsa-miR-197 |
| hsa-mir-197-prec | uc.41+ | -0.5966 | hsa-miR-197 |
| hsa-mir-197-prec | uc.204+ | -0.5663 | hsa-miR-197 |
| hsa-mir-197-prec | uc.177+ | -0.5607 | hsa-miR-197 |
| hsa-mir-197-prec | uc.278+ | -0.543 | hsa-miR-197 |
| hsa-mir-197-prec | uc.134+A | -0.5007 | hsa-miR-197 |
| hsa-mir-197-prec | uc.346+ | -0.4916 | hsa-miR-197 |
| hsa-mir-197-prec | uc.462+ | -0.4873 | hsa-miR-197 |
| hsa-mir-197-prec | uc.128+A | -0.4698 | hsa-miR-197 |
| hsa-mir-197-prec | uc.131+ | -0.4663 | hsa-miR-197 |
| hsa-mir-197-prec | uc.365+ | -0.4641 | hsa-miR-197 |
| hsa-mir-197-prec | uc.77+ | -0.4641 | hsa-miR-197 |
| hsa-mir-197-prec | uc.345+A | -0.4601 | hsa-miR-197 |
| hsa-mir-197-prec | uc.172+A | -0.4516 | hsa-miR-197 |
| hsa-mir-019b-1-prec | uc.117+ | -0.5477 | hsa-miR-19b |
| hsa-mir-019b-1-prec | uc.285+ | -0.4772 | hsa-miR-19b |
| hsa-mir-204-precNo2 | uc.287+A | -0.7123 | hsa-mir-204 |
| hsa-mir-204-precNo2 | uc.378+A | -0.6691 | hsa-mir-204 |
| hsa-mir-204-precNo2 | uc.445+A | -0.6689 | hsa-mir-204 |
| hsa-mir-204-precNo2 | uc.190+A | -0.6664 | hsa-mir-204 |
| hsa-mir-204-precNo2 | uc.354+A | -0.659 | hsa-mir-204 |
| hsa-mir-204-precNo2 | uc.275+ | -0.6581 | hsa-mir-204 |
| hsa-mir-204-precNo2 | uc.477+A | -0.6528 | hsa-mir-204 |
| hsa-mir-204-precNo2 | uc.43+ | -0.6526 | hsa-mir-204 |
| hsa-mir-204-precNo2 | uc.473+A | -0.6519 | hsa-mir-204 |
| hsa-mir-204-precNo2 | uc.462+A | -0.6483 | hsa-mir-204 |
| hsa-mir-204-precNo2 | uc.383+ | -0.6306 | hsa-mir-204 |

Figure 18 Continued

| miRNA probe on array | UCR probe on array | Correlations (Spearman Method) | miRNA |
|---|---|---|---|
| hsa-mir-204-precNo2 | uc.420+ | -0.614 | hsa-mir-204 |
| hsa-mir-204-precNo2 | uc.189+ | -0.6121 | hsa-mir-204 |
| hsa-mir-204-precNo2 | uc.20+ | -0.5883 | hsa-mir-204 |
| hsa-mir-204-precNo2 | uc.468+ | -0.5848 | hsa-mir-204 |
| hsa-mir-204-precNo2 | uc.88+ | -0.5815 | hsa-mir-204 |
| hsa-mir-204-precNo2 | uc.217+A | -0.5741 | hsa-mir-204 |
| hsa-mir-204-precNo2 | uc.362+A | -0.5707 | hsa-mir-204 |
| hsa-mir-204-precNo2 | uc.378+ | -0.5684 | hsa-mir-204 |
| hsa-mir-204-precNo2 | uc.8+ | -0.5606 | hsa-mir-204 |
| hsa-mir-204-precNo2 | uc.20+A | -0.5593 | hsa-mir-204 |
| hsa-mir-204-precNo2 | uc.412+A | -0.5556 | hsa-mir-204 |
| hsa-mir-204-precNo2 | uc.468+A | -0.5538 | hsa-mir-204 |
| hsa-mir-204-precNo2 | uc.388+ | -0.5469 | hsa-mir-204 |
| hsa-mir-204-precNo2 | uc.299+A | -0.5419 | hsa-mir-204 |
| hsa-mir-204-precNo2 | uc.153+A | -0.5392 | hsa-mir-204 |
| hsa-mir-204-precNo2 | uc.33+ | -0.5329 | hsa-mir-204 |
| hsa-mir-204-precNo2 | uc.73+A | -0.514 | hsa-mir-204 |
| hsa-mir-204-precNo2 | uc.63+ | -0.5134 | hsa-mir-204 |
| hsa-mir-204-precNo2 | uc.106+ | -0.5125 | hsa-mir-204 |
| hsa-mir-204-precNo2 | uc.234+ | -0.5107 | hsa-mir-204 |
| hsa-mir-204-precNo2 | uc.153+ | -0.5062 | hsa-mir-204 |
| hsa-mir-204-precNo2 | uc.18+ | -0.5051 | hsa-mir-204 |
| hsa-mir-204-precNo2 | uc.338+ | -0.4907 | hsa-mir-204 |
| hsa-mir-204-precNo2 | uc.456+A | -0.4881 | hsa-mir-204 |
| hsa-mir-204-precNo2 | uc.456+ | -0.4788 | hsa-mir-204 |
| hsa-mir-204-precNo2 | uc.217+ | -0.4772 | hsa-mir-204 |
| hsa-mir-204-precNo2 | uc.477+ | -0.4756 | hsa-mir-204 |
| hsa-mir-204-precNo2 | uc.182+ | -0.4648 | hsa-mir-204 |
| hsa-mir-204-precNo2 | uc.388+A | -0.4644 | hsa-mir-204 |
| hsa-mir-204-precNo2 | uc.190+ | -0.4643 | hsa-mir-204 |
| hsa-mir-204-precNo2 | uc.475+A | -0.461 | hsa-mir-204 |
| hsa-mir-204-precNo2 | uc.448+A | -0.4577 | hsa-mir-204 |
| hsa-mir-204-precNo2 | uc.427+ | -0.45 | hsa-mir-204 |
| hsa-mir-206-precNo1 | uc.181+A | -0.6652 | hsa-miR-206 |
| hsa-mir-206-precNo2 | uc.90+A | -0.6609 | hsa-mir-206 |
| hsa-mir-206-precNo2 | uc.298+ | -0.6521 | hsa-mir-206 |
| hsa-mir-206-precNo2 | uc.159+A | -0.6404 | hsa-mir-206 |
| hsa-mir-206-precNo2 | uc.278+A | -0.6383 | hsa-mir-206 |
| hsa-mir-206-precNo2 | uc.95+ | -0.6274 | hsa-mir-206 |
| hsa-mir-206-precNo2 | uc.291+ | -0.6115 | hsa-mir-206 |
| hsa-mir-206-precNo2 | uc.217+ | -0.5949 | hsa-mir-206 |
| hsa-mir-206-precNo2 | uc.480+ | -0.5927 | hsa-mir-206 |
| hsa-mir-206-precNo2 | uc.392+ | -0.5749 | hsa-mir-206 |
| hsa-mir-206-precNo2 | uc.156+ | -0.5645 | hsa-mir-206 |
| hsa-mir-206-precNo2 | uc.88+A | -0.5614 | hsa-mir-206 |
| hsa-mir-206-precNo1 | uc.125+A | -0.553 | hsa-miR-206 |
| hsa-mir-206-precNo1 | uc.366+ | -0.5487 | hsa-miR-206 |
| hsa-mir-206-precNo2 | uc.223+A | -0.5471 | hsa-mir-206 |
| hsa-mir-206-precNo2 | uc.475+A | -0.5422 | hsa-mir-206 |
| hsa-mir-206-precNo1 | uc.192+ | -0.5404 | hsa-miR-206 |
| hsa-mir-206-precNo1 | uc.230+ | -0.5395 | hsa-miR-206 |
| hsa-mir-206-precNo2 | uc.456+ | -0.5335 | hsa-mir-206 |
| hsa-mir-206-precNo2 | uc.477+ | -0.5185 | hsa-mir-206 |
| hsa-mir-206-precNo2 | uc.477+A | -0.5149 | hsa-mir-206 |
| hsa-mir-206-precNo2 | uc.378+ | -0.5001 | hsa-mir-206 |
| hsa-mir-206-precNo1 | uc.317+ | -0.4959 | hsa-miR-206 |
| hsa-mir-206-precNo1 | uc.388+ | -0.4836 | hsa-miR-206 |
| hsa-mir-206-precNo2 | uc.20+A | -0.4773 | hsa-mir-206 |
| hsa-mir-206-precNo2 | uc.287+A | -0.4719 | hsa-mir-206 |
| hsa-mir-206-precNo1 | uc.345+A | -0.4716 | hsa-miR-206 |
| hsa-mir-206-precNo2 | uc.448+A | -0.459 | hsa-mir-206 |
| hsa-mir-206-precNo1 | uc.31+ | -0.4561 | hsa-miR-206 |
| hsa-mir-206-precNo2 | uc.448+ | -0.4504 | hsa-mir-206 |
| hsa-mir-020-prec | uc.160+ | -0.6597 | hsa-miR-20a |
| hsa-mir-020-prec | uc.325+ | -0.6068 | hsa-miR-20a |
| hsa-mir-020-prec | uc.478+A | -0.5995 | hsa-miR-20a |
| hsa-mir-020-prec | uc.339+ | -0.5973 | hsa-miR-20a |
| hsa-mir-020-prec | uc.283+A | -0.5956 | hsa-miR-20a |
| hsa-mir-020-prec | uc.282+A | -0.593 | hsa-miR-20a |
| hsa-mir-020-prec | uc.465+A | -0.5781 | hsa-miR-20a |
| hsa-mir-020-prec | uc.167+ | -0.5697 | hsa-miR-20a |
| hsa-mir-020-prec | uc.327+A | -0.5497 | hsa-miR-20a |
| hsa-mir-020-prec | uc.117+ | -0.5329 | hsa-miR-20a |
| hsa-mir-020-prec | uc.48+A | -0.5303 | hsa-miR-20a |
| hsa-mir-020-prec | uc.269+A | -0.5251 | hsa-miR-20a |
| hsa-mir-020-prec | uc.300+A | -0.5206 | hsa-miR-20a |
| hsa-mir-020-prec | uc.213+ | -0.5038 | hsa-miR-20a |
| hsa-mir-020-prec | uc.170+ | -0.4696 | hsa-miR-20a |
| hsa-mir-020-prec | uc.346+ | -0.4629 | hsa-miR-20a |
| hsa-mir-020-prec | uc.84+A | -0.4629 | hsa-miR-20a |
| hsa-mir-020-prec | uc.285+ | -0.4605 | hsa-miR-20a |
| hsa-mir-020-prec | uc.153+A | -0.4507 | hsa-miR-20a |
| hsa-mir-21No1 | uc.33+A | -0.7553 | hsa-miR-21 |
| hsa-mir-21No1 | uc.153+A | -0.7091 | hsa-miR-21 |

Figure 18 Continued

| miRNA probe on array | UCR probe on array | Correlations (Spearman Method) | miRNA |
|---|---|---|---|
| hsa-mir-021-prec-17No1 | uc.88+ | -0.7013 | hsa-miR-21 |
| hsa-mir-021-prec-17No1 | uc.106- | -0.7002 | hsa-miR-21 |
| hsa-mir-021-prec-17No1 | uc.33+A | -0.698 | hsa-miR-21 |
| hsa-mir-21No1 | uc.106- | -0.6969 | hsa-miR-21 |
| hsa-mir-21No1 | uc.213+ | -0.695 | hsa-miR-21 |
| hsa-mir-021-prec-17No1 | uc.473+A | -0.6828 | hsa-miR-21 |
| hsa-mir-21No1 | uc.88+ | -0.6739 | hsa-miR-21 |
| hsa-mir-021-prec-17No1 | uc.217+A | -0.6636 | hsa-miR-21 |
| hsa-mir-021-prec-17No1 | uc.153- | -0.6594 | hsa-miR-21 |
| hsa-mir-021-prec-17No1 | uc.153+A | -0.6543 | hsa-miR-21 |
| hsa-mir-021-prec-17No1 | uc.427- | -0.6481 | hsa-miR-21 |
| hsa-mir-21No1 | uc.153+ | -0.6477 | hsa-miR-21 |
| hsa-mir-21No1 | uc.33+ | -0.6461 | hsa-miR-21 |
| hsa-mir-021-prec-17No1 | uc.263+ | -0.6454 | hsa-miR-21 |
| hsa-mir-21No1 | uc.420- | -0.6425 | hsa-miR-21 |
| hsa-mir-21No1 | uc.383+ | -0.6417 | hsa-miR-21 |
| hsa-mir-21No1 | uc.285+ | -0.6381 | hsa-miR-21 |
| hsa-mir-21No1 | uc.263+ | -0.6346 | hsa-miR-21 |
| hsa-mir-21No1 | uc.18+ | -0.6343 | hsa-miR-21 |
| hsa-mir-021-prec-17No1 | uc.20- | -0.634 | hsa-miR-21 |
| hsa-mir-021-prec-17No1 | uc.213+ | -0.6292 | hsa-miR-21 |
| hsa-mir-021-prec-17No1 | uc.448- | -0.6269 | hsa-miR-21 |
| hsa-mir-21No1 | uc.217+A | -0.6255 | hsa-miR-21 |
| hsa-mir-021-prec-17No1 | uc.462+A | -0.6247 | hsa-miR-21 |
| hsa-mir-021-prec-17No1 | uc.383- | -0.6235 | hsa-miR-21 |
| hsa-mir-021-prec-17No1 | uc.33+ | -0.6214 | hsa-miR-21 |
| hsa-mir-021-prec-17No1 | uc.275- | -0.6197 | hsa-miR-21 |
| hsa-mir-021-prec-17No1 | uc.378+A | -0.6197 | hsa-miR-21 |
| hsa-mir-21No1 | uc.473+A | -0.6179 | hsa-miR-21 |
| hsa-mir-021-prec-17No1 | uc.170+ | -0.6165 | hsa-miR-21 |
| hsa-mir-21No1 | uc.275+ | -0.6162 | hsa-miR-21 |
| hsa-mir-21No1 | uc.427- | -0.6122 | hsa-miR-21 |
| hsa-mir-21No1 | uc.388+A | -0.6096 | hsa-miR-21 |
| hsa-mir-021-prec-17No1 | uc.420- | -0.6093 | hsa-miR-21 |
| hsa-mir-021-prec-17No1 | uc.18+ | -0.6089 | hsa-miR-21 |
| hsa-mir-21No1 | uc.354+A | -0.6071 | hsa-miR-21 |
| hsa-mir-021-prec-17No1 | uc.354+A | -0.6069 | hsa-miR-21 |
| hsa-mir-21No1 | uc.327+A | -0.6025 | hsa-miR-21 |
| hsa-mir-21No1 | uc.20+ | -0.5999 | hsa-miR-21 |
| hsa-mir-021-prec-17No1 | uc.449+A | -0.5961 | hsa-miR-21 |
| hsa-mir-21No1 | uc.189- | -0.5936 | hsa-miR-21 |
| hsa-mir-021-prec-17No1 | uc.48+A | -0.5889 | hsa-miR-21 |
| hsa-mir-21No1 | uc.234- | -0.5854 | hsa-miR-21 |
| hsa-mir-021-prec-17No1 | uc.378- | -0.5807 | hsa-miR-21 |
| hsa-mir-21No1 | uc.448- | -0.5737 | hsa-miR-21 |
| hsa-mir-021-prec-17No1 | uc.267+A | -0.5709 | hsa-miR-21 |
| hsa-mir-21No1 | uc.48+A | -0.5696 | hsa-miR-21 |
| hsa-mir-021-prec-17No1 | uc.477+A | -0.5659 | hsa-miR-21 |
| hsa-mir-021-prec-17No1 | uc.73+A | -0.5624 | hsa-miR-21 |
| hsa-mir-21No1 | uc.73+A | -0.5593 | hsa-miR-21 |
| hsa-mir-021-prec-17No1 | uc.456+A | -0.5587 | hsa-miR-21 |
| hsa-mir-21No1 | uc.456+A | -0.5581 | hsa-miR-21 |
| hsa-mir-021-prec-17No1 | uc.44+A | -0.5571 | hsa-miR-21 |
| hsa-mir-21No1 | uc.346+ | -0.5571 | hsa-miR-21 |
| hsa-mir-21No1 | uc.378+A | -0.5569 | hsa-miR-21 |
| hsa-mir-021-prec-17No1 | uc.20+A | -0.5554 | hsa-miR-21 |
| hsa-mir-21No1 | uc.190+A | -0.5522 | hsa-miR-21 |
| hsa-mir-021-prec-17No1 | uc.234- | -0.5513 | hsa-miR-21 |
| hsa-mir-021-prec-17No1 | uc.388+A | -0.5497 | hsa-miR-21 |
| hsa-mir-021-prec-17No1 | uc.189- | -0.5494 | hsa-miR-21 |
| hsa-mir-021-prec-17No1 | uc.327+A | -0.548 | hsa-miR-21 |
| hsa-mir-021-prec-17No1 | uc.217- | -0.5479 | hsa-miR-21 |
| hsa-mir-021-prec-17No1 | uc.445+A | -0.5446 | hsa-miR-21 |
| hsa-mir-021-prec-17No1 | uc.285- | -0.5435 | hsa-miR-21 |
| hsa-mir-021-prec-17No1 | uc.190+A | -0.5417 | hsa-miR-21 |
| hsa-mir-21No1 | uc.44+A | -0.5414 | hsa-miR-21 |
| hsa-mir-21No1 | uc.462+A | -0.5363 | hsa-miR-21 |
| hsa-mir-21No1 | uc.172+A | -0.5303 | hsa-miR-21 |
| hsa-mir-21No1 | uc.151+A | -0.5301 | hsa-miR-21 |
| hsa-mir-21No1 | uc.170+ | -0.5291 | hsa-miR-21 |
| hsa-mir-021-prec-17No1 | uc.456+ | -0.5264 | hsa-miR-21 |
| hsa-mir-21No1 | uc.20+A | -0.5258 | hsa-miR-21 |
| hsa-mir-21No1 | uc.468- | -0.5256 | hsa-miR-21 |
| hsa-mir-021-prec-17No1 | uc.151+A | -0.5255 | hsa-miR-21 |
| hsa-mir-21No1 | uc.379+ | -0.523 | hsa-miR-21 |
| hsa-mir-21No1 | uc.412+A | -0.522 | hsa-miR-21 |
| hsa-mir-021-prec-17No1 | uc.362+A | -0.5192 | hsa-miR-21 |
| hsa-mir-21No1 | uc.463+A | -0.5152 | hsa-miR-21 |
| hsa-mir-021-prec-17No1 | uc.299+A | -0.5116 | hsa-miR-21 |
| hsa-mir-21No1 | uc.477+A | -0.5086 | hsa-miR-21 |
| hsa-mir-021-prec-17No1 | uc.468+A | -0.5035 | hsa-miR-21 |
| hsa-mir-21No1 | uc.468+A | -0.4983 | hsa-miR-21 |
| hsa-mir-21No1 | uc.388+ | -0.4914 | hsa-miR-21 |
| hsa-mir-021-prec-17No1 | uc.412+A | -0.4907 | hsa-miR-21 |

Figure 18 Continued

| miRNA probe on array | UCR probe on array | Correlations (Spearman Method) | miRNA |
|---|---|---|---|
| hsa-mir-21No1 | uc.445+A | -0.4896 | hsa-miR-21 |
| hsa-mir-21No1 | uc.299+A | -0.4883 | hsa-miR-21 |
| hsa-mir-021-prec-17No1 | uc.388+ | -0.4878 | hsa-miR-21 |
| hsa-mir-021-prec-17No1 | uc.331+A | -0.4855 | hsa-miR-21 |
| hsa-mir-21No1 | uc.287+A | -0.4752 | hsa-miR-21 |
| hsa-mir-021-prec-17No1 | uc.463+A | -0.4745 | hsa-miR-21 |
| hsa-mir-21No1 | uc.160+ | -0.4736 | hsa-miR-21 |
| hsa-mir-021-prec-17No1 | uc.263+A | -0.4725 | hsa-miR-21 |
| hsa-mir-21No1 | uc.77+ | -0.4692 | hsa-miR-21 |
| hsa-mir-021-prec-17No1 | uc.167+ | -0.4681 | hsa-miR-21 |
| hsa-mir-21No1 | uc.43+ | -0.4668 | hsa-miR-21 |
| hsa-mir-21No1 | uc.217+ | -0.4603 | hsa-miR-21 |
| hsa-mir-21No1 | uc.456+ | -0.4594 | hsa-miR-21 |
| hsa-mir-21No1 | uc.465+A | -0.4578 | hsa-miR-21 |
| hsa-mir-021-prec-17No1 | uc.95+ | -0.4522 | hsa-miR-21 |
| hsa-mir-21No1 | uc.263+A | -0.4515 | hsa-miR-21 |
| hsa-mir-21No1 | uc.128+A | -0.4498 | hsa-miR-21 |
| hsa-mir-21No1 | uc.183+ | -0.4488 | hsa-miR-21 |
| hsa-mir-21No1 | uc.331+A | -0.4487 | hsa-miR-21 |
| hsa-mir-210-prec | uc.159+A | -0.4855 | hsa-miR-210 |
| hsa-mir-210-prec | uc.296+ | -0.461 | hsa-miR-210 |
| hsa-mir-210-prec | uc.278+A | -0.4527 | hsa-miR-210 |
| hsa-mir-212-precNo1 | uc.483+ | -0.6884 | hsa-miR-212 |
| hsa-mir-212-precNo1 | uc.41+ | -0.6482 | hsa-miR-212 |
| hsa-mir-212-precNo1 | uc.77+ | -0.5846 | hsa-miR-212 |
| hsa-mir-212-precNo2 | uc.389+ | -0.5803 | hsa-miR-212 |
| hsa-mir-212-precNo1 | uc.229+ | -0.5656 | hsa-miR-212 |
| hsa-mir-212-precNo2 | uc.41+ | -0.5624 | hsa-miR-212 |
| hsa-mir-212-precNo1 | uc.128+A | -0.5609 | hsa-miR-212 |
| hsa-mir-212-precNo1 | uc.177+ | -0.5507 | hsa-miR-212 |
| hsa-mir-212-precNo2 | uc.34+A | -0.5308 | hsa-miR-212 |
| hsa-mir-212-precNo2 | uc.142+ | -0.5306 | hsa-miR-212 |
| hsa-mir-212-precNo1 | uc.172+A | -0.5202 | hsa-miR-212 |
| hsa-mir-212-precNo1 | uc.304+ | -0.5041 | hsa-miR-212 |
| hsa-mir-212-precNo1 | uc.345+ | -0.5016 | hsa-miR-212 |
| hsa-mir-212-precNo1 | uc.346+ | -0.4992 | hsa-miR-212 |
| hsa-mir-212-precNo1 | uc.73+ | -0.4991 | hsa-miR-212 |
| hsa-mir-212-precNo2 | uc.310+A | -0.4986 | hsa-miR-212 |
| hsa-mir-212-precNo2 | uc.466+A | -0.4863 | hsa-miR-212 |
| hsa-mir-212-precNo1 | uc.436+ | -0.4768 | hsa-miR-212 |
| hsa-mir-212-precNo2 | uc.478+ | -0.4719 | hsa-miR-212 |
| hsa-mir-212-precNo2 | uc.304+A | -0.4713 | hsa-miR-212 |
| hsa-mir-212-precNo2 | uc.483+ | -0.4628 | hsa-miR-212 |
| hsa-mir-212-precNo1 | uc.366+ | -0.4568 | hsa-miR-212 |
| hsa-mir-212-precNo1 | uc.349+ | -0.4532 | hsa-miR-212 |
| hsa-mir-214-prec | uc.466+A | -0.6614 | hsa-miR-214 |
| hsa-mir-214-prec | uc.136+ | -0.6576 | hsa-miR-214 |
| hsa-mir-214-prec | uc.426+ | -0.6547 | hsa-miR-214 |
| hsa-mir-214-prec | uc.229+ | -0.6505 | hsa-miR-214 |
| hsa-mir-214-prec | uc.345+A | -0.6157 | hsa-miR-214 |
| hsa-mir-214-prec | uc.73+ | -0.6091 | hsa-miR-214 |
| hsa-mir-214-prec | uc.366+ | -0.6015 | hsa-miR-214 |
| hsa-mir-214-prec | uc.349+ | -0.5879 | hsa-miR-214 |
| hsa-mir-214-prec | uc.204+ | -0.5678 | hsa-miR-214 |
| hsa-mir-214-prec | uc.278+ | -0.5276 | hsa-miR-214 |
| hsa-mir-214-prec | uc.345+ | -0.5223 | hsa-miR-214 |
| hsa-mir-214-prec | uc.177+ | -0.5221 | hsa-miR-214 |
| hsa-mir-214-prec | uc.483+ | -0.5202 | hsa-miR-214 |
| hsa-mir-214-prec | uc.462+ | -0.5156 | hsa-miR-214 |
| hsa-mir-214-prec | uc.185+ | -0.5051 | hsa-miR-214 |
| hsa-mir-214-prec | uc.346+ | -0.5041 | hsa-miR-214 |
| hsa-mir-214-prec | uc.131+ | -0.5017 | hsa-miR-214 |
| hsa-mir-214-prec | uc.41+ | -0.4941 | hsa-miR-214 |
| hsa-mir-214-prec | uc.262+A | -0.4932 | hsa-miR-214 |
| hsa-mir-214-prec | uc.125+A | -0.4836 | hsa-miR-214 |
| hsa-mir-214-prec | uc.134+A | -0.4761 | hsa-miR-214 |
| hsa-mir-214-prec | uc.192+ | -0.4684 | hsa-miR-214 |
| hsa-mir-215-precNo1 | uc.151+A | -0.45 | hsa-miR-215 |
| hsa-mir-218-2-precNo2 | uc.440+ | -0.6982 | hsa-miR-218 |
| hsa-mir-218-2-precNo2 | uc.456+ | -0.686 | hsa-miR-218 |
| hsa-mir-218-2-precNo2 | uc.477+A | -0.6519 | hsa-miR-218 |
| hsa-mir-218-2-precNo2 | uc.30+ | -0.6431 | hsa-miR-218 |
| hsa-mir-218-2-precNo2 | uc.473+A | -0.6284 | hsa-miR-218 |
| hsa-mir-218-2-precNo2 | uc.95+ | -0.6152 | hsa-miR-218 |
| hsa-mir-218-2-precNo2 | uc.287+A | -0.6065 | hsa-miR-218 |
| hsa-mir-218-2-precNo2 | uc.475+A | -0.6013 | hsa-miR-218 |
| hsa-mir-218-2-precNo2 | uc.283+ | -0.5944 | hsa-miR-218 |
| hsa-mir-218-2-precNo2 | uc.217+ | -0.5942 | hsa-miR-218 |
| hsa-mir-218-2-precNo2 | uc.20+A | -0.5892 | hsa-miR-218 |
| hsa-mir-218-2-precNo2 | uc.448+A | -0.5858 | hsa-miR-218 |
| hsa-mir-218-2-precNo2 | uc.427+ | -0.5846 | hsa-miR-218 |
| hsa-mir-218-2-precNo2 | uc.362+A | -0.5694 | hsa-miR-218 |
| hsa-mir-218-2-precNo2 | uc.378+ | -0.564 | hsa-miR-218 |
| hsa-mir-218-2-precNo2 | uc.275+ | -0.549 | hsa-miR-218 |

Figure 18 Continued

Calin GA

| miRNA probe on array | UCR probe on array | Correlations (Spearman Method) | miRNA |
|---|---|---|---|
| hsa-mir-218-2-precNo2 | uc.378+A | -0.5473 | hsa-miR-218 |
| hsa-mir-218-2-precNo2 | uc.170+ | -0.5371 | hsa-miR-218 |
| hsa-mir-218-2-precNo2 | uc.477+ | -0.5153 | hsa-miR-218 |
| hsa-mir-218-2-precNo2 | uc.468+A | -0.5117 | hsa-miR-218 |
| hsa-mir-218-2-precNo2 | uc.88+ | -0.5116 | hsa-miR-218 |
| hsa-mir-218-2-precNo2 | uc.86+A | -0.5041 | hsa-miR-218 |
| hsa-mir-218-2-precNo2 | uc.63+ | -0.5025 | hsa-miR-218 |
| hsa-mir-218-2-precNo2 | uc.363+ | -0.4995 | hsa-miR-218 |
| hsa-mir-218-2-precNo2 | uc.159+A | -0.4888 | hsa-miR-218 |
| hsa-mir-218-2-precNo2 | uc.331+A | -0.4886 | hsa-miR-218 |
| hsa-mir-218-2-precNo2 | uc.388+ | -0.488 | hsa-miR-218 |
| hsa-mir-218-2-precNo2 | uc.263+A | -0.4774 | hsa-miR-218 |
| hsa-mir-218-2-precNo2 | uc.200+ | -0.4738 | hsa-miR-218 |
| hsa-mir-218-2-precNo2 | uc.462+A | -0.4668 | hsa-miR-218 |
| hsa-mir-218-2-precNo2 | uc.190+A | -0.4628 | hsa-miR-218 |
| hsa-mir-218-2-precNo2 | uc.412+ | -0.4594 | hsa-miR-218 |
| hsa-mir-218-2-precNo2 | uc.445+A | -0.4551 | hsa-miR-218 |
| hsa-mir-218-2-precNo2 | uc.362+ | -0.4504 | hsa-miR-218 |
| hsa-mir-218-2-precNo2 | uc.456+A | -0.4495 | hsa-miR-218 |
| hsa-mir-218-2-precNo2 | uc.44+A | -0.4477 | hsa-miR-218 |
| hsa-mir-219-1No1 | uc.249+ | -0.4836 | hsa-miR-219 |
| hsa-mir-219-1No1 | uc.378+ | -0.4756 | hsa-miR-219 |
| hsa-mir-219-1No1 | uc.153+ | -0.4548 | hsa-miR-219 |
| hsa-mir-219-1No1 | uc.477+ | -0.4536 | hsa-miR-219 |
| hsa-mir-219-1No1 | uc.456+ | -0.4534 | hsa-miR-219 |
| hsa-mir-219-1No2 | uc.8+ | -0.6477 | hsa-mir-219-1 |
| hsa-mir-219-1No2 | uc.189+ | -0.583 | hsa-mir-219-1 |
| hsa-mir-219-1No2 | uc.190+A | -0.5699 | hsa-mir-219-1 |
| hsa-mir-219-1No2 | uc.477+A | -0.5555 | hsa-mir-219-1 |
| hsa-mir-219-1No2 | uc.420+ | -0.5343 | hsa-mir-219-1 |
| hsa-mir-219-1No2 | uc.378+ | -0.5441 | hsa-mir-219-1 |
| hsa-mir-219-1No2 | uc.412+A | -0.5309 | hsa-mir-219-1 |
| hsa-mir-219-1No2 | uc.412+ | -0.5279 | hsa-mir-219-1 |
| hsa-mir-219-1No2 | uc.468+A | -0.5259 | hsa-mir-219-1 |
| hsa-mir-219-1No2 | uc.462+A | -0.5229 | hsa-mir-219-1 |
| hsa-mir-219-1No2 | uc.388+ | -0.5183 | hsa-mir-219-1 |
| hsa-mir-219-1No2 | uc.354+A | -0.5059 | hsa-mir-219-1 |
| hsa-mir-219-1No2 | uc.287+A | -0.4809 | hsa-mir-219-1 |
| hsa-mir-219-1No2 | uc.190+ | -0.4782 | hsa-mir-219-1 |
| hsa-mir-219-1No2 | uc.217+ | -0.4717 | hsa-mir-219-1 |
| hsa-mir-219-1No2 | uc.43+ | -0.468 | hsa-mir-219-1 |
| hsa-mir-219-1No2 | uc.445+A | -0.4672 | hsa-mir-219-1 |
| hsa-mir-219-1No2 | uc.473+A | -0.4655 | hsa-mir-219-1 |
| hsa-mir-219-1No2 | uc.456+ | -0.4634 | hsa-mir-219-1 |
| hsa-mir-219-1No2 | uc.378+A | -0.461 | hsa-mir-219-1 |
| hsa-mir-219-1No2 | uc.275+ | -0.4607 | hsa-mir-219-1 |
| hsa-mir-219-1No2 | uc.339+ | -0.4497 | hsa-mir-219-1 |
| hsa-mir-219-1No2 | uc.477+ | -0.4488 | hsa-mir-219-1 |
| hsa-mir-221-prec | uc.282+A | -0.6378 | hsa-miR-221 |
| hsa-mir-221-prec | uc.325+ | -0.6289 | hsa-miR-221 |
| hsa-mir-221-prec | uc.346+A | -0.6232 | hsa-miR-221 |
| hsa-mir-221-prec | uc.339+ | -0.596 | hsa-miR-221 |
| hsa-mir-221-prec | uc.465+A | -0.5944 | hsa-miR-221 |
| hsa-mir-221-prec | uc.283+A | -0.5151 | hsa-miR-221 |
| hsa-mir-221-prec | uc.204+ | -0.4824 | hsa-miR-221 |
| hsa-mir-221-prec | uc.269+A | -0.4761 | hsa-miR-221 |
| hsa-mir-221-prec | uc.398+ | -0.4728 | hsa-miR-221 |
| hsa-mir-221-prec | uc.300+A | -0.4688 | hsa-miR-221 |
| hsa-mir-222-precNo2 | uc.331+A | -0.5434 | hsa-mir-222 |
| hsa-mir-222-precNo2 | uc.213+ | -0.5191 | hsa-mir-222 |
| hsa-mir-222-precNo2 | uc.419+A | -0.5138 | hsa-mir-222 |
| hsa-mir-222-precNo2 | uc.275+ | -0.5104 | hsa-mir-222 |
| hsa-mir-222-precNo2 | uc.465+A | -0.5054 | hsa-mir-222 |
| hsa-mir-222-precNo2 | uc.285+ | -0.5004 | hsa-mir-222 |
| hsa-mir-222-precNo2 | uc.420+ | -0.4996 | hsa-mir-222 |
| hsa-mir-222-precNo2 | uc.33+A | -0.4881 | hsa-mir-222 |
| hsa-mir-222-precNo2 | uc.172+A | -0.4818 | hsa-mir-222 |
| hsa-mir-222-precNo2 | uc.456+A | -0.4695 | hsa-mir-222 |
| hsa-mir-222-precNo2 | uc.282+A | -0.4683 | hsa-mir-222 |
| hsa-mir-222-precNo2 | uc.398+A | -0.4659 | hsa-mir-222 |
| hsa-mir-222-precNo2 | uc.173+ | -0.4619 | hsa-mir-222 |
| hsa-mir-222-precNo2 | uc.325+ | -0.4502 | hsa-mir-222 |
| hsa-mir-223-prec | uc.18+ | -0.5605 | hsa-miR-223 |
| hsa-mir-223-prec | uc.128+A | -0.5212 | hsa-miR-223 |
| hsa-mir-223-prec | uc.151+ | -0.5035 | hsa-miR-223 |
| hsa-mir-223-prec | uc.33+ | -0.496 | hsa-miR-223 |
| hsa-mir-223-prec | uc.177+ | -0.4948 | hsa-miR-223 |
| hsa-mir-223-prec | uc.468+ | -0.4941 | hsa-miR-223 |
| hsa-mir-223-prec | uc.483+A | -0.4941 | hsa-miR-223 |
| hsa-mir-223-prec | uc.388+A | -0.4912 | hsa-miR-223 |
| hsa-mir-223-prec | uc.172+A | -0.4797 | hsa-miR-223 |
| hsa-mir-223-prec | uc.299+A | -0.4656 | hsa-miR-223 |
| hsa-mir-223-prec | uc.483+ | -0.4587 | hsa-miR-223 |
| hsa-mir-223-prec | uc.151+A | -0.4559 | hsa-miR-223 |

Figure 18 Continued

| miRNA probe on array | UCR probe on array | Correlations (Spearman Method) | miRNA |
|---|---|---|---|
| hsa-mir-223-prec | uc.153+ | -0.4478 | hsa-miR-223 |
| hsa-mir-224-prec | uc.167+ | -0.533 | hsa-miR-224 |
| hsa-mir-224-prec | uc.217+A | -0.4895 | hsa-miR-224 |
| hsa-mir-224-prec | uc.462+A | -0.453 | hsa-miR-224 |
| hsa-mir-224-prec | uc.48+A | -0.4522 | hsa-miR-224 |
| hsa-mir-023a-prec | uc.389+ | -0.6337 | hsa-miR-23a |
| hsa-mir-023a-prec | uc.346+A | -0.623 | hsa-miR-23a |
| hsa-mir-023a-prec | uc.34+A | -0.5688 | hsa-miR-23a |
| hsa-mir-023a-prec | uc.24+A | -0.5396 | hsa-miR-23a |
| hsa-mir-023a-prec | uc.282+A | -0.5119 | hsa-miR-23a |
| hsa-mir-023a-prec | uc.478+ | -0.5053 | hsa-miR-23a |
| hsa-mir-023a-prec | uc.366+ | -0.4963 | hsa-miR-23a |
| hsa-mir-023a-prec | uc.192+ | -0.489 | hsa-miR-23a |
| hsa-mir-023a-prec | uc.310+A | -0.4631 | hsa-miR-23a |
| hsa-mir-023a-prec | uc.31+ | -0.4617 | hsa-miR-23a |
| hsa-mir-023a-prec | uc.125+A | -0.4556 | hsa-miR-23a |
| hsa-mir-023a-prec | uc.73+ | -0.4534 | hsa-miR-23a |
| hsa-mir-023a-prec | uc.398+ | -0.4503 | hsa-miR-23a |
| hsa-mir-023b-prec | uc.369+ | -0.6586 | hsa-miR-23b |
| hsa-mir-023b-prec | uc.478+ | -0.6064 | hsa-miR-23b |
| hsa-mir-023b-prec | uc.346+A | -0.5747 | hsa-miR-23b |
| hsa-mir-023b-prec | uc.192+ | -0.5196 | hsa-miR-23b |
| hsa-mir-023b-prec | uc.34+A | -0.481 | hsa-miR-23b |
| hsa-mir-023b-prec | uc.24+A | -0.4542 | hsa-miR-23b |
| hsa-mir-023b-prec | uc.341+A | -0.4531 | hsa-miR-23b |
| hsa-mir-024-2-prec | uc.462+A | -0.7119 | hsa-miR-24 |
| hsa-mir-024-2-prec | uc.427+ | -0.6964 | hsa-miR-24 |
| hsa-mir-024-2-prec | uc.44+A | -0.6715 | hsa-miR-24 |
| hsa-mir-024-1-precNo1 | uc.465+A | -0.6419 | hsa-miR-24 |
| hsa-mir-024-2-prec | uc.167+ | -0.6385 | hsa-miR-24 |
| hsa-mir-024-2-prec | uc.153+ | -0.6366 | hsa-miR-24 |
| hsa-mir-024-2-prec | uc.73+A | -0.6354 | hsa-miR-24 |
| hsa-mir-024-2-prec | uc.48+A | -0.634 | hsa-miR-24 |
| hsa-mir-024-2-prec | uc.263+ | -0.627 | hsa-miR-24 |
| hsa-mir-024-2-prec | uc.275+ | -0.618 | hsa-miR-24 |
| hsa-mir-024-2-prec | uc.378+A | -0.6089 | hsa-miR-24 |
| hsa-mir-024-2-prec | uc.331+A | -0.608 | hsa-miR-24 |
| hsa-mir-024-2-prec | uc.456+A | -0.6023 | hsa-miR-24 |
| hsa-mir-024-1-precNo1 | uc.153+A | -0.5931 | hsa-miR-24 |
| hsa-mir-024-2-prec | uc.153+A | -0.5877 | hsa-miR-24 |
| hsa-mir-024-1-precNo1 | uc.160+ | -0.5875 | hsa-miR-24 |
| hsa-mir-024-2-prec | uc.327+A | -0.586 | hsa-miR-24 |
| hsa-mir-024-2-prec | uc.420+ | -0.584 | hsa-miR-24 |
| hsa-mir-024-2-prec | uc.448+ | -0.582 | hsa-miR-24 |
| hsa-mir-024-2-prec | uc.287+A | -0.5777 | hsa-miR-24 |
| hsa-mir-024-2-prec | uc.477+A | -0.5733 | hsa-miR-24 |
| hsa-mir-024-2-prec | uc.383+ | -0.5731 | hsa-miR-24 |
| hsa-mir-024-1-precNo1 | uc.327+A | -0.5722 | hsa-miR-24 |
| hsa-mir-024-2-prec | uc.88+ | -0.571 | hsa-miR-24 |
| hsa-mir-024-2-prec | uc.313+ | -0.5686 | hsa-miR-24 |
| hsa-mir-024-1-precNo1 | uc.48+A | -0.5656 | hsa-miR-24 |
| hsa-mir-024-2-prec | uc.338+ | -0.5638 | hsa-miR-24 |
| hsa-mir-024-2-prec | uc.473+A | -0.5601 | hsa-miR-24 |
| hsa-mir-024-1-precNo1 | uc.172+A | -0.5596 | hsa-miR-24 |
| hsa-mir-024-2-prec | uc.20+ | -0.5571 | hsa-miR-24 |
| hsa-mir-024-1-precNo1 | uc.283+A | -0.5557 | hsa-miR-24 |
| hsa-mir-024-2-prec | uc.362+ | -0.5555 | hsa-miR-24 |
| hsa-mir-024-2-prec | uc.166+ | -0.555 | hsa-miR-24 |
| hsa-mir-024-1-precNo1 | uc.339+ | -0.5534 | hsa-miR-24 |
| hsa-mir-024-2-prec | uc.456+ | -0.5533 | hsa-miR-24 |
| hsa-mir-024-2-prec | uc.20+A | -0.5502 | hsa-miR-24 |
| hsa-mir-024-2-prec | uc.217+A | -0.5496 | hsa-miR-24 |
| hsa-mir-024-1-precNo1 | uc.77+ | -0.547 | hsa-miR-24 |
| hsa-mir-024-2-prec | uc.190+A | -0.5469 | hsa-miR-24 |
| hsa-mir-024-2-prec | uc.299+A | -0.545 | hsa-miR-24 |
| hsa-mir-024-1-precNo1 | uc.285+ | -0.544 | hsa-miR-24 |
| hsa-mir-024-2-prec | uc.473+A | -0.541 | hsa-miR-24 |
| hsa-mir-024-2-prec | uc.234+ | -0.5386 | hsa-miR-24 |
| hsa-mir-024-2-prec | uc.378+ | -0.5368 | hsa-miR-24 |
| hsa-mir-024-1-precNo1 | uc.478+A | -0.5363 | hsa-miR-24 |
| hsa-mir-024-1-precNo1 | uc.153+ | -0.5355 | hsa-miR-24 |
| hsa-mir-024-2-prec | uc.33+A | -0.5343 | hsa-miR-24 |
| hsa-mir-024-2-prec | uc.448+A | -0.5342 | hsa-miR-24 |
| hsa-mir-024-2-prec | uc.170+ | -0.5333 | hsa-miR-24 |
| hsa-mir-024-1-precNo1 | uc.420+A | -0.5318 | hsa-miR-24 |
| hsa-mir-024-1-precNo1 | uc.167+ | -0.5288 | hsa-miR-24 |
| hsa-mir-024-1-precNo1 | uc.234+ | -0.5252 | hsa-miR-24 |
| hsa-mir-024-1-precNo1 | uc.427+ | -0.525 | hsa-miR-24 |
| hsa-mir-024-2-prec | uc.285+ | -0.5236 | hsa-miR-24 |
| hsa-mir-024-1-precNo1 | uc.151+ | -0.5232 | hsa-miR-24 |
| hsa-mir-024-2-prec | uc.117+ | -0.5203 | hsa-miR-24 |
| hsa-mir-024-2-prec | uc.465+A | -0.5181 | hsa-miR-24 |
| hsa-mir-024-1-precNo1 | uc.420+ | -0.5179 | hsa-miR-24 |
| hsa-mir-024-1-precNo1 | uc.170+ | -0.515 | hsa-miR-24 |

Figure 18 Continued

Calin 6A

| miRNA probe on array | UCR probe on array | Correlations (Spearman Method) | miRNA |
|---|---|---|---|
| hsa-mir-024-2-prec | uc.354+A | -0.515 | hsa-miR-24 |
| hsa-mir-024-1-precNo1 | uc.263+ | -0.5141 | hsa-miR-24 |
| hsa-mir-024-1-precNo1 | uc.106+ | -0.5046 | hsa-miR-24 |
| hsa-mir-024-1-precNo1 | uc.346+ | -0.5038 | hsa-miR-24 |
| hsa-mir-024-2-prec | uc.383+ | -0.5031 | hsa-miR-24 |
| hsa-mir-024-2-prec | uc.412+A | -0.5026 | hsa-miR-24 |
| hsa-mir-024-1-precNo1 | uc.375+ | -0.5003 | hsa-miR-24 |
| hsa-mir-024-1-precNo1 | uc.217+A | -0.4991 | hsa-miR-24 |
| hsa-mir-024-2-prec | uc.63+ | -0.4985 | hsa-miR-24 |
| hsa-mir-024-2-prec | uc.189+ | -0.4978 | hsa-miR-24 |
| hsa-mir-024-1-precNo1 | uc.173+ | -0.4949 | hsa-miR-24 |
| hsa-mir-024-2-prec | uc.317+ | -0.4926 | hsa-miR-24 |
| hsa-mir-024-1-precNo1 | uc.213+ | -0.4921 | hsa-miR-24 |
| hsa-mir-024-1-precNo1 | uc.456+A | -0.4912 | hsa-miR-24 |
| hsa-mir-024-2-prec | uc.33+ | -0.4913 | hsa-miR-24 |
| hsa-mir-024-2-prec | uc.362+A | -0.4899 | hsa-miR-24 |
| hsa-mir-024-2-prec | uc.88-A | -0.4895 | hsa-miR-24 |
| hsa-mir-024-1-precNo1 | uc.331+A | -0.4842 | hsa-miR-24 |
| hsa-mir-024-1-precNo1 | uc.419+A | -0.4814 | hsa-miR-24 |
| hsa-mir-024-1-precNo1 | uc.151+A | -0.4792 | hsa-miR-24 |
| hsa-mir-024-2-prec | uc.151+A | -0.4789 | hsa-miR-24 |
| hsa-mir-024-1-precNo1 | uc.378+A | -0.4758 | hsa-miR-24 |
| hsa-mir-024-1-precNo1 | uc.128+A | -0.4752 | hsa-miR-24 |
| hsa-mir-024-2-prec | uc.145+A | -0.4718 | hsa-miR-24 |
| hsa-mir-024-2-prec | uc.233+A | -0.4693 | hsa-miR-24 |
| hsa-mir-024-1-precNo1 | uc.462+A | -0.4678 | hsa-miR-24 |
| hsa-mir-024-1-precNo1 | uc.473+A | -0.4674 | hsa-miR-24 |
| hsa-mir-024-1-precNo1 | uc.354+A | -0.4668 | hsa-miR-24 |
| hsa-mir-024-1-precNo1 | uc.88+ | -0.4663 | hsa-miR-24 |
| hsa-mir-024-2-prec | uc.95+ | -0.4653 | hsa-miR-24 |
| hsa-mir-024-2-prec | uc.445+A | -0.4628 | hsa-miR-24 |
| hsa-mir-024-1-precNo1 | uc.33+A | -0.4612 | hsa-miR-24 |
| hsa-mir-024-2-prec | uc.300+ | -0.4609 | hsa-miR-24 |
| hsa-mir-024-1-precNo1 | uc.388+ | -0.459 | hsa-miR-24 |
| hsa-mir-024-2-prec | uc.160+ | -0.4583 | hsa-miR-24 |
| hsa-mir-024-1-precNo1 | uc.362+ | -0.4581 | hsa-miR-24 |
| hsa-mir-024-1-precNo1 | uc.233+A | -0.4572 | hsa-miR-24 |
| hsa-mir-024-1-precNo1 | uc.325+ | -0.4497 | hsa-miR-24 |
| hsa-mir-024-1-precNo1 | uc.20+ | -0.4492 | hsa-miR-24 |
| hsa-mir-025-prec | uc.389+ | -0.698 | hsa-miR-25 |
| hsa-mir-025-prec | uc.346+A | -0.6873 | hsa-miR-25 |
| hsa-mir-025-prec | uc.478+ | -0.6722 | hsa-miR-25 |
| hsa-mir-025-prec | uc.398+ | -0.6055 | hsa-miR-25 |
| hsa-mir-025-prec | uc.192+ | -0.5962 | hsa-miR-25 |
| hsa-mir-025-prec | uc.366+ | -0.5764 | hsa-miR-25 |
| hsa-mir-025-prec | uc.34+A | -0.5702 | hsa-miR-25 |
| hsa-mir-025-prec | uc.181+A | -0.5638 | hsa-miR-25 |
| hsa-mir-025-prec | uc.31+ | -0.5488 | hsa-miR-25 |
| hsa-mir-025-prec | uc.125+A | -0.5441 | hsa-miR-25 |
| hsa-mir-025-prec | uc.24+A | -0.5203 | hsa-miR-25 |
| hsa-mir-025-prec | uc.283+ | -0.4882 | hsa-miR-25 |
| hsa-mir-026a-2No1 | uc.128-A | -0.7743 | hsa-miR-26a |
| hsa-mir-026a-precNo1 | uc.73+A | -0.7387 | hsa-miR-26a |
| hsa-mir-026a-2No1 | uc.229+ | -0.7132 | hsa-miR-26a |
| hsa-mir-026a-2No1 | uc.177+ | -0.7103 | hsa-miR-26a |
| hsa-mir-026a-1No1 | uc.420+ | -0.6998 | hsa-miR-26a |
| hsa-mir-026a-2No1 | uc.173+A | -0.6956 | hsa-miR-26a |
| hsa-mir-026a-2No1 | uc.346+ | -0.6915 | hsa-miR-26a |
| hsa-mir-026a-1No1 | uc.106+ | -0.6852 | hsa-miR-26a |
| hsa-mir-026a-precNo1 | uc.456+A | -0.6713 | hsa-miR-26a |
| hsa-mir-026a-1No1 | uc.383+ | -0.6713 | hsa-miR-26a |
| hsa-mir-026a-1No1 | uc.73+A | -0.67 | hsa-miR-26a |
| hsa-mir-026a-1No1 | uc.18+ | -0.6691 | hsa-miR-26a |
| hsa-mir-026a-2No1 | uc.77+ | -0.6684 | hsa-miR-26a |
| hsa-mir-026a-precNo1 | uc.285+ | -0.6632 | hsa-miR-26a |
| hsa-mir-026a-1No1 | uc.153+A | -0.6606 | hsa-miR-26a |
| hsa-mir-026a-1No1 | uc.33+ | -0.6551 | hsa-miR-26a |
| hsa-mir-026a-1No1 | uc.213+ | -0.649 | hsa-miR-26a |
| hsa-mir-026a-1No1 | uc.33+A | -0.6486 | hsa-miR-26a |
| hsa-mir-026a-1No1 | uc.462+A | -0.6426 | hsa-miR-26a |
| hsa-mir-026a-2No1 | uc.463+ | -0.6256 | hsa-miR-26a |
| hsa-mir-026a-1No1 | uc.234+ | -0.622 | hsa-miR-26a |
| hsa-mir-026a-precNo1 | uc.477+A | -0.6198 | hsa-miR-26a |
| hsa-mir-026a-1No1 | uc.153+ | -0.6197 | hsa-miR-26a |
| hsa-mir-026a-1No1 | uc.412+A | -0.6184 | hsa-miR-26a |
| hsa-mir-026a-1No1 | uc.189+ | -0.6139 | hsa-miR-26a |
| hsa-mir-026a-1No1 | uc.299+A | -0.6133 | hsa-miR-26a |
| hsa-mir-026a-1No1 | uc.354+A | -0.6118 | hsa-miR-26a |
| hsa-mir-026a-1No1 | uc.327+A | -0.6113 | hsa-miR-26a |
| hsa-mir-026a-1No1 | uc.285+ | -0.6089 | hsa-miR-26a |
| hsa-mir-026a-precNo1 | uc.420+ | -0.6062 | hsa-miR-26a |
| hsa-mir-026a-2No1 | uc.151+ | -0.6037 | hsa-miR-26a |
| hsa-mir-026a-2No1 | uc.466+A | -0.6001 | hsa-miR-26a |
| hsa-mir-026a-1No1 | uc.378+ | -0.5995 | hsa-miR-26a |

Figure 18 Continued

| miRNA probe on array | UCR probe on array | Correlations (Spearman Method) | miRNA |
|---|---|---|---|
| hsa-mir-026a-precNo1 | uc.378+ | -0.5988 | hsa-miR-26a |
| hsa-mir-26a-2No1 | uc.173+ | -0.5976 | hsa-miR-26a |
| hsa-mir-026a-precNo1 | uc.462+A | -0.5953 | hsa-miR-26a |
| hsa-mir-026a-precNo1 | uc.412+A | -0.5948 | hsa-miR-26a |
| hsa-mir-26a-2No1 | uc.465+A | -0.5937 | hsa-miR-26a |
| hsa-mir-26a-1No1 | uc.217+A | -0.5922 | hsa-miR-26a |
| hsa-mir-26a-1No1 | uc.456+A | -0.5915 | hsa-miR-26a |
| hsa-mir-26a-1No1 | uc.477+A | -0.5892 | hsa-miR-26a |
| hsa-mir-026a-precNo1 | uc.383+ | -0.5886 | hsa-miR-26a |
| hsa-mir-26a-1No1 | uc.388+A | -0.5868 | hsa-miR-26a |
| hsa-mir-26a-1No1 | uc.44+A | -0.5867 | hsa-miR-26a |
| hsa-mir-26a-1No1 | uc.468+ | -0.5845 | hsa-miR-26a |
| hsa-mir-026a-precNo1 | uc.106+ | -0.584 | hsa-miR-26a |
| hsa-mir-26a-1No1 | uc.88+ | -0.582 | hsa-miR-26a |
| hsa-mir-26a-1No1 | uc.173+ | -0.581 | hsa-miR-26a |
| hsa-mir-26a-2No1 | uc.420+A | -0.5792 | hsa-miR-26a |
| hsa-mir-26a-1No1 | uc.388+ | -0.5703 | hsa-miR-26a |
| hsa-mir-026a-precNo1 | uc.189+ | -0.5662 | hsa-miR-26a |
| hsa-mir-26a-1No1 | uc.473+A | -0.565 | hsa-miR-26a |
| hsa-mir-26a-1No1 | uc.128+A | -0.5601 | hsa-miR-26a |
| hsa-mir-26a-1No1 | uc.263+ | -0.5601 | hsa-miR-26a |
| hsa-mir-26a-1No1 | uc.427+ | -0.5591 | hsa-miR-26a |
| hsa-mir-26a-1No1 | uc.190+A | -0.5586 | hsa-miR-26a |
| hsa-mir-26a-2No1 | uc.339+ | -0.5576 | hsa-miR-26a |
| hsa-mir-26a-1No1 | uc.420+A | -0.5559 | hsa-miR-26a |
| hsa-mir-26a-1No1 | uc.151+ | -0.5557 | hsa-miR-26a |
| hsa-mir-026a-precNo1 | uc.190+A | -0.5549 | hsa-miR-26a |
| hsa-mir-26a-1No1 | uc.8+ | -0.5511 | hsa-miR-26a |
| hsa-mir-26a-1No1 | uc.20+ | -0.5508 | hsa-miR-26a |
| hsa-mir-026a-precNo1 | uc.354+A | -0.5479 | hsa-miR-26a |
| hsa-mir-26a-1No1 | uc.445+A | -0.5467 | hsa-miR-26a |
| hsa-mir-026a-precNo1 | uc.213+ | -0.5444 | hsa-miR-26a |
| hsa-mir-26a-2No1 | uc.278+ | -0.544 | hsa-miR-26a |
| hsa-mir-026a-precNo1 | uc.299+A | -0.5424 | hsa-miR-26a |
| hsa-mir-26a-1No1 | uc.172+A | -0.5375 | hsa-miR-26a |
| hsa-mir-026a-precNo1 | uc.153+A | -0.5371 | hsa-miR-26a |
| hsa-mir-026a-precNo1 | uc.412+ | -0.5329 | hsa-miR-26a |
| hsa-mir-26a-1No1 | uc.177+ | -0.5315 | hsa-miR-26a |
| hsa-mir-26a-1No1 | uc.275+ | -0.5312 | hsa-miR-26a |
| hsa-mir-26a-2No1 | uc.349+ | -0.5307 | hsa-miR-26a |
| hsa-mir-26a-2No1 | uc.262+A | -0.5265 | hsa-miR-26a |
| hsa-mir-26a-1No1 | uc.151+A | -0.5261 | hsa-miR-26a |
| hsa-mir-026a-precNo1 | uc.217+ | -0.5257 | hsa-miR-26a |
| hsa-mir-026a-precNo1 | uc.217+A | -0.5248 | hsa-miR-26a |
| hsa-mir-026a-precNo1 | uc.44+A | -0.5238 | hsa-miR-26a |
| hsa-mir-026a-precNo1 | uc.234+ | -0.5182 | hsa-miR-26a |
| hsa-mir-026a-precNo1 | uc.327+A | -0.5149 | hsa-miR-26a |
| hsa-mir-026a-precNo1 | uc.20+ | -0.5143 | hsa-miR-26a |
| hsa-mir-026a-precNo1 | uc.78+ | -0.5101 | hsa-miR-26a |
| hsa-mir-26a-1No1 | uc.20+A | -0.5096 | hsa-miR-26a |
| hsa-mir-26a-1No1 | uc.217+ | -0.5081 | hsa-miR-26a |
| hsa-mir-26a-1No1 | uc.43+ | -0.508 | hsa-miR-26a |
| hsa-mir-26a-1No1 | uc.468+A | -0.5071 | hsa-miR-26a |
| hsa-mir-26a-1No1 | uc.378+A | -0.5064 | hsa-miR-26a |
| hsa-mir-026a-precNo1 | uc.427+ | -0.5063 | hsa-miR-26a |
| hsa-mir-026a-precNo1 | uc.456+ | -0.5047 | hsa-miR-26a |
| hsa-mir-026a-precNo1 | uc.190+ | -0.5041 | hsa-miR-26a |
| hsa-mir-26a-2No1 | uc.18+ | -0.503 | hsa-miR-26a |
| hsa-mir-026a-precNo1 | uc.20+A | -0.4995 | hsa-miR-26a |
| hsa-mir-026a-precNo1 | uc.153+ | -0.4987 | hsa-miR-26a |
| hsa-mir-026a-precNo1 | uc.388+ | -0.4984 | hsa-miR-26a |
| hsa-mir-026a-precNo1 | uc.287+A | -0.4972 | hsa-miR-26a |
| hsa-mir-26a-2No1 | uc.183+ | -0.4957 | hsa-miR-26a |
| hsa-mir-26a-2No1 | uc.285+ | -0.4952 | hsa-miR-26a |
| hsa-mir-26a-2No1 | uc.388+A | -0.494 | hsa-miR-26a |
| hsa-mir-026a-precNo1 | uc.18+ | -0.4894 | hsa-miR-26a |
| hsa-mir-026a-precNo1 | uc.275+ | -0.4886 | hsa-miR-26a |
| hsa-mir-026a-precNo1 | uc.33+A | -0.4872 | hsa-miR-26a |
| hsa-mir-26a-1No1 | uc.287+A | -0.4856 | hsa-miR-26a |
| hsa-mir-26a-2No1 | uc.8+ | -0.4815 | hsa-miR-26a |
| hsa-mir-26a-1No1 | uc.263+A | -0.48 | hsa-miR-26a |
| hsa-mir-026a-precNo1 | uc.473+A | -0.4796 | hsa-miR-26a |
| hsa-mir-026a-precNo1 | uc.468+ | -0.4789 | hsa-miR-26a |
| hsa-mir-026a-precNo1 | uc.33+ | -0.475 | hsa-miR-26a |
| hsa-mir-26a-1No1 | uc.33+A | -0.4745 | hsa-miR-26a |
| hsa-mir-26a-2No1 | uc.420+ | -0.4732 | hsa-miR-26a |
| hsa-mir-026a-precNo1 | uc.8+ | -0.4736 | hsa-miR-26a |
| hsa-mir-26a-2No1 | uc.463+A | -0.4722 | hsa-miR-26a |
| hsa-mir-26a-2No1 | uc.213+ | -0.4704 | hsa-miR-26a |
| hsa-mir-26a-1No1 | uc.190+ | -0.4692 | hsa-miR-26a |
| hsa-mir-026a-precNo1 | uc.263+ | -0.4632 | hsa-miR-26a |
| hsa-mir-026a-precNo1 | uc.420+A | -0.4616 | hsa-miR-26a |
| hsa-mir-026a-precNo1 | uc.43+ | -0.4589 | hsa-miR-26a |
| hsa-mir-026a-precNo1 | uc.378+A | -0.4581 | hsa-miR-26a |

Figure 18 Continued

| miRNA probe on array | UCR probe on array | Correlations (Spearman Method) | miRNA |
|---|---|---|---|
| hsa-mir-26a-1No1 | uc.774+ | -0.453 | hsa-miR-26a |
| hsa-mir-026a-precNo1 | uc.173+ | -0.4478 | hsa-miR-26a |
| hsa-mir-26a-1No2 | uc.229+ | -0.7848 | hsa-miR-26a-1 |
| hsa-mir-26a-1No2 | uc.466+A | -0.7637 | hsa-miR-26a-1 |
| hsa-mir-26a-1No2 | uc.177+ | -0.7241 | hsa-miR-26a-1 |
| hsa-mir-26a-1No2 | uc.349+ | -0.6869 | hsa-miR-26a-1 |
| hsa-mir-26a-1No2 | uc.346+ | -0.6334 | hsa-miR-26a-1 |
| hsa-mir-26a-1No2 | uc.128+A | -0.6276 | hsa-miR-26a-1 |
| hsa-mir-26a-1No2 | uc.172+A | -0.6271 | hsa-miR-26a-1 |
| hsa-mir-26a-1No2 | uc.483+ | -0.6171 | hsa-miR-26a-1 |
| hsa-mir-26a-1No2 | uc.77+ | -0.6104 | hsa-miR-26a-1 |
| hsa-mir-26a-1No2 | uc.426+ | -0.5757 | hsa-miR-26a-1 |
| hsa-mir-26a-1No2 | uc.151+ | -0.5346 | hsa-miR-26a-1 |
| hsa-mir-26a-1No2 | uc.134+A | -0.527 | hsa-miR-26a-1 |
| hsa-mir-26a-1No2 | uc.278+ | -0.524 | hsa-miR-26a-1 |
| hsa-mir-26a-1No2 | uc.8+ | -0.5154 | hsa-miR-26a-1 |
| hsa-mir-26a-1No2 | uc.362+A | -0.5069 | hsa-miR-26a-1 |
| hsa-mir-26a-1No2 | uc.204+ | -0.5047 | hsa-miR-26a-1 |
| hsa-mir-26a-1No2 | uc.173+ | -0.4692 | hsa-miR-26a-1 |
| hsa-mir-26a-1No2 | uc.134+ | -0.4678 | hsa-miR-26a-1 |
| hsa-mir-26a-1No2 | uc.165+ | -0.4653 | hsa-miR-26a-1 |
| hsa-mir-26a-1No2 | uc.73+ | -0.4614 | hsa-miR-26a-1 |
| hsa-mir-26a-1No2 | uc.420+A | -0.4584 | hsa-miR-26a-1 |
| hsa-mir-26a-1No2 | uc.136+ | -0.4485 | hsa-miR-26a-1 |
| hsa-mir-027a-prec | uc.159+A | -0.6883 | hsa-miR-27a |
| hsa-mir-027a-prec | uc.44+A | -0.6488 | hsa-miR-27a |
| hsa-mir-027a-prec | uc.73+A | -0.6343 | hsa-miR-27a |
| hsa-mir-027a-prec | uc.217+ | -0.6231 | hsa-miR-27a |
| hsa-mir-027a-prec | uc.443+ | -0.6211 | hsa-miR-27a |
| hsa-mir-027a-prec | uc.477+A | -0.6075 | hsa-miR-27a |
| hsa-mir-027a-prec | uc.475+A | -0.5957 | hsa-miR-27a |
| hsa-mir-027a-prec | uc.142+A | -0.5905 | hsa-miR-27a |
| hsa-mir-027a-prec | uc.287+A | -0.5796 | hsa-miR-27a |
| hsa-mir-027a-prec | uc.338+ | -0.5745 | hsa-miR-27a |
| hsa-mir-027a-prec | uc.20+A | -0.5728 | hsa-miR-27a |
| hsa-mir-027a-prec | uc.331+A | -0.5709 | hsa-miR-27a |
| hsa-mir-027a-prec | uc.95+ | -0.5648 | hsa-miR-27a |
| hsa-mir-027a-prec | uc.462+A | -0.5534 | hsa-miR-27a |
| hsa-mir-027a-prec | uc.278+A | -0.5491 | hsa-miR-27a |
| hsa-mir-027a-prec | uc.427+ | -0.5478 | hsa-miR-27a |
| hsa-mir-027a-prec | uc.291+ | -0.5375 | hsa-miR-27a |
| hsa-mir-027a-prec | uc.223+A | -0.5367 | hsa-miR-27a |
| hsa-mir-027a-prec | uc.90+A | -0.5292 | hsa-miR-27a |
| hsa-mir-027a-prec | uc.263+ | -0.5258 | hsa-miR-27a |
| hsa-mir-027a-prec | uc.456+ | -0.5236 | hsa-miR-27a |
| hsa-mir-027a-prec | uc.298+ | -0.5211 | hsa-miR-27a |
| hsa-mir-027a-prec | uc.299+ | -0.5208 | hsa-miR-27a |
| hsa-mir-027a-prec | uc.48+A | -0.5141 | hsa-miR-27a |
| hsa-mir-027a-prec | uc.475+ | -0.506 | hsa-miR-27a |
| hsa-mir-027a-prec | uc.378+ | -0.504 | hsa-miR-27a |
| hsa-mir-027a-prec | uc.412+ | -0.4942 | hsa-miR-27a |
| hsa-mir-027a-prec | uc.448+A | -0.4864 | hsa-miR-27a |
| hsa-mir-027a-prec | uc.275+ | -0.486 | hsa-miR-27a |
| hsa-mir-027a-prec | uc.456+A | -0.4804 | hsa-miR-27a |
| hsa-mir-027a-prec | uc.477+ | -0.4748 | hsa-miR-27a |
| hsa-mir-027a-prec | uc.388+ | -0.4692 | hsa-miR-27a |
| hsa-mir-027a-prec | uc.117+ | -0.462 | hsa-miR-27a |
| hsa-mir-027a-prec | uc.299+A | -0.4552 | hsa-miR-27a |
| hsa-mir-027a-prec | uc.362+A | -0.4492 | hsa-miR-27a |
| hsa-mir-027a-prec | uc.363+ | -0.448 | hsa-miR-27a |
| hsa-mir-029a-2No1 | uc.33+A | -0.7241 | hsa-miR-29a |
| hsa-mir-029a-2No1 | uc.18+ | -0.7165 | hsa-miR-29a |
| hsa-mir-029a-2No1 | uc.153+A | -0.7101 | hsa-miR-29a |
| hsa-mir-029a-2No1 | uc.106+ | -0.6964 | hsa-miR-29a |
| hsa-mir-029a-2No1 | uc.173+A | -0.6841 | hsa-miR-29a |
| hsa-mir-029a-2No1 | uc.420+ | -0.6822 | hsa-miR-29a |
| hsa-mir-029a-2No1 | uc.308+A | -0.6634 | hsa-miR-29a |
| hsa-mir-029a-2No1 | uc.33+ | -0.6613 | hsa-miR-29a |
| hsa-mir-029a-2No1 | uc.313+ | -0.6581 | hsa-miR-29a |
| hsa-mir-029a-2No1 | uc.354+A | -0.6547 | hsa-miR-29a |
| hsa-mir-029a-2No1 | uc.363+ | -0.6536 | hsa-miR-29a |
| hsa-mir-029a-2No1 | uc.346+ | -0.6487 | hsa-miR-29a |
| hsa-mir-029a-2No1 | uc.77+ | -0.6462 | hsa-miR-29a |
| hsa-mir-029a-2No1 | uc.234+ | -0.6449 | hsa-miR-29a |
| hsa-mir-029a-2No1 | uc.128+A | -0.6403 | hsa-miR-29a |
| hsa-mir-029a-2No1 | uc.327+A | -0.6293 | hsa-miR-29a |
| hsa-mir-029a-2No1 | uc.153+ | -0.6226 | hsa-miR-29a |
| hsa-mir-029a-2No1 | uc.265+ | -0.6206 | hsa-miR-29a |
| hsa-mir-029a-2No1 | uc.468+ | -0.6194 | hsa-miR-29a |
| hsa-mir-029a-2No1 | uc.177+ | -0.6136 | hsa-miR-29a |
| hsa-mir-029a-2No1 | uc.217+A | -0.598 | hsa-miR-29a |
| hsa-mir-029a-2No1 | uc.462+A | -0.5977 | hsa-miR-29a |
| hsa-mir-029a-2No1 | uc.88+ | -0.5851 | hsa-miR-29a |
| hsa-mir-029a-2No1 | uc.465+A | -0.5818 | hsa-miR-29a |

Figure 18 Continued

| miRNA probe on array | UCR probe on array | Correlations (Spearman Method) | miRNA |
|---|---|---|---|
| hsa-mir-029a-2No1 | uc.427+ | -0.5884 | hsa-miR-29a |
| hsa-mir-029a-2No1 | uc.263+ | -0.5658 | hsa-miR-29a |
| hsa-mir-029a-2No1 | uc.190+A | -0.5606 | hsa-miR-29a |
| hsa-mir-029a-2No1 | uc.473+A | -0.5553 | hsa-miR-29a |
| hsa-mir-029a-2No1 | uc.189+ | -0.5484 | hsa-miR-29a |
| hsa-mir-029a-2No1 | uc.173+ | -0.5473 | hsa-miR-29a |
| hsa-mir-029a-2No1 | uc.20+ | -0.5473 | hsa-miR-29a |
| hsa-mir-029a-2No1 | uc.456+A | -0.5383 | hsa-miR-29a |
| hsa-mir-029a-2No1 | uc.412+A | -0.5377 | hsa-miR-29a |
| hsa-mir-029a-2No1 | uc.483+A | -0.5375 | hsa-miR-29a |
| hsa-mir-029a-2No1 | uc.151+ | -0.5365 | hsa-miR-29a |
| hsa-mir-029a-2No1 | uc.151+A | -0.5348 | hsa-miR-29a |
| hsa-mir-029a-2No1 | uc.445+A | -0.5315 | hsa-miR-29a |
| hsa-mir-029a-2No1 | uc.468+A | -0.5282 | hsa-miR-29a |
| hsa-mir-029a-2No1 | uc.183+ | -0.5259 | hsa-miR-29a |
| hsa-mir-029a-2No1 | uc.420+A | -0.5204 | hsa-miR-29a |
| hsa-mir-029a-2No1 | uc.275+ | -0.5156 | hsa-miR-29a |
| hsa-mir-029a-2No1 | uc.388+ | -0.5115 | hsa-miR-29a |
| hsa-mir-029a-2No1 | uc.378+A | -0.4976 | hsa-miR-29a |
| hsa-mir-029a-2No1 | uc.8+ | -0.4922 | hsa-miR-29a |
| hsa-mir-029a-2No1 | uc.43+ | -0.4883 | hsa-miR-29a |
| hsa-mir-029a-2No1 | uc.48+A | -0.4857 | hsa-miR-29a |
| hsa-mir-029a-2No1 | uc.160+ | -0.4856 | hsa-miR-29a |
| hsa-mir-029a-2No1 | uc.44+A | -0.4708 | hsa-miR-29a |
| hsa-mir-029a-2No1 | uc.229+ | -0.4696 | hsa-miR-29a |
| hsa-mir-029a-2No1 | uc.96+ | -0.4694 | hsa-miR-29a |
| hsa-mir-029a-2No1 | uc.378+ | -0.4688 | hsa-miR-29a |
| hsa-mir-029a-2No1 | uc.299+A | -0.4679 | hsa-miR-29a |
| hsa-mir-029a-2No1 | uc.483+ | -0.4599 | hsa-miR-29a |
| hsa-mir-029a-2No1 | uc.73+A | -0.4546 | hsa-miR-29a |
| hsa-mir-029a-2No1 | uc.339+ | -0.4531 | hsa-miR-29a |
| hsa-mir-29b-1No1 | uc.33+A | -0.807 | hsa-miR-29b |
| hsa-mir-29b-1No1 | uc.106+ | -0.8012 | hsa-miR-29b |
| hsa-mir-102-prec-1 | uc.106+ | -0.7814 | hsa-miR-29b |
| hsa-mir-29b-1No1 | uc.153+A | -0.7787 | hsa-miR-29b |
| hsa-mir-102-prec-1 | uc.33+A | -0.7718 | hsa-miR-29b |
| hsa-mir-29b-1No1 | uc.18+ | -0.7641 | hsa-miR-29b |
| hsa-mir-102-prec-1 | uc.383+ | -0.7596 | hsa-miR-29b |
| hsa-mir-29b-1No1 | uc.213+ | -0.7533 | hsa-miR-29b |
| hsa-mir-29b-1No1 | uc.420+ | -0.7426 | hsa-miR-29b |
| hsa-mir-102-prec-1 | uc.153+A | -0.7399 | hsa-miR-29b |
| hsa-mir-29b-1No1 | uc.153+ | -0.7381 | hsa-miR-29b |
| hsa-mir-29b-1No1 | uc.354+A | -0.7284 | hsa-miR-29b |
| hsa-mir-102-prec-1 | uc.18+ | -0.7283 | hsa-miR-29b |
| hsa-mir-29b-1No1 | uc.234+ | -0.7262 | hsa-miR-29b |
| hsa-mir-29b-1No1 | uc.88+ | -0.7207 | hsa-miR-29b |
| hsa-mir-29b-1No1 | uc.383+ | -0.7198 | hsa-miR-29b |
| hsa-mir-102-prec-1 | uc.153+ | -0.7124 | hsa-miR-29b |
| hsa-mir-102-prec-1 | uc.462+A | -0.7117 | hsa-miR-29b |
| hsa-mir-102-prec-1 | uc.354+A | -0.7044 | hsa-miR-29b |
| hsa-mir-29b-1No1 | uc.462+A | -0.6981 | hsa-miR-29b |
| hsa-mir-102-prec-1 | uc.420+ | -0.694 | hsa-miR-29b |
| hsa-mir-102-prec-1 | uc.263+ | -0.6934 | hsa-miR-29b |
| hsa-mir-102-prec-1 | uc.468+ | -0.6931 | hsa-miR-29b |
| hsa-mir-29b-1No1 | uc.33+ | -0.6924 | hsa-miR-29b |
| hsa-mir-102-prec-1 | uc.213+ | -0.6881 | hsa-miR-29b |
| hsa-mir-29b-1No1 | uc.217+A | -0.6856 | hsa-miR-29b |
| hsa-mir-29b-1No1 | uc.263+ | -0.6855 | hsa-miR-29b |
| hsa-mir-102-prec-1 | uc.88+ | -0.6851 | hsa-miR-29b |
| hsa-mir-29b-1No1 | uc.473+A | -0.683 | hsa-miR-29b |
| hsa-mir-29b-1No1 | uc.468+ | -0.6816 | hsa-miR-29b |
| hsa-mir-29b-1No1 | uc.327+A | -0.6814 | hsa-miR-29b |
| hsa-mir-29b-1No1 | uc.189+ | -0.6811 | hsa-miR-29b |
| hsa-mir-102-prec-1 | uc.190+A | -0.6782 | hsa-miR-29b |
| hsa-mir-102-prec-1 | uc.473+A | -0.671 | hsa-miR-29b |
| hsa-mir-102-prec-1 | uc.33+ | -0.6708 | hsa-miR-29b |
| hsa-mir-102-prec-1 | uc.20+ | -0.6697 | hsa-miR-29b |
| hsa-mir-29b-2=102prec7.1=7.2 | uc.465+A | -0.6666 | hsa-miR-29b |
| hsa-mir-102-prec-1 | uc.427+ | -0.6642 | hsa-miR-29b |
| hsa-mir-29b-1No1 | uc.388+A | -0.6638 | hsa-miR-29b |
| hsa-mir-102-prec-1 | uc.275+ | -0.6635 | hsa-miR-29b |
| hsa-mir-102-prec-1 | uc.234+ | -0.662 | hsa-miR-29b |
| hsa-mir-102-prec-1 | uc.456+A | -0.6592 | hsa-miR-29b |
| hsa-mir-29b-1No1 | uc.20+ | -0.6588 | hsa-miR-29b |
| hsa-mir-102-prec-1 | uc.217+A | -0.6576 | hsa-miR-29b |
| hsa-mir-29b-1No1 | uc.427+ | -0.6568 | hsa-miR-29b |
| hsa-mir-29b-1No1 | uc.275+ | -0.6548 | hsa-miR-29b |
| hsa-mir-29b-1No1 | uc.190+A | -0.6547 | hsa-miR-29b |
| hsa-mir-29b-1No1 | uc.388+ | -0.6521 | hsa-miR-29b |
| hsa-mir-29b-1No1 | uc.456+A | -0.6521 | hsa-miR-29b |
| hsa-mir-102-prec-1 | uc.378+ | -0.6481 | hsa-miR-29b |
| hsa-mir-29b-1No1 | uc.468+A | -0.6473 | hsa-miR-29b |
| hsa-mir-29b-1No1 | uc.412+A | -0.6464 | hsa-miR-29b |
| hsa-mir-102-prec-1 | uc.388+ | -0.6424 | hsa-miR-29b |

Figure 18 Continued

| miRNA probe on array | UCR probe on array | Correlations (Spearman Method) | miRNA |
|---|---|---|---|
| hsa-mir-29b-1No1 | uc.378+ | -0.6417 | hsa-miR-29b |
| hsa-mir-29b-1No1 | uc.445+A | -0.6408 | hsa-miR-29b |
| hsa-mir-102-prec-1 | uc.189+ | -0.6373 | hsa-miR-29b |
| hsa-mir-102-prec-1 | uc.73+A | -0.6347 | hsa-miR-29b |
| hsa-mir-102-prec-1 | uc.20+A | -0.6344 | hsa-miR-29b |
| hsa-mir-102-prec-1 | uc.267+A | -0.6329 | hsa-miR-29b |
| hsa-mir-102-prec-1 | uc.477+A | -0.6322 | hsa-miR-29b |
| hsa-mir-102-prec-1 | uc.368+A | -0.6321 | hsa-miR-29b |
| hsa-mir-29b-1No1 | uc.73+A | -0.6311 | hsa-miR-29b |
| hsa-mir-102-prec-1 | uc.468+A | -0.6279 | hsa-miR-29b |
| hsa-mir-29b-1No1 | uc.285+ | -0.6218 | hsa-miR-29b |
| hsa-mir-29b-1No1 | uc.378+A | -0.6176 | hsa-miR-29b |
| hsa-mir-29b-1No1 | uc.378+A | -0.6157 | hsa-miR-29b |
| hsa-mir-102-prec-1 | uc.412+A | -0.6069 | hsa-miR-29b |
| hsa-mir-102-prec-1 | uc.217+ | -0.6014 | hsa-miR-29b |
| hsa-mir-102-prec-1 | uc.445+A | -0.598 | hsa-miR-29b |
| hsa-mir-29b-1No1 | uc.43+ | -0.5968 | hsa-miR-29b |
| hsa-mir-29b-1No1 | uc.477+A | -0.5946 | hsa-miR-29b |
| hsa-mir-29b-1No1 | uc.20+A | -0.5915 | hsa-miR-29b |
| hsa-mir-102-prec-1 | uc.327+A | -0.5913 | hsa-miR-29b |
| hsa-mir-29b-1No1 | uc.173+ | -0.5912 | hsa-miR-29b |
| hsa-mir-29b-1No1 | uc.287+A | -0.5847 | hsa-miR-29b |
| hsa-mir-29b-2=102prec7.1=7.2 | uc.173+ | -0.5795 | hsa-miR-29b |
| hsa-mir-29b-1No1 | uc.128+A | -0.5777 | hsa-miR-29b |
| hsa-mir-102-prec-1 | uc.43+ | -0.574 | hsa-miR-29b |
| hsa-mir-29b-1No1 | uc.172+A | -0.5726 | hsa-miR-29b |
| hsa-mir-29b-2=102prec7.1=7.2 | uc.151+ | -0.5721 | hsa-miR-29b |
| hsa-mir-29b-1No1 | uc.299+A | -0.5715 | hsa-miR-29b |
| hsa-mir-29b-1No1 | uc.448+ | -0.5623 | hsa-miR-29b |
| hsa-mir-29b-1No1 | uc.44+A | -0.5602 | hsa-miR-29b |
| hsa-mir-29b-1No1 | uc.8+ | -0.5596 | hsa-miR-29b |
| hsa-mir-102-prec-1 | uc.299+A | -0.5586 | hsa-miR-29b |
| hsa-mir-29b-2=102prec7.1=7.2 | uc.151+A | -0.558 | hsa-miR-29b |
| hsa-mir-102-prec-1 | uc.44+A | -0.5579 | hsa-miR-29b |
| hsa-mir-102-prec-1 | uc.190+ | -0.5573 | hsa-miR-29b |
| hsa-mir-29b-1No1 | uc.151+A | -0.5569 | hsa-miR-29b |
| hsa-mir-102-prec-1 | uc.285+ | -0.5563 | hsa-miR-29b |
| hsa-mir-29b-1No1 | uc.170+ | -0.5562 | hsa-miR-29b |
| hsa-mir-102-prec-1 | uc.483+A | -0.5488 | hsa-miR-29b |
| hsa-mir-102-prec-1 | uc.448+ | -0.5482 | hsa-miR-29b |
| hsa-mir-102-prec-1 | uc.263+A | -0.5465 | hsa-miR-29b |
| hsa-mir-102-prec-1 | uc.456+ | -0.5464 | hsa-miR-29b |
| hsa-mir-29b-1No1 | uc.217+ | -0.5452 | hsa-miR-29b |
| hsa-mir-29b-1No1 | uc.483+A | -0.5409 | hsa-miR-29b |
| hsa-mir-29b-1No1 | uc.420+A | -0.5406 | hsa-miR-29b |
| hsa-mir-29b-2=102prec7.1=7.2 | uc.420+ | -0.5394 | hsa-miR-29b |
| hsa-mir-29b-1No1 | uc.190+ | -0.5323 | hsa-miR-29b |
| hsa-mir-102-prec-1 | uc.170+ | -0.5312 | hsa-miR-29b |
| hsa-mir-29b-1No1 | uc.263+A | -0.5248 | hsa-miR-29b |
| hsa-mir-29b-1No1 | uc.77+ | -0.5215 | hsa-miR-29b |
| hsa-mir-29b-1No1 | uc.151+ | -0.5207 | hsa-miR-29b |
| hsa-mir-29b-1No1 | uc.362+ | -0.5194 | hsa-miR-29b |
| hsa-mir-29b-1No1 | uc.177+ | -0.5176 | hsa-miR-29b |
| hsa-mir-102-prec-1 | uc.151+A | -0.517 | hsa-miR-29b |
| hsa-mir-29b-2=102prec7.1=7.2 | uc.420+A | -0.5147 | hsa-miR-29b |
| hsa-mir-29b-1No1 | uc.456+ | -0.5118 | hsa-miR-29b |
| hsa-mir-29b-1No1 | uc.182+ | -0.5111 | hsa-miR-29b |
| hsa-mir-29b-2=102prec7.1=7.2 | uc.77+ | -0.5099 | hsa-miR-29b |
| hsa-mir-102-prec-1 | uc.448+A | -0.5098 | hsa-miR-29b |
| hsa-mir-29b-2=102prec7.1=7.2 | uc.128+A | -0.5098 | hsa-miR-29b |
| hsa-mir-102-prec-1 | uc.48+A | -0.5069 | hsa-miR-29b |
| hsa-mir-102-prec-1 | uc.362+ | -0.5056 | hsa-miR-29b |
| hsa-mir-29b-1No1 | uc.346+ | -0.5014 | hsa-miR-29b |
| hsa-mir-102-prec-1 | uc.362+A | -0.5013 | hsa-miR-29b |
| hsa-mir-29b-1No1 | uc.362+A | -0.4977 | hsa-miR-29b |
| hsa-mir-29b-2=102prec7.1=7.2 | uc.172+A | -0.4976 | hsa-miR-29b |
| hsa-mir-29b-2=102prec7.1=7.2 | uc.300+A | -0.4972 | hsa-miR-29b |
| hsa-mir-102-prec-1 | uc.8+ | -0.497 | hsa-miR-29b |
| hsa-mir-29b-2=102prec7.1=7.2 | uc.134+ | -0.4959 | hsa-miR-29b |
| hsa-mir-29b-2=102prec7.1=7.2 | uc.269+A | -0.4947 | hsa-miR-29b |
| hsa-mir-29b-1No1 | uc.183+ | -0.492 | hsa-miR-29b |
| hsa-mir-102-prec-1 | uc.182+ | -0.4911 | hsa-miR-29b |
| hsa-mir-29b-1No1 | uc.48+A | -0.491 | hsa-miR-29b |
| hsa-mir-29b-1No1 | uc.10+ | -0.4825 | hsa-miR-29b |
| hsa-mir-102-prec-1 | uc.477+ | -0.4808 | hsa-miR-29b |
| hsa-mir-102-prec-1 | uc.173+ | -0.4807 | hsa-miR-29b |
| hsa-mir-29b-2=102prec7.1=7.2 | uc.33+A | -0.4764 | hsa-miR-29b |
| hsa-mir-102-prec-1 | uc.63+ | -0.4762 | hsa-miR-29b |
| hsa-mir-29b-1No1 | uc.63+ | -0.4738 | hsa-miR-29b |
| hsa-mir-102-prec-1 | uc.172+A | -0.4735 | hsa-miR-29b |
| hsa-mir-29b-1No1 | uc.449+A | -0.4733 | hsa-miR-29b |
| hsa-mir-29b-2=102prec7.1=7.2 | uc.325+ | -0.466 | hsa-miR-29b |
| hsa-mir-29b-2=102prec7.1=7.2 | uc.183+ | -0.4653 | hsa-miR-29b |
| hsa-mir-29b-2=102prec7.1=7.2 | uc.419+A | -0.4647 | hsa-miR-29b |

Figure 18 Continued

| miRNA probe on array | UCR probe on array | Correlations (Spearman Method) | miRNA |
|---|---|---|---|
| hsa-mir-29b-2=102prec7.1=7.2 | uc.364+ | -0.4619 | hsa-miR-29b |
| hsa-mir-29b-1No1 | uc.248+ | -0.4617 | hsa-miR-29b |
| hsa-mir-29b-1No1 | uc.233+A | -0.4594 | hsa-miR-29b |
| hsa-mir-102-prec-1 | uc.200+ | -0.4591 | hsa-miR-29b |
| hsa-mir-102-prec-1 | uc.248+ | -0.4555 | hsa-miR-29b |
| hsa-mir-29b-1No1 | uc.477+ | -0.455 | hsa-miR-29b |
| hsa-mir-29b-1No1 | uc.465+A | -0.454 | hsa-miR-29b |
| hsa-mir-29b-1No1 | uc.167+ | -0.4507 | hsa-miR-29b |
| hsa-mir-29b-1No1 | uc.200+ | -0.4495 | hsa-miR-29b |
| hsa-mir-029c-prec | uc.106+ | -0.7586 | hsa-miR-29c |
| hsa-mir-029c-prec | uc.153+A | -0.7466 | hsa-miR-29c |
| hsa-mir-029c-prec | uc.354+A | -0.7247 | hsa-miR-29c |
| hsa-mir-029c-prec | uc.383+ | -0.7195 | hsa-miR-29c |
| hsa-mir-029c-prec | uc.33+A | -0.7185 | hsa-miR-29c |
| hsa-mir-029c-prec | uc.462+A | -0.7154 | hsa-miR-29c |
| hsa-mir-029c-prec | uc.456+A | -0.7066 | hsa-miR-29c |
| hsa-mir-029c-prec | uc.190+A | -0.7064 | hsa-miR-29c |
| hsa-mir-029c-prec | uc.234+ | -0.7034 | hsa-miR-29c |
| hsa-mir-029c-prec | uc.18+ | -0.7017 | hsa-miR-29c |
| hsa-mir-029c-prec | uc.468+ | -0.6997 | hsa-miR-29c |
| hsa-mir-029c-prec | uc.427+ | -0.6947 | hsa-miR-29c |
| hsa-mir-029c-prec | uc.388+ | -0.6915 | hsa-miR-29c |
| hsa-mir-029c-prec | uc.213+ | -0.688 | hsa-miR-29c |
| hsa-mir-029c-prec | uc.153+ | -0.6869 | hsa-miR-29c |
| hsa-mir-029c-prec | uc.73+A | -0.6835 | hsa-miR-29c |
| hsa-mir-029c-prec | uc.430+ | -0.6784 | hsa-miR-29c |
| hsa-mir-029c-prec | uc.263+ | -0.67 | hsa-miR-29c |
| hsa-mir-029c-prec | uc.473+A | -0.6687 | hsa-miR-29c |
| hsa-mir-029c-prec | uc.275+ | -0.6662 | hsa-miR-29c |
| hsa-mir-029c-prec | uc.20+ | -0.6608 | hsa-miR-29c |
| hsa-mir-029c-prec | uc.287+A | -0.6604 | hsa-miR-29c |
| hsa-mir-029c-prec | uc.477+A | -0.6599 | hsa-miR-29c |
| hsa-mir-029c-prec | uc.317+A | -0.6569 | hsa-miR-29c |
| hsa-mir-029c-prec | uc.378+ | -0.6539 | hsa-miR-29c |
| hsa-mir-029c-prec | uc.20+A | -0.6522 | hsa-miR-29c |
| hsa-mir-029c-prec | uc.88+ | -0.647 | hsa-miR-29c |
| hsa-mir-029c-prec | uc.378+A | -0.6368 | hsa-miR-29c |
| hsa-mir-029c-prec | uc.33+ | -0.6322 | hsa-miR-29c |
| hsa-mir-029c-prec | uc.388+A | -0.6228 | hsa-miR-29c |
| hsa-mir-029c-prec | uc.412+A | -0.6209 | hsa-miR-29c |
| hsa-mir-029c-prec | uc.189+ | -0.6208 | hsa-miR-29c |
| hsa-mir-029c-prec | uc.468+A | -0.6189 | hsa-miR-29c |
| hsa-mir-029c-prec | uc.445+A | -0.6083 | hsa-miR-29c |
| hsa-mir-029c-prec | uc.217+ | -0.6001 | hsa-miR-29c |
| hsa-mir-029c-prec | uc.43+ | -0.5863 | hsa-miR-29c |
| hsa-mir-029c-prec | uc.327+A | -0.5852 | hsa-miR-29c |
| hsa-mir-029c-prec | uc.44+A | -0.5792 | hsa-miR-29c |
| hsa-mir-029c-prec | uc.170+ | -0.5568 | hsa-miR-29c |
| hsa-mir-029c-prec | uc.265+ | -0.5559 | hsa-miR-29c |
| hsa-mir-029c-prec | uc.299+A | -0.555 | hsa-miR-29c |
| hsa-mir-029c-prec | uc.263+A | -0.5516 | hsa-miR-29c |
| hsa-mir-029c-prec | uc.448+ | -0.5515 | hsa-miR-29c |
| hsa-mir-029c-prec | uc.362+ | -0.5513 | hsa-miR-29c |
| hsa-mir-029c-prec | uc.448+A | -0.5469 | hsa-miR-29c |
| hsa-mir-029c-prec | uc.190+ | -0.5464 | hsa-miR-29c |
| hsa-mir-029c-prec | uc.48+A | -0.545 | hsa-miR-29c |
| hsa-mir-029c-prec | uc.362+A | -0.5366 | hsa-miR-29c |
| hsa-mir-029c-prec | uc.456+ | -0.5164 | hsa-miR-29c |
| hsa-mir-029c-prec | uc.151+A | -0.5074 | hsa-miR-29c |
| hsa-mir-029c-prec | uc.173+ | -0.5017 | hsa-miR-29c |
| hsa-mir-029c-prec | uc.200+ | -0.4979 | hsa-miR-29c |
| hsa-mir-029c-prec | uc.477+ | -0.4973 | hsa-miR-29c |
| hsa-mir-029c-prec | uc.8+ | -0.4934 | hsa-miR-29c |
| hsa-mir-029c-prec | uc.63+ | -0.4934 | hsa-miR-29c |
| hsa-mir-029c-prec | uc.483+A | -0.4923 | hsa-miR-29c |
| hsa-mir-029c-prec | uc.173+A | -0.4851 | hsa-miR-29c |
| hsa-mir-029c-prec | uc.420+A | -0.4814 | hsa-miR-29c |
| hsa-mir-029c-prec | uc.182+ | -0.4763 | hsa-miR-29c |
| hsa-mir-029c-prec | uc.248+ | -0.4746 | hsa-miR-29c |
| hsa-mir-029c-prec | uc.233+A | -0.4698 | hsa-miR-29c |
| hsa-mir-029c-prec | uc.10+ | -0.4508 | hsa-miR-29c |
| hsa-mir-029c-prec | uc.128+A | -0.4479 | hsa-miR-29c |
| hsa-mir-030a-precNo1 | uc.282+A | -0.7 | hsa-miR-30a-5p |
| hsa-mir-030a-precNo1 | uc.465+A | -0.633 | hsa-miR-30a-5p |
| hsa-mir-030a-precNo1 | uc.325+ | -0.6138 | hsa-miR-30a-5p |
| hsa-mir-030a-precNo1 | uc.346+A | -0.5258 | hsa-miR-30a-5p |
| hsa-mir-030a-precNo1 | uc.339+ | -0.5164 | hsa-miR-30a-5p |
| hsa-mir-030a-precNo1 | uc.151+A | -0.5097 | hsa-miR-30a-5p |
| hsa-mir-030a-precNo1 | uc.142+ | -0.4975 | hsa-miR-30a-5p |
| hsa-mir-030a-precNo1 | uc.285+ | -0.4758 | hsa-miR-30a-5p |
| hsa-mir-030a-precNo1 | uc.142+A | -0.4757 | hsa-miR-30a-5p |
| hsa-mir-030a-precNo1 | uc.73+ | -0.4573 | hsa-miR-30a-5p |
| hsa-mir-030a-precNo1 | uc.173+A | -0.4541 | hsa-miR-30a-5p |
| hsa-mir-030a-precNo1 | uc.346+ | -0.4496 | hsa-miR-30a-5p |

Figure 18 Continued

| miRNA probe on array | UCR probe on array | Correlations (Spearman Method) | miRNA |
|---|---|---|---|
| hsa-mir-030c-prec | uc.420+ | -0.6341 | hsa-miR-30c |
| hsa-mir-30c-1No1 | uc.339+ | -0.6083 | hsa-miR-30c |
| hsa-mir-30c-1No1 | uc.346- | -0.5928 | hsa-miR-30c |
| hsa-mir-030c-prec | uc.189+ | -0.5918 | hsa-miR-30c |
| hsa-mir-30c-1No1 | uc.172+A | -0.5838 | hsa-miR-30c |
| hsa-mir-030c-prec | uc.339+ | -0.5644 | hsa-miR-30c |
| hsa-mir-030c-prec | uc.285+ | -0.5631 | hsa-miR-30c |
| hsa-mir-30c-1No1 | uc.285+ | -0.5623 | hsa-miR-30c |
| hsa-mir-30c-1No1 | uc.177+ | -0.545 | hsa-miR-30c |
| hsa-mir-030c-prec | uc.299+A | -0.5439 | hsa-miR-30c |
| hsa-mir-30c-1No1 | uc.213+ | -0.5393 | hsa-miR-30c |
| hsa-mir-030c-prec | uc.172-A | -0.5363 | hsa-miR-30c |
| hsa-mir-30c-1No1 | uc.278+ | -0.532 | hsa-miR-30c |
| hsa-mir-30c-1No1 | uc.151+ | -0.531 | hsa-miR-30c |
| hsa-mir-030c-prec | uc.468+ | -0.5264 | hsa-miR-30c |
| hsa-mir-030c-prec | uc.73+A | -0.5231 | hsa-miR-30c |
| hsa-mir-030c-prec | uc.213+ | -0.5135 | hsa-miR-30c |
| hsa-mir-30c-1No1 | uc.229+ | -0.5097 | hsa-miR-30c |
| hsa-mir-030c-prec | uc.128+A | -0.5093 | hsa-miR-30c |
| hsa-mir-30c-1No1 | uc.159- | -0.508 | hsa-miR-30c |
| hsa-mir-30c-1No1 | uc.465+A | -0.5036 | hsa-miR-30c |
| hsa-mir-30c-1No1 | uc.128+A | -0.5012 | hsa-miR-30c |
| hsa-mir-030c-prec | uc.278+ | -0.498 | hsa-miR-30c |
| hsa-mir-30c-1No1 | uc.420- | -0.4974 | hsa-miR-30c |
| hsa-mir-30c-1No1 | uc.466+A | -0.4963 | hsa-miR-30c |
| hsa-mir-30c-1No1 | uc.77+ | -0.4963 | hsa-miR-30c |
| hsa-mir-30c-1No1 | uc.349+ | -0.496 | hsa-miR-30c |
| hsa-mir-30c-1No1 | uc.234+ | -0.4921 | hsa-miR-30c |
| hsa-mir-30c-1No1 | uc.173- | -0.488 | hsa-miR-30c |
| hsa-mir-030c-prec | uc.465+A | -0.4874 | hsa-miR-30c |
| hsa-mir-030c-prec | uc.173+ | -0.4871 | hsa-miR-30c |
| hsa-mir-30c-1No1 | uc.18+ | -0.4869 | hsa-miR-30c |
| hsa-mir-030c-prec | uc.234+ | -0.4851 | hsa-miR-30c |
| hsa-mir-030c-prec | uc.8+ | -0.4843 | hsa-miR-30c |
| hsa-mir-030c-prec | uc.160- | -0.484 | hsa-miR-30c |
| hsa-mir-030c-prec | uc.151+ | -0.4826 | hsa-miR-30c |
| hsa-mir-30c-1No1 | uc.419+A | -0.4825 | hsa-miR-30c |
| hsa-mir-30c-1No1 | uc.153+A | -0.4823 | hsa-miR-30c |
| hsa-mir-030c-prec | uc.33+A | -0.481 | hsa-miR-30c |
| hsa-mir-030c-prec | uc.217+A | -0.4775 | hsa-miR-30c |
| hsa-mir-030c-prec | uc.419+A | -0.4775 | hsa-miR-30c |
| hsa-mir-030c-prec | uc.177+ | -0.4754 | hsa-miR-30c |
| hsa-mir-030c-prec | uc.233+A | -0.4738 | hsa-miR-30c |
| hsa-mir-030c-prec | uc.18+ | -0.4729 | hsa-miR-30c |
| hsa-mir-030c-prec | uc.153+A | -0.472 | hsa-miR-30c |
| hsa-mir-30c-1No1 | uc.468+ | -0.4717 | hsa-miR-30c |
| hsa-mir-030c-prec | uc.183+ | -0.4713 | hsa-miR-30c |
| hsa-mir-030c-prec | uc.262+A | -0.4678 | hsa-miR-30c |
| hsa-mir-30c-1No1 | uc.388+A | -0.464 | hsa-miR-30c |
| hsa-mir-030c-prec | uc.134+A | -0.462 | hsa-miR-30c |
| hsa-mir-030c-prec | uc.354+A | -0.4614 | hsa-miR-30c |
| hsa-mir-030c-prec | uc.262+A | -0.4607 | hsa-miR-30c |
| hsa-mir-30c-1No1 | uc.33+ | -0.4602 | hsa-miR-30c |
| hsa-mir-030c-prec | uc.412+A | -0.4571 | hsa-miR-30c |
| hsa-mir-30c-1No1 | uc.183+ | -0.4554 | hsa-miR-30c |
| hsa-mir-30c-1No1 | uc.299+A | -0.4544 | hsa-miR-30c |
| hsa-mir-30c-1No1 | uc.33+A | -0.4504 | hsa-miR-30c |
| hsa-mir-030c-prec | uc.420+A | -0.4491 | hsa-miR-30c |
| hsa-mir-030c-prec | uc.44+A | -0.4483 | hsa-miR-30c |
| hsa-mir-030c-prec | uc.466+A | -0.4481 | hsa-miR-30c |
| hsa-mir-030d-precNo2 | uc.325+ | -0.6363 | hsa-miR-30d |
| hsa-mir-030d-precNo2 | uc.465+A | -0.6086 | hsa-miR-30d |
| hsa-mir-030d-precNo2 | uc.262+A | -0.533 | hsa-miR-30d |
| hsa-mir-030d-precNo2 | uc.339+ | -0.4846 | hsa-miR-30d |
| hsa-mir-30eNo1 | uc.285+ | -0.6838 | hsa-miR-30e-5p |
| hsa-mir-30eNo1 | uc.420+ | -0.6583 | hsa-miR-30e-5p |
| hsa-mir-30eNo1 | uc.33+A | -0.6517 | hsa-miR-30e-5p |
| hsa-mir-30eNo1 | uc.153+A | -0.6433 | hsa-miR-30e-5p |
| hsa-mir-30eNo1 | uc.73+A | -0.6378 | hsa-miR-30e-5p |
| hsa-mir-30eNo1 | uc.213+ | -0.631 | hsa-miR-30e-5p |
| hsa-mir-30eNo1 | uc.234+ | -0.6107 | hsa-miR-30e-5p |
| hsa-mir-30eNo1 | uc.327+A | -0.6071 | hsa-miR-30e-5p |
| hsa-mir-30eNo1 | uc.18+ | -0.5974 | hsa-miR-30e-5p |
| hsa-mir-30eNo1 | uc.462+A | -0.5968 | hsa-miR-30e-5p |
| hsa-mir-30eNo1 | uc.186+ | -0.595 | hsa-miR-30e-5p |
| hsa-mir-30eNo1 | uc.275+ | -0.5876 | hsa-miR-30e-5p |
| hsa-mir-30eNo1 | uc.388+A | -0.5848 | hsa-miR-30e-5p |
| hsa-mir-30eNo1 | uc.44+A | -0.5762 | hsa-miR-30e-5p |
| hsa-mir-30eNo1 | uc.189+ | -0.5713 | hsa-miR-30e-5p |
| hsa-mir-30eNo1 | uc.153+ | -0.5619 | hsa-miR-30e-5p |
| hsa-mir-30eNo1 | uc.33+ | -0.5613 | hsa-miR-30e-5p |
| hsa-mir-30eNo1 | uc.465+A | -0.561 | hsa-miR-30e-5p |
| hsa-mir-30eNo1 | uc.88+ | -0.5554 | hsa-miR-30e-5p |
| hsa-mir-30eNo1 | uc.173+ | -0.5536 | hsa-miR-30e-5p |

Figure 18 Continued

| miRNA probe on array | UCR probe on array | Correlations (Spearman Method) | miRNA |
|---|---|---|---|
| hsa-mir-30eNo1 | uc.354+A | -0.5512 | hsa-miR-30e-5p |
| hsa-mir-30eNo1 | uc.383+ | -0.5499 | hsa-miR-30e-5p |
| hsa-mir-30eNo1 | uc.388+ | -0.5358 | hsa-miR-30e-5p |
| hsa-mir-30eNo1 | uc.299+A | -0.5345 | hsa-miR-30e-5p |
| hsa-mir-30eNo1 | uc.217+A | -0.5278 | hsa-miR-30e-5p |
| hsa-mir-30eNo1 | uc.151+A | -0.5268 | hsa-miR-30e-5p |
| hsa-mir-30eNo1 | uc.173+A | -0.5259 | hsa-miR-30e-5p |
| hsa-mir-30eNo1 | uc.346+ | -0.5253 | hsa-miR-30e-5p |
| hsa-mir-30eNo1 | uc.151+ | -0.5234 | hsa-miR-30e-5p |
| hsa-mir-30eNo1 | uc.183+ | -0.5203 | hsa-miR-30e-5p |
| hsa-mir-30eNo1 | uc.456+A | -0.519 | hsa-miR-30e-5p |
| hsa-mir-30eNo1 | uc.8+ | -0.5157 | hsa-miR-30e-5p |
| hsa-mir-30eNo1 | uc.427+ | -0.5153 | hsa-miR-30e-5p |
| hsa-mir-30eNo1 | uc.117+ | -0.5067 | hsa-miR-30e-5p |
| hsa-mir-30eNo1 | uc.177+ | -0.5023 | hsa-miR-30e-5p |
| hsa-mir-30eNo1 | uc.167+ | -0.4966 | hsa-miR-30e-5p |
| hsa-mir-30eNo1 | uc.77+ | -0.4959 | hsa-miR-30e-5p |
| hsa-mir-30eNo1 | uc.412+A | -0.4889 | hsa-miR-30e-5p |
| hsa-mir-30eNo1 | uc.263+ | -0.4869 | hsa-miR-30e-5p |
| hsa-mir-30eNo1 | uc.473+A | -0.4836 | hsa-miR-30e-5p |
| hsa-mir-30eNo1 | uc.128+A | -0.4823 | hsa-miR-30e-5p |
| hsa-mir-30eNo1 | uc.190+A | -0.4798 | hsa-miR-30e-5p |
| hsa-mir-30eNo1 | uc.468+ | -0.4794 | hsa-miR-30e-5p |
| hsa-mir-30eNo1 | uc.46+A | -0.47 | hsa-miR-30e-5p |
| hsa-mir-30eNo1 | uc.420+A | -0.4697 | hsa-miR-30e-5p |
| hsa-mir-30eNo1 | uc.478+A | -0.4692 | hsa-miR-30e-5p |
| hsa-mir-30eNo1 | uc.20+A | -0.466 | hsa-miR-30e-5p |
| hsa-mir-30eNo1 | uc.190+ | -0.4496 | hsa-miR-30e-5p |
| hsa-mir-032-precNo2 | uc.478+ | -0.6778 | hsa-miR-32 |
| hsa-mir-032-precNo2 | uc.1+ | -0.6241 | hsa-miR-32 |
| hsa-mir-032-precNo2 | uc.475+ | -0.483 | hsa-miR-32 |
| hsa-mir-032-precNo2 | uc.192+ | -0.471 | hsa-miR-32 |
| hsa-mir-032-precNo2 | uc.389+ | -0.4667 | hsa-miR-32 |
| hsa-mir-320No1 | uc.263+A | -0.6262 | hsa-miR-320 |
| hsa-mir-320No1 | uc.273+ | -0.618 | hsa-miR-320 |
| hsa-mir-320No1 | uc.160+ | -0.6056 | hsa-miR-320 |
| hsa-mir-320No1 | uc.339+ | -0.6013 | hsa-miR-320 |
| hsa-mir-320No1 | uc.265+A | -0.5776 | hsa-miR-320 |
| hsa-mir-320No1 | uc.349+ | -0.563 | hsa-miR-320 |
| hsa-mir-320No2 | uc.229+ | -0.5378 | hsa-mir-320 |
| hsa-mir-320No2 | uc.466+A | -0.5314 | hsa-mir-320 |
| hsa-mir-320No1 | uc.135+ | -0.5267 | hsa-miR-320 |
| hsa-mir-320No1 | uc.73+ | -0.5223 | hsa-miR-320 |
| hsa-mir-320No1 | uc.400+A | -0.5113 | hsa-miR-320 |
| hsa-mir-320No1 | uc.229+ | -0.508 | hsa-miR-320 |
| hsa-mir-320No1 | uc.204+ | -0.475 | hsa-miR-320 |
| hsa-mir-320No1 | uc.317+ | -0.4726 | hsa-miR-320 |
| hsa-mir-320No1 | uc.398+ | -0.4724 | hsa-miR-320 |
| hsa-mir-320No1 | uc.285+ | -0.4659 | hsa-miR-320 |
| hsa-mir-320No1 | uc.196+A | -0.4629 | hsa-miR-320 |
| hsa-mir-320No1 | uc.377+A | -0.4596 | hsa-miR-320 |
| hsa-mir-320No2 | uc.345+ | -0.4594 | hsa-mir-320 |
| hsa-mir-320No1 | uc.465+A | -0.4551 | hsa-miR-320 |
| hsa-miR-324-5pNo1 | uc.378+ | -0.6435 | hsa-miR-324-5p |
| hsa-miR-324-5pNo1 | uc.86+ | -0.6372 | hsa-miR-324-5p |
| hsa-miR-324-5pNo1 | uc.287+A | -0.6257 | hsa-miR-324-5p |
| hsa-miR-324-5pNo1 | uc.477+A | -0.6203 | hsa-miR-324-5p |
| hsa-miR-324-5pNo1 | uc.473+A | -0.6191 | hsa-miR-324-5p |
| hsa-miR-324-5pNo1 | uc.468+A | -0.6112 | hsa-miR-324-5p |
| hsa-miR-324-5pNo1 | uc.217+A | -0.6071 | hsa-miR-324-5p |
| hsa-miR-324-5pNo1 | uc.463+A | -0.5899 | hsa-miR-324-5p |
| hsa-miR-324-5pNo1 | uc.63+ | -0.5893 | hsa-miR-324-5p |
| hsa-miR-324-5pNo1 | uc.445+A | -0.5876 | hsa-miR-324-5p |
| hsa-miR-324-5pNo1 | uc.477+ | -0.5781 | hsa-miR-324-5p |
| hsa-miR-324-5pNo1 | uc.383+ | -0.5754 | hsa-miR-324-5p |
| hsa-miR-324-5pNo1 | uc.153+ | -0.5736 | hsa-miR-324-5p |
| hsa-miR-324-5pNo1 | uc.354+A | -0.5702 | hsa-miR-324-5p |
| hsa-miR-324-5pNo1 | uc.378+A | -0.5702 | hsa-miR-324-5p |
| hsa-miR-324-5pNo1 | uc.170+ | -0.5645 | hsa-miR-324-5p |
| hsa-miR-324-5pNo1 | uc.20+A | -0.562 | hsa-miR-324-5p |
| hsa-miR-324-5pNo1 | uc.182+ | -0.5558 | hsa-miR-324-5p |
| hsa-miR-324-5pNo1 | uc.217+ | -0.5518 | hsa-miR-324-5p |
| hsa-miR-324-5pNo1 | uc.190+A | -0.5457 | hsa-miR-324-5p |
| hsa-miR-324-5pNo1 | uc.362+A | -0.5423 | hsa-miR-324-5p |
| hsa-miR-324-5pNo1 | uc.106+ | -0.5351 | hsa-miR-324-5p |
| hsa-miR-324-5pNo1 | uc.43+ | -0.5339 | hsa-miR-324-5p |
| hsa-miR-324-5pNo1 | uc.263+ | -0.5321 | hsa-miR-324-5p |
| hsa-miR-324-5pNo1 | uc.190+ | -0.5253 | hsa-miR-324-5p |
| hsa-miR-324-5pNo1 | uc.33+ | -0.5147 | hsa-miR-324-5p |
| hsa-miR-324-5pNo1 | uc.189+ | -0.51 | hsa-miR-324-5p |
| hsa-miR-324-5pNo1 | uc.333+ | -0.5086 | hsa-miR-324-5p |
| hsa-miR-324-5pNo1 | uc.20+ | -0.4955 | hsa-miR-324-5p |
| hsa-miR-324-5pNo1 | uc.383+ | -0.4933 | hsa-miR-324-5p |
| hsa-miR-324-5pNo1 | uc.95+ | -0.4919 | hsa-miR-324-5p |

Figure 18 Continued

Calin GA

| miRNA probe on array | UCR probe on array | Correlations (Spearman Method) | miRNA |
|---|---|---|---|
| hsa-miR-324-5pNo1 | uc.234+ | -0.4877 | hsa-miR-324-5p |
| hsa-miR-324-5pNo1 | uc.275+ | -0.4865 | hsa-miR-324-5p |
| hsa-miR-324-5pNo1 | uc.420+ | -0.4815 | hsa-miR-324-5p |
| hsa-miR-324-5pNo1 | uc.86+A | -0.4798 | hsa-miR-324-5p |
| hsa-miR-324-5pNo1 | uc.153+A | -0.4773 | hsa-miR-324-5p |
| hsa-miR-324-5pNo1 | uc.362+ | -0.4721 | hsa-miR-324-5p |
| hsa-miR-324-5pNo1 | uc.468+ | -0.4715 | hsa-miR-324-5p |
| hsa-miR-324-5pNo1 | uc.412+ | -0.4669 | hsa-miR-324-5p |
| hsa-miR-324-5pNo1 | uc.289+A | -0.457 | hsa-miR-324-5p |
| hsa-miR-324-5pNo1 | uc.413+A | -0.4554 | hsa-miR-324-5p |
| hsa-miR-324-5pNo1 | uc.475+A | -0.4516 | hsa-miR-324-5p |
| hsa-miR-324-5pNo1 | uc.448+A | -0.4483 | hsa-miR-324-5p |
| hsa-mir-328No1 | uc.229+ | -0.6749 | hsa-miR-328 |
| hsa-mir-328No1 | uc.483+ | -0.6617 | hsa-miR-328 |
| hsa-mir-328No1 | uc.466+A | -0.5846 | hsa-miR-328 |
| hsa-mir-328No1 | uc.128+A | -0.5712 | hsa-miR-328 |
| hsa-mir-328No1 | uc.177+ | -0.5702 | hsa-miR-328 |
| hsa-mir-328No1 | uc.346+ | -0.5528 | hsa-miR-328 |
| hsa-mir-328No1 | uc.77+ | -0.5454 | hsa-miR-328 |
| hsa-mir-328No1 | uc.172+A | -0.5328 | hsa-miR-328 |
| hsa-mir-328No1 | uc.142+ | -0.4902 | hsa-miR-328 |
| hsa-mir-328No1 | uc.345+ | -0.4807 | hsa-miR-328 |
| hsa-mir-328No1 | uc.41+ | -0.4667 | hsa-miR-328 |
| hsa-mir-331No2 | uc.366+ | -0.5883 | hsa-miR-331 |
| hsa-mir-331No2 | uc.125+A | -0.5796 | hsa-miR-331 |
| hsa-mir-331No2 | uc.345+A | -0.5671 | hsa-miR-331 |
| hsa-mir-331No2 | uc.136+ | -0.548 | hsa-miR-331 |
| hsa-mir-331No2 | uc.73+ | -0.5026 | hsa-miR-331 |
| hsa-mir-331No2 | uc.192+ | -0.4928 | hsa-miR-331 |
| hsa-mir-331No2 | uc.330+ | -0.4886 | hsa-miR-331 |
| hsa-mir-331No2 | uc.31+ | -0.4558 | hsa-miR-331 |
| hsa-mir-033b-prec | uc.159+A | -0.5238 | hsa-miR-33b |
| hsa-mir-340No2 | uc.383+ | -0.5595 | hsa-miR-340 |
| hsa-mir-340No2 | uc.462+A | -0.5231 | hsa-miR-340 |
| hsa-mir-340No2 | uc.20+A | -0.4993 | hsa-miR-340 |
| hsa-mir-340No2 | uc.48+A | -0.4757 | hsa-miR-340 |
| hsa-mir-340No2 | uc.63+ | -0.4736 | hsa-miR-340 |
| hsa-mir-340No2 | uc.477+ | -0.4717 | hsa-miR-340 |
| hsa-mir-340No2 | uc.153+ | -0.4698 | hsa-miR-340 |
| hsa-mir-340No2 | uc.20+ | -0.4698 | hsa-miR-340 |
| hsa-mir-340No2 | uc.263+ | -0.4673 | hsa-miR-340 |
| hsa-mir-340No2 | uc.287+A | -0.4579 | hsa-miR-340 |
| hsa-mir-340No2 | uc.468+A | -0.4483 | hsa-miR-340 |
| hsa-mir-340No2 | uc.368+ | -0.4477 | hsa-miR-340 |
| hsa-mir-342No1 | uc.192+ | -0.7322 | hsa-miR-342 |
| hsa-mir-342No1 | uc.389+ | -0.7241 | hsa-miR-342 |
| hsa-mir-342No1 | uc.478+ | -0.6819 | hsa-miR-342 |
| hsa-mir-342No1 | uc.366+ | -0.6742 | hsa-miR-342 |
| hsa-mir-342No2 | uc.136+ | -0.5518 | hsa-miR-342 |
| hsa-mir-342No1 | uc.125+A | -0.5505 | hsa-miR-342 |
| hsa-mir-342No1 | uc.346+A | -0.5347 | hsa-miR-342 |
| hsa-mir-342No1 | uc.24+A | -0.5191 | hsa-miR-342 |
| hsa-mir-342No1 | uc.73+ | -0.5188 | hsa-miR-342 |
| hsa-mir-342No1 | uc.181+A | -0.5034 | hsa-miR-342 |
| hsa-mir-342No1 | uc.330+ | -0.5023 | hsa-miR-342 |
| hsa-mir-342No2 | uc.110+A | -0.4937 | hsa-miR-342 |
| hsa-mir-342No1 | uc.31+ | -0.4617 | hsa-miR-342 |
| hsa-mir-342No1 | uc.345+A | -0.4516 | hsa-miR-342 |
| hsa-mir-346No1 | uc.462+ | -0.6113 | hsa-miR-346 |
| hsa-mir-346No1 | uc.204+ | -0.6083 | hsa-miR-346 |
| hsa-mir-346No1 | uc.229+ | -0.544 | hsa-miR-346 |
| hsa-mir-346No1 | uc.345+ | -0.5396 | hsa-miR-346 |
| hsa-mir-346No1 | uc.131+ | -0.4891 | hsa-miR-346 |
| hsa-mir-346No1 | uc.41+ | -0.4822 | hsa-miR-346 |
| hsa-mir-346No1 | uc.73+ | -0.4746 | hsa-miR-346 |
| hsa-mir-346No1 | uc.177+ | -0.4563 | hsa-miR-346 |
| hsa-mir-346No1 | uc.483+ | -0.4557 | hsa-miR-346 |
| hsa-mir-346No1 | uc.345+ | -0.4534 | hsa-miR-346 |
| hsa-mir-346No1 | uc.192+ | -0.4531 | hsa-miR-346 |
| hsa-mir-346No1 | uc.349+ | -0.4507 | hsa-miR-346 |
| hsa-mir-346No1 | uc.366+ | -0.4497 | hsa-miR-346 |
| hsa-miR-373No1 | uc.181+A | -0.7063 | hsa-miR-373 |
| hsa-miR-373No1 | uc.125+A | -0.681 | hsa-miR-373 |
| hsa-miR-373No1 | uc.366+ | -0.6479 | hsa-miR-373 |
| hsa-miR-373No1 | uc.345+A | -0.6197 | hsa-miR-373 |
| hsa-miR-373No1 | uc.192+ | -0.5652 | hsa-miR-373 |
| hsa-miR-373No1 | uc.330+ | -0.5647 | hsa-miR-373 |
| hsa-miR-373No1 | uc.317+ | -0.4556 | hsa-miR-373 |
| hsa-mir-009-3No1 | uc.477+A | -0.6051 | hsa-miR-9 |
| hsa-mir-009-1No1 | uc.345+A | -0.6035 | hsa-miR-9 |
| hsa-mir-009-1No1 | uc.125+A | -0.5789 | hsa-miR-9 |
| hsa-mir-009-3No1 | uc.287+A | -0.555 | hsa-miR-9 |
| hsa-mir-009-1No1 | uc.31+ | -0.5493 | hsa-miR-9 |
| hsa-mir-009-1No1 | uc.192+ | -0.5477 | hsa-miR-9 |

Figure 18 Continued

| miRNA probe on array | UCR probe on array | Correlations (Spearman Method) | miRNA |
|---|---|---|---|
| hsa-mir-009-1No1 | uc.366+ | -0.5438 | hsa-miR-9 |
| hsa-mir-009-3No1 | uc.477+ | -0.5428 | hsa-miR-9 |
| hsa-mir-009-3No1 | uc.217+ | -0.5426 | hsa-miR-9 |
| hsa-mir-009-3No1 | uc.378+ | -0.5219 | hsa-miR-9 |
| hsa-mir-009-3No1 | uc.159+A | -0.5153 | hsa-miR-9 |
| hsa-mir-009-1No1 | uc.230+ | -0.5152 | hsa-miR-9 |
| hsa-mir-009-3No1 | uc.382+A | -0.4909 | hsa-miR-9 |
| hsa-mir-009-3No1 | uc.95+ | -0.4895 | hsa-miR-9 |
| hsa-mir-009-3No1 | uc.448+A | -0.4804 | hsa-miR-9 |
| hsa-mir-009-1No1 | uc.136+ | -0.4591 | hsa-miR-9 |
| hsa-mir-009-3No1 | uc.475+A | -0.453 | hsa-miR-9 |
| hsa-mir-009-3No1 | uc.338+ | -0.4525 | hsa-miR-9 |
| hsa-mir-009-3No1 | uc.412+ | -0.451 | hsa-miR-9 |
| hsa-mir-009-3No1 | uc.20+A | -0.4482 | hsa-miR-9 |
| hsa-mir-092-prec-X=092-2 | uc.478+ | -0.7591 | hsa-miR-92 |
| hsa-mir-092-prec-13=092-1No2 | uc.478+ | -0.7553 | hsa-miR-92 |
| hsa-mir-092-prec-13=092-1No2 | uc.389+ | -0.7431 | hsa-miR-92 |
| hsa-mir-092-prec-X=092-2 | uc.192+ | -0.7375 | hsa-miR-92 |
| hsa-mir-092-prec-X=092-2 | uc.389+ | -0.7308 | hsa-miR-92 |
| hsa-mir-092-prec-13=092-1No2 | uc.192+ | -0.7224 | hsa-miR-92 |
| hsa-mir-092-prec-13=092-1No2 | uc.346+A | -0.7064 | hsa-miR-92 |
| hsa-mir-092-prec-13=092-1No2 | uc.366+ | -0.6828 | hsa-miR-92 |
| hsa-mir-092-prec-X=092-2 | uc.346+A | -0.6735 | hsa-miR-92 |
| hsa-mir-092-prec-X=092-2 | uc.366+ | -0.6722 | hsa-miR-92 |
| hsa-mir-092-prec-13=092-1No2 | uc.24+A | -0.5623 | hsa-miR-92 |
| hsa-mir-092-prec-X=092-2 | uc.181+A | -0.5452 | hsa-miR-92 |
| hsa-mir-092-prec-X=092-2 | uc.24+A | -0.5418 | hsa-miR-92 |
| hsa-mir-092-prec-13=092-1No2 | uc.34+A | -0.5234 | hsa-miR-92 |
| hsa-mir-092-prec-X=092-2 | uc.125+A | -0.523 | hsa-miR-92 |
| hsa-mir-092-prec-X=092-2 | uc.34+A | -0.5132 | hsa-miR-92 |
| hsa-mir-092-prec-13=092-1No2 | uc.341+A | -0.5126 | hsa-miR-92 |
| hsa-mir-092-prec-X=092-2 | uc.73+ | -0.503 | hsa-miR-92 |
| hsa-mir-092-prec-X=092-2 | uc.31+ | -0.4945 | hsa-miR-92 |
| hsa-mir-092-prec-13=092-1No2 | uc.31+ | -0.4884 | hsa-miR-92 |
| hsa-mir-092-prec-13=092-1No2 | uc.125+A | -0.4787 | hsa-miR-92 |
| hsa-mir-092-prec-13=092-1No2 | uc.230+ | -0.4743 | hsa-miR-92 |
| hsa-mir-092-prec-13=092-1No2 | uc.181+A | -0.4655 | hsa-miR-92 |
| hsa-mir-092-prec-13=092-1No2 | uc.204+A | -0.4646 | hsa-miR-92 |
| hsa-mir-092-prec-13=092-1No2 | uc.73+ | -0.4646 | hsa-miR-92 |
| hsa-mir-092-prec-13=092-1No2 | uc.398+ | -0.4624 | hsa-miR-92 |
| hsa-mir-092-prec-X=092-2 | uc.341+A | -0.4594 | hsa-miR-92 |
| hsa-mir-092-prec-X=092-2 | uc.230+ | -0.4581 | hsa-miR-92 |
| hsa-mir-093-prec-7.1=093-1 | uc.465+A | -0.6446 | hsa-miR-93 |
| hsa-mir-093-prec-7.1=093-1 | uc.346+A | -0.6245 | hsa-miR-93 |
| hsa-mir-093-prec-7.1=093-1 | uc.167+ | -0.6053 | hsa-miR-93 |
| hsa-mir-093-prec-7.1=093-1 | uc.283+A | -0.5887 | hsa-miR-93 |
| hsa-mir-093-prec-7.1=093-1 | uc.478+A | -0.5851 | hsa-miR-93 |
| hsa-mir-093-prec-7.1=093-1 | uc.300+A | -0.5787 | hsa-miR-93 |
| hsa-mir-093-prec-7.1=093-1 | uc.283+A | -0.5446 | hsa-miR-93 |
| hsa-mir-093-prec-7.1=093-1 | uc.84+A | -0.5424 | hsa-miR-93 |
| hsa-mir-093-prec-7.1=093-1 | uc.325+ | -0.531 | hsa-miR-93 |
| hsa-mir-093-prec-7.1=093-1 | uc.269+A | -0.5227 | hsa-miR-93 |
| hsa-mir-093-prec-7.1=093-1 | uc.352+ | -0.4992 | hsa-miR-93 |
| hsa-mir-093-prec-7.1=093-1 | uc.398+ | -0.495 | hsa-miR-93 |
| hsa-mir-093-prec-7.1=093-1 | uc.160+ | -0.4929 | hsa-miR-93 |
| hsa-mir-093-prec-7.1=093-1 | uc.117+ | -0.482 | hsa-miR-93 |
| hsa-mir-093-prec-7.1=093-1 | uc.48+A | -0.4761 | hsa-miR-93 |
| hsa-mir-093-prec-7.1=093-1 | uc.299+ | -0.4755 | hsa-miR-93 |
| hsa-mir-093-prec-7.1=093-1 | uc.339+ | -0.4717 | hsa-miR-93 |
| hsa-mir-093-prec-7.1=093-1 | uc.110+A | -0.4521 | hsa-miR-93 |
| hsa-mir-095-prec-4 | uc.204+ | -0.6042 | hsa-miR-95 |
| hsa-mir-095-prec-4 | uc.345+ | -0.5157 | hsa-miR-95 |
| hsa-mir-095-prec-4 | uc.73+ | -0.5079 | hsa-miR-95 |
| hsa-mir-095-prec-4 | uc.192+ | -0.4705 | hsa-miR-95 |
| hsa-mir-095-prec-4 | uc.41+ | -0.4661 | hsa-miR-95 |
| hsa-mir-095-prec-4 | uc.346+A | -0.4615 | hsa-miR-95 |
| hsa-mir-095-prec-4 | uc.366+ | -0.4572 | hsa-miR-95 |
| hsa-mir-095-prec-4 | uc.465+A | -0.451 | hsa-miR-95 |
| hsa-mir-095-prec-4 | uc.341+A | -0.4507 | hsa-miR-95 |
| hsa-mir-095-prec-4 | uc.462+ | -0.4506 | hsa-miR-95 |

Figure 18 Continued

ULTRACONSERVED REGIONS ENCODING NCRNAS

CROSS-REFERENCE TO RELATED APPLICATIONS

This application claims the benefit of PCT application No. PCT/US08/072,081 filed Aug. 4, 2008 which claims priority to U.S. Provisional Application 60/963,329 filed Aug. 3, 2007, the disclosures of which are incorporated herein by reference.

STATEMENT REGARDING FEDERALLY SPONSORED RESEARCH

This invention was not made with any Government support and the Government has no rights in this invention.

BACKGROUND

Taken as a whole, cancers are a significant source of mortality and morbidity in the U.S. and throughout the world. However, cancers are a large and varied class of diseases with diverse etiologies. Researchers therefore have been unable to develop treatments or diagnostic tests which cover more than a few types of cancer.

For example, cancers are associated with many different classes of chromosomal features. One such class of chromosomal features are perturbations in the genomic structure of certain genes, such as the deletion or mutation of tumor suppressor genes. The activation of proto-oncogenes by gene amplification or promoter activation (e.g., by viral integration), epigenetic modifications (e.g., a change in DNA methylation) and chromosomal translocations can also cause cancerigenesis. Such perturbations in the genomic structure which are involved in the etiology of cancers are called "cancer-associated genomic regions" or "CAGRs."

Chromosomal fragile sites are another class of chromosomal feature implicated in the etiology of cancers. Chromosomal fragile sites are regions of genomic DNA which show an abnormally high occurrence of gaps or breaks when DNA synthesis is perturbed during metaphase. These fragile sites are categorized as "rare" or "common." As their name suggests, rare fragile sites are uncommon. Such sites are associated with di- or tri-nucleotide repeats, can be induced in metaphase chromosomes by folic acid deficiency, and segregate in a Mendelian manner. An exemplary rare fragile site is the Fragile X site.

Common fragile sites are revealed when cells are grown in the presence of aphidocolin or 5-azacytidine, which inhibit DNA polymerase. At least eighty-nine common fragile sites have been identified, and at least one such site is found on every human chromosome. Thus, while their function is poorly understood, common fragile sites represent a basic component of the human chromosome structure.

Induction of fragile sites in vitro leads to increased sister-chromatid exchange and a high rate of chromosomal deletions, amplifications and translocations, while fragile sites have been colocalized with chromosome breakpoints in vivo. Also, most common fragile sites studied in tumor cells contain large, intra-locus deletions or translocations, and a number of tumors have been identified with deletions in multiple fragile sites. Chromosomal fragile sites are therefore mechanistically involved in producing many of the chromosomal lesions commonly seen in cancer cells.

All malignant cells have specific alterations at DNA loci that encode genes for oncoproteins or tumor suppressors (Balmain et al., 2003; Wooster and Weber, 2003). This common feature has recently been expanded to include a large class of non-coding RNAs (ncRNAs) called microRNAs (miRNAs) (Ambros, 2004) that are also involved in cancer initiation and progression (Calin et al., 2002; Croce and Cann, 2005; Berezikov and Plasterk, 2005a; Esquela-Kerscher and Slack, 2006; Calin and Croce, 2006a). mRNAs affect the regulation of gene expression at both the transcriptional and post-transcriptional levels (Ambros, 2003; Ambros, 2004).

The extent of involvement of miRNAs and the involvement of other classes of ncRNAs in human tumorigenesis is unknown. Therefore, there is a need for further research into the molecular mechanisms and signal transduction pathways altered in cancer.

There is a further need for the identification of new molecular markers and potential therapeutic agents.

The ultraconserved regions (UCRs) of the human genome (Bejerano et al., 2004b) are also miRNAs that are almost completely conserved among various species (Berezikov et al., 2005b). For example, the active molecules of the miR-16-1/miR-15a cluster, has been shown to be an essential player in the initiation of chronic lymphocytic leukemia (CLL) (Calin et al., 2005a), and are completely conserved in human, mouse and rat and highly conserved in nine out of the ten sequenced primate species (Berezikov et al., 2005b). Comparative sequence analysis has identified a number of highly conserved genomic sequences. Some of these regions do not produce a transcript that is translated into protein and are therefore considered to be non-genic. Various names have been applied to this class of sequences: conserved non-genic sequences (CNGs) (Dermitzakis et al., 2005), conserved non-coding sequences (CNSs/CNCs) (Meisler, 2001), multiple species conserved sequences (MCSs) (Thomas et al., 2003) or highly conserved regions (HCRs) (Duret et al., 1993).

UCRs are a subset of conserved sequences that are located in both intra- and inter-genic regions. They are absolutely conserved (100%) between orthologous regions of the human, rat, and mouse genomes (Bejerano et al., 2004b). In contrast to other regions of conserved sequence, 53% of the UCRs have been classified as non-exonic ('N', 256/481 without evidence of encoding protein), while the other 47% have been designated either exonic ('E', 111/481, that overlap mRNA of known protein-coding genes), or possibly exonic ('P', 114/481, with inconclusive evidence of overlap with protein coding genes).

A large portion of transcription products of the non-coding functional genomic regions have significant RNA secondary structures and are components of clusters containing other sequences with functional non-coding significance (Bejerano et al., 2004a). The UCRs represent a small fraction of the human genome that are likely to be functional but not encoding proteins, and have been called the "dark matter" of the human genome (Bejerano et al., 2004a). Because of the high degree of conservation, the UCRs may have fundamental functional importance for the ontogeny and phylogeny of mammals and other vertebrates. This was illustrated by the recent finding of a distal enhancer and an ultraconserved exon derived from a novel retroposon active in lobe-finned fishes and terrestrial vertebrates more than 400 million years ago and maintained as active in a "living fossil" coelacanth (Bejerano et al., 2006).

Further experimental proof of the functional importance of UCRs is based on analysis of mice with targeted mutations. Megabase deletions of gene deserts that lack ultraconserved elements or highly conserved sequences resulted in viable mice that developed apparently without detectable phenotypes (Nobrega et al., 2004). By contrast, gene deserts containing several UCRs (such as the two gene deserts surrounding the DA CHI gene on human chromosome 13g21.33) were shown to contain long-range enhancers, some of them composed of UCR sequences (Nobrega et al., 2003).

In spite of considerable research into therapies for cancer-related diseases, these diseases remain difficult to diagnose and treat effectively. Accordingly, there is a need in the art for improved methods for diagnosing and/or treating cancer. The present invention fulfills these needs and further provides other related advantages.

SUMMARY OF INVENTION

Described herein is a thorough genomic interrogation of the status of UCRs in a large panel of human leukemias and carcinomas.

We investigated the genome-wide expression of UCRs in various normal and cancer samples, and we assessed the relationship between the genomic location of these sequences and the known regions involved in cancers.

Furthermore, we identified a functional role for miRNAs in the transcriptional regulation of cancer-associated UCRs.

Also described herein is evidence in cancer systems that a differentially expressed UCR could alter the functional characteristics of malignant cells.

Also described herein, by combining these data with the elaborate models involving miRNAs in human tumorigenesis, is a model in which alteration in both coding and non-coding RNAs cooperate in the initiation and progression of malignancy.

In one broad aspect, there is described herein are methods for differentiate human cancers comprising using one or more transcribed ultraconserved regions (T-UCR) expression profiles where the association between the genomic location of UCRs and the analyzed cancer-related genomic elements is highly statistically significant and comparable to that reported for miRNA Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. Northern blots showing the expression of various UCRs in normal tissues. In the case of uc.246(E) and uc.269A (N), the presence of the long transcript was confirmed by the RACE cloning experiments. For some tissues, duplicate samples were procured to confirm reproducibility. Normalization was performed with U6. The arrows on the left side show the identified transcripts.

FIG. 1B. T-UCRs 291 and 73A expression (normalized to 18S rRNA) was confirmed by qRT-PCR (graphs) and microarray analyses (Normalized number under the graph) in normal CD5+/CD19+ lymphocytes and malignant CLL samples. P-values were significant for both qRT-PCR and microarray data statistical comparison. Each box represents the distribution of expression measured for normals (blue) and CLL patients (red), ends of the boxes define the 25th and 75th percentiles, a line indicates the median, bars define the 10th and 90th percentiles.

FIG. 1C. Number of UCRs expressed in one or more of 19 tissues, as revealed by microarray analysis; UCR type (E, N, P) numbers are indicated. Four types of transcription were found: ubiquitously expressed UCRs (in 18 or 19 out of 19 different tissues), UCRs expressed in the majority of tissues (10 to 17), UCRs expressed in a minority of tissues (2 to 9) and tissue-specifically expressed UCRs.

FIG. 1D. Percentage of each UCR type (E, N, P) that is ubiquitously transcribed (both uni- and bi-directionally) in all the analyzed tissues; the absolute numbers for each UCR type are shown in the boxes.

FIG. 1E. Expression of the sense or antisense strand UCRs 73, 133 and 269, relative to 18S rRNA, in CD19+ B cells from three different donors. Sense/antisense strand specific real-time RT-PCR was used to validate the strand specific expression of the UCRs observed with microarray analysis; the average+1-standard deviation of microarray results for CDS+ samples is under each graph. Microarray probes are named as follows: the sense genomic probe is named "+", while the probe to the complementary sequence is named "A+".

FIGS. 3A-3E. T-UCRs represent direct targets of miRNAs:

FIG. 3A. Examples of sites of complementarity T-UCR:: miRNA. The uc.348::miR-155 pairing is shown as an example of low levels of complementarity in contrast with the other 4 interacting paired genes for which higher levels of complementarity are found.

FIG. 3B. The correlation by qRT-PCR for miR-155, uc.160 and uc.346A expression in 9 CLL patients. Lymphocytes from four different individuals were used as normal controls.

FIG. 3C. The direct miRNA::T-UCR interaction. Relative repression of firefly luciferase expression standardized to a transfection control, *Renilla* luciferase. pGL-3 (Promega) was used as the empty vector. All the experiments were performed four to eight times in triplicate (n=12-24).

FIG. 3D. The effects of miR-155 transfection in MEG-01 cells on expression levels of uc.160 and uc.346A. Effects were measured by qRT-PCR at 0, 24 and 48 hours post-transfection.

FIG. 3E. Two scatter plots between expression values of mir-24-1 and uc.160 and of miR-155 and uc.346A are presented. The regression line shows the negative correlation between these two genes. The name of the corresponding array probes are presented on the Y and X axes. Both probes recognize the mature form of the miRNA gene.

FIG. 4A. The expression inhibition by various siRNAs in COLO-320 cells. As reference value we used a siRNA control from Dharmacon. The most effective two siRNAs and a pool of four different siRNAs, including these two, were used.

FIG. 4B. The antiproliferative effects of reduction in uc.73A(P) gene expression using siRNA-uc73A in COLO-320 colorectal cancer cells. All the results represent the median of three independent triplicate experiments. The levels of uc. 73A (P) expression were measured by RT-PCR. Two asterisks indicate a statistically significant effect at P<0.01, while one at P<0.05.

FIG. 4C. Reduced levels of uc.73A(P) (using various siRNAs) results in enhanced apoptosis as shown by the Annexin-V staining assay in COLO-329 cells. As reference value we used a siRNA control from Dharmacon.

FIG. 4D. Inhibition of uc.73A(P) by various siRNAs did not influence SW620 colon cancer cell survival. All the results represent the median of three independent triplicate experiments.

FIG. 5. UCR expression in human normal and malignant tissues by Northern blot. The expression for uc.192(N) and uc.246(E) in normal mononuclear cells (MNC) and CLL samples is presented. Normalization was done with U6 probe. The arrows on the left side show the identified transcripts. Under the gel image there are the averages of UCR normalized expression values in CLL and MNC samples from microarray experiments; p-values were from ANOVA statistic.

FIG. 6. UCR expression in human normal and malignant tissues by qRT-PCR. Relative gene expression by qRT-PCR in CD5+/CD19+ positive lymphocytes and human chronic lymphocytic leukemia (CLL) samples. UCR microarray values of CLL and CD5+ samples are indicated under the graph; p-values were from ANOVA statistic.

FIG. 11. Downregulation by small interfering of uc.73A(P) induces apoptosis in COLO-320 cells but not in SW-620 cells. Data obtained with caspase-3 assay in COLO-320 (upper panel), where a significant increase in apoptotic cells is found, and in the control cells SW620 (lower panel), where no difference could be found. COLO-320 express high levels of uc.73A(P), while in SW620 the expression is comparable with the normal colon levels.

FIG. 12—Table 1. Most significant differentially expressed UCRs in leukemias and carcinomas.

FIG. 13—Table 2. Mixed effect Poisson regression results as association of UCRs with regions of interest.

FIG. 14—Table 3. T-UCRs whose expression inversely correlates with complementary miRNA differentially expressed in CLL patients.

Figure 15:
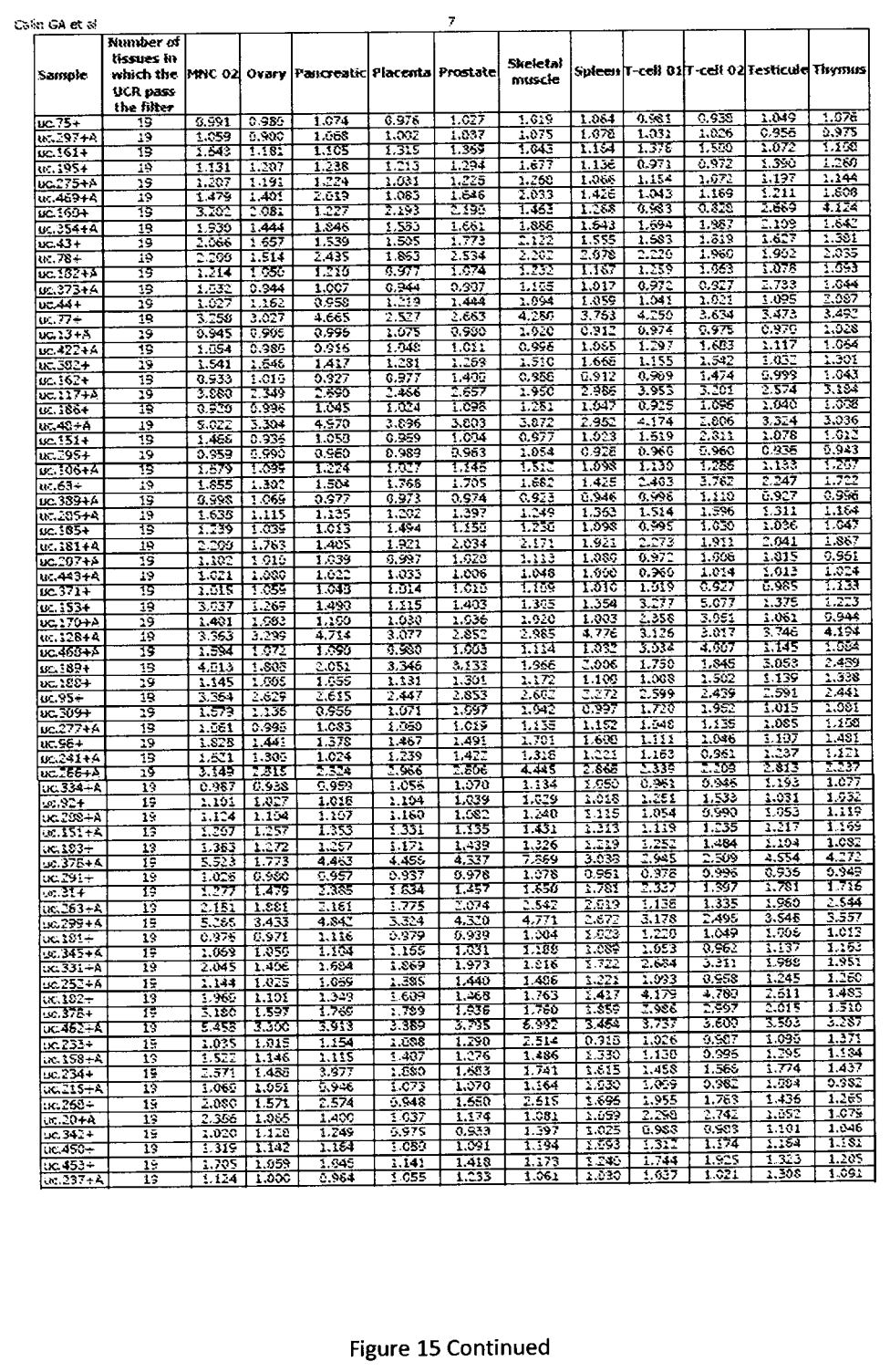

FIG. 15—Table 4. T-UCRs expression in 22 human normal tissues (3 in duplicate, from 2 different individuals).

FIG. 16—Table 5. T-UCRs differentially expressed in CLL, CRC and HCC identified by ANOVA analysis at P<0.005 (GeneSpring GX software).

FIG. 17—Table 6. Genomic location of UCRs is correlated with CAGR. (databases as in (Bejerano et al., 2004); (Cahn et al., 2004)).

FIG. 18—Table 7. Negative correlations between the expression of miRNAs and T-UCRs in CLL patients. All validated negative correlation by FDR method at 0.01 threshold, or 1% of false positive results, and with an R correlation lower as 0.40 were considered.

DESCRIPTION OF EMBODIMENTS

Figure 1A:
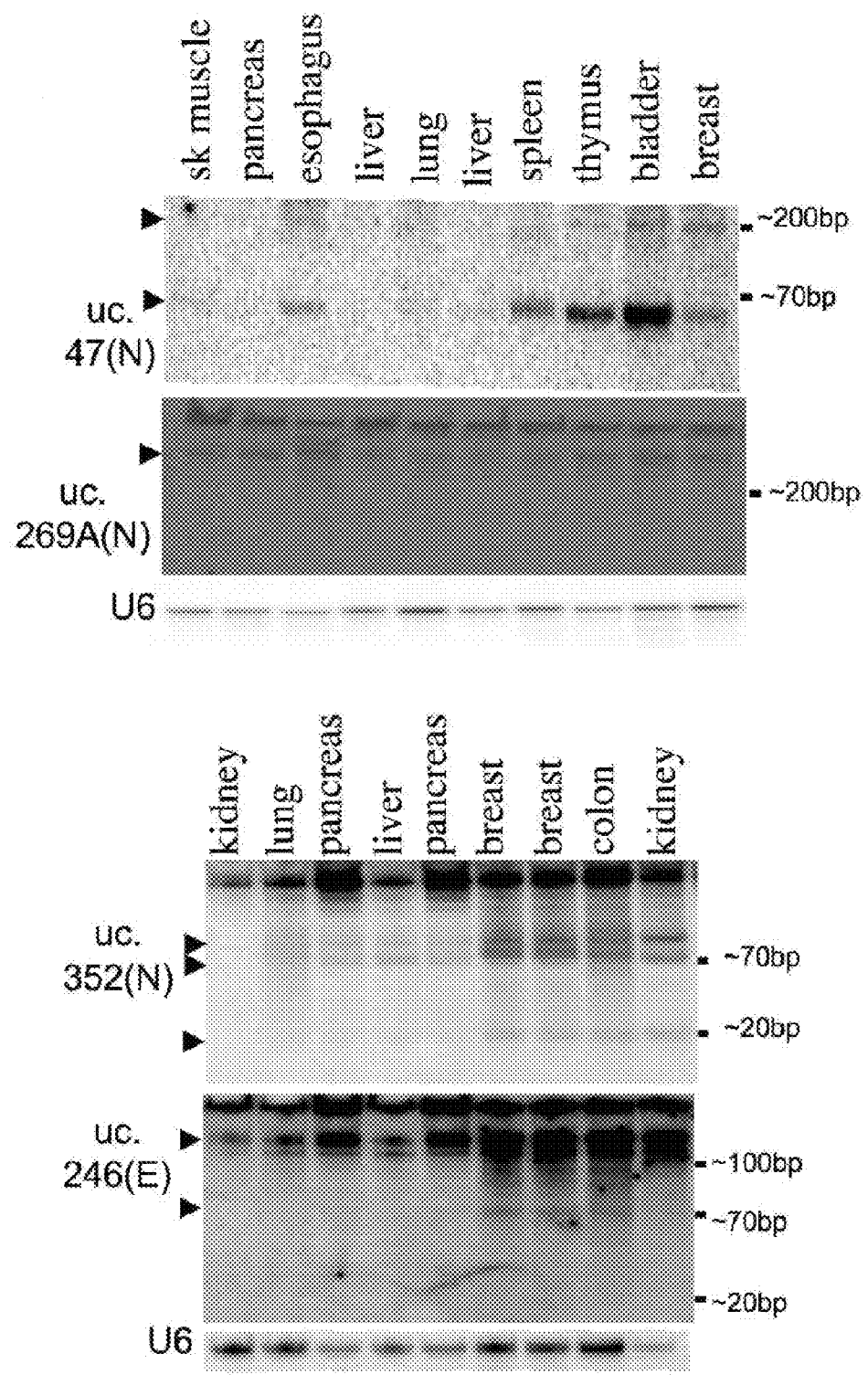
FIGS. 1A-1E. Transcriptional characteristics of various types of UCRs.

As used herein, a "CAGR" includes any region of the genomic DNA that comprises a genetic or epigenetic change (or the potential for a genetic or epigenetic change) that differs from normal DNA, and which is correlated with a cancer. Exemplary genetic changes include single- and double-stranded breaks (including common breakpoint regions in or near possible oncogenes or tumor-suppressor genes); chromosomal translocations; mutations, deletions, insertions (including viral, plasmid or transposon integrations) and amplifications (including gene duplications) in the DNA; minimal regions of loss-of-heterozygosity (LOH) suggestive of the presence of tumor-suppressor genes; and minimal regions of amplification suggestive of the presence of oncogenes. Exemplary epigenetic changes include any changes in DNA methylation patterns (e.g., DNA hyper- or hypo-methylation, especially in promoter regions).

Many of the known miR genes in the human genome are in or near CAGRs, including 80 miR genes that are located exactly in minimal regions of LOH or minimal regions of amplification correlated to a variety of cancers. Other miR genes are located in or near breakpoint regions, deleted areas, or regions of amplification.

For example, cancers associated with CAGRs include leukemia (e.g., AML, CLL, pro-lymphocytic leukemia), lung cancer (e.g., small cell and non-small cell lung carcinoma), esophageal cancer, gastric cancer, colorectal cancer, brain cancer (e.g., astrocytoma, glioma, glioblastoma, medulloblastoma, meningioma, neuroblastoma), bladder cancer, breast cancer, cervical cancer, epithelial cancer, nasopharyngeal cancer (e.g., oral or laryngeal squamous cell carcinoma), lymphoma (e.g., follicular lymphoma), uterine cancer (e.g., malignant fibrous histiocytoma), hepatic cancer (e.g., hepatocellular carcinoma), head-and-neck cancer (e.g., head-and-neck squamous cell carcinoma), renal cancer, male germ cell tumors, malignant mesothelioma, myelodysplastic syndrome, ovarian cancer, pancreatic or biliary cancer, prostate cancer, thyroid cancer (e.g., sporadic follicular thyroid tumors), and urothelial cancer.

As used herein, a "FRA" includes any rare or common fragile site in a chromosome; e.g., one that can be induced by subjecting a cell to stress during DNA replication. For example, a rare FRA can be induced by subjecting the cell to folic acid deficiency during DNA replication. A common FRA can be induced by treating the cell with aphidocolin or 5-azacytidine during DNA replication. The identification or induction of chromosomal fragile sites is within the skill in the art; see, e.g., Arlt et al. (2003), Cytogenet. Genome Res. 100:92-100 and Arlt et al. (2002), Genes, Chromosomes and Cancer 33:82-92, the entire disclosures of which are herein incorporated by reference.

Approximately 20% of the known human miR genes are located in (13 miRs) or within 3 Mb (22 miRs) of cloned FRAs. Indeed, the relative incidence of miR genes inside fragile sites occurs at a rate 9.12 times higher than in non-fragile sites. Moreover, after studying 113 fragile sites in a human karyotype, it was found that 61 miR genes are located in the same chromosomal band as a FRA.

For example, cancers associated with FRAs include bladder cancer, esophageal cancer, lung cancer, stomach cancer, kidney cancer, cervical cancer, ovarian cancer, breast cancer, lymphoma, Ewing sarcoma, hematopoietic tumors, solid tumors and leukemia.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Genome-wide profiling reveals extensive transcription of ultraconserved regions (UCRs) in normal human tissues.

To investigate the involvement of UCRs in human cancers, we analyzed 481 genomic regions longer than 200 bp (Bejerano et al., 2004b) by Northern blot, quantitative PCR (qRT-PCR) and microarray.

Both exonic (E) and non-exonic (N) UCR probes detected transcripts (in sense or antisense—A, orientation) over a large range of lengths from various normal tissues (FIG. 1A and FIG. 5).

The length of two of the transcripts was confirmed by cloning the cDNA by 5'- and 3'-RACE for the exonic uc.246 (E) from normal human colon and the non-exonic uc.269A (N) from normal human bone marrow. Neither of these cDNAs contained open reading frames (ORFs) of significant length, confirming their likely non-protein coding nature. These non-spliced full-length cDNAs, that we named non-coding ultraconserved genes, nc-UCGs, are of variable length (about 0.8 kb for the ultraconserved gene UCG.246 and about 1.8 kb and 2.8 kb for the ultraconserved gene UCG.269A).

Transcription of these nc-UCGs may be initiated from poly-adenine rich genomic regions, as was recently proposed for several long ncRNAs from mouse (Furuno et al., 2006).

Figure 1B:
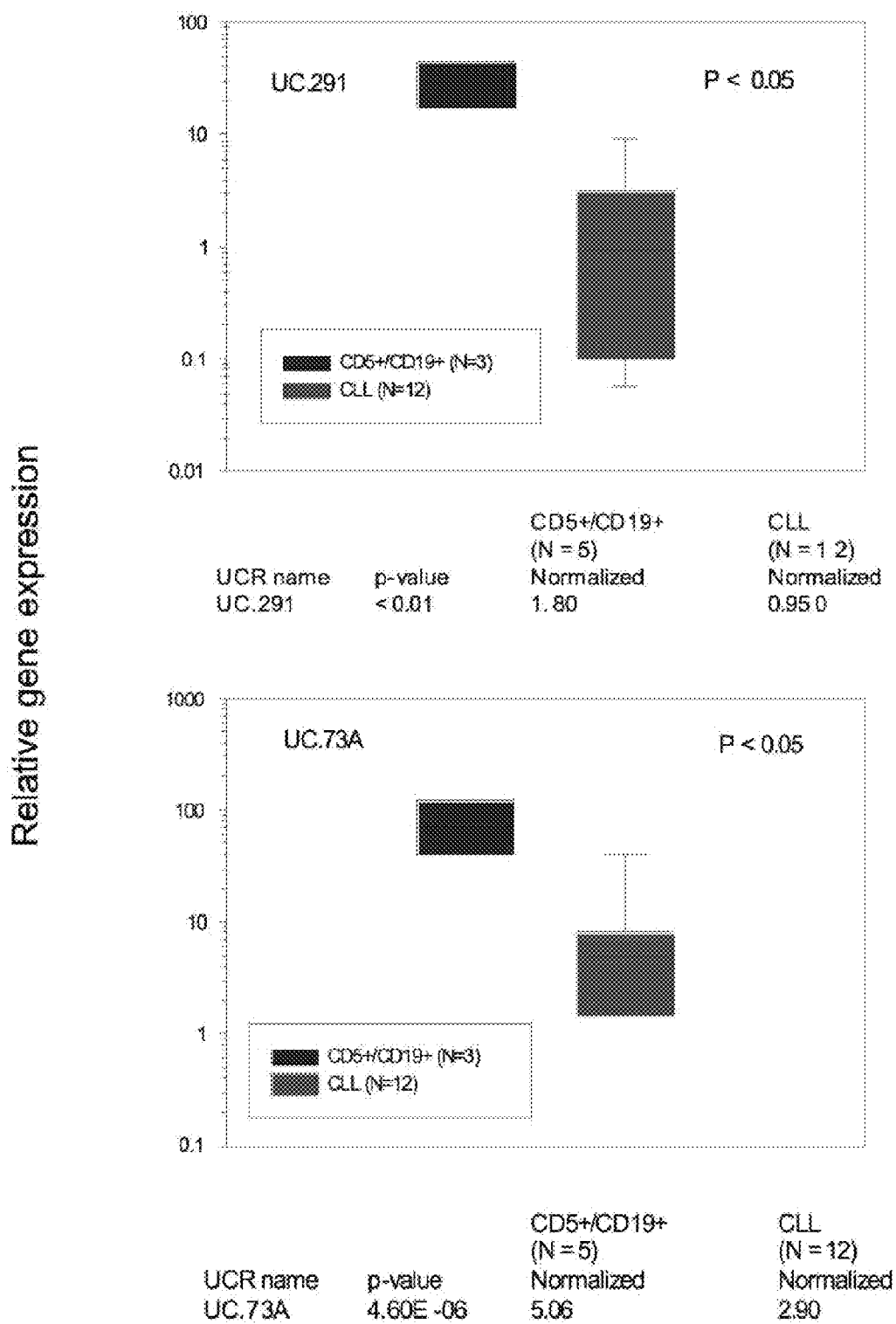

We compared the transcription levels of several UCRs from normal and disease tissue using microarray analysis followed by qRT-PCR and Northern blot confirmation. The expression of uc.291(P) and uc. 73A(P) was significantly higher in normal CD5+/CD 19+ lymphocytes than in CLL cells (P<0.05) (FIG. 1B). The data obtained with this microarray platform has been confirmed in various studies (Cahn et al., 2005a; Yanaihara et al., 2006; Volinia et al., 2006).

The strength of our data is reinforced by the fact that two independent sets of normal CD5 cells were included in microarray and quantitative RT-PCR experiments. When both uc.291(P) and uc.73A(P) were investigated by qRT-PCR and microarray in two different sets of CD5/CD19 positive B cells and malignant B cells, the differential expression was statistically significant by both assays (FIG. 1B).

Furthermore, qRT-PCR and Northern blotting for eleven and six UCRs, respectively, gave results that were concordant with microarray results (FIG. 5 and FIG. 6).

Figure 1C:
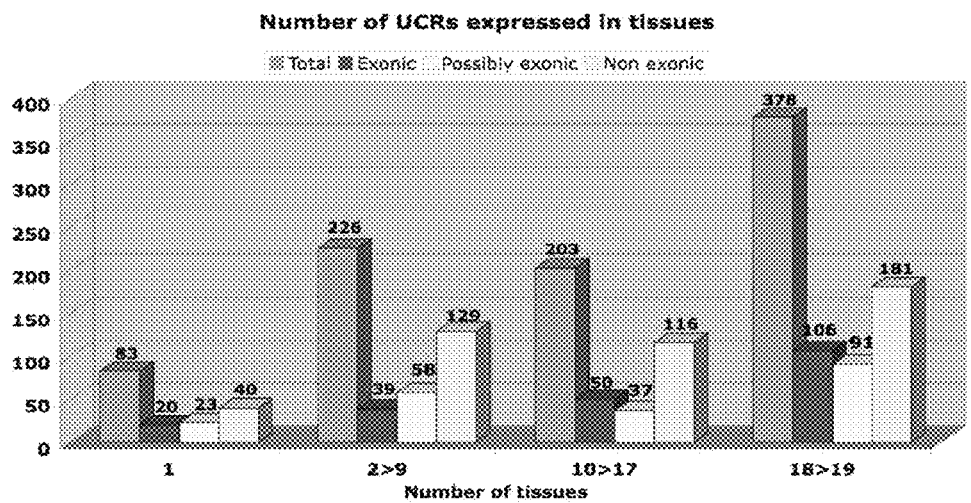

Using microarray analysis, we found that the majority of transcribed UCRs (that we named here T-UCRs) were expressed in normal human tissues both ubiquitously and in a tissue-specific manner (FIG. 1C).

About 34% of putative T-UCRs (325/962) had hybridization signals with an intensity over background (calculated as average signal of blank spots+2 SD) in all 19 tissue samples. The highest number of T-UCRs was found in B cells, while the lowest was in ovary. About 93% of the UCRs (890 of 962) were expressed over background in at least one sample, and therefore we considered these as T-UCRs. The three different types of UCRs were transcribed with similar frequencies: 41% of exonic UCRs, 33% of possibly exonic UCRs and 30% of non-exonic UCRs.

Figure 1D:
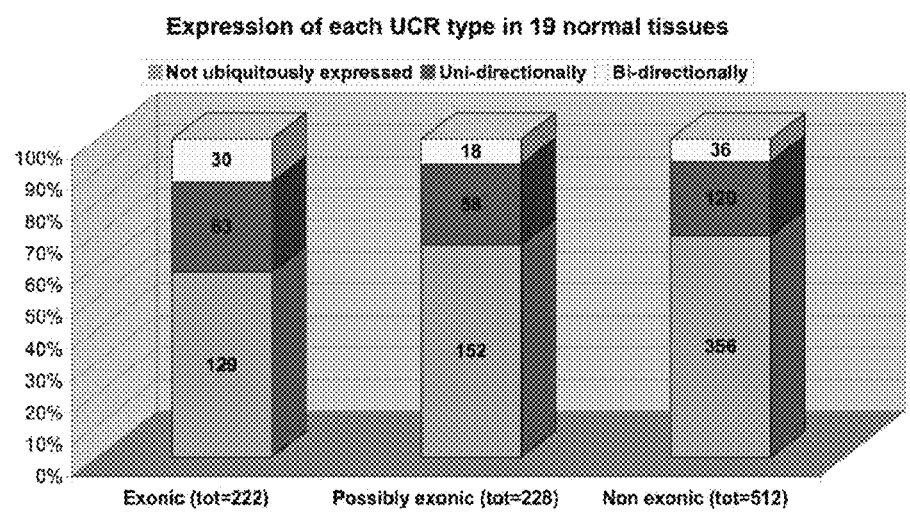
Figure 1E:
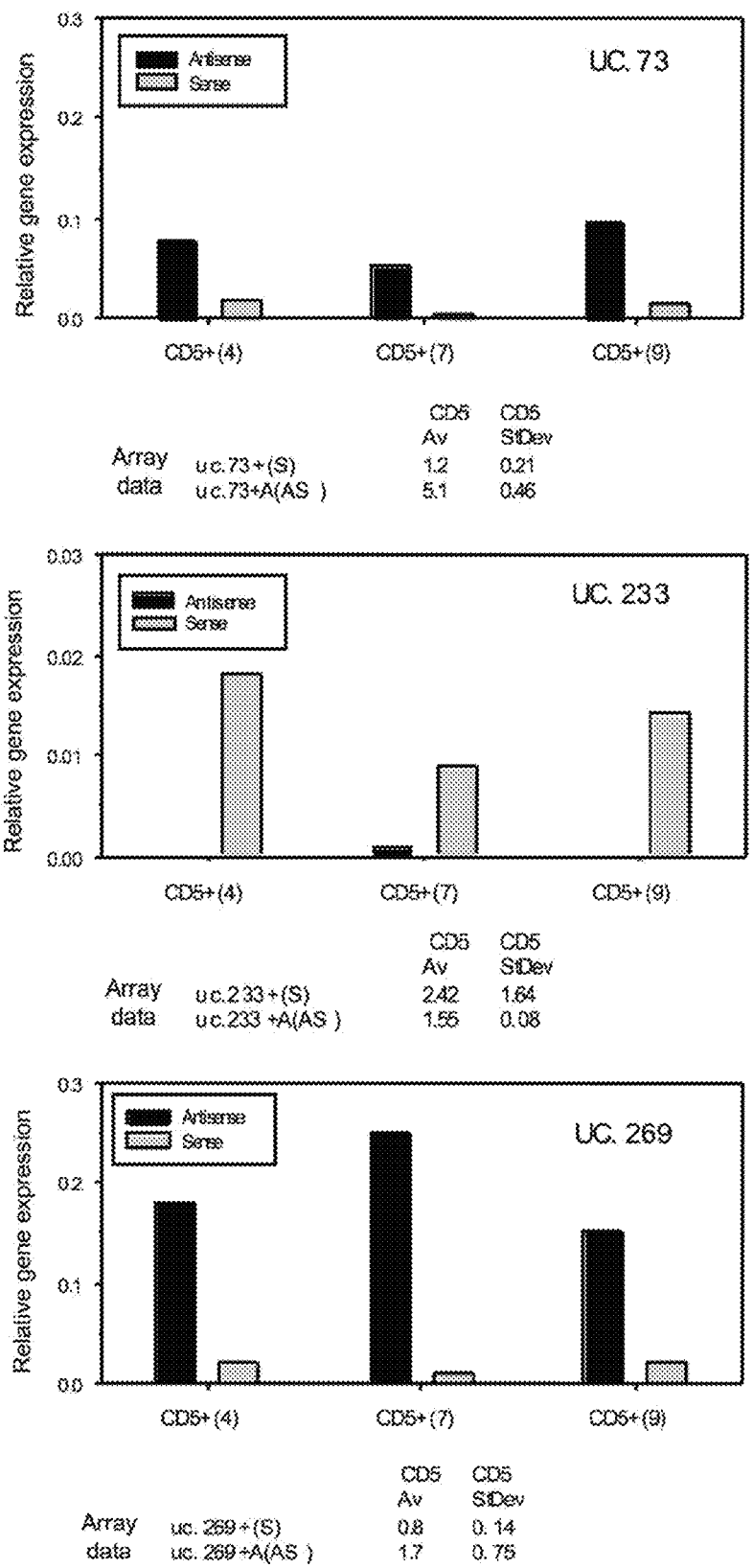

The microarray platform contains putative T-UCRs in both sense and anti-sense orientation. Eighty-four of the 962 UCRs (9%) were bidirectionally transcribed, while 241 were transcribed only from one strand, in all the normal tissues analyzed (FIG. 1D, FIG. 1E and Table 4).

Since identification of bidirectional transcription by microarray analysis may be hindered by trace contamination with genomic DNA, we performed a comparison of microarray results with strand-specific qRT-PCR for uc.2 69(N), uc.233(E) and uc. 73(P). In all three instances the data were concordant, showing predominant transcription from one strand (FIG. 1E).

Of note, out of the 156 non-exonic T-UCRs expressed in all 19 tissues, 92 (~60%) are intergenic, while 64 are intronic. Of the latter, 37 are in the antisense orientation compared with the host gene, suggesting that about 83% (129/156) of the non-exonic T-UCRs did not represent intronic transcription of long precursor transcripts of known host genes, but bona fide independent noncoding transcripts.

Figure 2A:
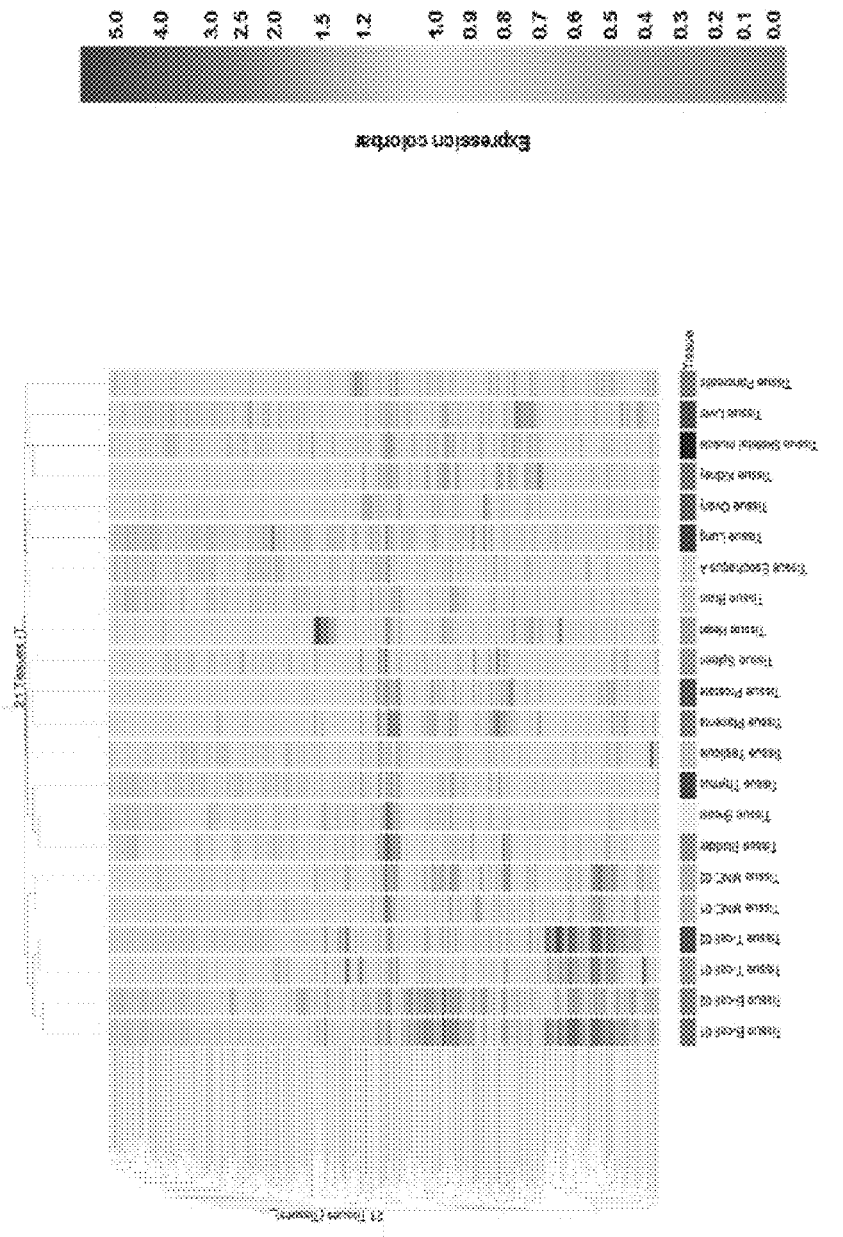
FIGS. 2A-2B. Hierarchical clustering of tissues and tumors according to UCRs expression. Unsupervised cluster of (FIG. 2A) 22 normal human tissues and (FIG. 2A\B) 133 leukemias and carcinomas made using the non-exonic UCRs of the chip. Some of the T-UCRs that well differentiate the tissue types (FIG. 2A) or carcinomas from leukemias (FIG. 2B) are expanded at the right. Samples are in columns, T-UCRs in rows. A green colored gene is down-regulated compared to its median expression in all samples, red is up-regulated and yellow means no variation. The complete UCRs profile of tissues and tumors can be found in FIGS. 5 and 6.
Figure 7:
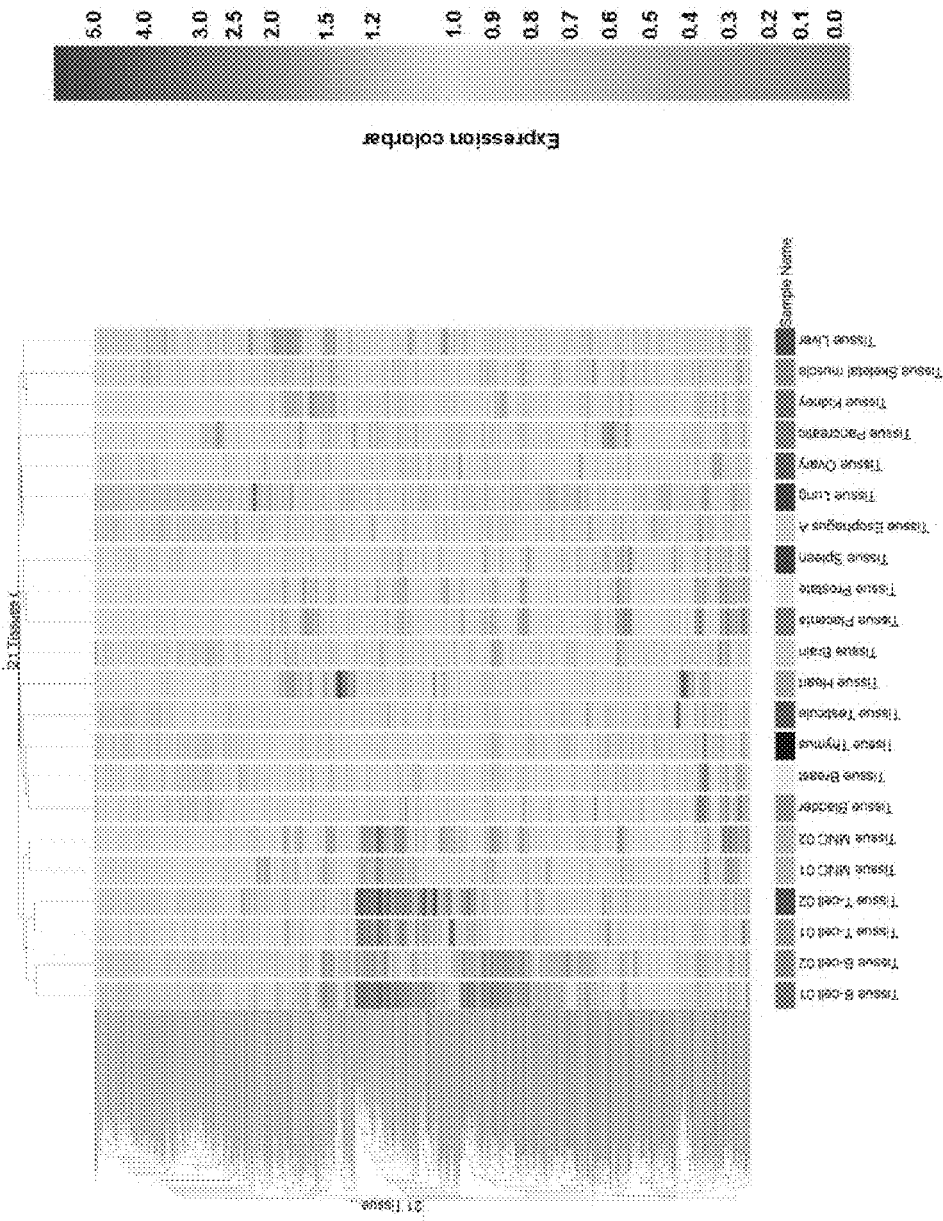
FIG. 7. T-UCR expression profile of 22 normal human tissues. Clustering of tissues and UCRs revealed a distinct pattern of UCRs expression in normal human tissues. Samples are shown in columns, T-UCRs in rows. A green colored gene is down-regulated compared to its median expression in all samples, red is up-regulated and yellow means no variation.

As with miRNAs (Liu et al., 2004), we performed a hierarchical clustering of T-UCR expression in hematopoietic tissues (represented by B lymphocytes, T lymphocytes and mononuclear cells, each collected from two healthy individuals) and non-hematopoietic tissues. The same types of tissue from different individuals were clustered as closest neighbors (FIG. 2A and FIG. 7).

These findings demonstrate that UCRs represent, in a significant proportion of cases, non-coding transcripts in normal human tissues and that the expression of these T-UCRs is tissue-specific.

Distinct UCR Signatures in Human Leukemias and Carcinomas

Since extensive gene expression alterations in cancer cells have been widely described for both protein coding genes and miRNAs (Esquela-Kerscher and Slack, 2006; Calin and Croce, 2006a; Calin and Croce, 2006b; Lu et al., 2005), we investigated the expression of UCRs in a panel of 173 samples, including 133 human cancers and 40 corresponding normal tissues.

Figure 2B:
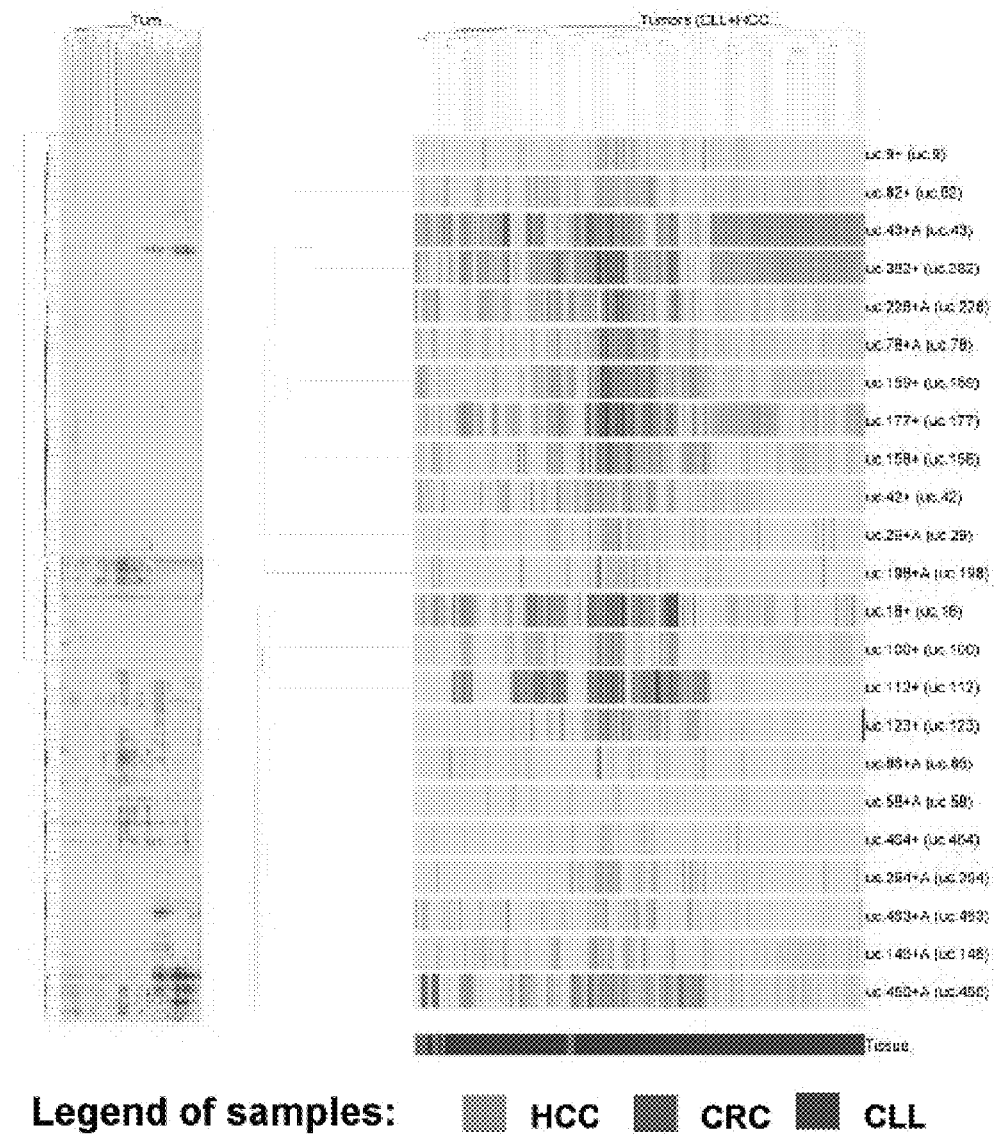
Figure 2B:
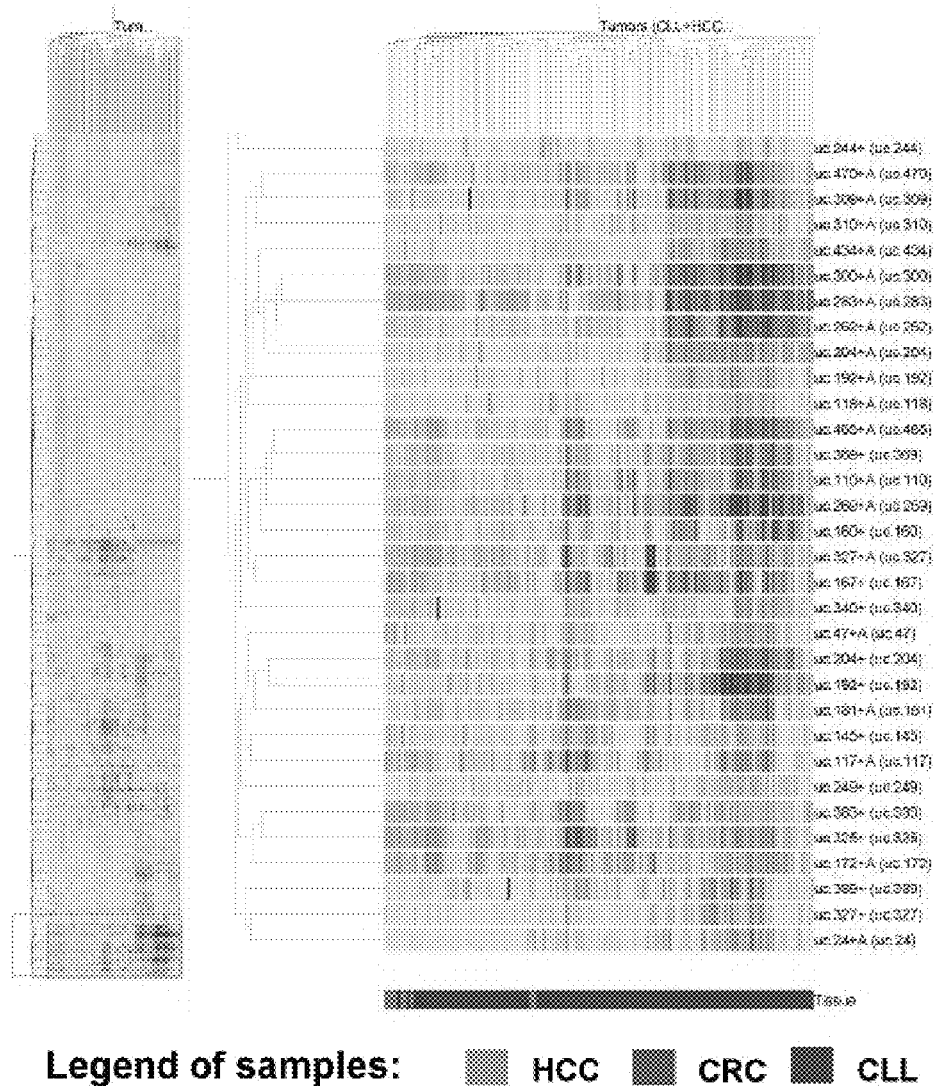
Figure 8:
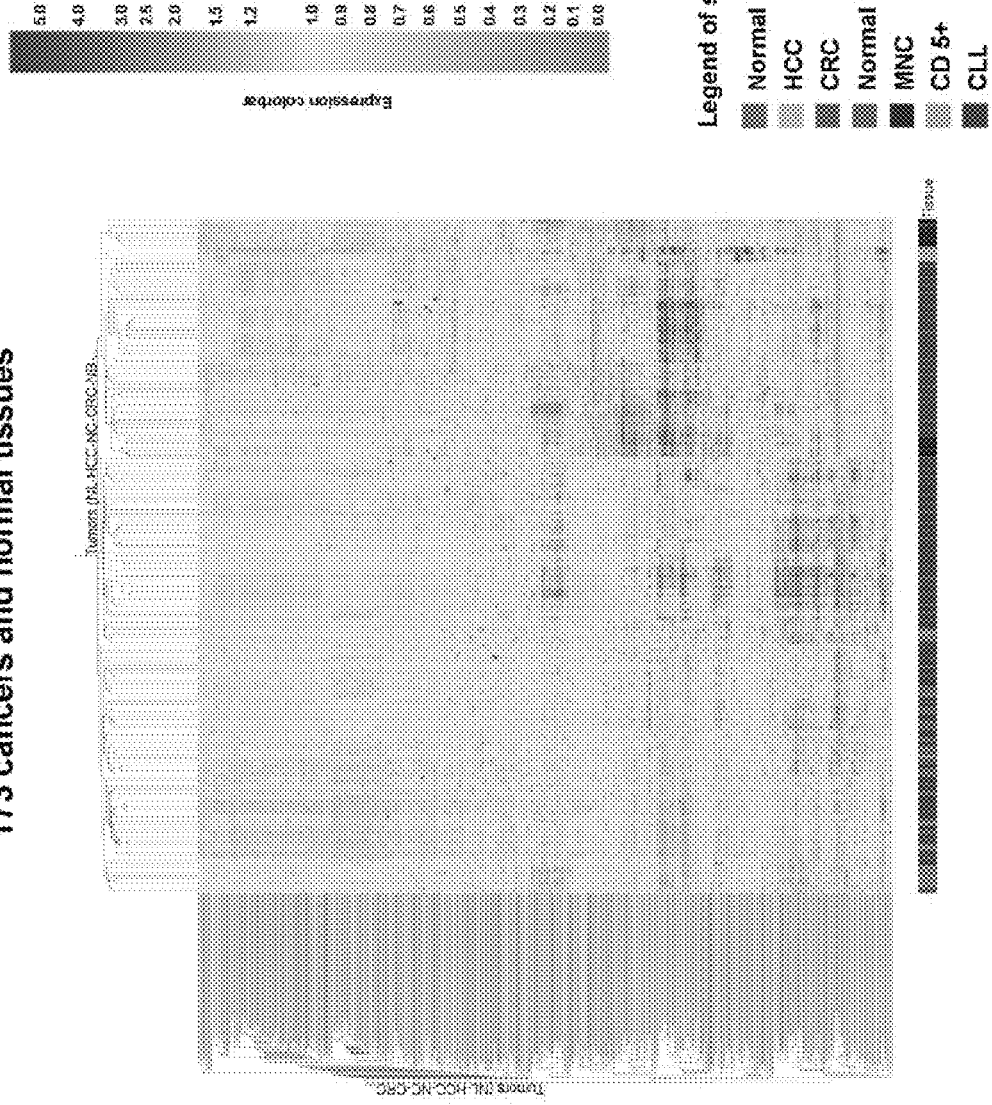
FIG. 8. T-UCR expression profile of 173 cancers and corresponding normal tissues. Samples from leukemia and normal blood cells are separated from cancer and tissue of epithelial origin. Samples are shown in columns, T-UCRs in rows. A green colored gene is down-regulated compared to its median expression in all samples, red is up-regulated and yellow means no variation.

Hierarchical clustering of the samples showed that various types of cancers clustered differently according to their developmental origins: the leukemias (CLL) and normal hematopoietic tissues were branched separately from the colorectal (CRC) and hepatocellular carcinomas (HCC) with their normal counterparts (FIG. 8); moreover, specific groups of UCRs seemed to be differentially expressed in tumor types (FIG. 2B).

Since different tissues have specific UCR signatures, this clustering pattern could be the consequence of different tissue-specific origin of the tumors. Thus, we compared the expression of UCRs between the normal and tumor cells of the same origin. Out of 962 possible T-UCRs, 88 (9.1%) were differentially expressed at a highly statistically significant level (P<0.005) in at least one type of cancer (Table 1 and Table 5).

We found both down-regulated and up-regulated T-UCRs in cancers compared to the expression in corresponding normal tissues. By comparing each cancer type with the corresponding normal tissues, we found that the CLL signature was composed of 19 UCRs (8 up- and 11 down-regulated), the CRC signature of 61 UCRs (59 up- and 2 down-regulated), and the HCC signature of 8 UCRs (3 up- and 5 down-regulated) (Table 5).

Eighteen transcripts of the signatures were exonic UCRs (20%), 28 were possibly exonic UCRs (32%) and 42 were non-exonic UCRs (48%). Of the 18 exonic T-UCRs, 9 represented the anti-sense direction of the known host protein-coding gene transcripts. We therefore demonstrated that the T-UCR expression profiles can be used to differentiate human cancers.

UCRs are Frequently Located at Fragile Sites and Genomic Regions Involved in Cancers We compared the genomic location of UCRs with that of previously reported non-random genetic alterations identified in human tumors and cloned fragile sites (FRA) as described (Calin et al., 2004b). We used the set of 186 miRNAs previously reported (Cahn et al., 2004b) and a set of 297 zinc finger protein-coding genes (ZNF) (genome.ucsc.edu), a well known family of transcription factors shown to be associated with cancer (Huntley et al., 2006).

We previously reported that miRNA genes are frequently located at FRA sites, HOX genes clusters and genomic regions involved in cancer, such as minimal regions of loss of heterozygosity (LOH), and minimal regions of amplification, globally named cancer associated genomic regions (CAGR) (Calin et al., 2004b).

A recent study, using high-resolution array comparative genomic hybridization (aCGH), confirmed that miRNA loci exhibit genomic alterations at high frequency in human cancers (Zhang and al, 2006). Furthermore, by analyzing the miRNA expression in NCI-60 cell lines, another group found that the candidate tumor-suppressor and oncogenic miRNAs are located in CAGRs (Gaur et al, 2007).

Here, we show that the association between the genomic location of UCRs and the analyzed cancer-related genomic elements is highly statistically significant and comparable to that reported for miRNAs. The ZNF transcription factors did not show any significant association with any of the analyzed regions of interest (Table 2 and Table 6).

There was a similar lack of association for the smaller family of protein-coding genes involved in RNA splicing (80 genes, data not shown). For example, the probability for the association of UCRs or miRNAs with minimal LOH regions versus non-deleted genomic regions was less than 0.001 in both instances (IRR of 2.02 and 4.08, respectively). As an internal control, we used the human papilloma virus 16 (HPV 16) integration sites, which frequently occur in FRA sites. If UCRs are significantly associated with FRA, then we expected to fin an association with the HPV 16 integration site. This is exactly what we observed for both UCRs and miRNAs, but not for ZNF protein-coding genes (Table 2) or for the protein-coding genes involved in RNA splicing (data not shown).

Additional data illustrate the importance of the genomic location of UCRs. First, we found that the ubiquitously expressed T-UCRs (expressed in 18 or 19 normal tissues in FIG. 1C) are significantly more frequently located in CAGRs (P<0.005, Fisher exact test) when compared with all other UCRs (97 out of 189 vs. 71 out of 292). Second, T-UCRs differentially expressed in human cancers are located in CAGRs specifically associated with that type of cancer. For example, the chromosomal region 13g21.33-g22.2 has been linked to susceptibility to familial CLL (Ng et al, 2007). No mutations were found in any of the 13 protein-coding genes screened within this interval.

We identified a cluster of seven UCRs (uc.347 to uc.353) located within this CAGR. Two of them, uc.349A(P) and uc.352(N) are among the T-UCRs that are differentially expressed between normal and malignant B-CLL CD5 positive cells.

This suggests, at least in this case, that it is not the protein-coding genes but the UCRs that represent the "unknown" culprits located in the CAGR. Together these data provide evidence that the UCRs are located in genomic regions altered during the malignant process, and suggest that T-UCRs could be candidate genes for cancer susceptibility.

Negative Regulation of T-UCRs by Direct Interaction with MicroRNAs

In order to begin to functionally characterize some UCRs involved in human cancers, we performed a genome-wide expression study in the same set of CLL samples investigated above. We found that a signature of five UCRs, uc.269A(N), uc.160(N), uc.215(N), uc.346A(P) and uc.348(N), was able to differentiate between two main CLL prognosis groups previously differentiated by the expression of 70-kDa zeta-associated protein (ZAP-70).

These five T-UCRs displayed variations in their expression level that was negatively correlated with the miRNA expression signature reported in CLL (Cahn et al., 2005a) (Table 3).

While not wishing to be bound by theory, the inventor herein now believes that this finding raises the possibility of complex regulatory mechanisms between miRNAs and T-UCRs. We identified, by sequence alignments, that three out of the 5 UCRs have significant antisense complementarity with 5 out of the 13 miRNAs from the signature, giving rise to six possible interacting pairs: uc.160:: miR-24, uc.160:: miR-155, uc.160:: miR-223, uc.160::miR-146a, uc.346A::miR-155, and uc.-348::miR-29b (FIG. 3A).

In this analyzed set of miRNA::UCR pairs, the 5'-end "6 base seed" complementarity rule described for miRNA::mRNA interaction was valid; furthermore, the levels of 3'-end complementarity could be variable: more than 60% complementarity for miR-24:: uc160 or miR-155::uc.346A pairs to less than 25% for the miR-155:: uc.160 pair. As a control, when randomly generated combinations of five UCRs and 13 miRNAs were compared, the sense and antisense complementarity was not significant.

Negative correlations between the microarray expression values of specific T-UCRs and predicted interactor miRNAs was confirmed by qRT-PCR for selected T-UCRs and miRNAs from lymphocytes of an independent set of CLL patients and normal controls (FIG. 3B).

We performed in vitro assays of miRNA::UCR interaction involving miR-155 which is overexpressed in the aggressive form of CLL (Calin et al., 2005) some lymphomas and carcinomas (E is et al., 2005; Kluiver et al., 2005; Volinia et al., 2006), and miR-24-1 and miR29-b which carry mutations in primary transcripts from CLL patients (Calin et al., 2005a).

Figure 3C:
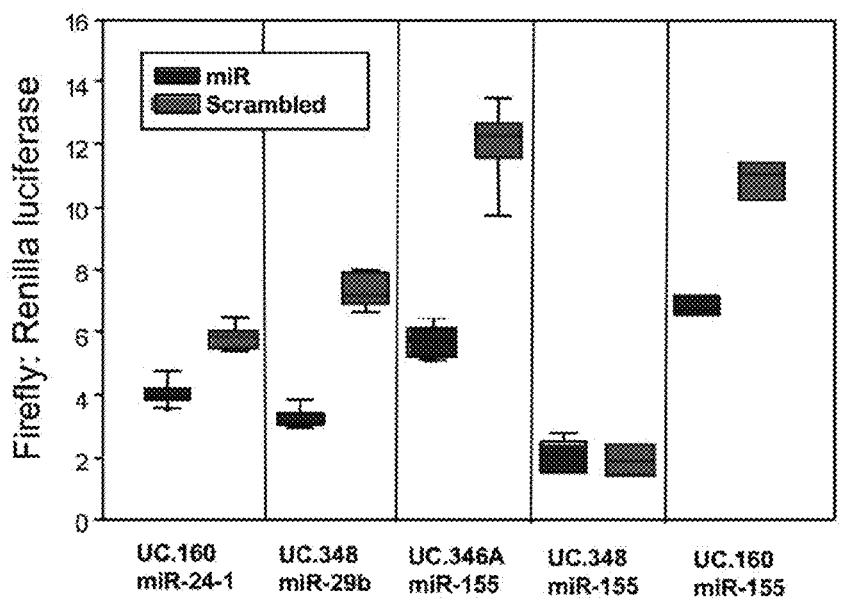

We cloned the UCRs uc.160(N), uc.346A(P) and uc.348 (N) in luciferase reporter vectors to assess the possible direct interaction with miR-155, miR-24-1 or miR-29-b. We observed consistent and reproducible reduction in luciferase expression with four miR::T-UCR pairings consistent with interactions taking place in vitro (FIG. 3C).

By contrast, uc.348(N) did not interact with miR155 as indicated by the luciferase assay, a result that is in concordance with the positive expression correlation of these two genes in CLL patients and the low sequence complementarity (FIG. 3A).

Interactions In Vivo

Figure 3D:
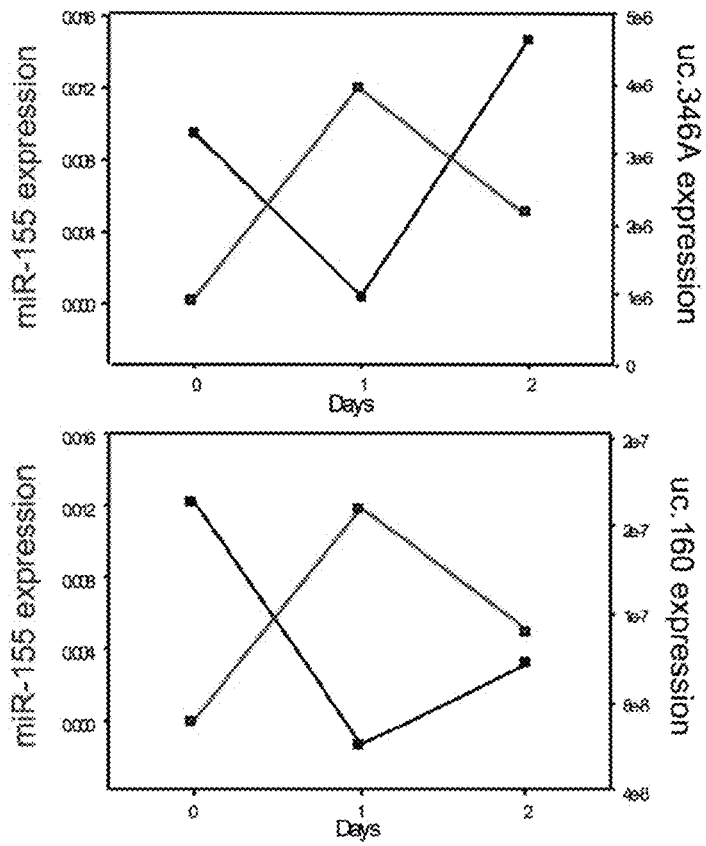

In order to determine if these interactions occur in vivo, we transfected miR-155 into MEG01 leukemia cells and assessed the levels of uc.346A and uc.160 (both well expressed in this cell line). At 24 hours after transfection, miR-155 significantly reduced the expression level of both T-UCRs; after 48 hours, the reduction of exogenous miR-155 levels was paralleled by an increase in T-UCR expression (FIG. 3D).

This reversible effect supports a regulation of T-UCR by specific miRNAs. As this interaction was proven for the genes of the "ZAP-70 signature", we investigated the correlations between the expression of all miRNAs and T-UCRs at the genome-wide level in all 50 CLL patients. Interestingly, we found a significant negative correlation (at a false detection rate (FDR) of less than 0.01) between 87 miRNAs (out of 235 spotted on the chip, 37%) and T-UCRs expression levels (Table 7).

Figure 3E:
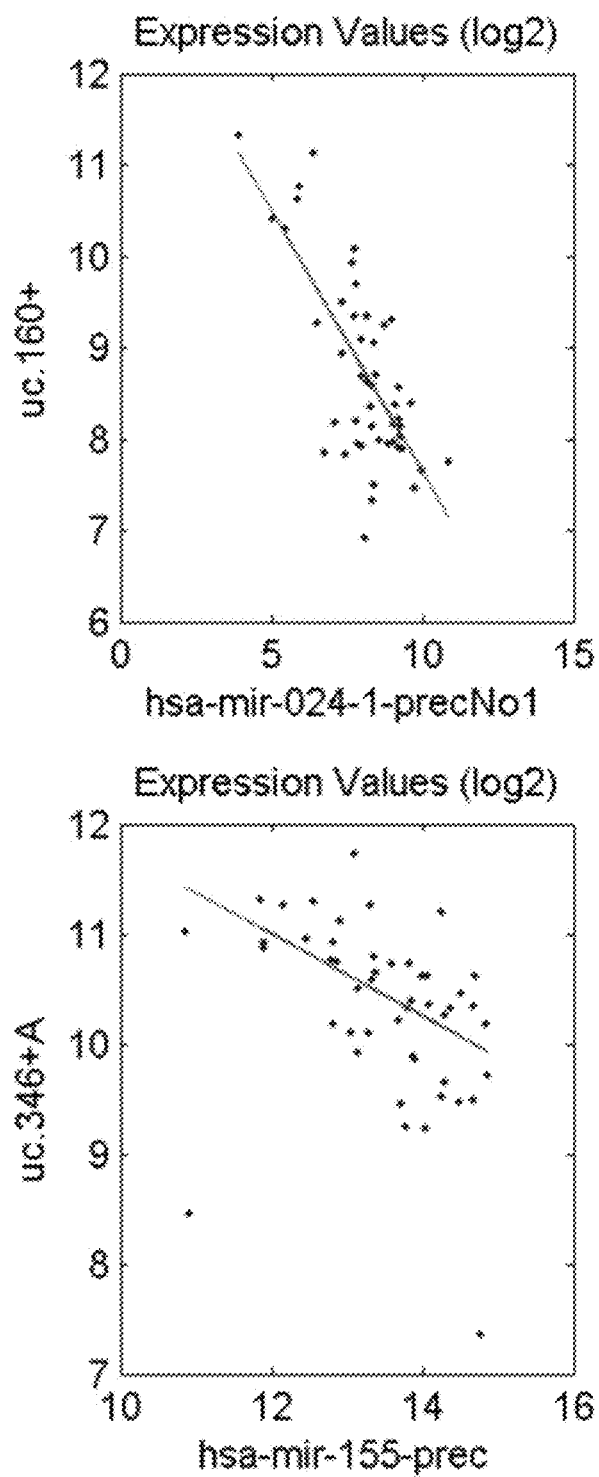

Furthermore, among the correlated genes we identified the miR-24-1:: uc.160 and the miR155:: uc346A(P) pairs, experimentally proven to interact (FIG. 3E).

Moreover, miR-155 and uc.348, that did not interact experimentally, were not members of this list. Other pairs of possible interactors for which we identified positive luciferase assays were miR-15-a:: uc.78 and miR16:: uc. 78 (data not shown). Therefore, non-coding T-UCRs represent possible targets of miRNAs, and these interactions may have biological and prognostic significance for cancer patients.

T-UCRs May Act as Oncogenes

Figure 9:
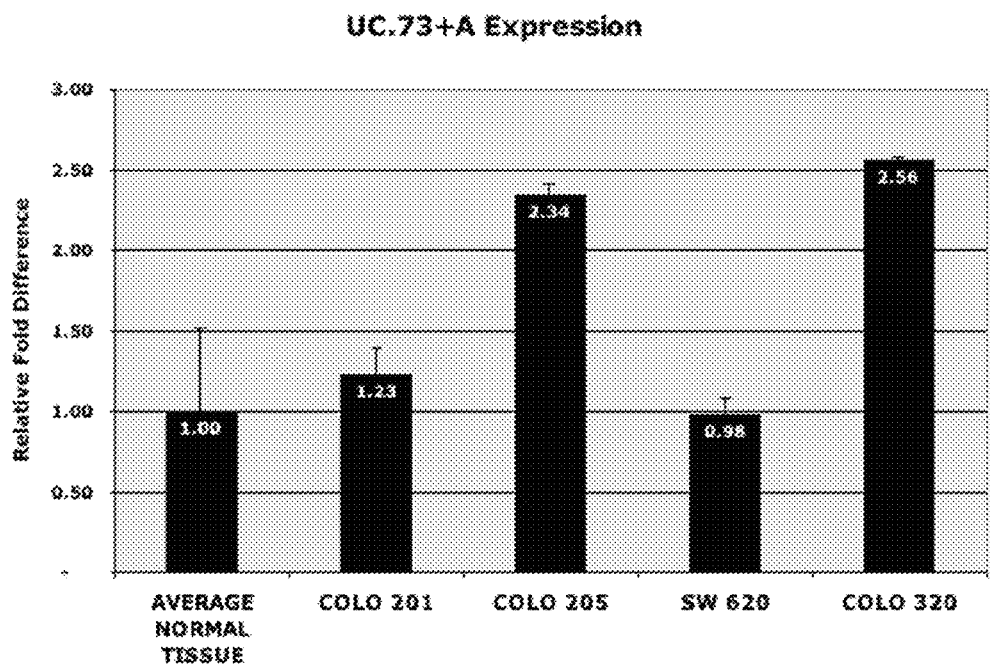
FIG. 9. The expression of uc.73A(P) gene in various colon cancer cell lines by quantitative RT-PCR. The expression in normal colon represents the median value of 4 different samples. For normalization we used beta-actin.

To expand the functional characterization of T-UCR, we examined the biological effects of uc. 73A (P) in a cancer model. Since this is one of the most statistically significant up-regulated T-UCRs in colon cancers (P<0.001), we decided to investigate the effects of its downregulation in COLO-320 colorectal cancer cells that expressed high levels of uc.73A (P). As a control we used the SW620 colon cancer cells in which the expression of this gene does not differ from normal colonic cells (FIG. 9).

Figure 4A:
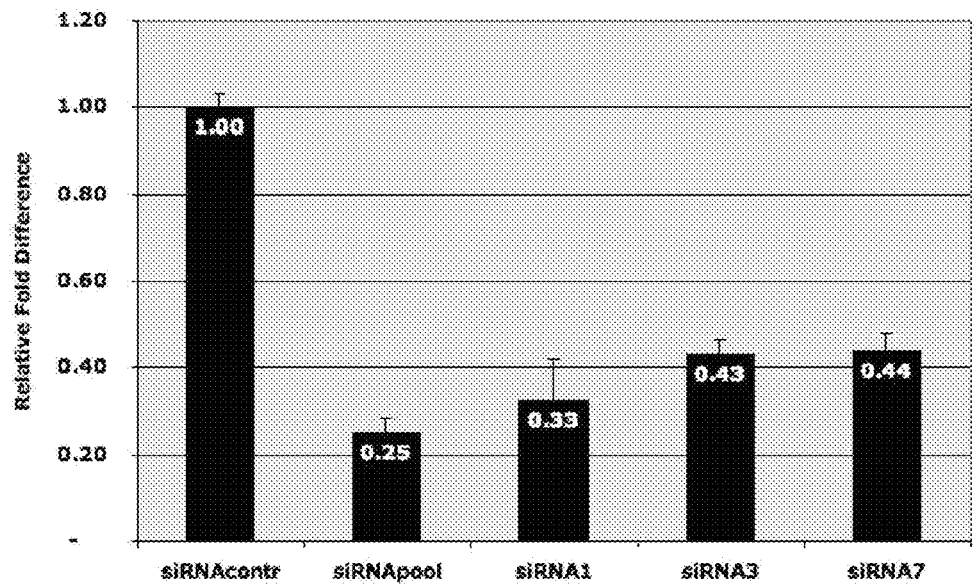
FIGS. 4A-4D. T-UCR 73A(P) is acting as an oncogene in colon cancer cells.
Figure 10:
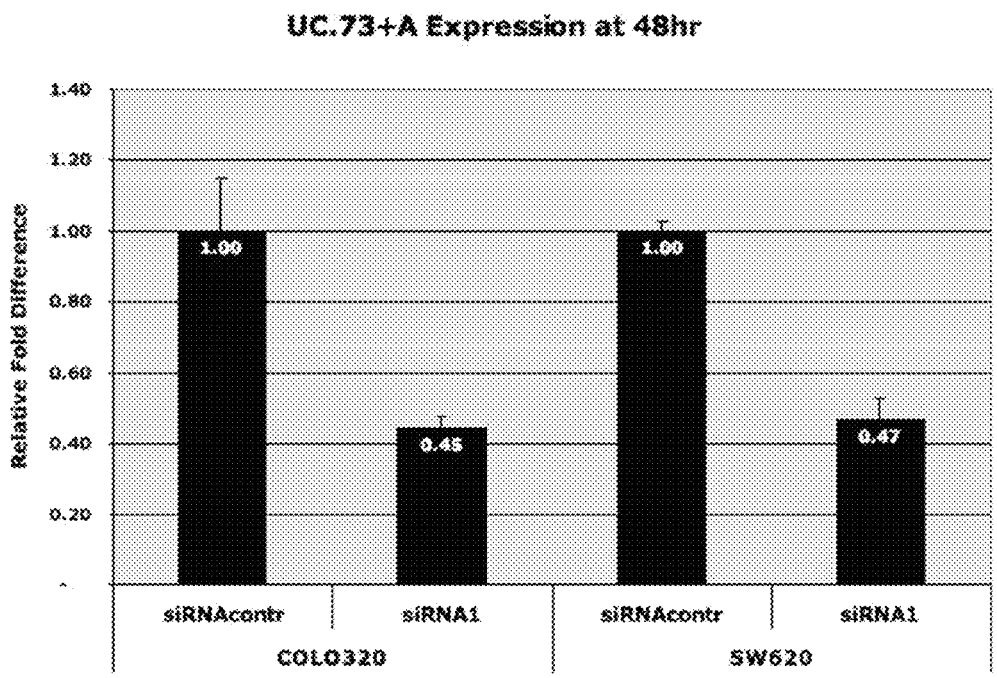
FIG. 10. The uc.73A(P) inhibition by siRNA1 in COLO-320 and SW-620 cells at 48 hrs. Comparable levels of inhibition in respect with a siRNA of control (Dharmacom) were achieved in both types of cells. In spite of this, the biological effects were seen only in COLO-320 cells, where the T-UCR is overexpressed about 2.5 times when compared with expression in normal colon.

Two small interfering RNAs (siRNA1 and siRNA3), as well as a pool of four siRNAs (siRNApool), were designed to target uc. 73A(P) and transfected into COLO-320 and SW620 cells. There was significantly less expression of uc.73A(P) after 48 (FIG. 4A and FIG. 10), 72 and 144 hours (data not shown) in the COLO-320 cells treated with siRNAs 1, 3 and pool. The same was found also for SW-620 cells (FIG. 6).

Figure 4B:
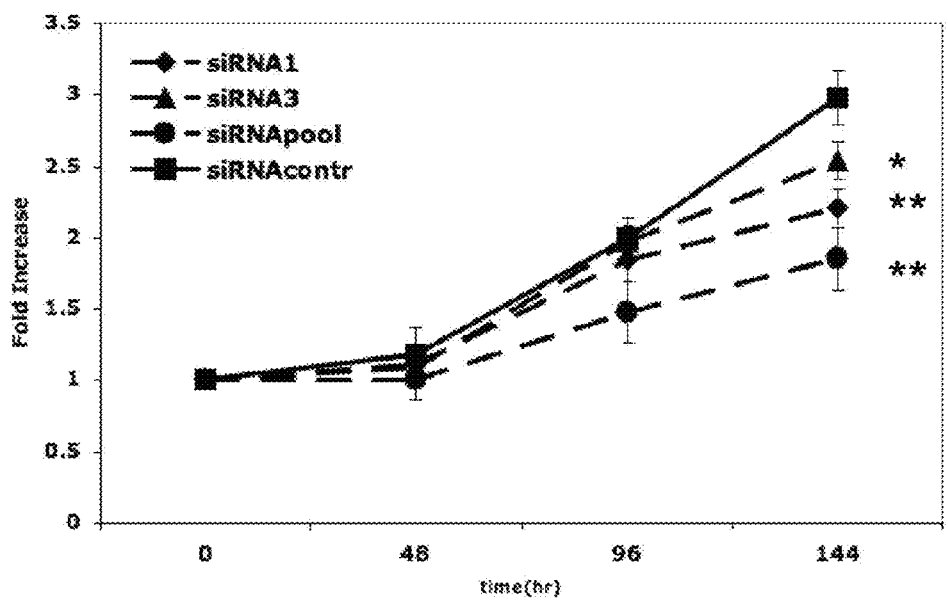

The growth of COLO-320 cells was significantly reduced after 144 hours of treatment with specific siRNA compared to both untreated (null) or siRNA-treated control cells (P<0.05 at 96 hrs and P<0.005 at 144 hrs) (FIG. 4B).

Figure 4C:
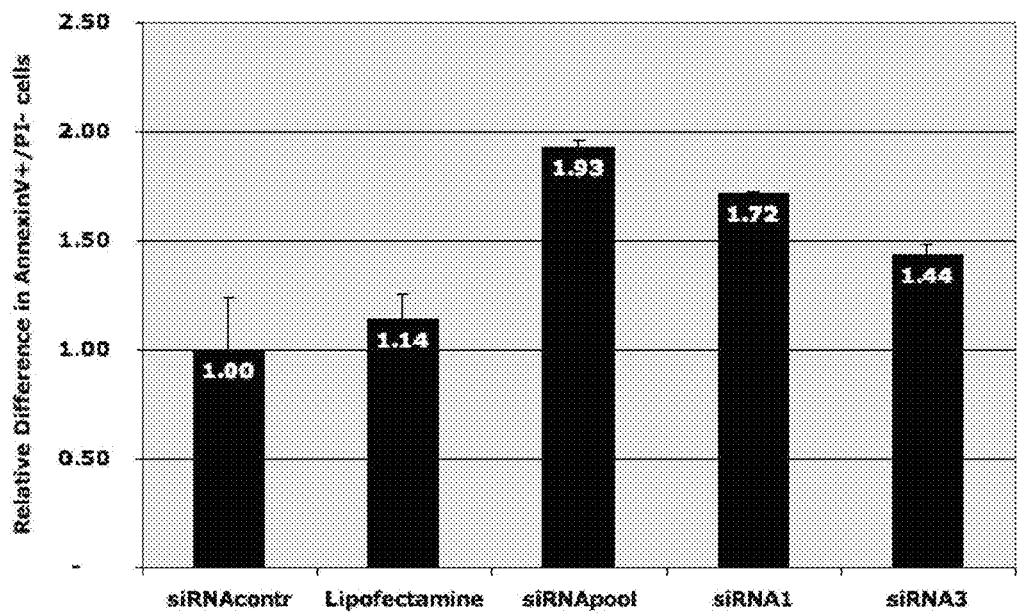
Figure 4D:
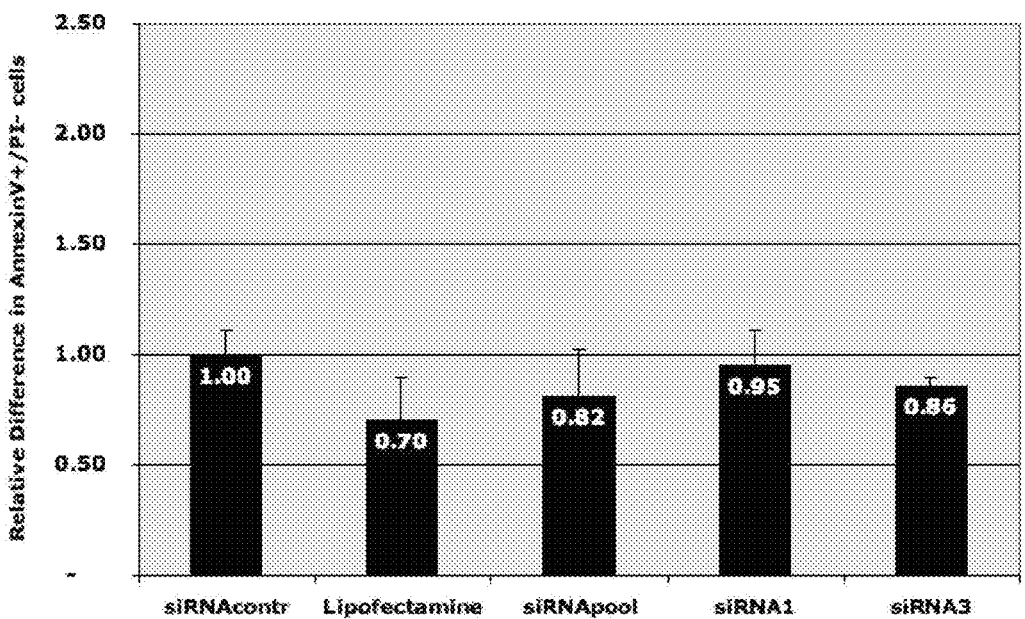

In comparison, proliferation of the SW620 control cells was not significantly changed (P=0.83 and P=0.23 at 96 and 144 hrs, respectively) (data not shown). Cell cycle studies revealed an increase in the sub-G1 fraction of cells (suggesting the presence of apoptotic cells, data not shown) in COLO-320 cells, but not in SW620 cells, a finding confirmed by the apoptosis-specific AnnexinV assay (FIG. 4C and FIG. 4D) and by caspase-3 assay (FIG. 11).

Furthermore, the intensity of effects on cell proliferation and survival were proportional with the degree of inhibition by siRNAs (FIG. 4).

These data suggest that in colorectal cancers, uc. 73A(P) behaves like an oncogene by increasing the number of malignant cells as a consequence of reduced apoptosis.

DISCUSSION

According to the dogma of molecular oncology, cancer is a genetic disease involving tumor-suppressor and oncogenic proteins (Bishop, 1991; Hunter, 1991; Weinberg, 1991). Recent findings strongly support the involvement of microRNAs in the pathogenesis of a majority of analyzed cancers, and add a new layer of complexity to the molecular architecture of human cancers (Calin et al., 2002; Esquela-Kerscher and Slack, 2006; Calin and Croce, 2006a). MiRNAs represent, however, just a particular group of ncRNAs involved in human cancers. It has been shown that antisense intronic ncRNA levels correlate with the degree of tumor differentiation in prostate cancer (Reis et al., 2005) and that MALAT-1 ncRNA expression predicts metastasis and survival in early stage non-small cell lung cancer (Ji et al., 2003), suggesting a deeper link between ncRNAs and tumor biology.

To clearly address this question, we investigated at the genomic level a full new class of ncRNAs, namely the transcribed non-coding ultraconserved regions (T-UCRs). We used bioinformatics tools to demonstrate that the UCRs are located in genomic regions targeted during the malignant process indicative of a putative involvement in human tumorigenesis.

As now shown herein, we were able to clone by RACE amplification cDNAs corresponding to uc.246(E) and uc.269A(N), proving that the UCRs are bona fide genes (named herein as nc-UCGs) that are expressed and can be cloned by standard methods.

Various expression techniques including Northern blot, qRT-PCR and genome-wide microarray profiling, proved that UCRs are frequently transcribed and that there are distinct signatures in human leukemias and carcinomas. We focused on chronic lymphocytic leukemia, the most frequent adult leukemia in the Western world (Chiorazzi et al., 2005), on colorectal carcinoma, one of the most common cancers in industrialized countries (de la Chapelle, 2004) and on hepatocellular carcinoma, the most rapidly increasing type of cancer in America (Wilson, 2005).

We found that for all the tumor types examined, the malignant cells have a unique spectrum of expressed UCRs when compared with the corresponding normal cells, suggesting that significant variations in T-UCR expression are involved in the malignant process.

Characterizing the functional significance of T-UCR alterations in human cancers is not a trivial task. A myriad of putative functions of T-UCRs can be hypothesized, including an antisense inhibitory role for protein coding genes or other non-codingRNAs, or a role as "aspecific" miRNAs, meaning miRNAs with peculiarities such as very long precursors (e.g. uc.339(P) which has a precursor length that is double the usual miRNA). This puzzle becomes more complicated by the fact that several UCRs do not act like genes and were found to have regulatory functions as enhancers (Nobrega et al., 2003; Pennacchio et al., 2006), while others represent exons of protein coding genes with known/unknown cancer connections. A particularly interesting region is the DA CHI locus that contains 7 UCRs in about 700 kb (Bejerano et al., 2004b). Three of the UCRs from this region are differentially expressed in analyzed cancers, two of which are members of the CLL signature. The majority of scanned conserved regions from this locus in a mouse model are enhancers, including the uc.351(N) that was not expressed in any of the analyzed tissues in our study.

Interestingly, the only two regions that failed to have enhancer function are uc.348(N) and uc.352(N), both classified as non-coding and both differentially expressed in human cancers. Further increasing the interest in these specific T-UCRs, is the finding that this genomic region has been linked to susceptibility to familial CLL and that none of the known protein-coding genes were mutated (Ng et al, 2007).

Recently, it was found that short blocks of several tens of by from the noncoding parts of the human genome (named pyknons) occur within nearly all known protein coding genes (Rigoutsos et al., 2006). While the pyknons are distinct from the UCRs, the ultraconserved element containing the highest number of pyknons (four) was uc. 73(P), which we found to be one of the most differentially expressed T-UCRs in both CLL and CRC. These intriguing observations suggest a possible regulatory role for uc. 73(P) on the coding genes with complementary sequences.

Further expanding the involvement of this T-UCR in human cancers, we were able to prove an oncogenic function for uc.73(P) in colon cancer, as diminution of its over-expression induced apoptosis and had antiproliferative effects specifically in colon cancer cells abnormally expressing this T-UCR.

Our findings that another class of ncRNAs, the T-UCRs, is consistently altered at the genomic level in a high percentage of analyzed leukemias and carcinomas, support a model in which both coding and non-coding genes are involved and cooperate in human tumorigenesis (Calin and Croce, 2006b).

Furthermore, correlations between the expression of UCRs and miRNAs in CLL patients raise the intriguing possibility of complex functional regulatory pathways in which two or more types of ncRNAs interact and influence the phenotype.

We also demonstrated the existence of the miRNA::T-UCR interaction in which two different types of ncRNAs are interacting.

We found that nc-UCGs are consistently altered at the genomic level in a high percentage of leukemias and carcinomas, and may interact with miRNAs in leukemias. The findings provide support for a model in which both coding and non-coding genes are involved in and cooperate in human tumorigenesis.

Example I

Experimental Procedures

A) RACE Cloning and Expression Analysis by Microarray, qRT-PCR and Northern Blot
  1) RACE Cloning
  The expression of six UCRs (uc.47(N), uc.110(N), uc.192 (N), uc.246(E), uc.269A(N) and uc.352(N)) was analyzed in brain, testis, bone marrow, small intestine, colon and liver tissue using various combinations of PCR primers designed to amplify short products. These products included 40-mers used for probes in microarray analysis and the complete >200 bp UCR sequence. Two of the UCR products, one exonic, uc.246(E) and one non-exonic, uc.269A(N), were cloned by Rapid Amplification of cDNA Ends (RACE) in both 5' and 3' directions. The sources of tissue from which sequences were cloned were bone marrow, leukocytes, fetal brain and colon according to the manufacturer protocol (Marathon-ready cDNAs, Clontech, Palo Alto, Calif.).
  2) UCR Expression Study by Microarray.
  Total RNA was extracted with Trizol (Invitrogen, Carlsbad, Calif.) from 19 normal human tissues (Liu et al., 2004) and from 50 CLL samples from patients diagnosed with CLL. Informed consent was obtained from all patients at the CLL Research Consortium institutions in the US. As controls, CDS+ B cells from 6 healthy individuals (four distinct samples, two being pools from two different healthy individuals) and mononuclear cells (MNC) from 3 individuals were used as reported in (Calin et al., 2005a). RNA was also extracted from 78 primary colorectal carcinomas, 21 normal colonic mucosas, 9 primary hepatocellular carcinomas and 4 normal livers, collected at the University of Ferrara, University of Bologna and University Tor Vergata, Rome (Italy). All samples were obtained with written informed consent according to institutional guidelines for the protection of human subjects.

Microarray chips were developed with a total of 481 human UCR sequences as in (soe.ucsc.edu/-jill/ultra). For each UCR two 40-mer probes were designed, one corresponding to the sense genomic sequence (named "+") and the other to the complementary sequence (named "A+"). The design criteria were as described (Liu et al., 2004). Each oligo was printed in duplicate in two different slide locations, and therefore quadruplicate numerical values were available for analysis. Several thousand (3484) blank spots were used for background subtraction. RNA extraction and microarray experiments, consisting of the UCR microarray assembly, target preparation and array hybridization, were performed as described in detail elsewhere (Liu et al., 2004; Calin et al., 2004a).

Briefly, 5 µg of RNA from each tissue sample was labeled with biotin by reverse transcription using random hexamers. Hybridization was carried out on the second version of our miRNA-chip (ArrayExpress accession number: A-MEXP-258) which contained the 962 UCR probes, 238 probes for mature miRNA and 143 probes for precursor miRNAs. Each oligo was printed in duplicate in two different slide locations. Hybridization signals were detected by biotin binding of a Streptavidin-Alexa647 conjugate (one-color signal) using a GenePix 4000B scanner (Axon Instruments). Images were quantified using the GenePix Pro 6.0 (Axon Instruments).

Raw data were normalized and analyzed in GeneSpring GX 7.3 (Agilent Technologies, Santa Clara, Calif.). Expression data of the 22 tissue samples were normalized with Lowess function in Bioconductor (Limma package) and then were median centered using GeneSpring normalization; the threshold used to determine the level of UCR expression was calculated as the average of blank spots+2 SD (standard deviation). Tumors were normalized using the on-chip and on-gene median normalization of the GeneSpring software. Hierarchical cluster analysis was done using average linkage and Pearson correlation as measures of similarity. Statistical comparisons of tumors and normal tissues were performed by filtering on fold change and then using the ANOVA (Analysis of Variance) statistic of the GeneSpring software and the Benjamin and Hochberg correction for reduction of false positives. The filter on fold-change was set on 1.2 because this threshold, already used for microRNAs analyzed with the same chip [see for examples (Cahn et al., 2005a; Cimmino et al., 2005; Iorio et al., 2005)], was demonstrated to reflect a real biological difference. The T-UCRs differentially expressed among CLL patients, grouped in accordance to 70-kDa zeta-associated protein (ZAP-70) expression, were identified by combining the ANOVA results with the SAM (Significance Analysis of Microarray) and PAM (Prediction Analysis of Microarrays) analysis. Their expression was compared to that of microRNAs (Calin et al., 2005a). All data were submitted using MIAMExpress to the ArrayExpress database and could be retrieve using the accession number E-TABM-184.

3) Quantitative RT-PCR for UCRs.
  Quantitative RT-PCR was the first method we used to confirm the microarray results. We validated the microarray data for eleven UCRs, including uc. 73 (P)/73A (P), uc.135(E), uc.160(N), uc.233(E)/233A(E), uc.269(N)/269A(N), uc.289 (N), uc.291(P), and uc.346A(P) in various combinations of samples, including 15 to 17 randomly selected CLL samples from the array set of 50, and various normal CD 19+/CD5+ B cells and B and T lymphocyte controls by qRT-PCR. An additional set of 3 normal CD19+/CD5+ positive B cells, not used for microarray studies, was purchased from AllCells (Berkeley, Calif.), and used as an independent confirmation set. In all instances the qRT-PCR data confirmed the microarray data. RNA was treated with RNase-free DNase I and reverse transcribed to cDNA using random primers and SuperScript II reverse transcriptase. To determine if the sense or antisense UCR transcript was expressed, total RNA was reverse transcribed using Thermoscript RT and a gene specific (i.e. sense or antisense) primer. RT conditions were as described (Schmittgen et al., 2004). cDNA was amplified using real-time PCR and SYBR green detection using PCR primers designed to amplify the same 40 bp regions as the oligo probe on the microarray. The relative amount of each UCR to 18S rRNA was determined using the equation 2"dcT, where dCT=(CTUCR−CT18s rRNA). Relative gene expression data were multiplied by 106 to simplify the presentation.

4) Northern Blot Analysis of T-UCRs.

We analyzed five UCRs, uc.110(N), uc.192(N), uc.246(E), uc.269A(N) and uc.352(N), by Northern blot, two of which were then cloned by RACE experiments. For a sixth one, the uc. 47(N), the data are not shown. Total RNA was electrophoresed on 15% PAA-urea gels (Calin et al., 2002). RNA sources included 11 normal tissues (breast, liver, lung, kidney and pancreas) in duplicate or triplicate (purchased from Ambion and Clontech) and 4 normal MNC samples and 16 CLL samples prepared in the laboratory. As this represents the investigation by Northern blot of UCR expression, we used multiple samples from the same tissues to confirm data reproducibility. The probes were designed to be identical with the oligonucleotides on the chip in order to detect the same transcripts as the microarray, and the hybridization was done as described (Cahn et al., 2002).

B) Databases and Statistical Analyses.

1) Databases for Genomic Locations.

The UCR databases used for all the studies reported here are as published (Bejerano et al., 2004b). We restricted our analyses to 481 segments longer than 200 base pairs (bp). The Fragile site (FRA) database and the cancer associated genomic regions (CAGR) databases are as previously published (Cain et al., 2004b).

2) Statistical Analyses for Genomic Locations.

To test hypotheses associating the incidence of ultra-conserved regions (UCRs) with fragile sites, amplified regions in cancer, and deletion regions in cancer, we utilized random effect Poisson and negative binomial regression models. Under these models, "events" were defined as the number of UCRs, and exposure "time" (i.e. fragile site versus non-fragile site) was defined as non-overlapping lengths of the region of interest. The "length" of a region was exact, if known, or estimated as 1 Mb if unknown. For example, for each chromosome the total length of all non-overlapping fragile sites was computed and was used as the exposure time for fragile sites. We then counted the number of UCRs occurring within fragile sites for each chromosome. The remaining length of each chromosome (total Mb−fragile sites Mb) was assumed to be non-fragile, and the remaining UCRs in each chromosome were assumed to occur in the non-fragile region. Then for each region, alternative random effects models, the zero-inflated Poisson and the zero-inflated negative binomial models were fitted, and, of the three, the best model was selected using the Akaike's Information Criteria (based on the log likelihood and number of parameters). This same approach was used for analysis of the data from expression of zinc finger proteins. The best fitting model for fragile sites with UCRs and LOH with zinc finger proteins was the zero-inflated negative binomial. For all other cases, the Poisson model is reported. When the number of categories with zero events was more than expected for a Poisson distribution, the zero-inflated negative binomial model was preferred. When the total number of events was too small for a region, the model likelihoods were unable to converge, and results are not reported. The random effect in the Poisson, zero-inflated Poisson and zero-inflated negative binomial regression models, was the individual chromosome, in that data within a chromosome was assumed to be correlated. The fixed effect in each model consisted of an indicator variable(s) for the type of region being compared. We report the incidence rate ratio (IRR), 2-sided 95% confidence interval of the incidence rate ratio, and 2-sided p-values for testing the hypothesis that the incident rate ratio is 1.0. An IRR significantly>1 indicates an increase in the number of UCRs within a region over that expected by chance.

The proportions of clustering of miRNAs and zinc finger proteins were compared using an asymptotic test of the difference in two independent proportions, where we report the difference, 95% confidence interval of the difference, and p-value. Of note, the ZNF transcription factor class of genes showed a significantly lower clustering (a cluster defined as the location of at least two genes from the same class at less than 50 kb genomic distance) when compared with the microRNAs (32%, 95/297 clustered ZNF genes versus 48%, 90/186 clustered miRNAs, difference=16.4%, 95% CI= (7.5%, 25.2%), P<0.001). All computations were completed using STATA v7.0 and StatXact v7.0.

Statistical Analyses for Negative Correlations Between Microarray Expression of UCRs and miRNAs.

A detailed description is provided in the Example II and data therein. Briefly, the input data was constituted by a list of T-UCRs and by a list of miRNAs (the "seeds") and the corresponding matrix of expression values. We calculated r, the Spearman rank coefficient of correlation for each pair of (miR, UC) genes; namely, we evaluate the P-values of the correlation tests and select the genes whose correlation value is significant at a given value of rejection. Given the high number of correlation tests performed, P-values were corrected for multiple testing by using the false detection rate (FDR), as in (Benjamini and Hochberg, 1995). In this way, P-values control the number of false positive over the number of truly null tests, while FDR controls the number of false positive over the number of significant tests.

C) Functional Studies

1) UCRs Down-Regulation by Direct Interaction with MicroRNAs.

The genomic sequences of uc.160, uc.346A and uc.348 were cloned into pGL3-control vector (Clontech) using the XbaI site immediately downstream from the stop codon of luciferase. Human megakaryocytic MEG-O1 and the cervical carcinoma HeLa cell lines were grown as recommended by the ATCC. Cells were co-transfected in 12-well plates using siPORT neoFX (Ambion) according to the manufacturer's protocol using 0.4 µg of the firefly luciferase reporter vector and 0.08 µg of the control vector containing *Renilla* luciferase, pRL-TK (Promega). For each well 10 nM of miRNA-sense precursor and scrambled oligonucleotides (Ambion) were used. Firefly and *Renilla* luciferase activities were measured consecutively using the Dual-luciferase assays (Promega) 24 hr after transfection. All experiments were performed in triplicate on four to six different days (n=12 to 18).

Expression of both the ultraconserved RNA and the mature miRNA was analyzed using real-time PCR. Expression of the UCR RNA was determined by real-time PCR as described above. Expression of the mature miRNA was performed using TaqMan looped primer assays to miR-155 (Applied Biosystems) as described (Chen et al., 2005). Mature miRNA expression was presented as 2-dCT where dCT=CTmiRNA−CT1 ss rRNA); data was multiplied by 106 to simplify presentation.

For the patient correlation a set of 13 samples was used (including 9 CLL patients and 4 normal lymphocyte samples) and miR-155, uc.346A and uc.160 levels were analyzed as described herein. For the identification of the "in vivo" effects in MEGO1 of miR-155 transfection, the levels of uc.346A and uc.160 were measured by qRT-PCR as described at 0, 24 and 48 hrs post-transfection with the pre-miRNA 155 (Ambion) using Lipofectamine reagent.

2) Effects on Cancer Cell Proliferation by uc. 73A(P) Inhibition.

The siRNA against the uc. 73A(P) were designed using the Dharmacon algorithm (Dharmacon siDESIGN (harmacon.com/sidesign)) entering the complete sequence of the UCR. The eight highest rank target sequences were tested. The performance was assessed after 48, 72 and 144 hour post-transfection by semi-quantitative RT-PCR. The most effective two siRNAs and a pool of four different siRNAs, including these two, were used. We named these as siRNA1, siRNA3 and siRNApool. For the cell growth assay, the human colon cancer cell lines COLO-320 and SW620 were grown in RPMI1640 medium supplemented with 10% FBS and $1\times10^4$ cells were plated in 96-well plate a day before transfection. The cells were transfected with siRNA-uc.73A(P) at a final concentration of 200 nM by using Lipofectamine 2000 (Invitrogen, Carlsbad, Calif., USA) according to the manufacturer's protocol. The siCONTROL Non-Targeting siRNA Pool (Dharmacon Research, LaFayette, Colo., USA) was used as negative control. The transfection was repeated under the same conditions every two days, at 48 and 96 hour. To evaluate the cell number the CellTiter 96 Aqueous One Solution Cell Proliferation Assay (Promega U.S., Madison, Wis., USA) was used. The readings were performed at 0, 48, 96, and 144 hours, respectively measuring the absorbance at 490 nm using an ELISA plate reader (Spectra MAX, Molecular Devices, Sunnyvale, Calif., USA). The cell growth assay was performed three times in triplicate for each treatment. The statistical differences between the number of cells at various time points with respect to time 0, was calculated using the t test.

For both cell cycle and apoptosis assays, cells were plated in 6 well plates at $6\times10^5$ cells per well. The day after and then every 48 hrs, the cells were transfected with 200 nM siRNA. The cells were collected and fixed in cold 70% ethanol for at least 30 minutes. The Propidium Iodide (PI) staining was performed at 48, 96, and 144 hours in a 50 µg/mL PI (Sigma Aldrich, St. Louis, Mo.) and 5.1 g/mL RNAse DNAse free (Roche Diagnostics, Indianapolis, Ind., USA) PBS Solution. The apoptosis staining was performed with the Annexin V-FITC Apoptosis Detection Kit (BD Pharmingen, San Jose, Calif., USA) and with the PE-conjugated monoclonal active Caspase-3 antibody apoptosis kit (BD Biosciences) at 0 and 144 hours according to the manufacturer's procedure using an FACS Calibur (BD Biosciences, San Jose, Calif., USA) to acquire the data. Each experiment was performed three times.

The GeneBank accession numbers for the cloned T-UCRs described in this study are as followings: DQ644536 (UCG.246), DQ644537 (UCG.269A, short form), and DQ644538 (UCG.269A, long form).

Example II

Experimental Procedures

Statistical Analyses for Negative Correlations Between Microarray Expression of UCRs and miRNAs.

The input data were constituted by a list of UCGs and by a list of miRNAs (the "seeds") and the corresponding matrix of expression values. We calculated r, the Spearman rank coefficient of correlation, a non-parametric measure of data trend correlation based on rankings, for each pair of (miR, UCR) genes; namely, we evaluate the P-values of the correlation tests and selected the genes whose correlation value is significant at a given value of rejection. Evaluation of P-values was performed assuming that the correlation values are distributed using Student's t cumulative distribution, with a number of degrees of freedom corresponding to the number of samples in the microarray experiment. The P-values measure the 'goodness' of the single correlations (among couples of genes), therefore, to understand if the real correlation derives by chance or represents a biologically important information, we choose the method of permutations, changing the order of the samples for each row (miR or UCR) and calculating the correlations between pair of genes (miR, UCR) with different changed samples orders. We repeated the samples permutation and computed correlations 100 times, in this way, every real correlation has 100 random correlations to compare with. Using all (100*n° MIR*n° UC) random correlations and real correlations, we recalculated P-values based on random correlations ranking and position of the real correlations.

Given the high number of correlation tests performed, P-values were corrected for multiple testing by using the false detection rate (FDR), as defined by (Benjamini and Hochberg, 1995). In this way, P-values control the number of false positive over the number of truly null tests, while FDR controls the number of false positive over the number of significant tests. Several ways of estimating this number have been proposed, and we adopted the solution devised by Tom Nichols (see froi.sourceforge.net/documents/technical/matlab/FDR), that rescales the P-value obtained on a single test multiplying it by a combination of indexes related to the total number of tests performed. Correction was performed on a seed by seed basis, meaning that the genes in the seeds list were considered independent tests. This statistically validated tripe filtering allows the targeted extraction of a shortlist of candidate genes, thus saving resources for the following costly and time-consuming genetic analysis.

To build a scatter plot between miR-24-1 and uc.160 expression values, we plotted a regression line by using MatLab function ROBUSTFIT to explain hypotheses of negative correlation between these two genes. Notice that only 11.67% (7/60) of points (pairs of expression values) are outlier.

Example III

Additional Examples and Information

As used herein miR and UCRs are used interchangeably; including in a non-limiting manner: a "miR gene product,"

"microRNA," "miR," or "miRNA" refers to the unprocessed (e.g., precursor) or processed (e.g., mature) RNA transcript from a miR gene.

Diagnosis Using UCRs (miRNAs)

In one aspect, there is provided herein methods of diagnosing whether a subject has, or is at risk for developing, a cancer, comprising measuring the level of at least one UCR in a test sample from the subject and comparing the level of the miR gene product in the test sample to the level of a corresponding miR gene product in a control sample. As used herein, a "subject" can be any mammal that has, or is suspected of having, a cancer. In a preferred embodiment, the subject is a human who has, or is suspected of having, a cancer.

The level of at least one miR gene product can be measured in a biological sample (e.g., cells, tissues) obtained from the subject. For example, a tissue sample (e.g., from a tumor) can be removed from a subject suspected of having a cancer-related disease by conventional biopsy techniques. In another embodiment, a blood sample can be removed from the subject, and blood cells (e.g., white blood cells) can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. A reference miR expression standard for the biological sample can also be used as a control.

An alteration (e.g., an increase or decrease) in the level of a miR gene product in the sample obtained from the subject, relative to the level of a corresponding miR gene product in a control sample, is indicative of the presence of a cancer-related disease in the subject.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample.

In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample.

The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences and include, but are not limited to, probes having at least about 70%, 75%, 80%, 85%, 90%, 95%, 98%, 99% or complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

In one non-limiting example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl) deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference.

In one non-limiting example, suitable probes for in situ hybridization of a given miR gene product can be produced from the nucleic acid sequences, and include, but are not limited to, probes having at least about 70%, 75%, 80%, 85%, 90%, 95%, 98%, 99% or complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in cancer cells.

As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancerous (e.g., tumor) tissue, and within cancerous tissue, different prognosis states (for example, good or poor long term survival prospects) may be determined. By comparing expression profiles of the cancer tissue in different states, information regarding which genes are important (including both up- and down-regulation of genes) in each of these states is obtained. The identification of sequences that are differentially expressed in cancer tissue, as well as differential expression resulting in different prognostic outcomes, allows the use of this information in a number of ways.

In one non-limiting example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the cancer expression profile or convert a poor prognosis profile to a better prognosis profile.

Accordingly, there is also provided herein methods of diagnosing whether a subject has, or is at risk for developing, a cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, cancer.

In one embodiment, the microarray comprises miRNA-specific probe oligonucleotides for a substantial portion of all known human miRNAs. In a particular embodiment, the microarray comprises miRNA-specific probe oligonucleotides for one or more miRNAs selected from the group consisting of miR29a, miR-29b, miR-29c and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/ 30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample.

According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool allows for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer-related disease quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal).

More preferably, the profile recorded includes the intensity of the signal from each hybridization. The profile is compared to the hybridization profile generated from a normal, i.e., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

There is also provided herein methods of determining the prognosis of a subject with a cancer, comprising measuring the level of at least one miR gene product, which is associated with a particular prognosis in a cancer-related disease (e.g., a good or positive prognosis, a poor or adverse prognosis), in a test sample from the subject.

According to these methods, an alteration in the level of a miR gene product that is associated with a particular prognosis in the test sample, as compared to the level of a corresponding miR gene product in a control sample, is indicative of the subject having a cancer with a particular prognosis. In one embodiment, the miR gene product is associated with an adverse (i.e., poor) prognosis. Examples of an adverse prognosis include, but are not limited to, low survival rate and rapid disease progression. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of cancers. Therefore, altering the level of the miR gene product (e.g., by decreasing the level of a miR gene product that is up-regulated in cancer cells, by increasing the level of a miR gene product that is down-regulated in cancer cells) may successfully treat the cancer.

Accordingly, there is further provided herein methods of inhibiting tumorigenesis in a subject who has, or is suspected of having, a cancer wherein at least one miR gene product is deregulated (e.g., down-regulated, up-regulated) in the cancer cells of the subject. When the at least one isolated miR gene product is down-regulated in the cancer cells (e.g., miR-29 family), the method comprises administering an effective amount of the at least one isolated miR gene product, or an isolated variant or biologically-active fragment thereof, such that proliferation of cancer cells in the subject is inhibited.

For example, when a miR gene product is down-regulated in a cancer cell in a subject, administering an effective amount of an isolated miR gene product to the subject can inhibit proliferation of the cancer cell. The isolated miR gene product that is administered to the subject can be identical to the endogenous wild-type miR gene product (e.g., a miR gene product) that is down-regulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with a cancer. In certain embodiments, the biologically-active fragment is at least about 5, 7, 10, 12, 15, or 17 nucleotides in length.

In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of at least one compound for inhibiting expression of the at least one miR gene product, referred to herein as miR gene expression-inhibition compounds, such that proliferation of the cancer cells is inhibited. In a particular embodiment, the at least one miR expression-inhibition compound is specific for a miR gene product selected from the group consisting miR29 family, including miR-29a, miR-29b, miR-29c, and combinations thereof.

The terms "treat", "treating" and "treatment", as used herein, refer to ameliorating symptoms associated with a disease or condition, for example, a cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from a cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5 to about 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to one particular embodiment, the isolated miR gene products described herein can be used for the manufacture of a medicament for treating a cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/

0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol*, 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), Nature 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., a cancer). One skilled in the art can readily determine an effective amount of a miR expression-inhibition compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibition compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression of (e.g., inhibit translation of, induce cleavage or destruction of) the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product.

Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups.

Exemplary enzymatic nucleic acids for use in the present methods include de novo methyltransferases, including DNMT3A and DNMT3B, as described in the Examples herein.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer.

As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibition compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibition compounds can be administered to a subject by any means suitable for delivering these compounds to cancer cells of the subject. For example, the miR gene products or miR expression-inhibition compounds can be administered by methods suitable to transfect cells of the subject with these compounds, or with nucleic acids comprising sequences encoding these compounds.

In one embodiment, the cells are transfected with a plasmid or viral vector comprising sequences encoding at least one miR gene product or miR gene expression-inhibition compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibition compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibition compound can be administered to the subject either as naked RNA, in combination with a delivery reagent, or as a nucleic acid (e.g., a recombinant plasmid or viral vector) comprising sequences that express the miR gene product or miR gene product expression-inhibition compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression-inhibition compounds, and techniques for delivering such plasmids and vectors to cancer cells, are discussed herein and/or are well known in the art.

In a particular embodiment, liposomes are used to deliver a miR gene product or miR gene expression-inhibition compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone;

linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating a cancer.

In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in cancer cells relative to suitable control cells.

In other embodiments, the pharmaceutical compositions of the invention comprise at least one miR expression-inhibition compound. In a particular embodiment, the at least one miR gene expression-inhibition compound is specific for a miR gene whose expression is greater in cancer cells than control cells.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising sequences encoding them) (e.g., 0.1 to 90% by weight), or a physiologically-acceptable salt thereof, mixed with a pharmaceutically-acceptable carrier. In certain embodiments, the pharmaceutical compositions of the invention additionally comprise one or more anti-cancer agents (e.g., chemotherapeutic agents). The pharmaceutical formulations of the invention can also comprise at least one miR gene product or miR gene expression-inhibition compound (or at least one nucleic acid comprising sequences encoding them), which are encapsulated by liposomes and a pharmaceutically-acceptable carrier. In one embodiment, the pharmaceutical composition comprises a miR gene or gene product that is one or more of miR29a, miR-29b and miR-29c.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising sequences encoding them) that is resistant to degradation by nucleases.

One skilled in the art can readily synthesize nucleic acids that are nuclease resistant, for example, by incorporating one or more ribonucleotides that is modified at the 2'-position into the miR gene product. Suitable 2'-modified ribonucleotides include those modified at the 2'-position with fluoro, amino, alkyl, alkoxy, and O-allyl.

Pharmaceutical Compositions

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising sequences encoding them) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising sequences encoding them) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, FOLFOX4.

Inhibitors of Tumorigenesis

There is also provided herein methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in cancer cells. An increase in the level of the miR gene product in the cell after the agent is provided, relative to a suitable control cell (e.g., agent is not provided), is indicative of the test agent being an inhibitor of tumorigenesis.

In other embodiments, the method comprises providing a test agent to a cell and measuring the level of at least one miR gene product associated with increased expression levels in cancer cells. A decrease in the level of the miR gene product in the cell after the agent is provided, relative to a suitable control cell (e.g., agent is not provided), is indicative of the test agent being an inhibitor of tumorigenesis. In a particular embodiment, at least one miR gene product associated with increased expression levels in cancer cells is selected from the group consisting of miR29a, miR-29b, miR-29c, and combinations thereof.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described hereinabove.

Example IV

Methods, Reagents and Kits for Diagnosing, Staging, Prognosing, Monitoring and Treating Cancer-Related Diseases It is to be understood that all examples herein are to be considered non-limiting in their scope. Various aspects are described in further detail in the following subsections.

Diagnostic Methods

In one embodiment, there is provided a diagnostic method of assessing whether a patient has a cancer-related disease or has higher than normal risk for developing a cancer-related disease, comprising the steps of comparing the level of expression of a marker in a patient sample and the normal level of expression of the marker in a control, e.g., a sample from a patient without a cancer-related disease.

A significantly higher level of expression of the marker in the patient sample as compared to the normal level is an indication that the patient is afflicted with a cancer-related disease or has higher than normal risk for developing a cancer-related disease.

The markers are selected such that the positive predictive value of the methods is at least about 10%, and in certain non-limiting embodiments, about 25%, about 50% or about 90%. Also preferred for use in the methods are markers that are differentially expressed, as compared to normal cells, by at least two-fold in at least about 20%, and in certain non-limiting embodiments, about 50% or about 75%.

In one diagnostic method of assessing whether a patient is afflicted with a cancer-related disease (e.g., new detection ("screening"), detection of recurrence, reflex testing), the method comprises comparing: a) the level of expression of a marker in a patient sample, and b) the normal level of expression of the marker in a control non-cancer-related disease sample. A significantly higher level of expression of the marker in the patient sample as compared to the normal level is an indication that the patient is afflicted with a cancer-related disease.

There is also provided diagnostic methods for assessing the efficacy of a therapy for inhibiting a cancer-related disease in a patient. Such methods comprise comparing: a) expression of a marker in a first sample obtained from the patient prior to providing at least a portion of the therapy to the patient, and b) expression of the marker in a second sample obtained from the patient following provision of the portion of the therapy. A significantly lower level of expression of the marker in the second sample relative to that in the first sample is an indication that the therapy is efficacious for inhibiting a cancer-related disease in the patient.

It will be appreciated that in these methods the "therapy" may be any therapy for treating a cancer-related disease including, but not limited to, pharmaceutical compositions, gene therapy and biologic therapy such as the administering of antibodies and chemokines. Thus, the methods described herein may be used to evaluate a patient before, during and after therapy, for example, to evaluate the reduction in disease state.

In certain aspects, the diagnostic methods are directed to therapy using a chemical or biologic agent. These methods comprise comparing: a) expression of a marker in a first sample obtained from the patient and maintained in the presence of the chemical or biologic agent, and b) expression of the marker in a second sample obtained from the patient and maintained in the absence of the agent. A significantly lower level of expression of the marker in the second sample relative to that in the first sample is an indication that the agent is efficacious for inhibiting a cancer-related disease in the patient. In one embodiment, the first and second samples can be portions of a single sample obtained from the patient or portions of pooled samples obtained from the patient.

Methods for Assessing Prognosis

There is also provided a monitoring method for assessing the progression of a cancer-related disease in a patient, the method comprising: a) detecting in a patient sample at a first time point, the expression of a marker; b) repeating step a) at a subsequent time point in time; and c) comparing the level of expression detected in steps a) and b), and therefrom monitoring the progression of a cancer-related disease in the patient. A significantly higher level of expression of the marker in the sample at the subsequent time point from that of the sample at the first time point is an indication that the cancer-related disease has progressed, whereas a significantly lower level of expression is an indication that the cancer-related disease has regressed.

There is further provided a diagnostic method for determining whether a cancer-related disease has worsened or is likely to worsen in the future, the method comprising comparing: a) the level of expression of a marker in a patient sample, and b) the normal level of expression of the marker in a control sample. A significantly higher level of expression in the patient sample as compared to the normal level is an indication that the cancer-related disease has worsened or is likely to worsen in the future.

Methods for Assessing Inhibitory, Therapeutic and/or Harmful Compositions

There is also provided a test method for selecting a composition for inhibiting a cancer-related disease in a patient. This method comprises the steps of: a) obtaining a sample comprising cells from the patient; b) separately maintaining aliquots of the sample in the presence of a plurality of test compositions; c) comparing expression of a marker in each of the aliquots; and d) selecting one of the test compositions which significantly reduces the level of expression of the marker in the aliquot containing that test composition, relative to the levels of expression of the marker in the presence of the other test compositions.

There is additionally provided a test method of assessing the harmful potential of a compound in causing a cancer-related disease. This method comprises the steps of: a) maintaining separate aliquots of cells in the presence and absence of the compound; and b) comparing expression of a marker in each of the aliquots. A significantly higher level of expression of the marker in the aliquot maintained in the presence of the compound, relative to that of the aliquot maintained in the absence of the compound, is an indication that the compound possesses such harmful potential.

In addition, there is further provided a method of inhibiting a cancer-related disease in a patient. This method comprises the steps of: a) obtaining a sample comprising cells from the patient; b) separately maintaining aliquots of the sample in the presence of a plurality of compositions; c) comparing expression of a marker in each of the aliquots; and d) administering to the patient at least one of the compositions which significantly lowers the level of expression of the marker in the aliquot containing that composition, relative to the levels of expression of the marker in the presence of the other compositions.

The level of expression of a marker in a sample can be assessed, for example, by detecting the presence in the sample of: the corresponding marker protein or a fragment of the protein (e.g. by using a reagent, such as an antibody, an antibody derivative, an antibody fragment or single-chain antibody, which binds specifically with the protein or protein fragment) the corresponding marker nucleic acid (e.g. a nucleotide transcript, or a complement thereof), or a fragment of the nucleic acid (e.g. by contacting transcribed polynucleotides obtained from the sample with a substrate having affixed thereto one or more nucleic acids having the entire or a segment of the nucleic acid sequence or a complement thereof) a metabolite which is produced directly (i.e., catalyzed) or indirectly by the corresponding marker protein.

Any of the aforementioned methods may be performed using at least one or a plurality (e.g., 2, 3, 5, or 10 or more) of cancer-related disease markers. In such methods, the level of expression in the sample of each of a plurality of markers, at least one of which is a marker, is compared with the normal level of expression of each of the plurality of markers in samples of the same type obtained from control humans not afflicted with a cancer-related disease. A significantly altered (i.e., increased or decreased as specified in the above-described methods using a single marker) level of expression in the sample of one or more markers, or some combination thereof, relative to that marker's corresponding normal or control level, is an indication that the patient is afflicted with a cancer-related disease. For all of the aforementioned methods, the marker(s) are selected such that the positive predictive value of the method is at least about 10%.

Examples of Candidate Agents

The candidate agents may be pharmacologic agents already known in the art or may be agents previously unknown to have any pharmacological activity. The agents may be naturally arising or designed in the laboratory. They may be isolated from microorganisms, animals or plants, or may be produced recombinantly, or synthesized by any suitable chemical method. They may be small molecules, nucleic acids, proteins, peptides or peptidomimetics. In certain embodiments, candidate agents are small organic compounds having a molecular weight of more than 50 and less than about 2,500 daltons. Candidate agents comprise functional groups necessary for structural interaction with proteins. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. There are, for example, numerous means available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. In certain embodiments, the candidate agents can be obtained using any of the numerous approaches in combinatorial library methods art, including, by non-limiting example: biological libraries; spatially addressable parallel solid phase or solution phase libraries; synthetic library methods requiring deconvolution; the "one-bead one-compound" library method; and synthetic library methods using affinity chromatography selection.

In certain further embodiments, certain pharmacological agents may be subjected to directed or random chemical modifications, such as acylation, alkylation, esterification, amidification, etc. to produce structural analogs.

The same methods for identifying therapeutic agents for treating a cancer-related disease can also be used to validate lead compounds/agents generated from in vitro studies.

The candidate agent may be an agent that up- or down-regulates one or more cancer-related disease response pathways. In certain embodiments, the candidate agent may be an antagonist that affects such pathway.

Methods for Treating a Cancer-Related Disease

There is provided herein methods for treating, inhibiting, relieving or reversing a cancer-related disease response. In the methods described herein, an agent that interferes with a signaling cascade is administered to an individual in need thereof, such as, but not limited to, cancer-related disease patients in whom such complications are not yet evident and those who already have at least one cancer-related disease response.

In the former instance, such treatment is useful to prevent the occurrence of such cancer-related disease response and/or reduce the extent to which they occur. In the latter instance, such treatment is useful to reduce the extent to which such cancer-related disease response occurs, prevent their further development or reverse the cancer-related disease response.

In certain embodiments, the agent that interferes with the cancer-related disease response cascade may be an antibody specific for such response.

Expression of Markers

Expression of a marker can be inhibited in a number of ways, including, by way of a non-limiting example, an antisense oligonucleotide can be provided to the cancer-related disease cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the cancer-related disease cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit cancer-related disease cells of the patient.

Any marker or combination of markers, as well as any certain markers in combination with the markers, may be used in the compositions, kits and methods described herein. In general, it is desirable to use markers for which the difference between the level of expression of the marker in cancer-related disease cells and the level of expression of the same marker in normal cells is as great as possible. Although this difference can be as small as the limit of detection of the method for assessing expression of the marker, it is desirable that the difference be at least greater than the standard error of the assessment method, and, in certain embodiments, a difference of at least 2-, 3-, 4-, 5-, 6-, 7-, 8-, 9-, 10-, 15-, 20-, 100-, 500-, 1000-fold or greater than the level of expression of the same marker in normal tissue.

It is recognized that certain marker proteins are secreted to the extracellular space surrounding the cells. These markers are used in certain embodiments of the compositions, kits and methods, owing to the fact that such marker proteins can be detected in a cancer-associated body fluid sample, which may be more easily collected from a human patient than a tissue biopsy sample. In addition, in vivo techniques for detection of a marker protein include introducing into a subject a labeled antibody directed against the protein. For example, the antibody can be labeled with a radioactive marker whose presence and location in a subject can be detected by standard imaging techniques.

In order to determine whether any particular marker protein is a secreted protein, the marker protein is expressed in, for example, a mammalian cell, such as a human cell line, extracellular fluid is collected, and the presence or absence of the protein in the extracellular fluid is assessed (e.g. using a labeled antibody which binds specifically with the protein).

It will be appreciated that patient samples containing tissue and/or fluid cells may be used in the methods described herein. In these embodiments, the level of expression of the marker can be assessed by assessing the amount (e.g., absolute amount or concentration) of the marker in a sample. The cell sample can, of course, be subjected to a variety of post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

It will also be appreciated that the markers may be shed from the cells into the digestive system, the blood stream and/or interstitial spaces. The shed markers can be tested, for example, by examining the serum or plasma.

The compositions, kits and methods can be used to detect expression of marker proteins having at least one portion which is displayed on the surface of cells which express it. For example, immunological methods may be used to detect such proteins on whole cells, or computer-based sequence analysis methods may be used to predict the presence of at least one extracellular domain (i.e., including both secreted proteins and proteins having at least one cell-surface domain). Expression of a marker protein having at least one portion which is displayed on the surface of a cell which expresses it may be detected without necessarily lysing the cell (e.g., using a labeled antibody which binds specifically with a cell-surface domain of the protein).

Expression of a marker may be assessed by any of a wide variety of methods for detecting expression of a transcribed nucleic acid or protein. Non-limiting examples of such methods include immunological methods for detection of secreted, cell-surface, cytoplasmic or nuclear proteins, protein purification methods, protein function or activity assays, nucleic acid hybridization methods, nucleic acid reverse transcription methods and nucleic acid amplification methods.

In a particular embodiment, expression of a marker is assessed using an antibody (e.g., a radio-labeled, chromophore-labeled, fluorophore-labeled or enzyme-labeled antibody), an antibody derivative (e.g., an antibody conjugated with a substrate or with the protein or ligand of a protein-ligand pair), or an antibody fragment (e.g., a single-chain antibody, an isolated antibody hypervariable domain, etc.) which binds specifically with a marker protein or fragment thereof, including a marker protein which has undergone all or a portion of its normal post-translational modification.

In another particular embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many methods of detecting mutations or variants (e.g., single nucleotide polymorphisms, deletions, etc.) of a marker may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, it is desired that the hybridization be performed under stringent hybridization conditions.

Biomarker Assays

In certain embodiments, the biomarker assays can be performed using mass spectrometry or surface plasmon resonance. In various embodiment, the method of identifying an agent active against al cancer-related disease can include a) providing a sample of cells containing one or more markers or derivative thereof; b) preparing an extract from said cells; c) mixing said extract with a labeled nucleic acid probe containing a marker binding site; and, d) determining the formation of a complex between the marker and the nucleic acid probe in the presence or absence of the test agent. The determining step can include subjecting said extract/nucleic acid probe mixture to an electrophoretic mobility shift assay.

In certain embodiments, the determining step comprises an assay selected from an enzyme linked immunoabsorption assay (ELISA), fluorescence based assays and ultra high throughput assays, for example surface plasmon resonance (SPR) or fluorescence correlation spectroscopy (FCS) assays. In such embodiments, the SPR sensor is useful for direct real-time observation of biomolecular interactions since SPR is sensitive to minute refractive index changes at a metal-dielectric surface. SPR is a surface technique that is sensitive to changes of $10^5$ to $10^{-6}$ refractive index (RI) units within approximately 200 nm of the SPR sensor/sample interface. Thus, SPR spectroscopy is useful for monitoring the growth of thin organic films deposited on the sensing layer.

Because the compositions, kits, and methods rely on detection of a difference in expression levels of one or more markers, it is desired that the level of expression of the marker is significantly greater than the minimum detection limit of the method used to assess expression in at least one of normal cells and cancer-affected cells.

It is understood that by routine screening of additional patient samples using one or more of the markers, it will be realized that certain of the markers are over-expressed in cells of various types, including specific cancer-related diseases.

In addition, as a greater number of patient samples are assessed for expression of the markers and the outcomes of the individual patients from whom the samples were obtained are correlated, it will also be confirmed that altered expression of certain of the markers are strongly correlated with a cancer-related disease and that altered expression of other markers are strongly correlated with other diseases. The compositions, kits, and methods are thus useful for characterizing one or more of the stage, grade, histological type, and nature of a cancer-related disease in patients.

When the compositions, kits, and methods are used for characterizing one or more of the stage, grade, histological type, and nature of a cancer-related disease in a patient, it is desired that the marker or panel of markers is selected such that a positive result is obtained in at least about 20%, and in certain embodiments, at least about 40%, 60%, or 80%, and in substantially all patients afflicted with a cancer-related disease of the corresponding stage, grade, histological type, or nature. The marker or panel of markers invention can be selected such that a positive predictive value of greater than about 10% is obtained for the general population (in a non-limiting example, coupled with an assay specificity greater than 80%).

When a plurality of markers are used in the compositions, kits, and methods, the level of expression of each marker in a patient sample can be compared with the normal level of expression of each of the plurality of markers in non-cancer samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with a cancer-related disease. When a plurality of markers is used, 2, 3, 4, 5, 8, 10, 12, 15, 20, 30, or 50 or more individual markers can be used; in certain embodiments, the use of fewer markers may be desired.

In order to maximize the sensitivity of the compositions, kits, and methods (i.e. by interference attributable to cells of non-tissue and/or fluid origin in a patient sample), it is desirable that the marker used therein be a marker which has a restricted tissue distribution, e.g., normally not expressed in a non-tissue cells.

It is recognized that the compositions, kits, and methods will be of particular utility to patients having an enhanced risk of developing a cancer-related disease and their medical advisors. Patients recognized as having an enhanced risk of developing a cancer-related disease include, for example, patients having a familial history of a cancer-related disease.

The level of expression of a marker in normal human cells can be assessed in a variety of ways. In one embodiment, this normal level of expression is assessed by assessing the level of expression of the marker in a portion of cells which appear to be normal and by comparing this normal level of expression with the level of expression in a portion of the cells which is suspected of being abnormal. Alternately, and particularly as further information becomes available as a result of routine performance of the methods described herein, population-average values for normal expression of the markers may be used. In other embodiments, the "normal" level of expression of a marker may be determined by assessing expression of the marker in a patient sample obtained from a non-cancer-afflicted patient, from a patient sample obtained from a patient before the suspected onset of a cancer-related disease in the patient, from archived patient samples, and the like.

There is also provided herein compositions, kits, and methods for assessing the presence of cancer-related disease cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions, in the kits, or the methods used to assess levels of marker expression in the sample.

Methods of Producing Antibodies

There is also provided herein a method of making an isolated hybridoma which produces an antibody useful for assessing whether a patient is afflicted with a cancer-related disease. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro). A vertebrate, for example, a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods. Hybridomas formed in this manner are then screened using standard methods to identify one or more hybridomas which produce an antibody which specifically binds with the marker protein or a fragment thereof. There is also provided herein hybridomas made by this method and antibodies made using such hybridomas.

Methods of Assessing Efficacy

There is also provided herein a method of assessing the efficacy of a test compound for inhibiting cancer-related disease cells. As described herein, differences in the level of expression of the markers correlate with the abnormal state of the cells. Although it is recognized that changes in the levels of expression of certain of the markers likely result from the abnormal state of the cells, it is likewise recognized that changes in the levels of expression of other of the markers induce, maintain, and promote the abnormal state of those cells. Thus, compounds which inhibit a cancer-related disease in a patient will cause the level of expression of one or more of the markers to change to a level nearer the normal level of expression for that marker (i.e. the level of expression for the marker in normal cells).

This method thus comprises comparing expression of a marker in a first cell sample and maintained in the presence of the test compound and expression of the marker in a second cell sample and maintained in the absence of the test compound. A significantly reduced expression of a marker in the presence of the test compound is an indication that the test compound inhibits a cancer-related disease. The cell samples may, for example, be aliquots of a single sample of normal cells obtained from a patient, pooled samples of normal cells obtained from a patient, cells of a normal cell line, aliquots of a single sample of cancer-related disease cells obtained from a patient, pooled samples of cancer-related disease cells obtained from a patient, cells of a cancer-related disease cell line, or the like.

In one embodiment, the samples are cancer-related disease cells obtained from a patient and a plurality of compounds believed to be effective for inhibiting various cancer-related diseases are tested in order to identify the compound which is likely to best inhibit the cancer-related disease in the patient.

This method may likewise be used to assess the efficacy of a therapy for inhibiting a cancer-related disease in a patient. In this method, the level of expression of one or more markers in a pair of samples (one subjected to the therapy, the other not subjected to the therapy) is assessed. As with the method of assessing the efficacy of test compounds, if the therapy induces a significantly lower level of expression of a marker then the therapy is efficacious for inhibiting a cancer-related disease. As above, if samples from a selected patient are used in this method, then alternative therapies can be assessed in vitro in order to select a therapy most likely to be efficacious for inhibiting a cancer-related disease in the patient.

Methods for Assessing Harmful Potentials

As described herein, the abnormal state of human cells is correlated with changes in the levels of expression of the markers. There is also provided a method for assessing the harmful potential of a test compound. This method comprises maintaining separate aliquots of human cells in the presence and absence of the test compound. Expression of a marker in each of the aliquots is compared. A significantly higher level of expression of a marker in the aliquot maintained in the presence of the test compound (relative to the aliquot maintained in the absence of the test compound) is an indication that the test compound possesses a harmful potential. The relative harmful potential of various test compounds can be assessed by comparing the degree of enhancement or inhibition of the level of expression of the relevant markers, by comparing the number of markers for which the level of expression is enhanced or inhibited, or by comparing both.

Isolated Proteins and Antibodies

One aspect pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein").

When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein can be a polypeptide which is, for example, 10, 25, 50, 100 or more amino acids in length.

Moreover, other biologically active portions, in which other regions of the marker protein are deleted, can be prepared by recombinant techniques and evaluated for one or more of the functional activities of the native form of the marker protein. In certain embodiments, useful proteins are substantially identical (e.g., at least about 40%, and in certain embodiments, 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

In addition, libraries of segments of a marker protein can be used to generate a variegated population of polypeptides for screening and subsequent selection of variant marker proteins or segments thereof.

Predictive Medicine

There is also provided herein uses of the animal models and markers in the field of predictive medicine in which diagnostic assays, prognostic assays, pharmacogenomics, and monitoring clinical trials are used for prognostic (predictive) purposes to thereby treat an individual prophylactically. Accordingly, there is also provided herein diagnostic assays for determining the level of expression of one or more marker proteins or nucleic acids, in order to determine whether an individual is at risk of developing a cancer-related disease. Such assays can be used for prognostic or predictive purposes to thereby prophylactically treat an individual prior to the onset of the cancer-related disease.

In another aspect, the methods are useful for at least periodic screening of the same individual to see if that individual has been exposed to chemicals or toxins that change his/her expression patterns.

Yet another aspect pertains to monitoring the influence of agents (e.g., drugs or other compounds administered either to inhibit a cancer-related disease or to treat or prevent any other disorder (e.g., in order to understand any system effects that such treatment may have) on the expression or activity of a marker in clinical trials.

Pharmacogenomics

The markers are also useful as pharmacogenomic markers. As used herein, a "pharmacogenomic marker" is an objective biochemical marker whose expression level correlates with a specific clinical drug response or susceptibility in a patient. The presence or quantity of the pharmacogenomic marker expression is related to the predicted response of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected.

Monitoring Clinical Trials

Monitoring the influence of agents (e.g., drug compounds) on the level of expression of a marker can be applied not only in basic drug screening, but also in clinical trials. For example, the effectiveness of an agent to affect marker expression can be monitored in clinical trials of subjects receiving treatment for a cancer-related disease.

In one non-limiting embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly.

For example, increased expression of the marker gene(s) during the course of treatment may indicate ineffective dosage and the desirability of increasing the dosage. Conversely, decreased expression of the marker gene(s) may indicate efficacious treatment and no need to change dosage.

Electronic Apparatus Readable Media, Systems, Arrays and Methods of Using Same

As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; and general hard disks and hybrids of these categories such as magnetic/optical storage media. The medium is adapted or configured for having recorded thereon a marker as described herein.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems.

As used herein, "recorded" refers to a process for storing or encoding information on the electronic apparatus readable medium. Those skilled in the art can readily adopt any method for recording information on media to generate materials comprising the markers described herein.

A variety of software programs and formats can be used to store the marker information of the present invention on the electronic apparatus readable medium. Any number of data processor structuring formats (e.g., text file or database) may be employed in order to obtain or create a medium having recorded thereon the markers. By providing the markers in readable form, one can routinely access the marker sequence information for a variety of purposes. For example, one skilled in the art can use the nucleotide or amino acid sequences in readable form to compare a target sequence or target structural motif with the sequence information stored within the data storage means. Search means are used to identify fragments or regions of the sequences which match a particular target sequence or target motif.

Thus, there is also provided herein a medium for holding instructions for performing a method for determining whether a subject has a cancer-related disease or a pre-disposition to a cancer-related disease, wherein the method comprises the steps of determining the presence or absence of a marker and based on the presence or absence of the marker, determining whether the subject has a cancer-related disease or a pre-disposition to a cancer-related disease and/or recommending a particular treatment for a cancer-related disease or pre-cancer-related disease condition.

There is also provided herein an electronic system and/or in a network, a method for determining whether a subject has a cancer-related disease or a pre-disposition to a cancer-related disease associated with a marker wherein the method comprises the steps of determining the presence or absence of the marker, and based on the presence or absence of the marker, determining whether the subject has a cancer-related disease or a pre-disposition to a cancer-related disease, and/or recommending a particular treatment for the cancer-related disease or pre-cancer-related disease condition. The method may further comprise the step of receiving phenotypic information associated with the subject and/or acquiring from a network phenotypic information associated with the subject.

Also provided herein is a network, a method for determining whether a subject has a cancer-related disease or a pre-disposition to a cancer-related disease associated with a marker, the method comprising the steps of receiving information associated with the marker, receiving phenotypic information associated with the subject, acquiring information from the network corresponding to the marker and/or a cancer-related disease, and based on one or more of the phenotypic information, the marker, and the acquired information, determining whether the subject has a cancer-related disease or a pre-disposition to a cancer-related disease. The method may further comprise the step of recommending a particular treatment for the cancer-related disease or pre-cancer-related disease condition.

There is also provided herein a business method for determining whether a subject has a cancer-related disease or a pre-disposition to a cancer-related disease, the method comprising the steps of receiving information associated with the marker, receiving phenotypic information associated with the subject, acquiring information from the network corresponding to the marker and/or a cancer-related disease, and based on one or more of the phenotypic information, the marker, and the acquired information, determining whether the subject has a cancer-related disease or a pre-disposition to a cancer-related disease. The method may further comprise the step of recommending a particular treatment for the cancer-related disease or pre-cancer-related disease condition.

Arrays

There is also provided herein an array that can be used to assay expression of one or more genes in the array. In one embodiment, the array can be used to assay gene expression in a tissue to ascertain tissue specificity of genes in the array. In this manner, up to about 7000 or more genes can be simultaneously assayed for expression. This allows a profile to be developed showing a battery of genes specifically expressed in one or more tissues.

In addition to such qualitative determination, there is provided herein the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined.

Such a determination is useful, for example, to know the effect of cell-cell interaction at the level of gene expression. If an agent is administered therapeutically to treat one cell type but has an undesirable effect on another cell type, the method provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a cancer-related disease, progression of a cancer-related disease, and processes, such as cellular transformation associated with a cancer-related disease.

The array is also useful for ascertaining the effect of the expression of a gene or the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

Surrogate Markers

The markers may serve as surrogate markers for one or more disorders or disease states or for conditions leading up to a cancer-related disease state. As used herein, a "surrogate marker" is an objective biochemical marker which correlates with the absence or presence of a disease or disorder, or with the progression of a disease or disorder. The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies, or when an assessment of disease progression is desired before a potentially dangerous clinical endpoint is reached.

The markers are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo.

Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations.

Protocols for Testing

The method of testing for cancer-related diseases comprises, for example measuring the expression level of each marker gene in a biological sample from a subject over time and comparing the level with that of the marker gene in a control biological sample.

When the marker gene is one of the genes described herein and the expression level is differentially expressed (for examples, higher or lower than that in the control), the subject is judged to be affected with a cancer-related disease. When the expression level of the marker gene falls within the permissible range, the subject is unlikely to be affected with a cancer-related disease.

The standard value for the control may be pre-determined by measuring the expression level of the marker gene in the control, in order to compare the expression levels. For example, the standard value can be determined based on the expression level of the above-mentioned marker gene in the control. For example, in certain embodiments, the permissible range is taken as ±2S.D. based on the standard value. Once the standard value is determined, the testing method may be performed by measuring only the expression level in a biological sample from a subject and comparing the value with the determined standard value for the control.

Expression levels of marker genes include transcription of the marker genes to mRNA, and translation into proteins. Therefore, one method of testing for a cancer-related disease is performed based on a comparison of the intensity of expression of mRNA corresponding to the marker genes, or the expression level of proteins encoded by the marker genes.

Probes

The measurement of the expression levels of marker genes in the testing for a cancer-related disease can be carried out according to various gene analysis methods. Specifically, one can use, for example, a hybridization technique using nucleic acids that hybridize to these genes as probes, or a gene amplification technique using DNA that hybridize to the marker genes as primers.

The probes or primers used for the testing can be designed based on the nucleotide sequences of the marker genes. The identification numbers for the nucleotide sequences of the respective marker genes are describer herein.

Further, it is to be understood that genes of higher animals generally accompany polymorphism in a high frequency. There are also many molecules that produce isoforms comprising mutually different amino acid sequences during the splicing process. Any gene associated with a cancer-related disease that has an activity similar to that of a marker gene is included in the marker genes, even if it has nucleotide sequence differences due to polymorphism or being an isoform.

It is also to be understood that the marker genes can include homologs of other species in addition to humans. Thus, unless otherwise specified, the expression "marker gene" refers to a homolog of the marker gene unique to the species or a foreign marker gene which has been introduced into an individual.

Also, it is to be understood that a "homolog of a marker gene" refers to a gene derived from a species other than a human, which can hybridize to the human marker gene as a probe under stringent conditions. Such stringent conditions are known to one skilled in the art who can select an appropriate condition to produce an equal stringency experimentally or empirically.

A polynucleotide comprising the nucleotide sequence of a marker gene or a nucleotide sequence that is complementary to the complementary strand of the nucleotide sequence of a marker gene and has at least 15 nucleotides, can be used as a primer or probe. Thus, a "complementary strand" means one strand of a double stranded DNA with respect to the other strand and which is composed of A:T (U for RNA) and G:C base pairs.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by an algorithm, BLAST, etc.

Such polynucleotides are useful as a probe to detect a marker gene, or as a primer to amplify a marker gene. When used as a primer, the polynucleotide comprises usually 15 bp to 100 bp, and in certain embodiments 15 bp to 35 bp of nucleotides. When used as a probe, a DNA comprises the whole nucleotide sequence of the marker gene (or the complementary strand thereof), or a partial sequence thereof that has at least 15 bp nucleotides. When used as a primer, the 3' region must be complementary to the marker gene, while the 5' region can be linked to a restriction enzyme-recognition sequence or a tag.

"Polynucleotides" may be either DNA or RNA. These polynucleotides may be either synthetic or naturally-occurring. Also, DNA used as a probe for hybridization is usually labeled. Those skilled in the art readily understand such labeling methods. Herein, the term "oligonucleotide" means a polynucleotide with a relatively low degree of polymerization. Oligonucleotides are included in polynucleotides.

Tests for Cancer-Related Diseases

Tests for a cancer-related disease using hybridization techniques can be performed using, for example, Northern hybridization, dot blot hybridization, or the DNA microarray technique. Furthermore, gene amplification techniques, such as the RT-PCR method may be used. By using the PCR amplification monitoring method during the gene amplification step in RT-PCR, one can achieve a more quantitative analysis of the expression of a marker gene.

In the PCR gene amplification monitoring method, the detection target (DNA or reverse transcript of RNA) is hybridized to probes that are labeled with a fluorescent dye and a quencher which absorbs the fluorescence. When the PCR proceeds and Taq polymerase degrades the probe with its 5'-3' exonuclease activity, the fluorescent dye and the quencher draw away from each other and the fluorescence is detected. The fluorescence is detected in real time. By simultaneously measuring a standard sample in which the copy number of a target is known, it is possible to determine the copy number of the target in the subject sample with the cycle number where PCR amplification is linear. Also, one skilled in the art recognizes that the PCR amplification monitoring method can be carried out using any suitable method.

The method of testing for a cancer-related disease can be also carried out by detecting a protein encoded by a marker gene. Hereinafter, a protein encoded by a marker gene is described as a "marker protein." For such test methods, for example, the Western blotting method, the immunoprecipitation method, and the ELISA method may be employed using an antibody that binds to each marker protein.

Antibodies used in the detection that bind to the marker protein may be produced by any suitable technique. Also, in order to detect a marker protein, such an antibody may be appropriately labeled. Alternatively, instead of labeling the antibody, a substance that specifically binds to the antibody, for example, protein A or protein G, may be labeled to detect the marker protein indirectly. More specifically, such a detection method can include the ELISA method.

A protein or a partial peptide thereof used as an antigen may be obtained, for example, by inserting a marker gene or a portion thereof into an expression vector, introducing the construct into an appropriate host cell to produce a transformant, culturing the transformant to express the recombinant protein, and purifying the expressed recombinant protein from the culture or the culture supernatant. Alternatively, the amino acid sequence encoded by a gene or an oligopeptide comprising a portion of the amino acid sequence encoded by a full-length cDNA are chemically synthesized to be used as an immunogen.

Furthermore, a test for a cancer-related disease can be performed using as an index not only the expression level of a marker gene but also the activity of a marker protein in a biological sample. Activity of a marker protein means the biological activity intrinsic to the protein. Various methods can be used for measuring the activity of each protein.

Even if a patient is not diagnosed as being affected with a cancer-related disease in a routine test in spite of symptoms suggesting these diseases, whether or not such a patient is suffering from a cancer-related disease can be easily determined by performing a test according to the methods described herein.

More specifically, in certain embodiments, when the marker gene is one of the genes described herein, an increase or decrease in the expression level of the marker gene in a patient whose symptoms suggest at least a susceptibility to a cancer-related disease indicates that the symptoms are primarily caused by a cancer-related disease.

In addition, the tests are useful to determine whether a cancer-related disease is improving in a patient. In other words, the methods described herein can be used to judge the therapeutic effect of a treatment for a cancer-related disease. Furthermore, when the marker gene is one of the genes described herein, an increase or decrease in the expression level of the marker gene in a patient, who has been diagnosed as being affected by a cancer-related disease, implies that the disease has progressed more.

The severity and/or susceptibility to a cancer-related disease may also be determined based on the difference in expression levels. For example, when the marker gene is one of the genes described herein, the degree of increase in the expression level of the marker gene is correlated with the presence and/or severity of a cancer-related disease.

Control of Expression of Marker

In addition, the expression itself of a marker gene can be controlled by introducing a mutation(s) into the transcriptional regulatory region of the gene. Those skilled in the art understand such amino acid substitutions. Also, the number of amino acids that are mutated is not particularly restricted, as long as the activity is maintained. Normally, it is within 50 amino acids, in certain non-limiting embodiments, within 30 amino acids, within 10 amino acids, or within 3 amino acids. The site of mutation may be any site, as long as the activity is maintained.

Screening Methods

In yet another aspect, there is provided herein screening methods for candidate compounds for therapeutic agents to treat a cancer-related disease. One or more marker genes are selected from the group of genes described herein. A therapeutic agent for a cancer-related disease can be obtained by selecting a compound capable of increasing or decreasing the expression level of the marker gene(s).

It is to be understood that the expression "a compound that increases the expression level of a gene" refers to a compound that promotes any one of the steps of gene transcription, gene translation, or expression of a protein activity. On the other hand, the expression "a compound that decreases the expression level of a gene", as used herein, refers to a compound that inhibits any one of these steps.

In particular aspects, the method of screening for a therapeutic agent for a cancer-related disease can be carried out either in vivo or in vitro. This screening method can be performed, for example, by (1) administering a candidate compound to an animal subject; (2) measuring the expression level of a marker gene(s) in a biological sample from the animal subject; or (3) selecting a compound that increases or decreases the expression level of a marker gene(s) as compared to that in a control with which the candidate compound has not been contacted.

In still another aspect, there is provided herein a method to assess the efficacy of a candidate compound for a pharmaceutical agent on the expression level of a marker gene(s) by contacting an animal subject with the candidate compound and monitoring the effect of the compound on the expression level of the marker gene(s) in a biological sample derived from the animal subject. The variation in the expression level of the marker gene(s) in a biological sample derived from the animal subject can be monitored using the same technique as used in the testing method described above. Furthermore, based on the evaluation, a candidate compound for a pharmaceutical agent can be selected by screening.

Kits

In another aspect, there is provided various diagnostic and test kits. In one embodiment, a kit is useful for assessing whether a patient is afflicted with a cancer-related disease. The kit comprises a reagent for assessing expression of a marker. In another embodiment, a kit is useful for assessing the suitability of a chemical or biologic agent for inhibiting a cancer-related disease in a patient. Such a kit comprises a reagent for assessing expression of a marker, and may also comprise one or more of such agents.

In a further embodiment, the kits are useful for assessing the presence of cancer-related disease cells or treating cancer-related diseases. Such kits comprise an antibody, an antibody derivative or an antibody fragment, which binds specifically with a marker protein or a fragment of the protein. Such kits may also comprise a plurality of antibodies, antibody derivatives or antibody fragments wherein the plurality of such antibody agents binds specifically with a marker protein or a fragment of the protein.

In an additional embodiment, the kits are useful for assessing the presence of cancer-related disease cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

The compositions, kits and methods described herein can have the following uses, among others: 1) assessing whether a patient is afflicted with a cancer-related disease; 2) assessing the stage of a cancer-related disease in a human patient; 3) assessing the grade of a cancer-related disease in a patient; 4) assessing the nature of a cancer-related disease in a patient; 5) assessing the potential to develop a cancer-related disease in a patient; 6) assessing the histological type of cells associated with a cancer-related disease in a patient; 7) making antibodies, antibody fragments or antibody derivatives that are useful for treating a cancer-related disease and/or assessing whether a patient is afflicted with a cancer-related disease; 8) assessing the presence of cancer-related disease cells; 9) assessing the efficacy of one or more test compounds for inhibiting a cancer-related disease in a patient; 10) assessing the efficacy of a therapy for inhibiting a cancer-related disease in a patient; 11) monitoring the progression of a cancer-related disease in a patient; 12) selecting a composition or therapy for inhibiting a cancer-related disease in a patient; 13) treating a patient afflicted with a cancer-related disease; 14) inhibiting a cancer-related disease in a patient; 15) assessing the harmful potential of a test compound; and 16) preventing the onset of a cancer-related disease in a patient at risk for developing a cancer-related disease.

The kits are useful for assessing the presence of cancer-related disease cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kits may optionally comprise additional components useful for performing the methods described herein. By way of example, the kit may comprise fluids (e.g. SSC buffer) suitable for annealing complementary nucleic acids or for binding an antibody with a protein with which it specifically binds, one or more sample compartments, an instructional material which describes performance of the method, a sample of normal cells, a sample of cancer-related disease cells, and the like.

Animal Model

Non-human animal model can be produced for assessment of at least one cancer-related disease. The method includes exposing the animal to repeated doses of at least one chemical believed to cause the cancer if interest. In certain aspects, the method further includes collecting one or more selected samples from the animal; and comparing the collected sample to one or more indicia of potential cancer initiation or development.

A method of producing the animal model includes: maintaining the animal in a specific chemical-free environment and sensitizing the animal with at least one chemical believed to cause the cancer. In certain embodiments, at least a part of the animal is sensitized by multiple sequential exposures.

A method of screening for an agent for effectiveness against at least one cancer-related disease generally includes: administering at least one agent to a test animal, determining whether the agent reduces or aggravates one or more symptoms of the cancer-related disease; correlating a reduction in one or more symptoms with effectiveness of the agent against the cancer-related disease; or correlating a lack of reduction in one or more symptoms with ineffectiveness of the agent. The animal model is useful for assessing one or more metabolic pathways that contribute to at least one of initiation, progression, severity, pathology, aggressiveness, grade, activity, disability, mortality, morbidity, disease sub-classification or other underlying pathogenic or pathological feature of at least one cancer-related disease. The analysis can be by one or more of: hierarchical clustering, signature network construction, mass spectroscopy proteomic analysis, surface plasmon resonance, linear statistical modeling, partial least squares discriminant analysis, and multiple linear regression analysis.

The animal model can be assessed for at least one cancer-related disease, by examining an expression level of one or more markers, or a functional equivalent thereto.

The animal models can be used for the screening of therapeutic agents useful for treating or preventing a cancer-related disease. Accordingly, the methods are useful for identifying therapeutic agents for treating or preventing a cancer-related disease. The methods comprise administering a candidate agent to an animal model made by the methods described herein, assessing at least one cancer-related disease response in the animal model as compared to a control animal model to which the candidate agent has not been administered. If at least one cancer-related disease response is reduced in symptoms or delayed in onset, the candidate agent is an agent for treating or preventing the cancer-related disease.

The animal models for a cancer-related disease can include an animal where the expression level of one or more marker genes or a gene functionally equivalent to the marker gene has been elevated in the animal model. A "functionally equivalent gene" as used herein generally is a gene that encodes a protein having an activity similar to a known activity of a protein encoded by the marker gene. A representative example of a functionally equivalent gene includes a counterpart of a marker gene of a subject animal, which is intrinsic to the animal.

The animal model for a cancer-related disease is useful for detecting physiological changes due to a cancer-related disease. In certain embodiments, the animal model is useful to reveal additional functions of marker genes and to evaluate drugs whose targets are the marker genes.

In one embodiment, an animal model for a cancer-related disease can be created by controlling the expression level of a counterpart gene or administering a counterpart gene. The method can include creating an animal model for a cancer-related disease by controlling the expression level of a gene selected from the group of genes described herein. In another embodiment, the method can include creating an animal model for a cancer-related disease by administering the protein encoded by a gene described herein, or administering an antibody against the protein. It is to be also understood, that in certain other embodiments, the marker can be over-expressed such that the marker can then be measured using appropriate methods.

In another embodiment, an animal model for a cancer-related disease can be created by introducing a gene selected from such groups of genes, or by administering a protein encoded by such a gene.

In another embodiment, a cancer-related disease can be induced by suppressing the expression of a gene selected from such groups of genes or the activity of a protein encoded by such a gene. An antisense nucleic acid, a ribozyme, or an RNAi can be used to suppress the expression. The activity of a protein can be controlled effectively by administering a substance that inhibits the activity, such as an antibody.

The animal model is useful to elucidate the mechanism underlying a cancer-related disease and also to test the safety of compounds obtained by screening. For example, when an animal model develops the symptoms of a cancer-related disease, or when a measured value involved in a certain a cancer-related disease alters in the animal, a screening system can be constructed to explore compounds having activity to alleviate the disease.

As used herein, the expression "an increase in the expression level" refers to any one of the following: where a marker gene introduced as a foreign gene is expressed artificially; where the transcription of a marker gene intrinsic to the subject animal and the translation thereof into the protein are enhanced; or where the hydrolysis of the protein, which is the translation product, is suppressed. As used herein, the expression "a decrease in the expression level" refers to either the state in which the transcription of a marker gene of the subject animal and the translation thereof into the protein are inhibited, or the state in which the hydrolysis of the protein, which is the translation product, is enhanced. The expression level of a gene can be determined, for example, by a difference in signal intensity on a DNA chip. Furthermore, the activity of the translation product—the protein—can be determined by comparing with that in the normal state.

It is also within the contemplated scope that the animal model can include transgenic animals, including, for example animals where a marker gene has been introduced and expressed artificially; marker gene knockout animals; and knock-in animals in which another gene has been substituted for a marker gene. A transgenic animal, into which an antisense nucleic acid of a marker gene, a ribozyme, a polynucleotide having an RNAi effect, or a DNA functioning as a decoy nucleic acid or such has been introduced, can be used as the transgenic animal. Such transgenic animals also include, for example, animals in which the activity of a marker protein has been enhanced or suppressed by introducing a mutation(s) into the coding region of the gene, or the amino acid sequence has been modified to become resistant or susceptible to hydrolysis. Mutations in an amino acid sequence include substitutions, deletions, insertions, and additions.

Therapeutic Applications

The invention is widely applicable to a variety of situations where it is desirable to be able to regulate the level of gene expression, such as by turning gene expression "on" and "off", in a rapid, efficient and controlled manner without causing pleiotropic effects or cytotoxicity. The invention may be particularly useful for gene therapy purposes in humans, in treatments for either genetic or acquired diseases. The general approach of gene therapy involves the introduction of one or more nucleic acid molecules into cells such that one or more gene products encoded by the introduced genetic material are produced in the cells to restore or enhance a functional activity. For reviews on gene therapy approaches Anderson, et al. (1992; Miller et al. (1992); Friedmann et al. (1989); and Cournoyer et al. (1990). However, current gene therapy vectors typically utilize constitutive regulatory elements which are responsive to endogenous transcriptions factors. These vector systems do not allow for the ability to modulate the level of gene expression in a subject. In contrast, the regulatory system of the invention provides this ability.

To use the system of the invention for gene therapy purposes, at least one DNA molecule is introduced into cells of a subject in need of gene therapy (e.g., a human subject suffering from a genetic or acquired disease) to modify the cells. The cells are modified to comprise: 1) nucleic acid encoding an inducible regulator of the invention in a form suitable for expression of the inducible regulator in the host cells; and 2) an siRNA (e.g., for therapeutic purposes) operatively linked to a tissue-specific promoter such as an s-ship1 promoter. A single DNA molecule encoding components of the regulatory system of the invention can be used, or alternatively, separate DNA molecules encoding each component can be used. The cells of the subject can be modified ex vivo and then introduced into the subject or the cells can be directly modified in vivo by conventional techniques for introducing nucleic acid into cells. Thus, the regulatory system of the invention offers the advantage over constitutive regulatory systems of allowing for modulation of the level of gene expression depending upon the requirements of the therapeutic situation.

Genes of particular interest to be knocked down or knocked out in cells of a subject for treatment of genetic or acquired diseases include those encoding a deleterious gene product, such as an abnormal protein. Examples of non-limiting specific diseases include anemia, blood-related cancers, Parkinson's disease, and diabetes.

The present invention can be applied to develop autologous or allogeneic cell lines for therapeutical purposes. For example, gene therapy applications of particular interest in cell and/or organ transplantation are utilized with the present invention. In exemplary embodiments, downregulation of transplantation antigens (such as, for example, by downregulation of beta2-microglobulin expression via siRNA) allows for transplantation of allogeneic cells while minimizing the risk of rejection by the patient's immune system. The present invention would allow for a switch off of the RNAi in case of adverse effects (e.g. uncontrollable replication of the transplanted cells).

Cells types that can be subjected to the present invention include hematopoietic stem cells, myoblasts, hepatocytes, lymphocytes, airway epithelium, skin epithelium, islets, dopaminergic neurons, keratinocytes, and so forth. For further descriptions of cell types, genes and methods for gene therapy see e.g., Armentano et al. (1990); Wolff et al. (1990); Chowdhury et al. (1991); Ferry et al. (1991); Quantin et al (1992); Dai et al. (1992); van Beusechem et al. (1992); Rosenfeld et al. (1992); Kay et al. (1992); Cristiano et al (1993); Hwu et al (1993); and Herz and Gerard (1993).

In particular embodiments of the present invention, there is a method of treating any disease condition amenable to treatment with an s-ship promoter. In specific embodiments, the method comprises preparing a polynucleotide construct having a region encoding a therapeutic or diagnostic (marker) gene that is operably linked to a promoter, wherein the gene encoded by the construct is for the treatment of the disease condition.

A. Pharmaceutical Formulations, Delivery, and Treatment Regimens

In an embodiment of the present invention, methods of treatment are contemplated. An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

B. Combination Treatments

The compounds and methods of the present invention may be used in the context of traditional therapies. In order to increase the effectiveness of a treatment with the compositions of the present invention, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery. Likewise, the treatment of a vascular disease or condition may involve both the present invention and conventional vascular agents or therapies.

Various combinations may be employed; for example, a host cell of the present invention is "A" and the secondary anti-cancer agent/therapy is "B": TABLE-US-00005 A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A Administration of the therapeutic expression constructs of the present invention to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

All patents, patent applications and references cited herein are incorporated in their entirety by reference. While the invention has been described and exemplified in sufficient detail for those skilled in this art to make and use it, various alternatives, modifications and improvements should be apparent without departing from the spirit and scope of the invention. One skilled in the art readily appreciates that the present invention is well adapted to carry out the objects and obtain the ends and advantages mentioned, as well as those inherent therein.

The methods and reagents described herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will also be readily apparent to a person skilled in the art that varying substitutions and modifications may be made to the invention disclosed herein without departing from the scope and spirit of the invention.

It should be understood that although the present invention has been specifically disclosed by preferred embodiments and optional features, modifications and variations of the concepts herein disclosed may be resorted to by those skilled in the art, and that such modifications and variations are considered to be within the scope of this invention as defined by the appended claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Unless otherwise defined, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (Glover ed., 1985); Oligonucleotide Synthesis (Gait ed., 1984); Mullis et al. U.S. Pat. No. 4,683,195; Nucleic Acid Hybridization (Hames & Higgins eds., 1984); Transcription And Translation (Hames & Higgins eds., 1984); Culture Of Animal Cells (R. I. Freshney, Alan R. Liss, Inc., 1987); Immobilized Cells And Enzymes (IRL Press, 1986); Perbal, A Practical Guide To Molecular Cloning (1984); the treatise, Methods In Enzymology (Academic Press, Inc., N.Y.); Gene Transfer Vectors For Mammalian Cells (Miller and Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (Weir and Blackwell, eds., 1986); The Laboratory Rat, editor in chief: Mark A. Suckow; authors: Sharp and LaRegina. CRC Press, Boston, 1988, which are incorporated herein by reference) and chemical methods.

REFERENCES

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

1. Ambros, V. (2003). MicroRNA pathways in flies and worms: growth, death, fat, stress, and timing. Cell 113, 673-676.
2. Ambros, V. (2004). The functions of animal microRNAs. Nature 431, 350-355.
3. Balmain, A., Gray, J. W., and Ponder, B. A. (2003). The genetics and genomics of cancer. Nat Genet. 33 Suppl, 238-244.
4. Bejerano, G., Haussler, D., and Blanchette, M. (2004a). Into the heart of darkness: large-scale clustering of human non-coding DNA. Bioinformatics 20, 140-148.
5. Bejerano, G., Pheasant, M., Makunin, I., Stephen, S., Kent, W. J., Mattick, J. S., and Haussler, D.
6. (2004b). Ultraconserved elements in the human genome. Science 304, 1321-1325. Benjamini Y and Hochberg Y. Controlling the False Discovery Rate: a Practical and Powerful
7. Approach to Multiple Testing. Journal of the Royal Statistical Society. B, 57, 289-300. Berezikov, E. and Plasterk, R. H. Camels and zebrafish, viruses and cancer: a microRNA update
8. (2005a). Hum Mol. Genet. 14, R183-90.
9. Berezikov, E., Guryev, V., van de Belt, J., Wienholds, E., Plasterk, R. H., and Cuppen, E. (2005b). Phylogenetic shadowing and computational identification of human microRNA genes. Cell 120, 21-24.
10. Bejerano, G., Lowe, C. B., Ahituv, N., King, B., Siepel, A., Salama, S. R., Rubin, E. M., Kent, W. J., and Haussler, D. (2006). A distal enhancer and an ultraconserved exon are derived from a novel retroposon. Nature 441, 87-90.
11. Bishop, J. M. (1991). Molecular themes in oncogenesis. Cell 64, 235-248.
12. Calin, G. A., Dumitru, C. D., Shimizu, M., Bichi, R., Zupo, S., Noch, E., Aldler, H., Rattan, S., Keating, M., Rai, K., et al. (2002). Frequent deletions and down-regulation of microRNA genes riR15 and miR16 at 13g14 in chronic lymphocytic leukemia. Proc Natl Acad Sc USA 99, 15524-15529.
13. Calin, G. A., Liu, C. G., Sevignani, C., Ferracin, M., Felli, N., Dumitru, C. D., Shimizu, M., Cimmino, A., Zupo, S., Dono, M., et al. (2004a). MicroRNA profiling reveals distinct signatures in B cell chronic lymphocytic leukemias. Proc Natl Acad Sci USA 101, 11755-11760.
14. Calin, G. A., Sevignani, C., Dumitru, C. D., Hyslop, T., Noch, E., Yendamuri, S., Shimizu, M., Rattan, S., Bullrich, F., Negrini; M., and Croce, C. M. (2004b). Human microRNA genes are frequently located at fragile sites and genomic regions involved in cancers. Proc Natl Acad Sci USA 101, 2999-3004.
15. Calin, G. A., Ferracin, M., Cimmino, A., Di Leva, G., Shimizu, M., Wojcik, S., Iorio, M. V., Visone, R., Sever, N. I., Fabbri, M., et al. (2005a). A Unique MicroRNA Signature Associated with Prognostic Factors and Disease Progression in B cell Chronic Lymphocytic Leukemia. N Engl J Med 352, 1667-1676.
16. Calin, G. A., and Croce, C. M. (2006a). MicroRNA signatures in human cancers. Nature Reviews Cancer 6, 857-866.
17. Calin, G. A., and Croce, C. M. (2006b). MicroRNA-cancer connection: the beginning of a new tale. Cancer Res 66, 7390-7394.
18. Chen, C., Ridzon, D. A., Broomer, A. J., Zhou, Z., Lee, D. H., Nguyen, J. T., Barbisin, M., Xu, N. L., Mahuvakar, V. R., Andersen, M. R., et al. (2005). Real-time quantification of microRNAs by stem-loop RT-PCR. Nucleic Acids Res 33, e179.
19. Chiorazzi, N., Rai, K. R., and Ferrarini, M. (2005). Chronic lymphocytic leukemia. N Engl J Med 352, 804-815.
20. Cimmino, A., Calin, G. A., Fabbri, M., Iorio, M. V., Ferracin, M., Shimizu, M., Wojcik, S. E., Aqeilan, R., Zupo, S., Dono, M., et al. (2005). miR-15 and miR-16 induce apoptosis by targeting BCL2. Proc Natl Acad Sc USA 102, 13944-13949.
21. Croce, C. M., and Cann, G. A. (2005). miRNAs, Cancer, and Stem Cell Division. Cell 122, 6-7. de la Chapelle, A. (2004). Genetic predisposition to colorectal cancer. Nature Reviews Cancer 4, 769-780.
22. Dermitzakis, E. T., Reymond, A., and Antonarakis, S. E. (2005). Conserved non-genic sequences—an unexpected feature of mammalian genomes. Nat Rev Genet. 6, 151-157.
23. Duret, L., Dorkeld, F., and Gautier, C. (1993). Strong conservation of non-coding sequences during vertebrates evolution: potential involvement in post-transcriptional regulation of gene expression. Nucleic Acids Res 21, 2315-2322.
24. E is, P. S., Tam, W., Sun, L., Chadburn, A., Li, Z., Gomez, M. F., Lund, E., and Dahlberg, J. E. (2005). Accumulation of miR-155 and BIC RNA in human B cell lymphomas. Proc Natl Acad Sci USA 102, 3627-3632.
25. Esquela-Kerscher, A., and Slack, F. J. (2006). Oncomirs—microRNAs with a role in cancer. Nat Rev Cancer 6, 259-269.
26. Furuno, M., Pang, K. C., Ninomiya, N., Fukuda, S., Frith, M. C., Bult, C., Kai, C., Kawai, J., Carninci, P., Hayashizaki, Y., et al. (2006). Clusters of internally primed transcripts reveal novel long noncoding RNAs. PLoS Genet. 2, e37.
27. Hunter, T. (1991). Cooperation between oncogenes. Cell 64, 249-270.
28. Huntley, S., Baggott, D. M., Hamilton, A. T., Tran-Gyamfi, M., Yang, S. C., Kim, J., Gordon, L., Branscomb, E., and Stubbs, S. (2006). A comprehensive catalog of human KRAB-associated zinc finger genes: Insights into the evolutionary history of a large family of transcriptional repressors. Genome Res 16:669-677.
29. Gaur A, Jewell D A, Liang Y, Ridzon D, Moore J H, Chen C, Ambros V R, Israel M A. Characterization of MicroRNA Expression Levels and Their Biological Correlates in Human Cancer Cell Lines. Cancer Res. 2007 Mar. 15; 67(6):2456-68.
30. Iorio, M. V., Ferracin, M., Liu, C. G., Veronese, A., Spizzo, R., Sabbioni, S., Magri, E., Pedriali, M., Fabbri, M., Campiglio, M., et al. (2005). microRNA gene expression deregulation in human breast cancer. Cancer Res 65, 7065-7070.
31. Ji, P., Diederichs, S., Wang, W., Boing, S., Metzger, R., Schneider, P. M., Tidow, N., Brandt, B., Buerger, H., Bulk, E., et al. (2003). MALAT-1, a novel noncoding RNA, and thymosin beta4 predict metastasis and survival in early-stage non-small cell lung cancer. Oncogene 22, 8031-8041.
32. Kluiver, J., Poppema, S., de Jong, D., Blokzijl, T., Harms, G., Jacobs, S., Kroesen, B. J., and van den Berg, A. (2005). BIC and miR-155 are highly expressed in Hodgkin, primary mediastinal and diffuse large B cell lymphomas. J Pathol 207, 243-249.
33. Liu, C.-G., Cahn, G. A., Meloon, B., Gamliel, N., Sevignani, C., Ferracin, M., Dumitru, D. C., Shimizu, M., Zupo, S., Dono, M., et al. (2004). An oligonucleotide microchip for genome-wide miRNA profiling in human and mouse tissues. Proc Natl Acad Sci USA 101, 9740-9744.
34. Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.
35. Meisler, M. H. (2001). Evolutionarily conserved noncoding DNA in the human genome: how much and what for? Genome Res 11, 1617-1618.
36. Ng, D., Toure, O., Wei, M. H., Arthur, D. C., Abbasi, F., Fontaine, L., Marti, G. E., Fraumeni, J. F. J., Goldin, L. R., Caporaso, N. E., and Toro, J. R. (2007). Identification of a novel chromosome region, 13q21.33-q22.2, for susceptibility genes in familial chronic lyinphocytic leukemia. Blood 109, 916-925.
37. Nobrega, M. A., Ovcharenko, I., Afzal, V., and Rubin, E. M. (2003). Scanning human gene deserts for long-range enhancers. Science 302, 413.
38. Nobrega, M. A., Zhu, Y., Plajzer-Frick, I., Afzal, V., and Rubin, E. M. (2004). Megabase deletions of gene deserts result in viable mice. Nature 431, 988-993.
39. Pennacchio, L. A., Ahituv, N., Moses, A. M., Prabhakar, S., Nobrega, M. A., Shoukry, M., Minovitsky, S., Dubchak, I., Holt, A., Lewis, K. D., et al. (2006). In vivo enhancer analysis of human conserved non-coding sequences. Nature November 5; [Epub ahead of print].
40. Raveche E S, Salerno E, Scaglione B J, Manohar V, Abbasi F, Lin Y C, Fredrickson T, Landgraf P, Ramachandra S, Huppi K, Toro J R, Zenger V E, Metcalf R A, Marti G E. Abnormal microRNA-16 locus with synteny to human 13814 linked to CLL in NZB mice. Blood. 2007 Mar. 9; [Epub ahead of print]
41. Reis, E. M., Louro, R., Nakaya, H. I., and Verjovski-Almeida, S. (2005). As antisense RNA gets intronic. OMICS 9.
42. Rhodes, D. R., and Chinnaiyan, A. M. (2005). Integrative analysis of the cancer transcriptome. Nat Genet. 37, Suppl: S31-37.
43. Rigoutsos, I., Huynh, T., Miranda, K., Tsirigos, A., McHardy, A., and Platt, D. (2006). Short blocks from the noncoding parts of the human genome have instances within nearly all known genes and relate to biological processes. Proc Natl Acad Sci USA 103, 66056610.
44. Schmittgen, T. D., Jiang, J., Liu, Q., and yang, L. (2004). A high-throughput method to monitor the expression of microRNA precursor. Nucleic Acid Research 32, 43-53.
45. Thomas, J. W., Touchman, J. W., Blakesley, R. W., Bouffard, G. G., Beckstrom-Sternberg, S. M., Margulies, E. H., Blanchette, M., Siepel, A. C., Thomas, P. J., McDowell, J. C., et al. (2003). Comparative analyses of multi-species sequences from targeted genomic regions. Nature 424, 788-793.
46. Volinia, S., Calin, G. A., Liu, C.-G., Ambs, S., Cimmino, A., Petrocca, F., Visone, R., Iorio, M.

47. V., Roldo, C., Ferracin, M., et al. (2006). A microRNA expression signature of human
48. solid tumors define cancer gene targets. Proc Natl Acad Sc USA 103, 2257-2261. Weinberg, R. A. (1991). Tumor suppressor genes. Science 254, 1138-1146.
49. Wilson, J. F. (2005). Liver cancer on the rise. Ann Intern Med 142, 1029-1032.
50. Wooster, R., and Weber, B. L. (2003). Breast and ovarian cancer. N Engl J Med 348, 2339-2347. Yanaihara, N., Caplen, N., Bowman, E., Kumamoto, K., Okamoto, A., Yokota, J., Tanaka, T.,
51. Calin, G. A., Liu, C. G., Croce, C. M., and Harris, C. C. (2006). microRNA Signature in
52. Lung Cancer Diagnosis and Prognosis. Cancer Cell 9, 189-198.
53. Zhang, L., and al, e. (2006). MicroRNAs exhibit high frequency genomic alterations in human cancer. Proc Natl Acad Sc USA 103, 9136-9141.

REFERENCES FOR EXAMPLE II

54. Bejerano, G., Pheasant, M., Makunin, I., Stephen, S., Kent, W. J., Mattick, J. S., and Haussler, D. (2004). Ultra-con served elements in the human genome. Science 304, 1321-1325.
55. Benjamini Y and Hochberg Y. Controlling the False Discovery Rate: a Practical and Powerful Approach to Multiple Testing. Journal of the Royal Statistical Society. B, 57, 289-300.
56. Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004). Human microRNA genes are frequently located at fragile sites and genomic regions involved in cancers. Proc Natl Acad Sci USA 101, 2999-3004.

What is claimed is:

1. A method to identify a relative risk in a vertebrate for developing chronic lymphocytic leukemia, comprising:
   (a) obtaining a nucleic acid-containing test sample from a vertebrate subject,
   (b) measuring, by laboratory analysis, a level of at least one transcribed ultra-conserved regions (T-UCR),
   (c) identifying whether the test sample expresses at least one T-UCR,
   (d) determining the relative risk for developing chronic lymphocytic leukemia by comparing the at least one T-UCR measured level to the level of a corresponding T-UCR in a control sample,
      wherein a decrease in the level of at least one T-UCR in the test sample, relative to the level of a corresponding T-UCR in a control sample, is indicative of the subject either having, or being at risk for developing chronic lymphocytic leukemia, wherein the at least one T-UCR is uc.160(N), and
   (e) measuring the level of at least one miR-155 in the test sample from said subject,
      wherein an increase in the level of the miR-155 in the test sample, relative to the level of a corresponding miR-155 in a control sample, is indicative of the subject either having, or being at risk for developing chronic lymphocytic leukemia.

2. The method of claim 1, further comprising measuring one or more additional T-URCs selected from: uc.269A(N) and uc.346A(P).

3. The method of claim 1, further comprising measuring at least one additional T-UCR selected from uc.215(N) and uc.348(N).

* * * * *

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acttccccct tctattatag cattagcaac g                                        31

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttaatgcata tcgtgatagg gg                                                  22

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcaatgcact attgcaagag cattattgca t                                        31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgccatgta cctgcctact tagcccaagg g                                        31
```

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggctcagtt cagcaggaac ag                                              22

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctaatgagac tgagtttaca gtgccataga                                      30

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tagcaccatt tgaaatcagt gtt                                             23

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggagataca acaagataac attaatgagt                                      30
```